United States Patent
Lee et al.

(10) Patent No.: US 12,064,426 B2
(45) Date of Patent: Aug. 20, 2024

(54) SELECTIVE INHIBITORS OF ROCK1 AND ROCK2 PROTEIN KINASES AND USES THEREOF

(71) Applicant: GENOSCO Inc., Billerica, MA (US)

(72) Inventors: Wongil Lee, Bedford, MA (US); William G. Devine, Woburn, MA (US); R. Bruce Diebold, Waltham, MA (US); So Young Hwang, Lexington, MA (US); Yunggeun Choi, Acton, MA (US); Yan Liu, Boston, MA (US); Sang-Ae Seung, Lexington, MA (US); Miyong Yong, Belmont, MA (US); Sewon Kim, Cambridge, MA (US); Jaekyoo Lee, North Andover, MA (US); Jong Sung Koh, Cambridge, MA (US)

(73) Assignee: GENOSCO Inc., Billerica, MA (US)

( * ) Notice: Subject to any disclaimer, the term of this patent is extended or adjusted under 35 U.S.C. 154(b) by 0 days.

(21) Appl. No.: 17/568,991

(22) Filed: Jan. 5, 2022

(65) Prior Publication Data

US 2023/0082993 A1 Mar. 16, 2023

Related U.S. Application Data

(60) Provisional application No. 63/134,458, filed on Jan. 6, 2021.

(51) Int. Cl.
| | | |
|---|---|---|
| *A61K 31/4725* | (2006.01) | |
| *A61K 31/4375* | (2006.01) | |
| *A61K 31/496* | (2006.01) | |
| *A61K 31/517* | (2006.01) | |
| *A61K 31/5377* | (2006.01) | |
| *A61K 31/5386* | (2006.01) | |
| *A61K 31/675* | (2006.01) | |
| *C07D 401/04* | (2006.01) | |
| *C07D 401/14* | (2006.01) | |
| *C07D 403/04* | (2006.01) | |
| *C07D 403/14* | (2006.01) | |
| *C07D 405/14* | (2006.01) | |
| *C07D 413/04* | (2006.01) | |
| *C07D 413/14* | (2006.01) | |
| *C07D 471/04* | (2006.01) | |
| *C07D 498/08* | (2006.01) | |
| *C07D 513/04* | (2006.01) | |
| *C07F 9/6558* | (2006.01) | |

(52) U.S. Cl.
CPC ...... *A61K 31/4725* (2013.01); *A61K 31/4375* (2013.01); *A61K 31/496* (2013.01); *A61K 31/517* (2013.01); *A61K 31/5377* (2013.01); *A61K 31/5386* (2013.01); *A61K 31/675* (2013.01); *C07D 401/04* (2013.01); *C07D 401/14* (2013.01); *C07D 403/04* (2013.01); *C07D 403/14* (2013.01); *C07D 405/14* (2013.01); *C07D 413/04* (2013.01); *C07D 413/14* (2013.01); *C07D 471/04* (2013.01); *C07D 498/08* (2013.01); *C07D 513/04* (2013.01); *C07F 9/65583* (2013.01); *C07B 2200/05* (2013.01)

(58) Field of Classification Search
CPC ............ A61K 31/4725; A61K 31/4375; A61K 31/496; A61K 31/517; A61K 31/5377; A61K 31/5386; A61K 31/675; C07D 401/04; C07D 401/14; C07D 403/04; C07D 403/14; C07D 405/14; C07D 413/14; C07D 471/04; C07D 498/08; C07D 513/04; C07F 9/65583; C07B 2200/05; A61L 31/675
See application file for complete search history.

(56) References Cited

FOREIGN PATENT DOCUMENTS

CN 107879975 A * 4/2018 ........... C07D 217/24

OTHER PUBLICATIONS

Dumas et al., "Ni-Catalyzed Reductive and Merged Photocatalytic Cross-Coupling Reactions [ . . . ]" ACS Omega 2020, 5, 42, 27591 (Year: 2020).*

Xu et al., "Hit-to-lead optimization and discovery of a potent, and orally bioavailable G protein coupled receptor kinase 2 (GRK2) inhibitor" Bioorganic & Medicinal Chemistry Letters 30 (2020) 127602 (Year: 2020).*

\* cited by examiner

*Primary Examiner* — Joseph R Kosack
*Assistant Examiner* — Jed A Kucharczk
(74) *Attorney, Agent, or Firm* — United One Law Group LLC; Kongsik Kim; Jhongwoo Peck

(57) ABSTRACT

The present invention relates to novel substituted bicyclic derivatives that can inhibit Rho-kinases and/or Rho-kinase mediated phosphorylation of myosin light chain phosphates, compositions comprising the derivatives, methods for preparing the derivatives, and methods for using the derivatives and/or compositions.

21 Claims, No Drawings

SELECTIVE INHIBITORS OF ROCK1 AND ROCK2 PROTEIN KINASES AND USES THEREOF

CROSS-REFERENCE TO RELATED APPLICATIONS

The present application claims priority to U.S. Provisional Application No. 63/134,458 filed Jan. 6, 2021, which is incorporated herein by reference.

TECHNICAL FIELD

The present invention relates to compounds capable of selectively inhibiting Rho-associated coiled-coil containing protein kinases (ROCK), compositions comprising the compounds, methods for preparing the compounds, and methods of using the compounds or compositions.

BACKGROUND

The Rho-associated coiled-coil containing protein kinases (ROCKs/Rho-kinase/Rho-associated kinase) are downstream effectors of small GTPase Rho (Rho A, Rho B, Rho C, and Rho E) and belong to the family of serine/threonine kinases. The active GTP bound form of Rho mediates several biological functions through the action of ROCKs, including smooth muscle contractions, cell motility, and cytokinesis. The ROCK proteins were identified in 1996 as proteins that bind to Rho GTPase. Two proteins were independently isolated as p160 and p164. Later, these were recognized as ROCK-1 and ROCK-2, respectively and as isoforms of the Rho-associated kinase. The two isoforms, ROCK-1 (ROCK-b/p160) and ROCK-2 (ROCK-a/p164), share 92% similarity in their amino acid sequence. Their structure comprises an N-terminally located catalytic kinase domain, followed by a coiled-coil containing region (600 amino acids) with a Rho-binding domain and a pleckstrin homology (PH) domain at the C terminus. They have varying locations, and distinct physiological roles have been identified for each. The ROCK-1 transcript (gene located on chromosome 18) is ubiquitous, with more prominent expression in liver, kidney, spleen, testis, thymus, and blood corpuscles, whereas ROCK-2 mRNA (chromosome 2) is expressed more abundantly in skeletal muscles and brain, suggesting that they have specialized roles in these locations.

ROCK inhibitors have been considered for use in numerous diseases, such as cerebral ischaemia, hypertension, erectile dysfunction, glaucoma, osteoporosis, cardiac hypertrophy, diabetic cardiomyopathy, retinopathy, pulmonary hypertension, and atherosclerosis. However, their implementation is limited because of a lack of knowledge regarding the involvement of the particular ROCK isoform. Whether isoform-specific targeting or combined ROCK inhibition would provide a better therapeutic outcome is yet to be verified. Despite their incomplete specificity towards the ROCK isoforms as well as other serine/threonine kinases, such as PRK2, PKC, cAMP-dependent protein kinase, and citron kinase, some nonspecific ROCK inhibitors have shown promising results in certain pathological states, such as glaucoma and hypertension. However, further work is required for isoform-selective ROCK inhibitors to be of clinical use, although several research-based studies have helped resolve, to some extent, ambiguity over ROCK-1 and ROCK-2-specific functions. Thus, a need for understanding the discreet functions of each isoform in a particular disorder still exists to help resolve issues of safety and specificity and expand the therapeutic applications of ROCK inhibitors.

SUMMARY

In one aspect, the present invention provides novel chemical compounds represented by Formula (1) below, which is capable of inhibiting Rho-associated coiled-coil forming protein serine/threonine kinases (ROCKs).

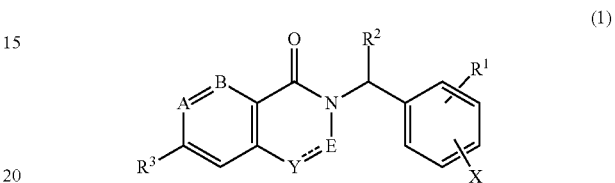

(1)

wherein A, B, E, X, Y, $R^1$, $R^2$ and $R^3$ are defined in the detailed description of the invention below.

In another aspect, the present invention provides pharmaceutically acceptable salts, diastereomers, enantiomers, racemates, hydrates, solvates, prodrugs of the novel compounds. Also, the present invention provides pharmaceutically acceptable salts, hydrates, or solvates of the diastereomers, enantiomers, or racemates.

In still another aspect, the present invention provides pharmaceutical compositions each comprising the compound, salt, diastereomer, enantiomer, racemate, hydrate, solvate, prodrug, or a combination thereof.

In yet another aspect, the present invention provides methods of treating or alleviating certain ROCK-mediated diseases or disorders by using the compounds, salts, diastereomers, enantiomers, racemates, hydrates, solvates, prodrugs, or compositions. Non-limiting examples of the diseases or disorders include cardiovascular, pulmonary, inflammatory, neurological, or proliferative diseases or disorders.

In a further aspect, the present invention provides methods of preparing the compounds, salts, diastereomers, enantiomers, racemates, hydrates, solvates, and prodrugs.

DETAILED DESCRIPTION

1. Compounds

In one aspect, the present invention provides a compound represented by Formula (1), a pharmaceutically acceptable salt, diastereomer, enantiomer, racemate, hydrate, solvate, or prodrug thereof:

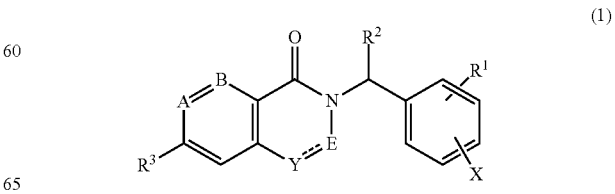

(1)

wherein:

X is H or halogen;

Y is N or $CR^4$;

A, B and E each are independently N or CH;

=== represents a single or double bond;

$R^1$ is H, F, Cl, OH, heteroaryl, $C_1$-$C_3$alkyl, $C_1$-$C_3$alkoxy, $C(O)_2R^5$, $NHS(O)_2R^5$, $S(O)_2R^5$, $C(O)NR^5R^6$, or $NHC(O)R^7$, wherein the heteroaryl, $C_1$-$C_3$alkyl or $C_1$-$C_3$alkoxy can be optionally substituted with one or more suitable substituents, for example, halogen, amino, hydroxyl or alkoxy;

$R^2$ is H or $C_1$-$C_3$alkyl, wherein the $C_1$-$C_3$alkyl can be optionally and independently substituted with one or more suitable substituents, for example, halogen, hydroxyl, $C_1$-$C_3$alkoxy or $NR^5R^6$;

$R^3$ is 5-6 membered heteroaryl, heterocycloalkyl, or unsaturated heterocycloalkyl, wherein the heteroaryl, heterocycloalkyl, or unsaturated heterocycloalkyl can be optionally substituted with one or more suitable substituents, for example, halogen, CN, $CHF_2$, $CF_3$, $C_1$-$C_3$alkyl, or amino, wherein the 5-6 membered heteroaryl, heterocycloalkyl, or unsaturated heterocycloalkyl has 1-3 heteroatoms selected from the group consisting of oxygen, nitrogen, and a combination thereof;

$R^4$ is H, halogen, CN, $CF_3$, $C_1$-$C_3$alkyl, $C_1$-$C_3$alkoxy, or $C_2$-$C_6$alkynyl, wherein the $C_1$-$C_3$alkyl or $C_2$-$C_6$alkynyl can be substituted with one or more suitable substituents, for example, amino, hydroxyl, $C_1$-$C_2NR^5R^6$ or $C_1$-$C_3$alkoxy;

$R^5$ is H or $C_1$-$C_3$alkyl, wherein the $C_1$-$C_3$alkyl can be optionally substituted with one or more suitable substituents, for example, halogen, amino, hydroxyl or alkoxy;

$R^6$ is H, $CD_3$, $C_1$-$C_6$alkyl, $C_3$-$C_7$cycloalkyl, aryl, heteroaryl, 8-10 membered bicyclic heteroaryl, 8-10 membered saturated or partially unsaturated bicyclic heteroaryl group, or 4-7 membered heterocycloalkyl comprising 1-2 heteroatoms selected from the group consisting of N, O, S, sulfoxide, and sulfone, wherein the $C_1$-$C_6$alkyl, $C_3$-$C_7$cycloalkyl, aryl or heteroaryl is optionally substituted with halogen, $NR^5R^6$, aryl, heteroaryl, heterocycloalkyl or $OR^5$, wherein when the 4-7 membered heterocycloalkyl has one nitrogen atom, the 4-7 membered heterocycloalkyl is optionally substituted with $R^6$, $C(O)R^5$, $S(O)_2NH_2$, $C(O)OR_5$, or $C(O)NHR^5$ at the nitrogen atom;

$R^7$ is $C_1$-$C_6$alkyl, $C_3$-$C_7$cycloalkyl, 4-7 membered heterocycloalkyl comprising 1-2 heteroatoms selected from N or O, 5-6 membered aryl, 5-6 membered heteroaryl, 8-10 membered bicyclic heteroaryl, or 8-10 membered saturated or partially unsaturated bicyclic heteroaryl, wherein the $C_1$-$C_6$alkyl, $C_3$-$C_7$cycloalkyl, 4-7 membered heterocycloalkyl comprising 1-2 heteroatoms selected from N or O, 5-6 membered aryl, 5-6 membered heteroaryl, 8-10 membered bicyclic heteroaryl, or 8-10 membered saturated or partially unsaturated bicyclic heteroaryl is optionally substituted with halogen, $C_1$-$C_3$alkyl, $OR^5$, $NH_2$ or 5-6 membered heteroaryl.

In some embodiments,

X is H or halogen;

Y is N or $CR^4$;

A, B and E each are independently N or CH;

=== is a single or double bond;

$R^1$ is H, F, Cl, OH, heteroaryl, $C_1$-$C_3$alkoxy, $C(O)OR_5$, $NHS(O)_2R^5$, $S(O)_2R^5$, $C(O)NR^5R^6$, or $NHC(O)R^7$, wherein the heteroaryl or $C_1$-$C_3$alkoxy is optionally substituted with one or more substituents selected from the group consisting of halogen, amino, hydroxyl, alkoxy, and a combination thereof;

$R^2$ is H or $C_1$-$C_3$alkyl, which is optionally substituted with one or more substituents selected from the group consisting of halogen, hydroxyl, $C_1$-$C_3$alkoxy, $NR^5R^6$, and a combination thereof;

$R^3$ is 5-6 membered heteroaryl or heterocycle, wherein the heteroaryl is optionally substituted with one or more substituents selected from the group consisting of halogen, CN, $CHF_2$, $CF_3$, $C_1$-$C_3$alkyl, amino, and a combination thereof, and wherein the 5-6 membered heteroaryl has 1-3 heteroatoms selected from the group consisting of oxygen, nitrogen, and a combination thereof;

$R^4$ is H, halogen, $CF_3$, CN, $C_1$-$C_3$alkyl, $C_1$-$C_3$alkoxy, or $C_2$-$C_6$alkynyl, wherein the $C_1$-$C_3$alkyl or $C_2$-$C_6$alkynyl is optionally substituted with one or more substituents selected from the group consisting of OH, $NH_2$, $C_1$-$C_2$amino, $C_1$-$C_2$hydroxyl, $C_1$-$C_2NR^5R^6$, $C_1$-$C_3$alkoxy, and a combination thereof;

$R^5$ is H or $C_1$-$C_3$alkyl, wherein the $C_1$-$C_3$alkyl is optionally substituted with one or more substituents selected from the group consisting of halogen, amino, hydroxyl, alkoxy, and a combination thereof;

$R^6$ is H, $CD_3$, $C_1$-$C_6$ alkyl, $C_3$-$C_7$ cycloalkyl, aryl, heteroaryl, 8-10 membered bicyclic heteroaryl, 8-10 membered saturated or partially unsaturated bicyclic heteroaryl group, or 4-7 membered heterocyclyl comprising 1-2 heteroatoms selected from the group consisting of N, O, S, and a combination thereof, wherein the $C_1$-$C_6$ alkyl, $C_3$-$C_7$cycloalkyl, aryl or heteroaryl is optionally substituted with one or more substituents selected from the group consisting of halogen, $NR^5R^6$, aryl, heteroaryl, and $OR^5$, and a combination thereof, and wherein when the 4-7 membered heterocyclyl has one nitrogen atom, the 4-7 membered heterocyclyl is optionally substituted with $C_1$-$C_3$ alkyl, $CF_3$, $C(O)R^5$, $S(O)_2NH_2$, $OCF_3$, $C(O)OR^5$, or $C(O)NHR^5$ at the nitrogen atom; and $R^7$ is $C_1$-$C_6$alkyl, $C_3$-$C_7$cycloalkyl, 4-7 membered heterocyclyl comprising 1-2 heteroatoms selected from the group consisting of N, O, and a combination thereof, 5-6 membered aryl, 5-6 membered heteroaryl, 8-10 membered bicyclic heteroaryl, 8-10 membered saturated or partially unsaturated bicyclic heteroaryl group, wherein the $C_1$-$C_6$alkyl or $C_3$-$C_7$ cycloalkyl is optionally substituted with one or more substituents selected from the group consisting of halogen, $C_1$-$C_3$ alkyl, $OR^5$, $NH_2$, 5-6 membered heteroaryl, and a combination thereof.

In some embodiments, X may be H, F, or Cl.

In some embodiments, $R^1$ may be H, F, Cl, OH, methoxy, heteroaryl, $C(O)OR^5$, $NHS(O)_2R^5$, $S(O)_2R^5$, $C(O)NR^5R^6$, or $NHC(O)R^7$, wherein the heteroaryl is optionally substituted with one or more substituents selected from the group consisting of halogen, amino, hydroxyl, alkoxy, and a combination thereof.

In some embodiments, $R^2$ may be H or $C_1$-$C_3$alkyl, which is optionally substituted with one or more substituents selected from the group consisting of hydroxyl, methoxy, ethoxy, $NH_2$, NHMe, $NMe_2$, and a combination thereof.

In some embodiments, $R^3$ may be one of the following group:

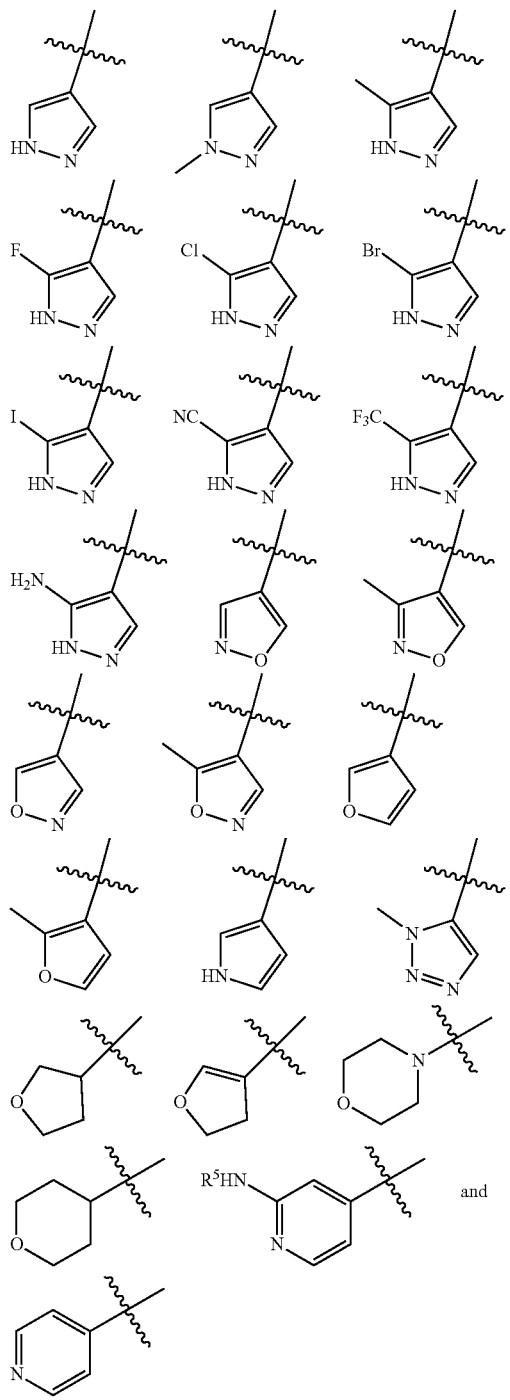

In some embodiments, $R^4$ may be H, Me, F, Cl, CN, $C_1$-$C_3$alkyl, or $C_2$-$C_4$alkynyl, wherein the $C_1$-$C_3$alkyl or $C_2$-$C_4$alkynyl is optionally substituted with one or more substituents selected from the group consisting of OH, $NH_2$, $NMe_2$, OMe, and a combination thereof.

In some embodiments, $R^5$ may be H or Me.

In some embodiments $R^6$ may be H, $CD_3$, $C_1$-$C_6$alkyl, $C_3$-$C_7$cycloalkyl, phenyl, heteroaryl, 8-10 membered bicyclic heteroaryl, 8-10 membered saturated or partially unsaturated bicyclic heteroaryl group, or 4-7 membered heterocyclyl comprising 1-2 heteroatoms selected from the group consisting of N, O, S, and a combination thereof, wherein the $C_1$-$C_6$ alkyl, $C_3$-$C_7$ cycloalkyl, phenyl, or heteroaryl is optionally substituted with one or more substituents selected from the group consisting of halogen, $CF_3$, OH, OMe, $NR^5R^6$, aryl, heteroaryl, and a combination thereof, and wherein when the 4-7 membered heterocyclyl has one nitrogen atom, the 4-7 membered heterocyclyl is optionally substituted with $C_1$-$C_3$ alkyl, $C(O)R^5$, $S(O)_2NH_2$, $OCF_3$, $C(O)OR^5$, or $C(O)NHR^5$ at the nitrogen atom.

In some embodiments, $R^7$ may be H, $C_1$-$C_6$alkyl, $C_3$-$C_7$cycloalkyl, 4-7 membered heterocyclyl comprising 1-2 heteroatoms selected from the group consisting of N, O, and a combination thereof, 5-6 membered aryl, 5-6 membered heteroaryl, 8-10 membered bicyclic heteroaryl, or 8-10 membered saturated or partially unsaturated bicyclic heteroaryl group, wherein the $C_1$-$C_6$ alkyl or $C_3$-$C_7$ cycloalkyl is optionally substituted with one or more substituents selected from the group consisting of halogen, $C_1$-$C_3$ alkyl, OH, OMe, $NH_2$, 5-6 membered heteroaryl, and a combination thereof.

The term "alkyl," used alone or as part of a larger moiety such as "arylalkyl" or "cycloalkyl" refers to a straight or branched hydrocarbon radical having from 1 to 10 carbon atoms, or from 1-8 carbon atoms, or from 1-6 carbon atoms, or from 1-4 carbon atoms (unless stated otherwise) and includes, for example, methyl, ethyl, n-propyl, iso-propyl, n-butyl, sec-butyl, isobutyl, tert-butyl, n-pentyl, iso-pentyl, n-hexyl and the like. An alkyl can be unsubstituted or substituted with one or more suitable substituents.

The term "cycloalkyl" refers to a monocyclic or polycyclic hydrocarbon ring group having from 3 to 10 carbon atoms, or from 3 to 7 carbon atoms, in the hydrocarbon ring (unless stated otherwise) and includes, for example, cyclopropyl, cycloheptyl, cyclooctyl, cyclodecyl, cyclobutyl, adamantyl, norpinanyl, decalinyl, norbornyl, cyclohexyl, cyclopentyl, and the like. A cycloalkyl group can be unsubstituted or substituted with one or more suitable substituents.

The term "hetero" refers to the replacement of at least one carbon atom member in a ring system with at least one heteroatom such as nitrogen, sulfur, sulfoxide, sulfone, and oxygen.

The term "heterocycloalkyl" means a non-aromatic saturated or a non-aromatic unsaturated monocyclic or a non-aromatic saturated or non-aromatic unsaturated polycyclic ring having from 2 to 9 carbon atoms, or from 2 to 7 carbon atoms, in the ring (unless stated otherwise) and at least one heteroatom, preferably, 1 to 4 heteroatoms selected from nitrogen, sulfur (including oxidized sulfur such as sulfone or sulfoxide) and oxygen. The ring or ring system of the heterocycloalkyl group can be linked to another moiety of the compound via a carbon atom or a nitrogen atom, if such an atom is present. A heterocycloalkyl group can have a total of 3-10, or 3-8, or 5-8, atoms in the ring system (unless otherwise stated). A heterocycloalkyl group can have one or more carbon-carbon double bonds or carbon-heteroatom double bonds in the ring group as long as the ring group is not rendered aromatic by their presence.

Examples of heterocycloalkyl groups include azetidinyl, aziridinyl, pyrrolidinyl, piperidinyl, piperazinyl, homopiperazinyl, morpholino, thiomorpholino, tetrahydrofuranyl, tetrahydrothiofuranyl, tetrahydropyranyl, pyranyl, and the like. A heterocycloalkyl group can be unsubstituted or substituted with one or more suitable substituents.

As used herein, the term "halo" includes fluoro, chloro, bromo, and iodo.

As used herein, the term "alkoxy" refers to the alkyl groups above bound through oxygen, examples of which include methoxy, ethoxy, iso-propoxy, tert-butoxy, and the like. In addition, alkoxy also refers to polyethers such as —O—(CH$_2$)$_2$O—CH$_3$, and the like. An alkoxy can be unsubstituted or substituted with one or more suitable substituents.

As used herein, the term "aryl" refers to unsubstituted or substituted aromatic monocyclic or polycyclic groups and includes, for example, carbocyclic aromatic groups such as phenyl, naphthyl and the like, as well as heteroaromatic groups such as pyridyl, furanyl, thiophenyl, and the like. The term "aryl" also includes an aromatic ring (such as a phenyl or pyridyl ring) fused to a non-aromatic carbocyclic or heterocyclic ring. The term "aryl" may be interchangeably used with "aryl ring," aromatic group," and "aromatic ring. Heteroaryl groups have 4 to 14 atoms in the heteroaromatic ring(s), 1 to 9 of which are independently selected from the group consisting of oxygen, sulfur and nitrogen. Heteroaryl groups have 1-3 heteroatoms in a 5-8 membered aromatic group. An aryl or heteroaryl can be a mono- or bicyclic aromatic group. Typical aryl and heteroaryl groups include, for example, phenyl, quinolinyl, indazoyl, indolyl, dihydrobenzodioxynyl, 3-chlorophenyl, 2,6-dibromophenyl, pyridyl, pyrimidinyl, 3-methylpyridyl, benzothienyl, 2,4,6-tribromophenyl, 4-ethylbenzothienyl, furanyl, 3,4-diethylfuranyl, naphthyl, 4,7-dichloronaphthyl, pyrrole, pyrazole, imidazole, thiazole, and the like. An aryl or heteroaryl can be unsubstituted or substituted with one or more suitable substituents.

As used herein, the term "hydroxyl" or "hydroxy" refers to —OH.

As used herein, the term "amino" refers to —NH$_2$.

As used herein, the term "hydroxyalkyl" refers to any hydroxyl derivative of alkyl radical. The term "hydroxyalkyl" includes any alkyl radical having one or more hydrogen atoms replaced by a hydroxy group.

As used herein, the term "arylalkyl" includes any alkyl radical having one or more hydrogen atoms replaced by an aryl group, e.g., a benzyl group, a phenethyl group, and the like.

A "substituent," as used herein, refers to a molecular moiety that is covalently bonded to an atom within a molecule of interest. For example, a ring substituent may be a moiety such as a halogen, alkyl group, haloalkyl group or other group that is covalently bonded to an atom (preferably a carbon or nitrogen atom) that is a ring member. Substituents of aromatic groups are generally covalently bonded to a ring carbon atom. The term "substitution" refers to replacing a hydrogen atom in a molecular structure with a substituent, such that the valence on the designated atom is not exceeded, and such that a chemically stable compound (i.e., a compound that can be isolated, characterized, and tested for biological activity) results from the substitution.

As described above, certain groups can be unsubstituted or substituted with one or more suitable substituents by other than hydrogen at one or more available positions, typically 1, 2, 3, 4 or 5 positions, by one or more suitable groups (which may be the same or different). Certain groups, when substituted, are substituted with 1, 2, 3 or 4 independently selected substituents. Suitable substituents include halo, alkyl, haloalkyl, aryl, hydroxy, alkoxy, hydroxyalkyl, amino, and the like.

As used herein, the term "pharmaceutically acceptable" refers a material, such as a carrier or diluent, which does not abrogate the biological activity or properties of the compounds described herein. Such materials are administered to an individual without causing undesirable biological effects or interacting in a deleterious manner with any of the components of the composition in which it is contained.

As used herein, the term "pharmaceutically acceptable salt" refers to a formulation of a compound that does not cause significant irritation to an organism to which it is administered and does not abrogate the biological activity and properties of the compounds described herein.

Pharmaceutically acceptable salt forms include pharmaceutically acceptable acidic/anionic or basic/cationic salts (UK Journal of Pharmaceutical and Biosciences Vol. 2(4), 01-04, 2014, which is incorporated herein by reference). Pharmaceutically acceptable acidic/anionic salts include acetate, benzenesulfonate, benzoate, bicarbonate, bitartrate, bromide, calcium edetate, camsylate, carbonate, chloride, citrate, dihydrochloride, edetate, edisylate, estolate, esylate, fumarate, glyceptate, gluconate, glutamate, glycollylarsanilate, hexylresorcinate, hydrobromide, hydrochloride, hydroxynaphthoate, iodide, isethionate, lactate, lactobionate, malate, maleate, malonate, mandelate, mesylate, methylsulfate, mucate, napsylate, nitrate, pamoate, pantothenate, phosphate/diphosphate, polygalacturonate, salicylate, stearate, subacetate, succinate, sulfate, hydrogensulfate, tannate, tartrate, teoclate, tosylate, and triethiodide salts. Pharmaceutically acceptable basic/cationic salts include, the sodium, potassium, calcium, magnesium, diethanolamine, N-methyl-D-glucamine, L-lysine, L-arginine, ammonium, ethanolamine, piperazine and triethanolamine salts.

A pharmaceutically acceptable acid salt is formed by reaction of the free base form of a compound of Formula 1 with a suitable inorganic or organic acid including, but not limited to, hydrobromic, hydrochloric, sulfuric, nitric, phosphoric, succinic, maleic, formic, acetic, propionic, fumaric, citric, tartaric, lactic, benzoic, salicylic, glutamic, aspartic, p-toluenesulfonic, benzenesulfonic, methanesulfonic, ethanesulfonic, naphthalenesulfonic such as 2-naphthalenesulfonic, or hexanoic acid. A pharmaceutically acceptable acid addition salt of a compound of Formula 1 can comprise or be, for example, a hydrobromide, hydrochloride, sulfate, nitrate, phosphate, succinate, maleate, formarate, acetate, propionate, fumarate, citrate, tartrate, lactate, benzoate, salicylate, glutamate, aspartate, p-toluenesulfonate, benzenesulfonate, methanesulfonate, ethanesulfonate, naphthalenesulfonate (e.g., 2-naphthalenesulfonate) or hexanoate salt.

The free acid or free base forms of the compounds of the invention may be prepared by methods known to those of ordinary skill in the art (e.g., for further details see L. D. Bigley, S. M. Berg, D. C. Monkhouse, in "*Encyclopedia of Pharmaceutical Technology*". Eds, J. Swarbrick and J. C. Boylam, Vol 13, Marcel Dekker, Inc., 1995, pp. 453-499; the entire teachings of which are incorporated herein by reference) from the corresponding base addition salt or acid addition salt form, respectively. For example, a compound of the invention in an acid addition salt form may be converted to the corresponding free base form by treating with a suitable base (e.g., ammonium hydroxide solution, sodium hydroxide, and the like). A compound of the invention in a base addition salt form may be converted to the corresponding free acid by treating with a suitable acid (e.g., hydrochloric acid, etc.).

Prodrug derivatives of the compounds of the invention may be prepared by methods known to those of ordinary skill in the art (e.g., for further details see Saulnier et al., *Bioorg. Med. Chem. Letters*, 1994, 4, 1985; Daniela Hartmann Jornada at. Al., *Molecules* 2016, 21, 42; the entire teachings of which are incorporated herein by reference). Protected derivatives of the compounds of the invention may be prepared by means known to those of ordinary skill in the art. A detailed description of techniques applicable to the creation of protecting groups and their removal can be found in T. W. Greene, "*Green's Protective Groups in Organic Chemistry,*" 4th edition, John Wiley and Sons, Inc., 2006, the entire teachings of which are incorporated herein by reference.

Compounds of the invention may be prepared as their individual stereoisomers by reaction of a racemic mixture of the compound with an optically active resolving agent to form a pair of diastereoisomeric compounds, separating the diastereomers and recovering the optically pure enantiomers. Resolution of enantiomers may be carried out using covalent diastereomeric derivatives of the compounds of the invention, or by using dissociable complexes (e.g., crystalline diastereomeric salts). Diastereomers have distinct physical properties (e.g., melting points, boiling points, solubility, reactivity, etc.) and may be readily separated by taking advantage of these dissimilarities. The diastereomers may be separated by chromatography, or by separation/resolution techniques based upon differences in solubility. The optically pure enantiomer is then recovered, along with the resolving agent, by any practical means that would not result in racemization. A more detailed description of the techniques applicable to the resolution of stereoisomers of compounds from their racemic mixture can be found in Jean Jacques, Andre Collet and Samuel H. Wilen, "*Enantiomers, Racemates and Resolutions*," John Wiley And Sons, Inc., 1981, the entire teachings of which are incorporated herein by reference.

As used herein, the term "solvate" refers to a complex of variable stoichiometry formed by a solute (in this invention, a compound of Formula 1 or a pharmaceutically acceptable salt thereof) and a solvent. Such solvents for the purpose of the invention may not interfere with the biological activity of the solute. Non-limiting examples of suitable solvents include water, acetone, methanol, ethanol and acetic acid. Preferably the solvent used is a pharmaceutically acceptable solvent. Non-limiting examples of suitable pharmaceutically acceptable solvents include water, ethanol and acetic acid.

2. Compositions

In another aspect, the present invention provides a pharmaceutical composition comprising the compound, salt, diastereomer, enantiomer, racemate, hydrate, solvate, prodrug, or a pharmaceutical combination thereof. The composition may further comprise an additional component. A non-limiting example of the additional component includes a pharmaceutically acceptable carrier, diluent, excipient, and a combination thereof.

As used herein, the term "pharmaceutical composition" refers to a mixture of a compound described herein with other chemical components, such as carriers, stabilizers, diluents, dispersing agents, suspending agents, thickening agents, and/or excipients.

As used herein, the term "pharmaceutical combination" means a product that results from the mixing or combining of more than one active ingredient.

As used herein, the term "acceptable" with respect to a formulation, composition or ingredient, as used herein, means having no persistent detrimental effect on the general health of the subject being treated.

As used herein, the term "carrier" refers to chemical compounds or agents that facilitate the incorporation of a compound described herein into cells or tissues.

As used herein, the term "diluent" refers to chemical compounds that are used to dilute a compound described herein prior to delivery. Diluents can also be used to stabilize compounds described herein.

Suitable pharmaceutically acceptable carriers, diluents, adjuvants, or excipients for use in the pharmaceutical compositions of the invention include tablets (coated tablets) made of for example collidone or shellac, gum Arabic, talc, titanium dioxide or sugar, capsules (gelatin), solutions (aqueous or aqueous-ethanolic solution), syrups containing the active substances, emulsions or inhalable powders (of various saccharides such as lactose or glucose, salts and mixture of these excipients with one another) and aerosols (propellant-containing or -free inhale solutions).

Excipients which may be used include, for example, water, pharmaceutically acceptable organic solvents such as paraffins (e.g., petroleum fractions), vegetable oils (e.g. groundnut or sesame oil), mono- or polyfunctional alcohols (e.g., ethanol or glycerol), carriers such as natural mineral powders (e.g., kaoline, clays, talc, chalk), synthetic mineral powders (e.g., highly dispersed silicic acid and silicates), sugars (e.g., cane sugar, lactose and glucose), emulsifiers (e.g., lignin, spent sulphite liquors, methylcellulose, starch and polyvinylpyrrolidone) and lubricants (e.g., magnesium stearate, talc, stearic acid and sodium lauryl sulphate).

3. Methods of Using Compounds or Compositions

In another aspect, the present invention provides methods of treating or alleviating certain protein kinase-mediated diseases or conditions by administering a subject or patient a therapeutically effective amount of the compound, salt, diastereomer, enantiomer, racemate, hydrate, solvate, prodrug, or composition. In some embodiments, the present invention provides methods of treating or alleviating certain ROCK-mediated diseases or disorders by administering a subject or patient a therapeutically effective amount of the compound, salt, diastereomer, enantiomer, racemate, hydrate, solvate, prodrug, or composition. In some embodiments, the present invention provides methods of treating or alleviating a disease or disorder in which ROCK is known to play a role.

In a further aspect, the present invention provides methods of inhibiting enzyme activity, particularly ROCK1, ROCK2, PKCδ, PKCθ, PRK1, GSK3, PRK2, NEK1 and NEK4 kinase activity, by administering a subject or patient a therapeutically effective amount of the compound, salt, diastereomer, enantiomer, racemate, hydrate, solvate, prodrug, or composition.

In yet another aspect, the present invention provides methods of inhibiting protein kinase activity, such as, for example, ROCK kinase activity, in a biological sample by contacting the biological sample with the compound, salt, diastereomer, enantiomer, racemate, hydrate, solvate, prodrug, or composition.

As used herein, the term "inhibitor" refers to a compound which inhibits one or more kinases described herein. For example, the term "ROCK inhibitor" refers to a compound which inhibits the ROCK receptor or reduces the signaling effect.

As used herein, the term "protein kinase-mediated disease" or a "disorder or disease or condition mediated by inappropriate protein kinase activity" refers to any disease state mediated or modulated by protein kinases described herein. Such disease states include, but are not limited to, fibrotic disorders; pulmonary fibrosis including cystic and idiopathic pulmonary fibrosis, radiation induced lung injury, liver fibrosis including cirrhosis, cardiac fibrosis including arterial fibrosis, endomyocardial fibrosis, old myocardial infraction, arterial stiffness, atherosclerosis, restenosis, arthrofibrosis, Crohn's disease, myelofibrosis, Peyronie's diseases, nephrogenic systemic fibrosis, progressive massive fibrosis, retroperitoneal cavity fibrosis, scleroderma/systemic sclerosis, mediastinal fibrosis, Keloids and hypertrophic scars, glial scaring, or renal fibrosis; cardiovascular disease or disorder, such as, for example, cerebral vasospasm, hypertension, atherosclerosis, angina, myocardial infarction, ischemic/reperfusion injury, stroke, bronchial asthma; glaucoma, pre-term labor, erectile dysfunction, or renal disease, such as, for example, chronic renal failure, chronic nephritis, diabetic nephropathy, and IgA nephropathia; a neurological disease or disorder, such as for example, spinal-cord injury, Alzheimer's disease, multiple sclerosis, or neuropathic pain; and proliferative disorders, such as, for example, retinopathy, fibrosis, or invasive/metastatic cancers. Such cancers include adenocarcinoma, adrenocortical cancer; bladder cancer; bone cancer; brain cancer; breast cancer; cancer of the buccal cavity; cervical cancer; colon cancer; colorectal cancer; endometrial or uterine carcinoma; epidermoid carcinoma; esophageal cancer; eye cancer; follicular carcinoma; gallbladder cancer; gastrointestinal cancer; cancer of the genitourinary tract; glioblastoma; hairy cell carcinoma; head and neck cancer; hepatic carcinoma; hepatocellular cancer; Hodgkin's disease; keratoacanthoma; kidney cancer; large cell carcinoma; cancer of the large intestine; laryngeal cancer; liver cancer; lung cancer, such as, for example, adenocarcinoma of the lung, small-cell lung cancer, squamous carcinoma of the lung, non-small cell lung cancer; melanoma; myeloproliferative disorders, neuroblastoma; ovarian cancer; papillary carcinoma; pancreatic cancer; cancer of the peritoneum; prostate cancer; rectal cancer; salivary gland carcinoma; sarcoma; squamous cell cancer; small cell carcinoma; cancer of the small intestine; stomach cancer; testicular cancer; thyroid cancer; and vulval cancer. In particular embodiments, the treated cancer is melanoma, breast cancer, colon cancer, or pancreatic cancer.

As used herein, the term "treat," "treating" or "treatment" refers to methods of alleviating, abating or ameliorating a disease or condition symptoms, preventing additional symptoms, ameliorating or preventing the underlying metabolic causes of symptoms, inhibiting the disease or condition, arresting the development of the disease or condition, relieving the disease or condition, causing regression of the disease or condition, relieving a condition caused by the disease or condition, or stopping the symptoms of the disease or condition either prophylactically and/or therapeutically.

As used herein, the term "subject" or "patient" encompasses mammals and non-mammals. Examples of mammals include, but are not limited to, humans, chimpanzees, apes monkeys, cattle, horses, sheep, goats, swine; rabbits, dogs, cats, rats, mice, guinea pigs, and the like. Examples of non-mammals include, but are not limited to, birds, fishes and the like.

As used herein, the term "administration" or "administering" of the subject compound refers to providing a compound of the invention and/or prodrugs thereof to a subject in need of treatment.

As used herein, the term "effective amount" or "therapeutically effective amount" refer to a sufficient amount of a compound described herein being administered which will relieve to some extent one or more of the symptoms of the disease or condition being treated. The result can be reduction and/or alleviation of the signs, symptoms, or causes of a disease, or any other desired alteration of a biological system. For example, an "effective amount" for therapeutic uses is the amount of the composition comprising a compound as disclosed herein required to provide a clinically significant decrease in disease symptoms. An appropriate "effective" amount in any individual case may be determined using techniques, such as a dose escalation study. By way of example only, a therapeutically effective amount of a compound of the invention may be in the range of e.g., about 0.01 mg/kg/day to about 1000 mg/kg/day, from about 0.1 mg/kg/day to about 500 mg/kg/day, from about 0.1 mg (×2)/kg/day to about 500 mg (×2)/kg/day.

The compounds of the present invention were screened against a kinase panel and inhibited the activity of at least one kinase on the panel. Examples of kinases include, but not limited to, ROCK1 and ROCK2.

The compounds described herein are inhibitors of ROCK kinase activity and have therapeutic benefit in the treatment of disorders associated with inappropriate kinase activity, in particular in the treatment and prevention of disease states mediated by kinases, including ROCK kinase. Therefore, the present invention provides methods of regulating and, in particular, inhibiting signal transduction cascades in which a kinase plays a role. The method generally involves administering to a subject or contacting a cell expressing the kinase with an effective amount of a compound described herein, a salt, a diastereomer, an enantiomer, a racemate, a hydrate, a solvate, a prodrug, and/or a composition thereof, to regulate or inhibit the signal transduction cascade. The methods are also used to regulate and, in particular, inhibit downstream processes or cellular responses elicited by activation of the particular kinase signal transduction cascade. The methods are also practiced in in vitro contexts or in in vivo contexts as a therapeutic approach towards the treatment or prevention of diseases characterized by, caused by, or associated with activation of the kinase-dependent signal transduction cascade.

For the therapeutic uses of compounds provided herein, including compounds of Formula 1, salts, diastereomers, enantiomers, racemates, hydrates, solvates, or prodrugs thereof, such compounds are administered in therapeutically effective amounts either alone or as part of a pharmaceutical composition. Accordingly, provided herein are pharmaceutical compositions, which comprise at least one compound provided herein, including at least one compound of Formula 1, a pharmaceutically acceptable salt, a diastereomer, an enantiomer, a racemate, a hydrate, a solvate, or prodrug thereof, and one or more pharmaceutically acceptable carriers, diluents, adjuvant or excipients.

In addition, such compounds and compositions are administered singly or in combination with one or more additional therapeutic agents. Non-limiting examples of the additional therapeutic agents may include immune checkpoint inhibitors and immunogenic cell death (ICD)-inducing chemotherapeutic agents. Non-limiting examples of the immune checkpoint inhibitor may include PD-1 inhibitors, PD-L1 inhibitors, and CTLA-4 inhibitors. Non-limiting examples of the immunogenic cell death (ICD)-inducing chemotherapeutic agent may include doxorubicin, idarubicin, mitoxantrone, tautomycin, calyculin A, salubrinal, oxaliplatin, bleomycin, and cyclophosphamide. The methods of administration of such compounds and compositions include, but are not limited to, intravenous administration, inhalation, oral administration, rectal administration, parenteral, intravitreal administration, subcutaneous administration, intramuscular administration, intranasal administration, dermal administration, topical administration, ophthalmic administration, buccal administration, tracheal administration, bronchial administration, sublingual administration or optic administration. Compounds provided herein are administered by way of known pharmaceutical formulations, including tablets, capsules or elixirs for oral administration, suppositories for rectal administration, sterile solutions or suspensions for parenteral or intramuscular administration, lotions, gels, ointments or creams for topical administration, and the like. In some embodiments, such pharmaceutical compositions are formulated as tablets, pills, capsules, a liquid, an inhalant, a nasal spray solution, a suppository, a solution, a gel, an emulsion, an ointment, eye drops or ear drops.

The therapeutically effective amount will vary depending on, among others, the disease indicated, the severity of the disease, the age and relative health of the subject, the potency of the compound administered, the mode of administration and the treatment desired. The required dosage will also vary depending on the mode of administration, the particular condition to be treated and the effect desired.

The compounds of Formula 1 are useful for inhibiting one or more protein kinases and for treating diseases and disorders that are mediated by the protein kinases, such as cancer, autoimmune diseases, fibrotic disorders, cardiovascular disease, and neurodegenerative diseases.

The term "biological sample," as used herein, means a sample outside an animal and includes, without limitation, cell cultures or extracts thereof, biopsied material obtained from an animal or extracts thereof; and blood, saliva, urine, feces, semen, tears, or other body fluids or extracts thereof Inhibition of kinase activity, particularly ROCK kinase activity, in a biological sample is useful for a variety of purposes known to one of skill in the art. Examples of such purposes include, but are not limited to, biological specimen storage and biological assays.

The term "ROCK-mediated disease" or "condition," as used herein, means any disease or other deleterious condition in which ROCK is known to play a role. ROCK participates in a variety of important physiological functions in the vasculature, including smooth muscle contraction; cell proliferation, such as, for example, vascular smooth muscle cell proliferation; and cell adhesion and migration (see Hu & Lee, *Expert Opin. Ther. Targets*, 9(4):715-36, 2005; Shimokawa & Takeshita, Arterioscler. Thromb. Vase. Biol. 25(9):1767-75, 2005). ROCK participates in inflammatory responses due to leukocyte migration, such as, for example, autoimmune disease and allergic reactions (see Wettschureck et al., *J. Mol. Med.* 80:629-38, 2002). Abnormal activation of the Rho/ROCK pathway has been observed in various disorders of the central nervous system (see Mueller et al, *Nature Rev.*, 4:387-98, 2005). In addition, ROCK has been implicated in tumor cell migration and invasion (Riento & Ridley, *Nature Rev.* 4:446-56, 2004) and in osteoporosis (Ohnaka et al., *Biochem. Biophys., Res. Commun.* 287(2):337-4, 2001).

Specifically, the present invention relates to a method of treating or lessening the severity of a cardiovascular disease or disorder, such as, for example, cerebral vasospasm, hypertension, atherosclerosis, angina, myocardial infarction, ischemic/reperfusion injury, stroke, bronchial asthma; glaucoma, pre-term labor, erectile dysfunction, or renal disease, such as, for example, chronic renal failure, chronic nephritis, diabetic nephropathy, and IgA nephropathia; a neurological disease or disorder, such as for example, spinal-cord injury, Alzheimer's disease, multiple sclerosis, or neuropathic pain; and proliferative disorders, such as, for example, retinopathy, fibrosis, or invasive/metastatic cancers. Such cancers include adenocarcinoma, adrenocortical cancer; bladder cancer; bone cancer; brain cancer; breast cancer; cancer of the buccal cavity; cervical cancer; colon cancer; colorectal cancer; endometrial or uterine carcinoma; epidermoid carcinoma; esophageal cancer; eye cancer; follicular carcinoma; gallbladder cancer; gastrointestinal cancer; cancer of the genitourinary tract; glioblastoma; hairy cell carcinoma; head and neck cancer; hepatic carcinoma; hepatocellular cancer; Hodgkin's disease; keratoacanthoma; kidney cancer; large cell carcinoma; cancer of the large intestine; laryngeal cancer; liver cancer; lung cancer, such as, for example, adenocarcinoma of the lung, small-cell lung cancer, squamous carcinoma of the lung, non-small cell lung cancer; melanoma; myeloproliferative disorders, neuroblastoma; ovarian cancer; papillary carcinoma; pancreatic cancer; cancer of the peritoneum; prostate cancer; rectal cancer; salivary gland carcinoma; sarcoma; squamous cell cancer; small cell carcinoma; cancer of the small intestine; stomach cancer; testicular cancer; thyroid cancer; and vulval cancer. In particular embodiments, the treated cancer is melanoma, breast cancer, colon cancer, or pancreatic cancer.

In another aspect, the invention provides a method of treating a fibrotic disorder in a subject comprising administering to the subject a therapeutically effective amount of a compound of Formula I. Non-limiting examples of fibrotic disorders are pulmonary fibrosis including cystic and idiopathic pulmonary fibrosis, radiation induced lung injury, liver fibrosis including cirrhosis, cardiac fibrosis including arterial fibrosis, endomyocardial fibrosis, old myocardial infraction, arterial stiffness, atherosclerosis, restenosis, arthrofibrosis, Crohn's disease, myelofibrosis, Peyronie's diseases, nephrogenic systemic fibrosis, progressive massive fibrosis, retroperitoneal cavity fibrosis, schleroderma/systemic sclerosis, mediastinal fibrosis, Keloids and hypertrophic scars, glial scaring, or renal fibrosis.

In one aspect, the present invention provides methods for treating a cell-proliferative disease or condition, such as cancer, comprising administering to a subject in need of such treatment a therapeutically effective amount of the compound of Formula 1, a pharmaceutically acceptable salt, a diastereomer, an enantiomer, a racemate, a hydrate, a solvate, a prodrug thereof, or a pharmaceutical composition or medicament thereof, wherein the cell proliferative disease or condition include, for example, lymphoma, osteosarcoma, melanoma, breast cancer, renal cancer, prostate cancer, colorectal cancer, thyroid cancer, ovarian cancer, pancreatic cancer, neuronal cancer, lung cancer, uterine cancer or gastrointestinal cancer. In one aspect, the present invention provides methods of inhibiting growth of cancer cells with the compound described herein, salt, diastereomer, enantiomer, racemate, hydrate, solvate, prodrug, or any combination thereof, or the composition described herein.

In certain embodiments, protein kinase-mediated diseases or conditions are inflammatory diseases or conditions, respiratory diseases or autoimmune diseases or conditions, such as asthma, chronic obstructive pulmonary disease (COPD), adult respiratory distress syndrome (ARDS), ulcerative colitis, Crohn's disease, bronchitis, dermatitis, allergic rhinitis, psoriasis, scleroderma, urticaria, rheumatoid arthritis, multiple sclerosis, cancer, breast cancer, HIV associated diseases or lupus.

In another aspect, the present invention provides methods for treating a neurological/neurodegenerative disease or condition by administering to a subject a therapeutically effective amount of the compound described herein, salt, diastereomer, enantiomer, racemate, hydrate, solvate, prodrug, or any combination thereof, or the composition described herein. In certain embodiment, such neurological/ neurodegenerative disease or condition includes, for example, Alzheimer's disease, cerebral edema, cerebral ischemia, multiple sclerosis, neuropathies, Parkinson's disease, blunt or surgical trauma (including post-surgical cognitive dysfunction and spinal cord or brain stem injury), as well as the neurological aspects of disorders such as degenerative disc disease and sciatica.

In another aspect, the present invention provides methods for treating a cardiovascular disease by administering to a subject a therapeutically effective amount of the compound described herein, salt, diastereomer, enantiomer, racemate, hydrate, solvate, prodrug, or any combination thereof, or the composition described herein. Such a cardiovascular disease affects the heart or blood vessels and includes, for example, atherosclerosis, arrhythmia, angina, myocardial ischemia, myocardial infarction, cardiac or vascular aneurysm, vasculitis, stroke, peripheral obstructive arteriopathy of a limb, an organ, or a tissue, reperfusion injury following ischemia of an organ or a tissue, endotoxic, surgical, or traumatic shock, hypertension, valvular heart disease, heart failure, abnormal blood pressure, vasoconstriction, vascular abnormality, or inflammation.

In another aspect, the present invention provides methods of treating cancer comprising administering to a subject in need a composition comprising a therapeutically effective amount of at least one of the compounds described herein, salts, diastereomers, enantiomers, racemates, hydrates, solvates, or prodrugs thereof and a therapeutically effective amount of at least one immune checkpoint inhibitor, wherein the cancer is adenocarcinoma, adrenocortical cancer, bladder cancer, bone cancer, brain cancer, breast cancer, buccal cavity cancer, cervical cancer, colon cancer, colorectal cancer, endometrial or uterine carcinoma, epidermoid carcinoma, esophageal cancer, eye cancer, follicular carcinoma, gallbladder cancer, gastrointestinal cancer, genitourinary tract cancer, glioblastoma, hairy cell carcinoma, head and neck cancer, hepatic carcinoma, hepatocellular cancer, Hodgkin's disease, keratoacanthoma, kidney cancer, large cell carcinoma, large intestine cancer, laryngeal cancer, liver cancer, lung adenocarcinoma, small-cell lung cancer, lung squamous carcinoma, non-small cell lung cancer, melanoma, a myeloproliferative disorder, neuroblastoma, ovarian cancer, papillary carcinoma, pancreatic cancer, peritoneal cancer, prostate cancer, rectal cancer, salivary gland carcinoma, sarcoma, squamous cell cancer, small cell carcinoma, small intestine cancer, stomach cancer, testicular cancer, thyroid cancer, vulvar cancer, or any combination thereof. Examples of the checkpoint inhibitor include, not being limited to, a PD-1 inhibitor, a PD-L1 inhibitor, and a CTLA-4 inhibitor.

In another aspect, the present invention provides methods of treating a cancer comprising administering to a subject in need a composition comprising a therapeutically effective amount of at least one of the compounds described herein, salts, diastereomers, enantiomers, racemates, hydrates, solvates, or prodrugs thereof and a therapeutically effective amount of at least one immunogenic cell death (ICD)-inducing chemotherapeutic, wherein the cancer is adenocarcinoma, adrenocortical cancer, bladder cancer, bone cancer, brain cancer, breast cancer, buccal cavity cancer, cervical cancer, colon cancer, colorectal cancer, endometrial or uterine carcinoma, epidermoid carcinoma, esophageal cancer, eye cancer, follicular carcinoma, gallbladder cancer, gastrointestinal cancer, genitourinary tract cancer, glioblastoma, hairy cell carcinoma, head and neck cancer, hepatic carcinoma, hepatocellular cancer, Hodgkin's disease, keratoacanthoma, kidney cancer, large cell carcinoma, large intestine cancer, laryngeal cancer, liver cancer, lung adenocarcinoma, small-cell lung cancer, lung squamous carcinoma, non-small cell lung cancer, melanoma, a myeloproliferative disorder, neuroblastoma, ovarian cancer, papillary carcinoma, pancreatic cancer, peritoneal cancer, prostate cancer, rectal cancer, salivary gland carcinoma, sarcoma, squamous cell cancer, small cell carcinoma, small intestine cancer, stomach cancer, testicular cancer, thyroid cancer, vulvar cancer, or any combination thereof. Examples of the immunogenic cell death (ICD)-inducing chemotherapeutic include, not being limited to, doxorubicin, idarubicin, mitoxantrone, tautomycin, calyculin A, salubrinal, oxaliplatin, bleomycin, and cyclophosphamide.

In the above methods for using the compound of the invention, the compound described herein, salt, diastereomer, enantiomer, racemate, hydrate, solvate, or prodrug thereof is administered to a system comprising cells or tissues. In certain embodiments, the compound described herein, a salt, a diastereomer, an enantiomer, a racemate, a hydrate, a solvate, a prodrug, or any combination thereof is administered to a human or animal subject. In still certain embodiments, a pharmaceutical composition or a medicament comprising at least one of the compound, the salt, the diastereomer, the enantiomer, the racemate, the hydrate, the solvate, the prodrug, or any combination thereof is administered to a human or animal subject.

4. Methods of Preparing Compounds

In a further aspect, the present invention provides methods of preparing the compounds, salts, diastereomers, enantiomers, racemates, hydrates, solvates, and prodrugs. In some embodiments, the compounds, salts, diastereomers, enantiomers, racemates, hydrates, solvates, or prodrugs may be prepared by methods including, but not limited to, one or more of the following methods:

(a) optionally converting a compound of the invention into a pharmaceutically acceptable salt;
(b) optionally converting a salt form of a compound of the invention to a non-salt form;
(c) optionally converting an unoxidized form of a compound of the invention into a pharmaceutically acceptable N-oxide;
(d) optionally resolving an individual isomer of a compound of the invention from a mixture of stereoisomers;
(e) optionally converting a non-derivatized compound of the invention into a pharmaceutically acceptable prodrug derivative; and
(f) optionally converting a prodrug derivative of a compound of the invention to its non-derivatized form.

Exemplary methods for preparing the compounds of the invention are described herein, including in the Examples, which will be described in detail below. Some embodiments of the invention provide processes for preparing the compounds of the present invention, as illustrated in Methods 1-5 below.

Method 1

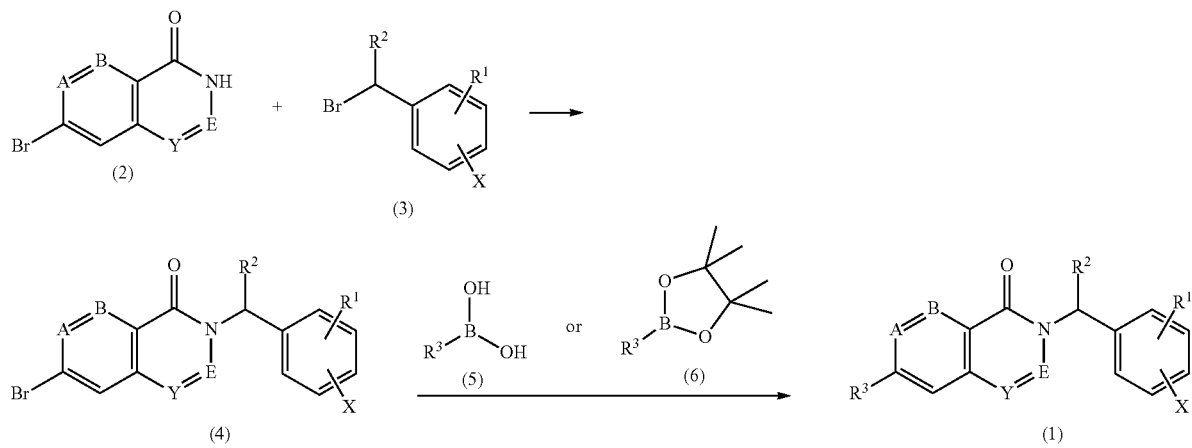

A bicyclic compound (2) was reacted with benzylbromide (3) in an organic solvent (DMF, acetone, acetonitrile or dichloromethane) in the presence of inorganic base ($K_2CO_3$, $Na_2CO_3$, $Cs_2CO_3$) or organic base (triethylamine, diisopropylethylamine, pyridine) at room temperature (RT)-100° C. for 5-16 hours to provide a benzyl bicyclic intermediate (4). The resulting intermediate (4) was reacted with a boronic acid (5) or a boronic ester (6) with Suzuki reaction condition using a palladium catalyst ($Pd(OAc)_2$, $Pd_2(dba)_3$, $Pd(PPh_3)_4$ or $Pd(dppf)Cl_2·DCM$) to provide the compound (1).

Method 2

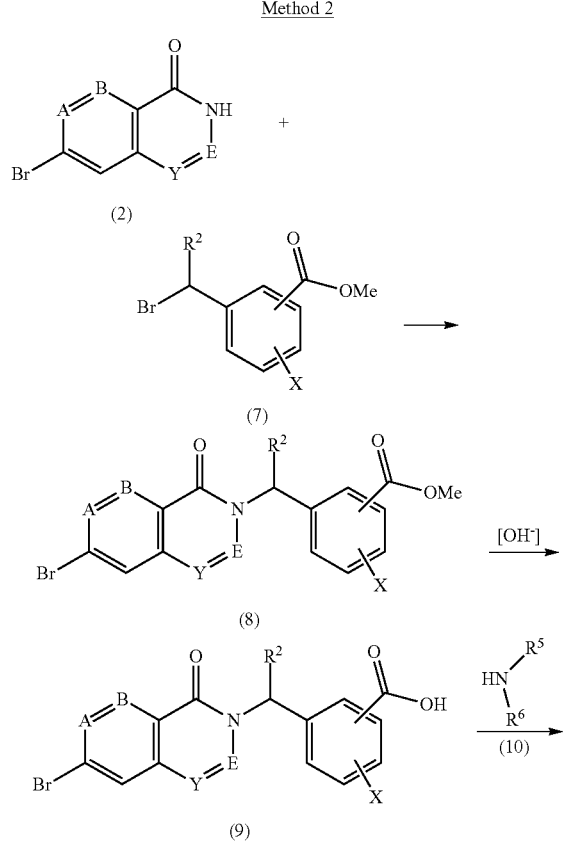

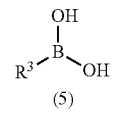

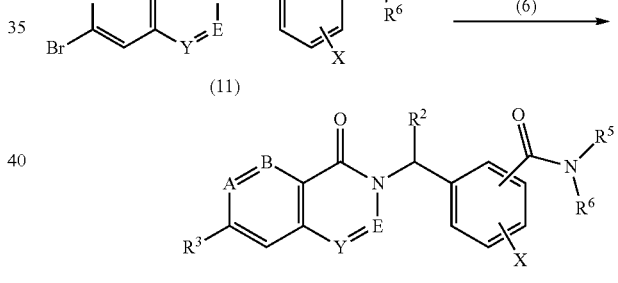

A bicyclic compound (2) was reacted with benzylbromide (7) in an organic solvent (DMF, acetone, acetonitrile or dichloromethane) in the presence of an inorganic base ($K_2CO_3$, $Na_2CO_3$ or $Cs_2CO_3$) or organic base (triethylamine, diisopropylethylamine or pyridine) at RT-100° C. for 5-16 hours to provide a benzyl bicyclic intermediate (8). The resulting intermediate (8) was converted to a benzoic acid (9) using a base (LiOH, NaOH or KOH) in mixture of water with a solvent (MeOH, THF) at RT-80° C. for 3-20 hours. The benzoic acid was coupled with an amine (10) by a coupling reagent (EDCI, HATU, HBTU, PyBop or ByBrop) in the presence of a base (triethylamine, diisopropylethylamine) in a solvent (DMF, THF, DCM) at RT-60° C. for 1-20 hours to give the compound (11). The resulting compound (11) was reacted with a boronic acid (5) or a boronic ester (6) with Suzuki reaction condition using a palladium catalyst ($Pd(OAc)_2$, $Pd_2(dba)_3$, $Pd(PPh_3)_4$ or $Pd(dppf)Cl_2$-DCM) in the presence of an inorganic base ($K_2CO_3$, $Na_2CO_3$ or $Cs_2CO_3$) to provide the compound (12).

Method 3

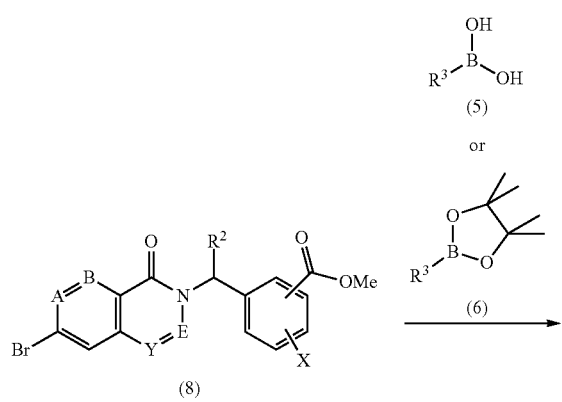

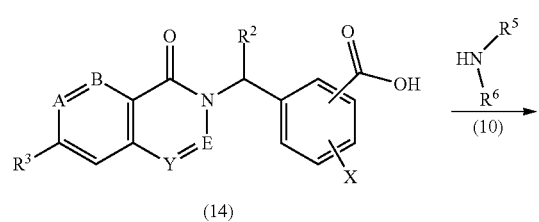

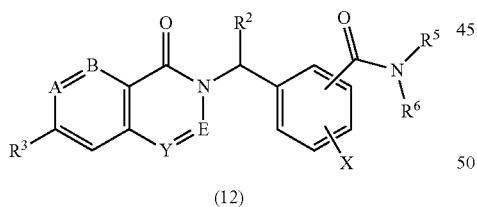

A benzyl bicyclic ester (8) was reacted with boronic acid (5) or a boronic ester (6) with Suzuki reaction condition using a palladium catalyst ($Pd(OAc)_2$, $Pd_2(dba)_3$, $Pd(PPh_3)_4$ or $Pd(dppf)Cl_2 \cdot DCM$) in the presence of an inorganic base ($K_2CO_3$, $Na_2CO_3$ or $Cs_2CO_3$) to provide the compound (13). The resulting compound (13) was converted to its benzoic acid (14) using a base (LiOH, NaOH or KOH) in mixture of water with a solvent (MeOH or THF) at RT-80° C. for 3-20 hours. The benzoic acid was coupled with an amine (10) by a coupling reagent (EDCI, HOBT, HBTU, PyBop or ByBrop) in the presence of a base (triethylamine, diisopropylethylamine) in a solvent (DMF, THF or DCM) at RT-60° C. for 1-20 hours to give the compound (12).

Method 4

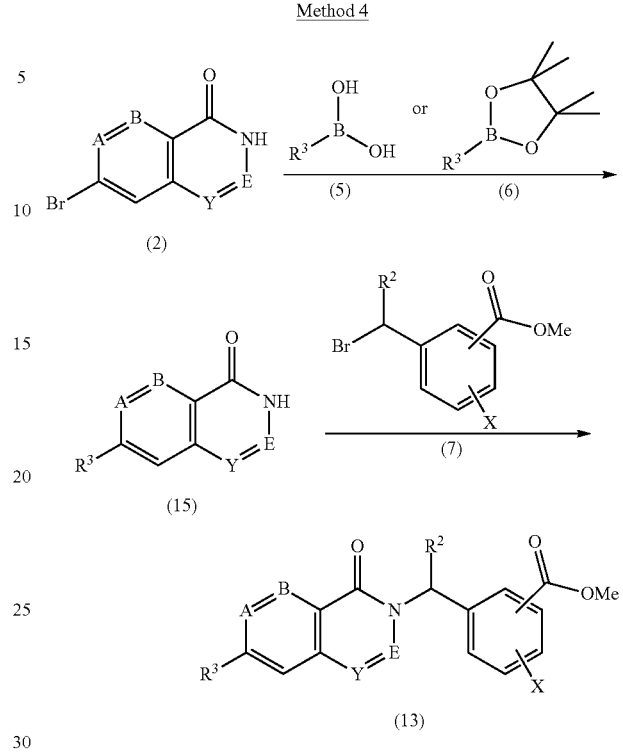

A bicyclic compound (2) was reacted with boronic acid (5) or a boronic ester (6) with Suzuki reaction condition using a palladium catalyst ($Pd(OAc)_2$, $Pd_2(dba)_3$, $Pd(PPh_3)_4$ or $Pd(dppf)Cl_2 \cdot DCM$) in the presence of an inorganic base ($K_2CO_3$, $Na_2CO_3$ or $Cs_2CO_3$) to provide a compound of 15. A bicyclic Suzuki adduct (15) was reacted with benzylbromide (7) in an organic solvent (DMF, acetone, acetonitrile or dichloromethane) in the presence of an inorganic base ($K_2CO_3$, $Na_2CO_3$ or $Cs_2CO_3$) or organic base (triethylamine, diisopropylethylamine or pyridine) at RT-100° C. for 5-16 hours to provide a benzyl bicyclic intermediate (13).

Method 5

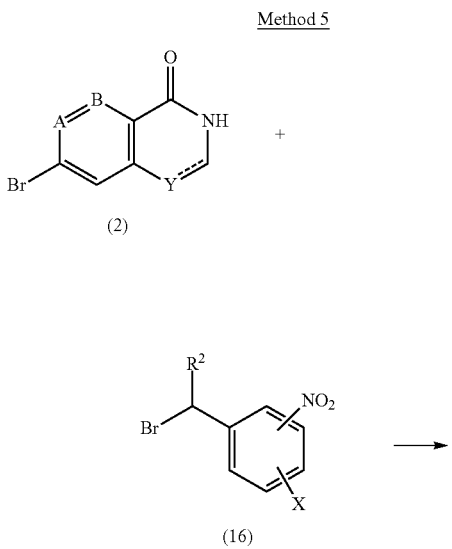

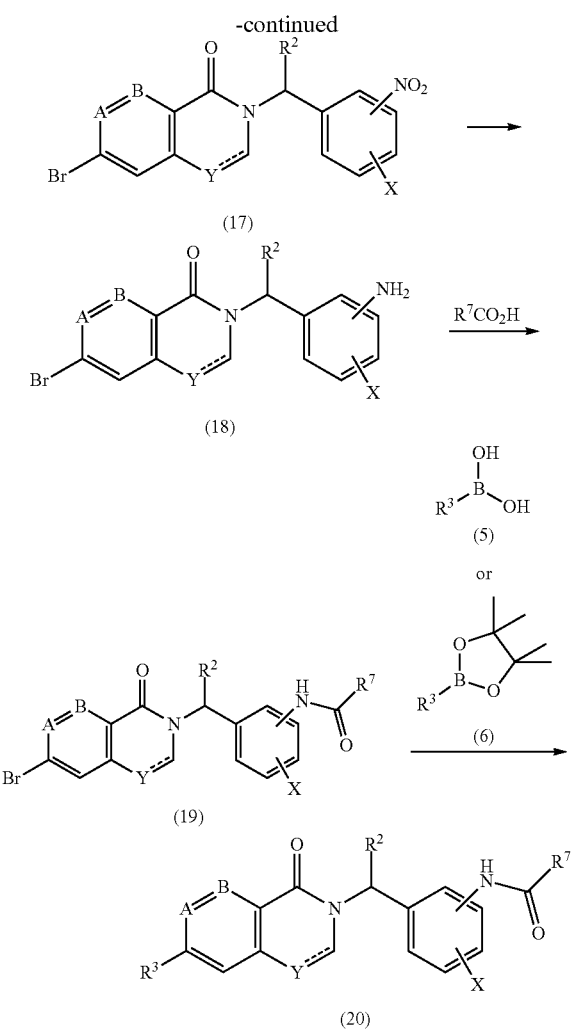

A bicyclic compound (2) was reacted with nitrobenzyl-bromide (16) in an organic solvent (DMF, acetone, acetonitrile or dichloromethane) in the presence of an inorganic base ($K_2CO_3$, $Na_2CO_3$ or $Cs_2CO_3$) or organic base (triethylamine, diisopropylethylamine or pyridine) at RT-100° C. for 5-16 hours to provide a benzyl bicyclic intermediate (17). The resulting intermediate (17) was converted to its aminobenzyl bicycle (18) by palladium catalyzed hydrogenation in a solvent (MeOH, EtOH, i-PrOH or EtOAc). The resulting compound (18) was coupled with an acid, $R^7COOH$, by a coupling reagent (EDCI, HOBT, HBTU, PyBop or ByBrop) in the presence of a base (triethylamine or diisopropylethylamine) in a solvent (DMF, THF or DCM) at RT-60° C. for 1-20 hours to give the compound (19). The resulting compound (19) was reacted with boronic acid (5) or a boronic ester (6) with Suzuki reaction condition using a palladium catalyst ($Pd(OAc)_2$, $Pd_2(dba)_3$, $Pd(PPh_3)_4$ or $Pd(dppf)Cl_2 \cdot DCM$) in the presence of an inorganic base ($K_2CO_3$, $Na_2CO_3$ or $Cs_2CO_3$) to provide the compound (20).

Non-limiting examples of the compounds described herein may include:

2-(3-Methoxybenzyl)-6-(1H-pyrazol-4-yl)-3,4-dihydroisoquinolin-1(2H)-one;
2-(3-Methoxybenzyl)-6-(1H-pyrazol-4-yl)isoquinolin-1(2H)-one;
2-(3-Hydroxybenzyl)-6-(1H-pyrazol-4-yl)isoquinolin-1(2H)-one;
2-(3-Methoxybenzyl)-6-(3-methyl-1H-pyrazol-4-yl)isoquinolin-1(2H)-one;
2-(3-Hydroxybenzyl)-6-(3-methyl-1H-pyrazol-4-yl)isoquinolin-1(2H)-one;
2-(3-Methoxybenzyl)-6-(3-(trifluoromethyl)-1H-pyrazol-4-yl)isoquinolin-1(2H)-one;
2-(3-Hydroxybenzyl)-6-(3-(trifluoromethyl)-1H-pyrazol-4-yl)isoquinolin-1(2H)-one;
2-(1-(3-Hydroxyphenyl)ethyl)-6-(3-(trifluoromethyl)-1H-pyrazol-4-yl)isoquinolin-1(2H)-one;
2-(3-Methoxybenzyl)-6-(3-methylisoxazol-4-yl)isoquinolin-1(2H)-one;
2-(3-Methoxybenzyl)-6-(1-methyl-1H-pyrazol-5-yl)isoquinolin-1(2H)-one
6-(3-(Difluoromethyl)-1H-pyrazol-4-yl)-2-(3-methoxybenzyl)isoquinolin-1(2H)-one;
2-(3-Hydroxybenzyl)-6-(3-methylisoxazol-4-yl)isoquinolin-1(2H)-one;
6-(3-(Difluoromethyl)-1H-pyrazol-4-yl)-2-(3-hydroxybenzyl)isoquinolin-1(2H)-one;
6-(3-(Difluoromethyl)-1H-pyrazol-4-yl)-2-(1-(3-hydroxyphenyl)ethyl)isoquinolin-1(2H)-one;
2-(3-Hydroxybenzyl)-6-(1-methyl-1H-pyrazol-5-yl)isoquinolin-1(2H)-one;
6-(2-Aminopyridin-4-yl)-2-(3-methoxybenzyl)isoquinolin-1(2H)-one;
6-(3-(Difluoromethyl)-1H-pyrazol-4-yl)-2-(3-fluoro-5-methoxybenzyl)isoquinolin-1(2H)-one;
6-(3-Chloro-1H-pyrazol-4-yl)-2-(3-fluoro-5-methoxybenzyl)isoquinolin-1(2H)-one;
6-(3-Chloro-1H-pyrazol-4-yl)-2-(3-methoxybenzyl)isoquinolin-1(2H)-one;
6-(3-Chloro-1H-pyrazol-4-yl)-2-(1-(3-methoxyphenyl)ethyl)isoquinolin-1(2H)-one;
6-(3-Chloro-1H-pyrazol-4-yl)-2-(3-hydroxybenzyl)isoquinolin-1(2H)-one;
6-(3-Chloro-1H-pyrazol-4-yl)-2-(1-(3-hydroxyphenyl)ethyl)isoquinolin-1(2H)-one;
2-(3-Methoxybenzyl)-6-(pyridin-4-yl)isoquinolin-1(2H)-one;
2-(3-Hydroxybenzyl)-6-(pyridin-4-yl)isoquinolin-1(2H)-one;
6-(2-Aminopyridin-4-yl)-2-(3-methoxybenzyl)isoquinolin-1(2H)-one;
6-(2-Aminopyridin-4-yl)-2-(1-(3-methoxyphenyl)ethyl)isoquinolin-1(2H)-one;
3-((1-Oxo-6-(1H-pyrazol-4-yl)isoquinolin-2(1H)-yl)methyl)-N-(2-(pyridin-2-yl)ethyl)benzamide;
N-Isopropyl-3-((1-oxo-6-(1H-pyrazol-4-yl)isoquinolin-2(1H)-yl)methyl)benzamide;
3-((1-Oxo-6-(1H-pyrazol-4-yl)isoquinolin-2(1H)-yl)methyl)-N-phenylbenzamide;
N-Benzyl-3-((1-oxo-6-(1H-pyrazol-4-yl)isoquinolin-2(1H)-yl)methyl)benzamide;
3-((6-(3-Methyl-1H-pyrazol-4-yl)-1-oxoisoquinolin-2(1H)-yl)methyl)-N-(2-(pyridin-2-yl)ethyl)benzamide;
N-(1-Methyl-1H-pyrazol-3-yl)-3-((6-(3-methyl-1H-pyrazol-4-yl)-1-oxoisoquinolin-2(1H)-yl)methyl)benzamide;
3-((6-(3-Methyl-1H-pyrazol-4-yl)-1-oxoisoquinolin-2(1H)-yl)methyl)-N-(3-(methylsulfonamido)benzyl)benzamide;
3-((6-(3-Methyl-1H-pyrazol-4-yl)-1-oxoisoquinolin-2(1H)-yl)methyl)-N-(3-sulfamoylphenyl)benzamide;
3-((6-(3-Methyl-1H-pyrazol-4-yl)-1-oxoisoquinolin-2(1H)-yl)methyl)-N-(3-(trifluoromethoxy)phenyl)benzamide;
3-((6-(3-Methyl-1H-pyrazol-4-yl)-1-oxoisoquinolin-2(1H)-yl)methyl)-N-(4-sulfamoylphenyl)benzamide;

3-((6-(3-Methyl-1H-pyrazol-4-yl)-1-oxoisoquinolin-2(1H)-yl)methyl)-N-(4-(methylsulfonamido)phenyl)benzamide;
3-((6-(3-Methyl-1H-pyrazol-4-yl)-1-oxoisoquinolin-2(1H)-yl)methyl)-N-(2-(trifluoromethoxy)phenyl)benzamide;
N-(6-Fluoropyridin-3-yl)-3-((6-(3-methyl-1H-pyrazol-4-yl)-1-oxoisoquinolin-2(1H)-yl)methyl)benzamide;
N-((6-Fluoropyridin-3-yl)methyl)-3-((6-(3-methyl-1H-pyrazol-4-yl)-1-oxoisoquinolin-2(1H)-yl)methyl)benzamide;
3-((6-(3-Methyl-1H-pyrazol-4-yl)-1-oxoisoquinolin-2(1H)-yl)methyl)-N-(2,2,2-trifluoroethyl)benzamide;
3-((1-Oxo-6-(3-(trifluoromethyl)-1H-pyrazol-4-yl)isoquinolin-2(1H)-yl)methyl)-N-(4-sulfamoylphenyl)benzamide;
N-(1-Methyl-1H-pyrazol-3-yl)-3-((1-oxo-6-(5-(trifluoromethyl)-1H-pyrazol-4-yl)isoquinolin-2(1H)-yl)methyl)benzamide;
N-((6-Fluoropyridin-3-yl)methyl)-3-((1-oxo-6-(3-(trifluoromethyl)-1H-pyrazol-4-yl)isoquinolin-2(1H)-yl)methyl)benzamide;
3-((1-Oxo-6-(3-(trifluoromethyl)-1H-pyrazol-4-yl)isoquinolin-2(1H)-yl)methyl)-N-(tetrahydro-2H-pyran-4-yl)benzamide;
3-((1-Oxo-6-(3-(trifluoromethyl)-1H-pyrazol-4-yl)isoquinolin-2(1H)-yl)methyl)-N-(piperidin-4-yl)benzamide;
N-(1-Methylpiperidin-4-yl)-3-((1-oxo-6-(3-(trifluoromethyl)-1H-pyrazol-4-yl)isoquinolin-2(1H)-yl)methyl)benzamide;
N-(1-(Oxetan-3-yl)piperidin-4-yl)-3-((1-oxo-6-(3-(trifluoromethyl)-1H-pyrazol-4-yl)isoquinolin-2(1H)-yl)methyl)benzamide;
N-(1-(2,2-Difluoroethyl)piperidin-4-yl)-3-((1-oxo-6-(3-(trifluoromethyl)-1H-pyrazol-4-yl)isoquinolin-2(1H)-yl)methyl)benzamide;
N-Cyclopropyl-3-((1-oxo-6-(3-(trifluoromethyl)-1H-pyrazol-4-yl)isoquinolin-2(1H)-yl)methyl)benzamide;
N-((1-Methylpiperidin-4-yl)methyl)-3-((1-oxo-6-(3-(trifluoromethyl)-1H-pyrazol-4-yl)isoquinolin-2(1H)-yl)methyl)benzamide;
3-((1-Oxo-6-(3-(trifluoromethyl)-1H-pyrazol-4-yl)isoquinolin-2(1H)-yl)methyl)-N-((tetrahydro-2H-pyran-4-yl)methyl)benzamide;
N-(Oxetan-3-ylmethyl)-3-((1-oxo-6-(3-(trifluoromethyl)-1H-pyrazol-4-yl)isoquinolin-2(1H)-yl)methyl)benzamide;
N-(2-(6-Fluoropyridin-2-yl)ethyl)-3-((1-oxo-6-(3-(trifluoromethyl)-1H-pyrazol-4-yl)isoquinolin-2(1H)-yl)methyl)benzamide;
3-((6-(3-(Difluoromethyl)-1H-pyrazol-4-yl)-1-oxoisoquinolin-2(1H)-yl)methyl)-N-((tetrahydro-2H-pyran-4-yl)methyl)benzamide;
3-((6-(3-(Difluoromethyl)-1H-pyrazol-4-yl)-1-oxoisoquinolin-2(1H)-yl)methyl)-N-((1-methylpiperidin-4-yl)methyl)benzamide;
3-((6-(3-(Difluoromethyl)-1H-pyrazol-4-yl)-1-oxoisoquinolin-2(1H)-yl)methyl)-N-(piperidin-4-ylmethyl)benzamide;
3-((6-(3-(Difluoromethyl)-1H-pyrazol-4-yl)-1-oxoisoquinolin-2(1H)-yl)methyl)-N-(oxetan-3-ylmethyl)benzamide;
3-((6-(3-(Difluoromethyl)-1H-pyrazol-4-yl)-1-oxoisoquinolin-2(1H)-yl)methyl)-5-fluoro-N-(oxetan-3-ylmethyl)benzamide;
3-((6-(3-(Difluoromethyl)-1H-pyrazol-4-yl)-1-oxoisoquinolin-2(1H)-yl)methyl)-5-fluoro-N-((tetrahydro-2H-pyran-4-yl)methyl)benzamide;
3-((6-(3-(Difluoromethyl)-1H-pyrazol-4-yl)-1-oxoisoquinolin-2(1H)-yl)methyl)-5-fluoro-N-(piperidin-4-ylmethyl)benzamide;
3-((6-(3-(Difluoromethyl)-1H-pyrazol-4-yl)-1-oxoisoquinolin-2(1H)-yl)methyl)-5-fluoro-N-((1-methylpiperidin-4-yl)methyl)benzamide;
3-((6-(3-Chloro-1H-pyrazol-4-yl)-1-oxoisoquinolin-2(1H)-yl)methyl)-N-(oxetan-3-ylmethyl)benzamide;
3-((6-(3-Chloro-1H-pyrazol-4-yl)-1-oxoisoquinolin-2(1H)-yl)methyl)-N-((1-methylpiperidin-4-yl)methyl)benzamide;
3-((6-(3-Chloro-1H-pyrazol-4-yl)-1-oxoisoquinolin-2(1H)-yl)methyl)-5-fluoro-N-(2-hydroxyethyl)benzamide;
3-((6-(1-Methyl-1H-pyrazol-5-yl)-1-oxoisoquinolin-2(1H)-yl)methyl)-N-((1-methylpiperidin-4-yl)methyl)benzamide;
3-Fluoro-5-((6-(1-methyl-1H-pyrazol-5-yl)-1-oxoisoquinolin-2(1H)-yl)methyl)-N-((1-methylpiperidin-4-yl)methyl)benzamide;
3-((6-(3-Chloro-1H-pyrazol-4-yl)-1-oxoisoquinolin-2(1H)-yl)methyl)-5-fluoro-N-((1 S,4S)-4-hydroxycyclohexyl)benzamide;
3-Fluoro-5-((6-(1-methyl-1H-pyrazol-5-yl)-1-oxoisoquinolin-2(1H)-yl)methyl)-N-(piperidin-4-ylmethyl)benzamide hydrochloride;
3-((6-(3-Methylisoxazol-4-yl)-1-oxoisoquinolin-2(1H)-yl)methyl)-N-(2,2,2-trifluoroethyl)benzamide;
N-(Cyclopropylmethyl)-3-((6-(3-methylisoxazol-4-yl)-1-oxoisoquinolin-2(1H)-yl)methyl)benzamide;
3-((6-(3-Methylisoxazol-4-yl)-1-oxoisoquinolin-2(1H)-yl)methyl)-N-(2-morpholinoethyl)benzamide;
3-((6-(3-Methylisoxazol-4-yl)-1-oxoisoquinolin-2(1H)-yl)methyl)-N-(2-(4-methylpiperazin-1-yl)ethyl)benzamide;
3-((6-(3-Methylisoxazol-4-yl)-1-oxoisoquinolin-2(1H)-yl)methyl)-N-(oxetan-3-ylmethyl)benzamide;
N-((1S,3S)-3-Hydroxycyclobutyl)-3-((6-(3-methylisoxazol-4-yl)-1-oxoisoquinolin-2(1H)-yl)methyl)benzamide;
N-((1R,3R)-3-Hydroxycyclobutyl)-3-((6-(3-methylisoxazol-4-yl)-1-oxoisoquinolin-2(1H)-yl)methyl)benzamide;
N-((1S,4S)-4-Hydroxycyclohexyl)-3-((6-(3-methylisoxazol-4-yl)-1-oxoisoquinolin-2(1H)-yl)methyl)benzamide;
N-((1R,4R)-4-Hydroxycyclohexyl)-3-((6-(3-methylisoxazol-4-yl)-1-oxoisoquinolin-2(1H)-yl)methyl)benzamide;
N-((6-Fluoropyridin-3-yl)methyl)-3-((6-(3-methylisoxazol-4-yl)-1-oxoisoquinolin-2(1H)-yl)methyl)benzamide;
3-((6-(3-Methylisoxazol-4-yl)-1-oxoisoquinolin-2(1H)-yl)methyl)-N-(tetrahydro-2H-pyran-4-yl)benzamide;
3-((6-(3-Methylisoxazol-4-yl)-1-oxoisoquinolin-2(1H)-yl)methyl)-N-((1-methylpiperidin-4-yl)methyl)benzamide;
3-((6-(3-Methylisoxazol-4-yl)-1-oxoisoquinolin-2(1H)-yl)methyl)-N-(piperidin-4-ylmethyl)benzamide hydrochloride;
3-((6-(3-Methylisoxazol-4-yl)-1-oxoisoquinolin-2(1H)-yl)methyl)-N-(piperidin-4-ylmethyl)benzamide hydrochloride;
N-((1-Cyclopropylpiperidin-4-yl)methyl)-3-((6-(3-methylisoxazol-4-yl)-1-oxoisoquinolin-2(1H)-yl)methyl)benzamide;
N-((1-Isopropylpiperidin-4-yl)methyl)-3-((6-(3-methylisoxazol-4-yl)-1-oxoisoquinolin-2(1H)-yl)methyl)benzamide;
N-((1-(3,3-Difluoroallyl)piperidin-4-yl)methyl)-3-((6-(3-methylisoxazol-4-yl)-1-oxoisoquinolin-2(1H)-yl)methyl)benzamide;
3-((6-(3-Methylisoxazol-4-yl)-1-oxoisoquinolin-2(1H)-yl)methyl)-N-((1-(2,2,2-trifluoroethyl)piperidin-4-yl)methyl)benzamide;

3-((6-(3-Methylisoxazol-4-yl)-1-oxoisoquinolin-2(1H)-yl) methyl)-N-((1-(oxetan-3-yl)piperidin-4-yl)methyl)benzamide;

3-((6-(3-Methylisoxazol-4-yl)-1-oxoisoquinolin-2(1H)-yl) methyl)-N-(piperidin-4-yl)benzamide;

N-((1-(2,2Difluoroethyl)piperidin-4-yl)methyl)-3-((6-(3-methylisoxazol-4-yl)-1-oxoisoquinolin-2(1H)-yl)methyl) benzamide;

3-((6-(3-Methylisoxazol-4-yl)-1-oxoisoquinolin-2(1H)-yl) methyl)-N-(1-(2,2,2-trifluoroethyl)piperidin-4-yl)benzamide;

3-((6-(3-Methylisoxazol-4-yl)-1-oxoisoquinolin-2(1H)-yl) methyl)-N-(1-(oxetan-3-yl)piperidin-4-yl)benzamide;

N-(1-Methyl-1H-pyrazol-3-yl)-3-((6-(3-methylisoxazol-4-yl)-1-oxoisoquinolin-2(1H)-yl)methyl)benzamide;

N-(Isoxazol-3-yl)-3-((6-(3-methylisoxazol-4-yl)-1-oxoisoquinolin-2(1H)-yl)methyl)benzamide;

N-(Isochroman-6-yl)-3-((6-(3-methylisoxazol-4-yl)-1-oxoisoquinolin-2(1H)-yl)methyl)benzamide;

N-(Isochroman-7-yl)-3-((6-(3-methylisoxazol-4-yl)-1-oxoisoquinolin-2(1H)-yl)methyl)benzamide;

3-((6-(3-Methylisoxazol-4-yl)-1-oxoisoquinolin-2(1H)-yl) methyl)-N-(4,5,6,7-tetrahydrothiazolo[4,5-c]pyridin-2-yl)benzamide;

N-(5-Methyl-4,5,6,7-tetrahydrothiazolo[4,5-c]pyridin-2-yl)-3-((6-(3-methylisoxazol-4-yl)-1-oxoisoquinolin-2 (1H)-yl)methyl)benzamide;

N-(5-Isopropyl-4,5,6,7-tetrahydrothiazolo[4,5-c]pyridin-2-yl)-3-((6-(3-methylisoxazol-4-yl)-1-oxoisoquinolin-2 (1H)-yl)methyl)benzamide;

3-((6-(3-Methylisoxazol-4-yl)-1-oxoisoquinolin-2(1H)-yl) methyl)-N-(1,2,3,4-tetrahydroisoquinolin-6-yl)benzamide;

N-(2-Methyl-1,2,3,4-tetrahydroisoquinolin-6-yl)-3-((6-(3-methylisoxazol-4-yl)-1-oxoisoquinolin-2(1H)-yl)methyl) benzamide;

N-(2-Isopropyl-1,2,3,4-tetrahydroisoquinolin-6-yl)-3-((6-(3-methylisoxazol-4-yl)-1-oxoisoquinolin-2(1H)-yl) methyl)benzamide;

N-(2-Cyclopropyl-1,2,3,4-tetrahydroisoquinolin-6-yl)-3-((6-(3-methylisoxazol-4-yl)-1-oxoisoquinolin-2(1H)-yl) methyl)benzamide;

3-((6-(3-Methylisoxazol-4-yl)-1-oxoisoquinolin-2(1H)-yl) methyl)-N-(1,2,3,4-tetrahydroisoquinolin-7-yl)benzamide;

N-(2-Methyl-1,2,3,4-tetrahydroisoquinolin-7-yl)-3-((6-(3-methylisoxazol-4-yl)-1-oxoisoquinolin-2(1H)-yl)methyl) benzamide;

N-(2-Hydroxyethyl)-3-((6-(3-methylisoxazol-4-yl)-1-oxoisoquinolin-2(1H)-yl)methyl)benzamide;

3-((6-(1-Methyl-1H-pyrazol-5-yl)-1-oxoisoquinolin-2(1H)-yl)methyl)-N-(2,2,2-trifluoroethyl)benzamide;

3-((6-(1-Methyl-1H-pyrazol-5-yl)-1-oxoisoquinolin-2(1H)-yl)methyl)-N-(tetrahydro-2H-pyran-4-yl)benzamide;

3-((6-(1-Methyl-1H-pyrazol-5-yl)-1-oxoisoquinolin-2(1H)-yl)methyl)-N-(piperidin-4-yl)benzamide;

3-((6-(1-Methyl-1H-pyrazol-5-yl)-1-oxoisoquinolin-2(1H)-yl)methyl)-N-(1-methylpiperidin-4-yl)benzamide;

N-(1-(2,2-Difluoroethyl)piperidin-4-yl)-3-((6-(1-methyl-1H-pyrazol-5-yl)-1-oxoisoquinolin-2(1H)-yl)methyl) benzamide;

3-((6-(1-Methyl-1H-pyrazol-5-yl)-1-oxoisoquinolin-2(1H)-yl)methyl)-N-(1-(2,2,2-trifluoroethyl)piperidin-4-yl)benzamide;

3-((6-(1-Methyl-1H-pyrazol-5-yl)-1-oxoisoquinolin-2(1H)-yl)methyl)-N-(1-(oxetan-3-yl)piperidin-4-yl)benzamide;

3-((6-(1-Methyl-1H-pyrazol-5-yl)-1-oxoisoquinolin-2(1H)-yl)methyl)-N-(oxetan-3-yl)benzamide;

3-((6-(1-Methyl-1H-pyrazol-5-yl)-1-oxoisoquinolin-2(1H)-yl)methyl)-N-(oxetan-3-ylmethyl)benzamide;

N-((3-Hydroxycyclobutyl)methyl)-3-((6-(1-methyl-1H-pyrazol-5-yl)-1-oxoisoquinolin-2(1H)-yl)methyl)benzamide;

3-((6-(1-Methyl-1H-pyrazol-5-yl)-1-oxoisoquinolin-2(1H)-yl)methyl)-N-((1-methylazetidin-3-yl)methyl)benzamide;

N-((6-Fluoropyridin-3-yl)methyl)-3-((6-(1-methyl-1H-pyrazol-5-yl)-1-oxoisoquinolin-2(1H)-yl)methyl)benzamide;

N-((1R,4R)-4-Hydroxycyclohexyl)-3-((6-(1-methyl-1H-pyrazol-5-yl)-1-oxoisoquinolin-2(1H)-yl)methyl)benzamide;

N-((1 S,4S)-4-Hydroxycyclohexyl)-3-((6-(1-methyl-1H-pyrazol-5-yl)-1-oxoisoquinolin-2(1H)-yl)methyl)benzamide;

N-((2-Fluoropyridin-4-yl)methyl)-3-((6-(1-methyl-1H-pyrazol-5-yl)-1-oxoisoquinolin-2(1H)-yl)methyl)benzamide;

N-(1-Isopropylpiperidin-4-yl)-3-((6-(1-methyl-1H-pyrazol-5-yl)-1-oxoisoquinolin-2(1H)-yl)methyl)benzamide;

N-(2-(Dimethylamino)ethyl)-3-((6-(1-methyl-1H-pyrazol-5-yl)-1-oxoisoquinolin-2(1H)-yl)methyl)benzamide;

N-Methyl-3-((1-oxo-6-(5-(trifluoromethyl)-1H-pyrazol-4-yl)isoquinolin-2(1H)-yl)methyl)benzamide;

N-(2-Methoxyethyl)-3-((6-(1-methyl-1H-pyrazol-5-yl)-1-oxoisoquinolin-2(1H)-yl)methyl)benzamide;

3-((6-(1-Methyl-1H-pyrazol-5-yl)-1-oxoisoquinolin-2(1H)-yl)methyl)-N-(5-methyl-4,5,6,7-tetrahydrothiazolo[4,5-c]pyridin-2-yl)benzamide;

3-((6-(1-Methyl-1H-pyrazol-5-yl)-1-oxoisoquinolin-2(1H)-yl)methyl)-N-(4,5,6,7-tetrahydrothiazolo[4,5-c]pyridin-2-yl)benzamide;

3-((6-(1-Methyl-1H-pyrazol-5-yl)-1-oxoisoquinolin-2(1H)-yl)methyl)-N-(1,2,3,4-tetrahydroisoquinolin-6-yl)benzamide;

N-(2-Methyl-1,2,3,4-tetrahydroisoquinolin-6-yl)-3-((6-(1-methyl-1H-pyrazol-5-yl)-1-oxoisoquinolin-2(1H)-yl) methyl)benzamide;

3-((6-(1-Methyl-1H-pyrazol-5-yl)-1-oxoisoquinolin-2(1H)-yl)methyl)-N-(1,2,3,4-tetrahydroisoquinolin-7-yl)benzamide;

N-(2-Cyclopropyl-1,2,3,4-tetrahydroisoquinolin-7-yl)-3-((6-(1-methyl-1H-pyrazol-5-yl)-1-oxoisoquinolin-2(1H)-yl)methyl)benzamide;

3-Fluoro-5-((1-oxo-6-(3-(trifluoromethyl)-1H-pyrazol-4-yl) isoquinolin-2(1H)-yl)methyl)-N-(4-sulfamoylphenyl) benzamide;

3-Fluoro-N-(1-methyl-1H-pyrazol-3-yl)-5-((1-oxo-6-(5-(trifluoromethyl)-1H-pyrazol-4-yl)isoquinolin-2(1H)-yl) methyl)benzamide;

3-Fluoro-N-((6-fluoropyridin-3-yl)methyl)-5-((1-oxo-6-(3-(trifluoromethyl)-1H-pyrazol-4-yl)isoquinolin-2(1H)-yl) methyl)benzamide;

3-Fluoro-5-((1-oxo-6-(3-(trifluoromethyl)-1H-pyrazol-4-yl) isoquinolin-2(1H)-yl)methyl)-N-(tetrahydro-2H-pyran-4-yl)benzamide;

3-Fluoro-5-((1-oxo-6-(3-(trifluoromethyl)-1H-pyrazol-4-yl) isoquinolin-2(1H)-yl)methyl)-N-(piperidin-4-yl)benzamide;

3-Fluoro-N-(1-methylpiperidin-4-yl)-5-((1-oxo-6-(3-(trifluoromethyl)-1H-pyrazol-4-yl)isoquinolin-2(1H)-yl) methyl)benzamide;

N-Cyclopropyl-3-fluoro-5-((1-oxo-6-(3-(trifluoromethyl)-1H-pyrazol-4-yl)isoquinolin-2(1H)-yl)methyl)benzamide;

3-Fluoro-N-((1-methylpiperidin-4-yl)methyl)-5-((1-oxo-6-(3-(trifluoromethyl)-1H-pyrazol-4-yl)isoquinolin-2(1H)-yl)methyl)benzamide;

3-Fluoro-5-((1-oxo-6-(3-(trifluoromethyl)-1H-pyrazol-4-yl)isoquinolin-2(1H)-yl)methyl)-N-((tetrahydro-2H-pyran-4-yl)methyl)benzamide;

3-Fluoro-N-(oxetan-3-ylmethyl)-5-((1-oxo-6-(3-(trifluoromethyl)-1H-pyrazol-4-yl)isoquinolin-2(1H)-yl)methyl)benzamide;

3-Fluoro-N-((1S,3S)-3-hydroxycyclobutyl)-5-((6-(3-methylisoxazol-4-yl)-1-oxoisoquinolin-2(1H)-yl)methyl)benzamide;

3-Fluoro-N-((1R,3R)-3-hydroxycyclobutyl)-5-((6-(3-methylisoxazol-4-yl)-1-oxoisoquinolin-2(1H)-yl)methyl)benzamide;

3-Fluoro-N-((1R,4R)-4-hydroxycyclohexyl)-5-((6-(3-methylisoxazol-4-yl)-1-oxoisoquinolin-2(1H)-yl)methyl)benzamide;

3-Fluoro-N-((1S,4S)-4-hydroxycyclohexyl)-5-((6-(3-methylisoxazol-4-yl)-1-oxoisoquinolin-2(1H)-yl)methyl)benzamide;

3-Fluoro-N-((1R,4R)-4-methoxycyclohexyl)-5-((6-(3-methylisoxazol-4-yl)-1-oxoisoquinolin-2(1H)-yl)methyl)benzamide;

3-Fluoro-N-((1S,4S)-4-methoxycyclohexyl)-5-((6-(3-methylisoxazol-4-yl)-1-oxoisoquinolin-2(1H)-yl)methyl)benzamide;

3-Fluoro-5-((6-(3-methylisoxazol-4-yl)-1-oxoisoquinolin-2(1H)-yl)methyl)-N-(2-morpholinoethyl)benzamide;

3-Fluoro-5-((6-(3-methylisoxazol-4-yl)-1-oxoisoquinolin-2(1H)-yl)methyl)-N-(2-(4-methylpiperazin-1-yl)ethyl)benzamide;

3-Fluoro-5-((6-(3-methylisoxazol-4-yl)-1-oxoisoquinolin-2(1H)-yl)methyl)-N-(oxetan-3-ylmethyl)benzamide;

3-Fluoro-N-((6-fluoropyridin-3-yl)methyl)-5-((6-(3-methylisoxazol-4-yl)-1-oxoisoquinolin-2(1H)-yl)methyl)benzamide;

3-Fluoro-5-((6-(3-methylisoxazol-4-yl)-1-oxoisoquinolin-2(1H)-yl)methyl)-N-(tetrahydro-2H-pyran-4-yl)benzamide;

3-Fluoro-5-((6-(3-methylisoxazol-4-yl)-1-oxoisoquinolin-2(1H)-yl)methyl)-N-((1-methylpiperidin-4-yl)methyl)benzamide;

3-Fluoro-5-((6-(3-methylisoxazol-4-yl)-1-oxoisoquinolin-2(1H)-yl)methyl)-N-(piperidin-4-ylmethyl)benzamide;

N-((1-Cyclopropylpiperidin-4-yl)methyl)-3-fluoro-5-((6-(3-methylisoxazol-4-yl)-1-oxoisoquinolin-2(1H)-yl)methyl)benzamide;

3-Fluoro-N-((1-isopropylpiperidin-4-yl)methyl)-5-((6-(3-methylisoxazol-4-yl)-1-oxoisoquinolin-2(1H)-yl)methyl)benzamide;

3-Fluoro-5-((6-(3-methylisoxazol-4-yl)-1-oxoisoquinolin-2(1H)-yl)methyl)-N-((1-(2,2,2-trifluoroethyl)piperidin-4-yl)methyl)benzamide;

3-Fluoro-5-((6-(3-methylisoxazol-4-yl)-1-oxoisoquinolin-2(1H)-yl)methyl)-N-((1-(oxetan-3-yl)piperidin-4-yl)methyl)benzamide;

3-Fluoro-5-((6-(3-methylisoxazol-4-yl)-1-oxoisoquinolin-2(1H)-yl)methyl)-N-(1-methylpiperidin-4-yl)benzamide;

3-Fluoro-N-(1-methyl-1H-pyrazol-3-yl)-5-((6-(3-methylisoxazol-4-yl)-1-oxoisoquinolin-2(1H)-yl)methyl)benzamide;

3-Fluoro-5-((6-(3-methylisoxazol-4-yl)-1-oxoisoquinolin-2(1H)-yl)methyl)-N-(4,5,6,7-tetrahydrothiazolo[4,5-c]pyridin-2-yl)benzamide;

3-Fluoro-N-(5-methyl-4,5,6,7-tetrahydrothiazolo[4,5-c]pyridin-2-yl)-5-((6-(3-methylisoxazol-4-yl)-1-oxoisoquinolin-2(1H)-yl)methyl)benzamide;

3-Fluoro-N-(5-isopropyl-4,5,6,7-tetrahydrothiazolo[4,5-c]pyridin-2-yl)-5-((6-(3-methylisoxazol-4-yl)-1-oxoisoquinolin-2(1H)-yl)methyl)benzamide;

3-Fluoro-5-((6-(3-methylisoxazol-4-yl)-1-oxoisoquinolin-2(1H)-yl)methyl)-N-(1,2,3,4-tetrahydroisoquinolin-7-yl)benzamide;

N-(2-Cyclopropyl-1,2,3,4-tetrahydroisoquinolin-7-yl)-3-fluoro-5-((6-(3-methylisoxazol-4-yl)-1-oxoisoquinolin-2(1H)-yl)methyl)benzamide;

3-Fluoro-5-((6-(3-methylisoxazol-4-yl)-1-oxoisoquinolin-2(1H)-yl)methyl)-N-(1,2,3,4-tetrahydroisoquinolin-6-yl)benzamide;

3-Fluoro-N-(2-methyl-1,2,3,4-tetrahydroisoquinolin-6-yl)-5-((6-(3-methylisoxazol-4-yl)-1-oxoisoquinolin-2(1H)-yl)methyl)benzamide;

3-Fluoro-N-((1R,4R)-4-hydroxycyclohexyl)-5-((6-(1-methyl-1H-pyrazol-5-yl)-1-oxoisoquinolin-2(1H)-yl)methyl)benzamide;

3-Fluoro-N-((1S,4S)-4-hydroxycyclohexyl)-5-((6-(1-methyl-1H-pyrazol-5-yl)-1-oxoisoquinolin-2(1H)-yl)methyl)benzamide;

3-Fluoro-5-((6-(1-methyl-1H-pyrazol-5-yl)-1-oxoisoquinolin-2(1H)-yl)methyl)-N-(tetrahydro-2H-pyran-4-yl)benzamide;

N-((3-Hydroxycyclobutyl)methyl)-3-((6-(1-methyl-1H-pyrazol-5-yl)-1-oxoisoquinolin-2(1H)-yl)methyl)benzamide;

3-((6-(1-Methyl-1H-pyrazol-5-yl)-1-oxoisoquinolin-2(1H)-yl)methyl)-N-((1-methylazetidin-3-yl)methyl)benzamide;

3-Fluoro-5-((6-(1-methyl-1H-pyrazol-5-yl)-1-oxoisoquinolin-2(1H)-yl)methyl)-N-((1-methylpiperidin-4-yl)methyl)benzamide;

3-Fluoro-5-((6-(1-methyl-1H-pyrazol-5-yl)-1-oxoisoquinolin-2(1H)-yl)methyl)-N-(piperidin-4-ylmethyl)benzamide;

3-Fluoro-N-((6-fluoropyridin-3-yl)methyl)-5-((6-(1-methyl-1H-pyrazol-5-yl)-1-oxoisoquinolin-2(1H)-yl)methyl)benzamide;

3-Fluoro-N-(1-isopropylpiperidin-4-yl)-5-((6-(1-methyl-1H-pyrazol-5-yl)-1-oxoisoquinolin-2(1H)-yl)methyl)benzamide;

3-Fluoro-5-((6-(1-methyl-1H-pyrazol-5-yl)-1-oxoisoquinolin-2(1H)-yl)methyl)-N-(1-methylpiperidin-4-yl)benzamide;

3-Fluoro-5-((6-(1-methyl-1H-pyrazol-5-yl)-1-oxoisoquinolin-2(1H)-yl)methyl)-N-(piperidin-4-yl)benzamide;

N-(2-(Dimethylamino)ethyl)-3-fluoro-5-((6-(1-methyl-1H-pyrazol-5-yl)-1-oxoisoquinolin-2(1H)-yl)methyl)benzamide;

3-Fluoro-N-(1-methyl-1H-pyrazol-3-yl)-5-((6-(1-methyl-1H-pyrazol-5-yl)-1-oxoisoquinolin-2(1H)-yl)methyl)benzamide;

N-(2-(2-Fluoropyridin-4-yl)ethyl)-3-((1-oxo-6-(pyridin-4-yl)isoquinolin-2(1H)-yl)methyl)benzamide;

3-((6-(2-Aminopyridin-4-yl)-1-oxoisoquinolin-2(1H)-yl)methyl)-N-benzylbenzamide;

3-((6-(2-Aminopyridin-4-yl)-1-oxoisoquinolin-2(1H)-yl)methyl)-N-(naphthalen-2-ylmethyl)benzamide;

N-(2-(Aminomethyl)benzyl)-3-((6-(2-aminopyridin-4-yl)-1-oxoisoquinolin-2(1H)-yl)methyl)benzamide;

3-((6-(2-Aminopyridin-4-yl)-1-oxoisoquinolin-2(1H)-yl)
methyl)-N-(2-(hydroxymethyl)benzyl)benzamide;
3-((6-(2-Aminopyridin-4-yl)-1-oxoisoquinolin-2(1H)-yl)
methyl)-N-phenethylbenzamide;
3-((6-(2-Aminopyridin-4-yl)-1-oxoisoquinolin-2(1H)-yl)
methyl)-N-(2-(pyridin-2-yl)ethyl)benzamide;
3-((6-(2-Aminopyridin-4-yl)-1-oxoisoquinolin-2(1H)-yl)
methyl)-N-(1,2,3,4-tetrahydroisoquinolin-7-yl)benzamide;
3-((6-(2-Aminopyridin-4-yl)-1-oxoisoquinolin-2(1H)-yl)
methyl)-N-(1,2,3,4-tetrahydroisoquinolin-6-yl)benzamide;
3-((6-(2-Aminopyridin-4-yl)-1-oxoisoquinolin-2(1H)-yl)
methyl)-N-(2-methyl-1,2,3,4-tetrahydroisoquinolin-6-yl)
benzamide;
3-((6-(2-Aminopyridin-4-yl)-1-oxoisoquinolin-2(1H)-yl)
methyl)-N-(4,5,6,7-tetrahydrothiazolo[5,4-c]pyridin-2-yl)benzamide;
3-((6-(2-Aminopyridin-4-yl)-1-oxoisoquinolin-2(1H)-yl)
methyl)-N-(5-methyl-4,5,6,7-tetrahydrothiazolo[5,4-c]
pyridin-2-yl)benzamide;
3-((6-(2-Aminopyridin-4-yl)-1-oxoisoquinolin-2(1H)-yl)
methyl)-N-((1S,4S)-4-hydroxycyclohexyl)benzamide;
3-((6-(2-Aminopyridin-4-yl)-1-oxoisoquinolin-2(1H)-yl)
methyl)-N-((1R,4R)-4-hydroxycyclohexyl)benzamide;
3-((6-(2-Aminopyridin-4-yl)-1-oxoisoquinolin-2(1H)-yl)
methyl)-N-(tetrahydro-2H-pyran-4-yl)benzamide;
3-((6-(2-Aminopyridin-4-yl)-1-oxoisoquinolin-2(1H)-yl)
methyl)-N-(oxetan-3-yl)benzamide;
3-((6-(2-Aminopyridin-4-yl)-1-oxoisoquinolin-2(1H)-yl)
methyl)-N-(isochroman-6-yl)benzamide;
3-((6-(2-Aminopyridin-4-yl)-1-oxoisoquinolin-2(1H)-yl)
methyl)-N-(isochroman-7-yl)benzamide;
3-((6-(2-Aminopyridin-4-yl)-1-oxoisoquinolin-2(1H)-yl)
methyl)-N-cyclopentylbenzamide;
3-((6-(2-Aminopyridin-4-yl)-1-oxoisoquinolin-2(1H)-yl)
methyl)-N-(1H-imidazol-2-yl)benzamide;
3-((6-(2-Aminopyridin-4-yl)-1-oxoisoquinolin-2(1H)-yl)
methyl)-N-(1-methyl-1H-pyrazol-3-yl)benzamide;
3-((6-(2-Aminopyridin-4-yl)-1-oxoisoquinolin-2(1H)-yl)
methyl)-5-fluoro-N-(1-methyl-1H-pyrazol-3-yl)benzamide;
3-((6-(2-Aminopyridin-4-yl)-1-oxoisoquinolin-2(1H)-yl)
methyl)-5-fluoro-N-(oxetan-3-yl)benzamide;
3-((6-(2-Aminopyridin-4-yl)-1-oxoisoquinolin-2(1H)-yl)
methyl)-N-(isoxazol-5-yl)benzamide;
3-((6-(2-Aminopyridin-4-yl)-1-oxoisoquinolin-2(1H)-yl)
methyl)-N-(isoxazol-3-yl)benzamide;
3-((6-(2-Aminopyridin-4-yl)-1-oxoisoquinolin-2(1H)-yl)
methyl)-5-fluoro-N-(isoxazol-3-yl)benzamide;
N-(Isoxazol-5-yl)-3-((6-morpholino-1-oxoisoquinolin-2
(1H)-yl)methyl)benzamide;
3-((6-Morpholino-1-oxoisoquinolin-2(1H)-yl)methyl)-N-
(oxetan-3-yl)benzamide;
3-Fluoro-5-((6-morpholino-1-oxoisoquinolin-2(1H)-yl)
methyl)-N-(oxetan-3-yl)benzamide;
3-Fluoro-N-((1S,3S)-3-hydroxycyclobutyl)-5-((6-morpholino-1-oxoisoquinolin-2(1H)-yl)methyl)benzamide;
3-Fluoro-N-((1R,3R)-3-hydroxycyclobutyl)-5-((6-morpholino-1-oxoisoquinolin-2(1H)-yl)methyl)benzamide;
3-Fluoro-5-((6-morpholino-1-oxoisoquinolin-2(1H)-yl)
methyl)-N-(tetrahydro-2H-pyran-4-yl)benzamide;
3-((6-Morpholino-1-oxoisoquinolin-2(1H)-yl)methyl)-N-
(tetrahydro-2H-pyran-4-yl)benzamide;
N-((1R,4R)-4-Hydroxycyclohexyl)-3-((6-morpholino-1-
oxoisoquinolin-2(1H)-yl)methyl)benzamide;
N-((1S,4S)-4-Hydroxycyclohexyl)-3-((6-morpholino-1-
oxoisoquinolin-2(1H)-yl)methyl)benzamide;
3-Fluoro-N-((1S,4S)-4-hydroxycyclohexyl)-5-((6-morpholino-1-oxoisoquinolin-2(1H)-yl)methyl)benzamide;
3-((6-Morpholino-1-oxoisoquinolin-2(1H)-yl)methyl)-N-
(2-morpholinoethyl)benzamide;
3-((6-Morpholino-1-oxoisoquinolin-2(1H)-yl)methyl)-N-
(piperidin-4-ylmethyl)benzamide;
N-((1-Methylpiperidin-4-yl)methyl)-3-((6-morpholino-1-
oxoisoquinolin-2(1H)-yl)methyl)benzamide;
N-((1-(2,2-Difluoroethyl)piperidin-4-yl)methyl)-3-((6-morpholino-1-oxoisoquinolin-2(1H)-yl)methyl)benzamide;
3-((6-Morpholino-1-oxoisoquinolin-2(1H)-yl)methyl)-N-
((1-(2,2,2-trifluoroethyl)piperidin-4-yl)methyl)benzamide;
3-Fluoro-5-((6-morpholino-1-oxoisoquinolin-2(1H)-yl)
methyl)-N-((1-(2,2,2-trifluoroethyl)piperidin-4-yl)
methyl)benzamide;
3-Fluoro-N-((1-methylpiperidin-4-yl)methyl)-5-((6-morpholino-1-oxoisoquinolin-2(1H)-yl)methyl)benzamide;
N-((1-Isopropylpiperidin-4-yl)methyl)-3-((6-morpholino-1-
oxoisoquinolin-2(1H)-yl)methyl)benzamide;
3-Fluoro-N-((1-isopropylpiperidin-4-yl)methyl)-5-((6-morpholino-1-oxoisoquinolin-2(1H)-yl)methyl)benzamide;
N-((1-Cyclopropylpiperidin-4-yl)methyl)-3-((6-morpholino-1-oxoisoquinolin-2(1H)-yl)methyl)benzamide;
N-((1-Cyclopropylpiperidin-4-yl)methyl)-3-fluoro-5-((6-
morpholino-1-oxoisoquinolin-2(1H)-yl)methyl)benzamide;
3-((6-Morpholino-1-oxoisoquinolin-2(1H)-yl)methyl)-N-
((1-(oxetan-3-yl)piperidin-4-yl)methyl)benzamide;
3-Fluoro-5-((6-morpholino-1-oxoisoquinolin-2(1H)-yl)
methyl)-N-((1-(oxetan-3-yl)piperidin-4-yl)methyl)benzamide;
3-Fluoro-5-((6-morpholino-1-oxoisoquinolin-2(1H)-yl)
methyl)-N-(2-morpholinoethyl)benzamide;
3-((6-Morpholino-1-oxoisoquinolin-2(1H)-yl)methyl)-N-
(2-morpholinoethyl)benzamide;
N-Methyl-3-((6-(2-methyl-1H-pyrrol-3-yl)-1-oxo-2,7-
naphthyridin-2(1H)-yl)methyl)benzamide;
N-(Methyl-d3)-3-((6-(2-methyl-1H-pyrrol-3-yl)-1-oxo-2,7-
naphthyridin-2(1H)-yl)methyl)benzamide;
N-Methyl-3-((6-(2-methyl-1H-pyrrol-3-yl)-1-oxo-2,7-
naphthyridin-2(1H)-yl)methyl)benzamide;
N-Methyl-3-((6-(2-methyl-1H-pyrrol-3-yl)-1-oxo-2,7-
naphthyridin-2(1H)-yl)methyl)benzamide;
N-(Methyl-D3)-3-((1-oxo-6-(5-(trifluoromethyl)-1H-pyrazol-4-yl)-2,7-naphthyridin-2(1H)-yl)methyl)benzamide;
N-Methyl-3-((1-oxo-6-(5-(trifluoromethyl)-1H-pyrazol-4-
yl)-2,7-naphthyridin-2(1H)-yl)methyl)benzamide;
N-(Methyl-D3)-3-((1-oxo-6-(5-(trifluoromethyl)-1H-pyrazol-4-yl)-2,7-naphthyridin-2(1H)-yl)methyl)benzamide;
3-((6-(3-Chloro-1H-pyrazol-4-yl)-1-oxo-2,7-naphthyridin-2
(1H)-yl)methyl)-N-methylbenzamide;
3-((6-(3-Chloro-1H-pyrazol-4-yl)-1-oxo-2,7-naphthyridin-2
(1H)-yl)methyl)-N-(methyl-d3)benzamide;
3-((6-(5-(Difluoromethyl)-1H-pyrazol-4-yl)-1-oxo-2,7-
naphthyridin-2(1H)-yl)methyl)-N-methylbenzamide;
3-((6-(5-(Difluoromethyl)-1H-pyrazol-4-yl)-1-oxo-2,7-
naphthyridin-2(1H)-yl)methyl)-N-(methyl-D3)benzamide;
N-Methyl-3-((6-(3-methyl-1H-pyrazol-4-yl)-1-oxo-2,7-
naphthyridin-2(1H)-yl)methyl)benzamide;
N-Methyl-3-((6-(1-methyl-1H-pyrazol-5-yl)-1-oxo-2,7-
naphthyridin-2(1H)-yl)methyl)benzamide;
N-Methyl-3-((6-(3-methylisoxazol-4-yl)-1-oxo-2,7-naphthyridin-2(1H)-yl)methyl)benzamide;

N-Methyl-3-((8-oxo-3-(5-(trifluoromethyl)-1H-pyrazol-4-yl)-1,7-naphthyridin-7(8H)-yl)methyl)benzamide;
N-Methyl-3-((3-(3-methylisoxazol-4-yl)-8-oxo-1,7-naphthyridin-7(8H)-yl)methyl)benzamide;
3-((6-(2-Aminopyridin-4-yl)-1-oxo-2,7-naphthyridin-2(1H)-yl)methyl)-N-methylbenzamide;
3-Fluoro-N-methyl-5-((6-(1-methyl-1H-pyrazol-5-yl)-1-oxo-2,7-naphthyridin-2(1H)-yl)methyl)benzamide;
3-Fluoro-N-methyl-5-((1-oxo-6-(5-(trifluoromethyl)-1H-pyrazol-4-yl)-2,7-naphthyridin-2(1H)-yl)methyl)benzamide;
3-Fluoro-N-methyl-5-((6-(2-methylfuran-3-yl)-1-oxo-2,7-naphthyridin-2(1H)-yl)methyl)benzamide;
3-Fluoro-N-methyl-5-((6-(5-methyl-1H-pyrazol-4-yl)-1-oxo-2,7-naphthyridin-2(1H)-yl)methyl)benzamide;
3-((6-(3-Chloro-1H-pyrazol-4-yl)-1-oxo-2,7-naphthyridin-2(1H)-yl)methyl)-5-fluoro-N-methylbenzamide;
3-Fluoro-N-methyl-5-((1-oxo-6-(3-(trifluoromethyl)-1H-pyrazol-4-yl)-2,7-naphthyridin-2(1H)-yl)methyl)benzamide;
3-((6-(2-Aminopyridin-4-yl)-1-oxoisoquinolin-2(1H)-yl)methyl)-5-fluoro-N-methylbenzamide;
3-((6-(3-(Difluoromethyl)-1H-pyrazol-4-yl)-1-oxo-2,7-naphthyridin-2(1H)-yl)methyl)-5-fluoro-N-methylbenzamide;
3-Fluoro-5-((6-(3-methyl-1H-pyrazol-4-yl)-1-oxo-2,7-naphthyridin-2(1H)-yl)methyl)-N-(tetrahydro-2H-pyran-4-yl)benzamide;
N-Ethyl-3-fluoro-5-((6-(3-methyl-1H-pyrazol-4-yl)-1-oxo-2,7-naphthyridin-2(1H)-yl)methyl)benzamide;
3-Fluoro-5-((6-(3-methyl-1H-pyrazol-4-yl)-1-oxo-2,7-naphthyridin-2(1H)-yl)methyl)-N-(tetrahydro-2H-pyran-4-yl)benzamide;
3-Fluoro-5-((6-(3-methyl-1H-pyrazol-4-yl)-1-oxo-2,7-naphthyridin-2(1H)-yl)methyl)-N-((1-methylpiperidin-4-yl)methyl)benzamide;
3-Fluoro-N-((1-methylpiperidin-4-yl)methyl)-5-((1-oxo-6-(3-(trifluoromethyl)-1H-pyrazol-4-yl)-2,7-naphthyridin-2(1H)-yl)methyl)benzamide;
3-Fluoro-N-(oxetan-3-ylmethyl)-5-((1-oxo-6-(3-(trifluoromethyl)-1H-pyrazol-4-yl)-2,7-naphthyridin-2(1H)-yl)methyl)benzamide;
3-Fluoro-N-(1-methylpiperidin-4-yl)-5-((1-oxo-6-(3-(trifluoromethyl)-1H-pyrazol-4-yl)-2,7-naphthyridin-2(1H)-yl)methyl)benzamide;
3-Fluoro-N-((1R,4R)-4-hydroxycyclohexyl)-5-((1-oxo-6-(3-(trifluoromethyl)-1H-pyrazol-4-yl)-2,7-naphthyridin-2(1H)-yl)methyl)benzamide;
3-((6-(3-Chloro-1H-pyrazol-4-yl)-1-oxo-2,7-naphthyridin-2(1H)-yl)methyl)-5-fluoro-N-(1-methylpiperidin-4-yl)benzamide;
3-((6-(3-Chloro-1H-pyrazol-4-yl)-1-oxo-2,7-naphthyridin-2(1H)-yl)methyl)-5-fluoro-N-((1 S,4S)-4-hydroxycyclohexyl)benzamide;
3-((6-(3-Chloro-1H-pyrazol-4-yl)-1-oxo-2,7-naphthyridin-2(1H)-yl)methyl)-5-fluoro-N-((1R,4R)-4-hydroxycyclohexyl)benzamide;
3-((6-(3-Chloro-1H-pyrazol-4-yl)-1-oxo-2,7-naphthyridin-2(1H)-yl)methyl)-5-fluoro-N-isopropylbenzamide;
3-Fluoro-5-((6-(3-methylisoxazol-4-yl)-1-oxo-2,7-naphthyridin-2(1H)-yl)methyl)-N-((1-methylpiperidin-4-yl)methyl)benzamide;
3-Fluoro-5-((6-(3-methylisoxazol-4-yl)-1-oxo-2,7-naphthyridin-2(1H)-yl)methyl)-N-((tetrahydro-2H-pyran-4-yl)methyl)benzamide;
3-Fluoro-5-((6-(3-methylisoxazol-4-yl)-1-oxo-2,7-naphthyridin-2(1H)-yl)methyl)-N-(2-morpholinoethyl)benzamide;
3-Fluoro-5-((6-(1-methyl-1H-pyrazol-5-yl)-1-oxo-2,7-naphthyridin-2(1H)-yl)methyl)-N-(2-(4-methylpiperazin-1-yl)ethyl)benzamide;
3-Fluoro-5-((6-(1-methyl-1H-pyrazol-5-yl)-1-oxo-2,7-naphthyridin-2(1H)-yl)methyl)-N-(oxetan-3-ylmethyl)benzamide;
3-Fluoro-5-((6-(1-methyl-1H-pyrazol-5-yl)-1-oxo-2,7-naphthyridin-2(1H)-yl)methyl)-N-((tetrahydro-2H-pyran-4-yl)methyl)benzamide;
3-Fluoro-5-((6-(1-methyl-1H-pyrazol-5-yl)-1-oxo-2,7-naphthyridin-2(1H)-yl)methyl)-N-(2-(pyridin-3-yl)ethyl)benzamide;
3-((6-(3-Bromo-1H-pyrazol-4-yl)-1-oxo-2,7-naphthyridin-2(1H)-yl)methyl)-5-fluoro-N-isopropylbenzamide;
3-((6-(3-Bromo-1H-pyrazol-4-yl)-1-oxo-2,7-naphthyridin-2(1H)-yl)methyl)-5-fluoro-N-((1-methylpiperidin-4-yl)methyl)benzamide;
3-((6-(3-(Difluoromethyl)-1H-pyrazol-4-yl)-1-oxo-2,7-naphthyridin-2(1H)-yl)methyl)-5-fluoro-N-((1-methylpiperidin-4-yl)methyl)benzamide;
N-Methyl-3-((6-(3-methylisoxazol-4-yl)-1-oxoisoquinolin-2(1H)-yl)methyl)benzamide;
N-Methyl-3-((1-oxo-6-(5-(trifluoromethyl)-1H-pyrazol-4-yl)isoquinolin-2(1H)-yl)methyl)benzamide;
N-(Methyl-D3)-3-((1-oxo-6-(5-(trifluoromethyl)-1H-pyrazol-4-yl)isoquinolin-2(1H)-yl)methyl)benzamide;
N-Methyl-3-(1-(1-oxo-6-(5-(trifluoromethyl)-1H-pyrazol-4-yl)isoquinolin-2(1H)-yl)ethyl)benzamide;
3-((4-Chloro-1-oxo-6-(5-(trifluoromethyl)-1H-pyrazol-4-yl)isoquinolin-2(1H)-yl)methyl)-N-methylbenzamide;
3-Fluoro-N-methyl-5-((1-oxo-6-(5-(trifluoromethyl)-1H-pyrazol-4-yl)isoquinolin-2(1H)-yl)methyl)benzamide;
3-Fluoro-N-(methyl-d3)-5-((1-oxo-6-(5-(trifluoromethyl)-1H-pyrazol-4-yl)isoquinolin-2(1H)-yl)methyl)benzamide;
3-Fluoro-N-methyl-5-(1-(1-oxo-6-(5-(trifluoromethyl)-1H-pyrazol-4-yl)isoquinolin-2(1H)-yl)ethyl)benzamide;
2-Fluoro-N-methyl-5-((1-oxo-6-(5-(trifluoromethyl)-1H-pyrazol-4-yl)isoquinolin-2(1H)-yl)methyl)benzamide;
3-Chloro-N-methyl-5-((1-oxo-6-(5-(trifluoromethyl)-1H-pyrazol-4-yl)isoquinolin-2(1H)-yl)methyl)benzamide;
3-((6-(5-(Difluoromethyl)-1H-pyrazol-4-yl)-1-oxoisoquinolin-2(1H)-yl)methyl)-N-methylbenzamide;
3-(1-(6-(5-(Difluoromethyl)-1H-pyrazol-4-yl)-1-oxoisoquinolin-2(1H)-yl)ethyl)-N-methylbenzamide;
N-(Methyl-d3)-3-(1-(6-(3-methylisoxazol-4-yl)-1-oxoisoquinolin-2(1H)-yl)ethyl)benzamide;
3-(1-(6-(5-(Difluoromethyl)-1H-pyrazol-4-yl)-1-oxoisoquinolin-2(1H)-yl)ethyl)-N-(methyl-D3)benzamide;
3-((6-(5-(Difluoromethyl)-1H-pyrazol-4-yl)-1-oxoisoquinolin-2(1H)-yl)methyl)-5-fluoro-N-methylbenzamide;
3-((6-(5-Chloro-1H-pyrazol-4-yl)-1-oxoisoquinolin-2(1H)-yl)methyl)-N-methylbenzamide;
3-((6-(5-Chloro-1H-pyrazol-4-yl)-1-oxoisoquinolin-2(1H)-yl)methyl)-N-(methyl-D3)benzamide;
3-(1-(6-(5-Chloro-1H-pyrazol-4-yl)-1-oxoisoquinolin-2(1H)-yl)ethyl)-N-methylbenzamide;
3-((6-(5-Chloro-1H-pyrazol-4-yl)-1-oxoisoquinolin-2(1H)-yl)methyl)-5-fluoro-N-methylbenzamide;
3-(1-(6-(5-Chloro-1H-pyrazol-4-yl)-1-oxoisoquinolin-2(1H)-yl)ethyl)-5-fluoro-N-methylbenzamide;
3-(1-(6-(5-Fluoro-1H-pyrazol-4-yl)-1-oxoisoquinolin-2(1H)-yl)ethyl)-N-methylbenzamide;

3-((6-(5-Fluoro-1H-pyrazol-4-yl)-1-oxoisoquinolin-2(1H)-yl)methyl)-N-(methyl-D3)benzamide;
3-((6-(5-Fluoro-1H-pyrazol-4-yl)-1-oxoisoquinolin-2(1H)-yl)methyl)-N-methylbenzamide;
3-Fluoro-5-(1-(6-(5-fluoro-1H-pyrazol-4-yl)-1-oxoisoquinolin-2(1H)-yl)ethyl)-N-methylbenzamide;
N-Methyl-3-((6-(1-methyl-1H-pyrazol-4-yl)-1-oxoisoquinolin-2(1H)-yl)methyl)benzamide;
3-((6-(Isoxazol-4-yl)-1-oxoisoquinolin-2(1H)-yl)methyl)-N-methylbenzamide;
N-Methyl-3-((6-(5-methylisoxazol-4-yl)-1-oxoisoquinolin-2(1H)-yl)methyl)benzamide;
3-((6-(Furan-3-yl)-1-oxoisoquinolin-2(1H)-yl)methyl)-N-methylbenzamide;
N-Methyl-3-((6-(2-methylfuran-3-yl)-1-oxoisoquinolin-2(1H)-yl)methyl)benzamide;
3-((6-(2,5-Dihydrofuran-3-yl)-1-oxoisoquinolin-2(1H)-yl)methyl)-N-methylbenzamide;
N-Methyl-3-((1-oxo-6-(1H-pyrrol-3-yl)isoquinolin-2(1H)-yl)methyl)benzamide;
N-Methyl-3-((6-(3-methylisoxazol-4-yl)-1-oxoisoquinolin-2(1H)-yl)methyl)benzamide;
N-(Methyl-d3)-3-((6-(3-methylisoxazol-4-yl)-1-oxoisoquinolin-2(1H)-yl)methyl)benzamide;
N-Methyl-3-(1-(6-(3-methylisoxazol-4-yl)-1-oxoisoquinolin-2(1H)-yl)ethyl)benzamide;
3-((4-Chloro-6-(3-methylisoxazol-4-yl)-1-oxoisoquinolin-2(1H)-yl)methyl)-N-methylbenzamide;
N-Methyl-6-((6-(3-methylisoxazol-4-yl)-1-oxoisoquinolin-2(1H)-yl)methyl)picolinamide;
N-Methyl-5-((6-(3-methylisoxazol-4-yl)-1-oxoisoquinolin-2(1H)-yl)methyl)nicotinamide;
N-Methyl-4-((6-(3-methylisoxazol-4-yl)-1-oxoisoquinolin-2(1H)-yl)methyl)picolinamide;
2-Fluoro-N-methyl-3-((6-(3-methylisoxazol-4-yl)-1-oxoisoquinolin-2(1H)-yl)methyl)benzamide;
3-Fluoro-N-methyl-5-((6-(3-methylisoxazol-4-yl)-1-oxoisoquinolin-2(1H)-yl)methyl)benzamide;
3-Fluoro-N-methyl-5-(1-(6-(3-methylisoxazol-4-yl)-1-oxoisoquinolin-2(1H)-yl)ethyl)benzamide;
2-Fluoro-N-methyl-5-((6-(3-methylisoxazol-4-yl)-1-oxoisoquinolin-2(1H)-yl)methyl)benzamide;
3-((4-Chloro-6-(3-methylisoxazol-4-yl)-1-oxoisoquinolin-2(1H)-yl)methyl)-5-fluoro-N-methylbenzamide;
3-Chloro-N-methyl-5-((6-(3-methylisoxazol-4-yl)-1-oxoisoquinolin-2(1H)-yl)methyl)benzamide;
N-Methyl-3-((6-(1-methyl-1H-pyrazol-5-yl)-1-oxoisoquinolin-2(1H)-yl)methyl)benzamide;
N-(Methyl-D3)-3-((6-(1-methyl-1H-pyrazol-5-yl)-1-oxoisoquinolin-2(1H)-yl)methyl)benzamide;
N-Methyl-3-(1-(6-(1-methyl-1H-pyrazol-5-yl)-1-oxoisoquinolin-2(1H)-yl)ethyl)benzamide;
3-Fluoro-N-methyl-5-((6-(1-methyl-1H-pyrazol-5-yl)-1-oxoisoquinolin-2(1H)-yl)methyl)benzamide;
3-Chloro-N-methyl-5-((6-(1-methyl-1H-pyrazol-5-yl)-1-oxoisoquinolin-2(1H)-yl)methyl)benzamide;
N-Methyl-3-((1-oxo-6-(pyridin-4-yl)isoquinolin-2(1H)-yl)methyl)benzamide;
3-((6-(2-Aminopyridin-4-yl)-1-oxoisoquinolin-2(1H)-yl)methyl)-N-methylbenzamide;
N-Methyl-3-((1-oxo-6-(pyridin-4-yl)isoquinolin-2(1H)-yl)methyl)benzamide;
3-((6-(2-Aminopyridin-4-yl)-1-oxoisoquinolin-2(1H)-yl)methyl)-N-methylbenzamide;
N-Methyl-3-((6-(1-methyl-1H-1,2,3-triazol-5-yl)-1-oxoisoquinolin-2(1H)-yl)methyl)benzamide;
N-Methyl-3-((6-morpholino-1-oxoisoquinolin-2(1H)-yl)methyl)benzamide;
3-Fluoro-N-methyl-5-((6-morpholino-1-oxoisoquinolin-2(1H)-yl)methyl)benzamide;
3-((6-(6-Oxa-3-azabicyclo[3.1.1]heptan-3-yl)-1-oxoisoquinolin-2(1H)-yl)methyl)-N-methylbenzamide;
(S)—N-Methyl-3-((6-(2-methylmorpholino)-1-oxoisoquinolin-2(1H)-yl)methyl)benzamide;
N-(3-((6-(2-Methylfuran-3-yl)-1-oxoisoquinolin-2(1H)-yl)methyl)phenyl)acetamide;
N-(3-Fluoro-5-((6-(2-methylfuran-3-yl)-1-oxoisoquinolin-2(1H)-yl)methyl)phenyl)acetamide;
N-(3-((6-(5-Methylisoxazol-4-yl)-1-oxoisoquinolin-2(1H)-yl)methyl)phenyl)acetamide;
N-(2-Fluoro-5-((6-(5-methylisoxazol-4-yl)-1-oxoisoquinolin-2(1H)-yl)methyl)phenyl)acetamide;
N-(3-((6-(3-Methyl-1H-pyrazol-4-yl)-1-oxoisoquinolin-2(1H)-yl)methyl)phenyl)acetamide;
N-(3-((1-Oxo-6-(3-(trifluoromethyl)-1H-pyrazol-4-yl)isoquinolin-2(1H)-yl)methyl)phenyl)acetamide;
N-(3-((1-Oxo-6-(3-(trifluoromethyl)-1H-pyrazol-4-yl)isoquinolin-2(1H)-yl)methyl)phenyl)isobutyramide;
N-(3-((1-Oxo-6-(3-(trifluoromethyl)-1H-pyrazol-4-yl)isoquinolin-2(1H)-yl)methyl)phenyl)tetrahydro-2H-pyran-4-carboxamide;
N-(3-((1-Oxo-6-(3-(trifluoromethyl)-1H-pyrazol-4-yl)isoquinolin-2(1H)-yl)methyl)phenyl)-3-(pyridin-2-yl)propenamide;
N-(3-((6-(3-(Difluoromethyl)-1H-pyrazol-4-yl)-1-oxoisoquinolin-2(1H)-yl)methyl)phenyl)acetamide;
N-(3-((6-(3-(Difluoromethyl)-1H-pyrazol-4-yl)-1-oxoisoquinolin-2(1H)-yl)methyl)phenyl)nicotinamide;
N-(3-((6-(3-(Difluoromethyl)-1H-pyrazol-4-yl)-1-oxoisoquinolin-2(1H)-yl)methyl)phenyl)oxetane-3-carboxamide;
N-(3-((6-(3-(Difluoromethyl)-1H-pyrazol-4-yl)-1-oxoisoquinolin-2(1H)-yl)methyl)phenyl)benzamide;
N-(3-((6-(3-Chloro-1H-pyrazol-4-yl)-1-oxoisoquinolin-2(1H)-yl)methyl)phenyl)acetamide;
N-(3-((6-(3-Chloro-1H-pyrazol-4-yl)-1-oxoisoquinolin-2(1H)-yl)methyl)phenyl)oxetane-3-carboxamide;
N-(3-((6-(3-Methylisoxazol-4-yl)-1-oxoisoquinolin-2(1H)-yl)methyl)phenyl)acetamide;
N-(3-((6-(3-Methylisoxazol-4-yl)-1-oxoisoquinolin-2(1H)-yl)methyl)phenyl)oxetane-3-carboxamide;
4-Fluoro-N-(3-((6-(3-methylisoxazol-4-yl)-1-oxoisoquinolin-2(1H)-yl)methyl)phenyl)benzamide;
N-(3-Fluoro-5-((6-(3-methylisoxazol-4-yl)-1-oxoisoquinolin-2(1H)-yl)methyl)phenyl)picolinamide;
N-(3-Fluoro-5-((6-(3-methylisoxazol-4-yl)-1-oxoisoquinolin-2(1H)-yl)methyl)phenyl)acetamide;
N-(3-((1-Oxo-6-(1H-pyrazol-4-yl)isoquinolin-2(1H)-yl)methyl)phenyl)acetamide;
N-(3-((6-(2-Aminopyridin-4-yl)-1-oxoisoquinolin-2(1H)-yl)methyl)-5-fluorophenyl)acetamide;
3-(3-Methoxybenzyl)-7-(1H-pyrazol-4-yl)quinazolin-4(3H)-one;
3-(3-Methoxybenzyl)-7-(3-methyl-1H-pyrazol-4-yl)quinazolin-4(3H)-one;
3-(3-Methoxybenzyl)-7-(3-(trifluoromethyl)-1H-pyrazol-4-yl)quinazolin-4(3H)-one;
3-(3-Methoxybenzyl)-7-(3-methylisoxazol-4-yl)quinazolin-4(3H)-one;
3-(3-Methoxybenzyl)-7-(1-methyl-1H-pyrazol-5-yl)quinazolin-4(3H)-one;
7-(3-(Difluoromethyl)-1H-pyrazol-4-yl)-3-(3-methoxybenzyl)quinazolin-4(3H)-one;

7-(3-(Difluoromethyl)-1H-pyrazol-4-yl)-3-(3-fluoro-5-methoxybenzyl)quinazolin-4(3H)-one;

7-(3-Chloro-1H-pyrazol-4-yl)-3-(3-fluoro-5-methoxybenzyl)quinazolin-4(3H)-one;

7-(3-Chloro-1H-pyrazol-4-yl)-3-(3-methoxybenzyl)quinazolin-4(3H)-one;

3-(3-Methoxybenzyl)-7-(pyridin-4-yl)quinazolin-4(3H)-one;

7-(2-Aminopyridin-4-yl)-3-(3-methoxybenzyl)quinazolin-4(3H)-one;

(R)-7-(2-Aminopyridin-4-yl)-3-(1-(3-methoxyphenyl)ethyl)quinazolin-4(3H)-one;

N-Methyl-3-((4-oxo-7-(1H-pyrazol-4-yl)quinazolin-3(4H)-yl)methyl)benzamide;

N-Methyl-3-((4-oxo-7-(5-(trifluoromethyl)-1H-pyrazol-4-yl)quinazolin-3(4H)-yl)methyl)benzamide;

N-(Methyl-D3)-3-((4-oxo-7-(5-(trifluoromethyl)-1H-pyrazol-4-yl)quinazolin-3(4H)-yl)methyl)benzamide;

N-Isopropyl-3-((4-oxo-7-(5-(trifluoromethyl)-1H-pyrazol-4-yl)quinazolin-3(4H)-yl)methyl)benzamide;

3-((4-Oxo-7-(5-(trifluoromethyl)-1H-pyrazol-4-yl)quinazolin-3(4H)-yl)methyl)-N-(2-(pyridin-4-yl)ethyl)benzamide;

N-Benzyl-3-((4-oxo-7-(5-(trifluoromethyl)-1H-pyrazol-4-yl)quinazolin-3(4H)-yl)methyl)benzamide;

3-((4-Oxo-7-(5-(trifluoromethyl)-1H-pyrazol-4-yl)quinazolin-3(4H)-yl)methyl)-N-(pyridin-4-ylmethyl)benzamide;

N-(4-(Methylsulfonamido)benzyl)-3-((4-oxo-7-(5-(trifluoromethyl)-1H-pyrazol-4-yl)quinazolin-3(4H)-yl)methyl)benzamide;

N-(1-Methyl-1H-pyrazol-3-yl)-3-((4-oxo-7-(5-(trifluoromethyl)-1H-pyrazol-4-yl)quinazolin-3(4H)-yl)methyl)benzamide;

N-(Isoxazol-3-yl)-3-((4-oxo-7-(5-(trifluoromethyl)-1H-pyrazol-4-yl)quinazolin-3(4H)-yl)methyl)benzamide;

3-((4-Oxo-7-(5-(trifluoromethyl)-1H-pyrazol-4-yl)quinazolin-3(4H)-yl)methyl)-N-(tetrahydro-2H-pyran-4-yl)benzamide;

N-(1-(Oxetan-3-yl)piperidin-4-yl)-3-((4-oxo-7-(5-(trifluoromethyl)-1H-pyrazol-4-yl)quinazolin-3(4H)-yl)methyl)benzamide;

N-(1-Methylpiperidin-4-yl)-3-((4-oxo-7-(5-(trifluoromethyl)-1H-pyrazol-4-yl)quinazolin-3(4H)-yl)methyl)benzamide;

3-((4-Oxo-7-(5-(trifluoromethyl)-1H-pyrazol-4-yl)quinazolin-3(4H)-yl)methyl)-N-((tetrahydro-2H-pyran-4-yl)methyl)benzamide;

N-(Oxetan-3-ylmethyl)-3-((4-oxo-7-(5-(trifluoromethyl)-1H-pyrazol-4-yl)quinazolin-3(4H)-yl)methyl)benzamide;

3-((4-Oxo-7-(5-(trifluoromethyl)-1H-pyrazol-4-yl)quinazolin-3(4H)-yl)methyl)-N-(piperidin-4-ylmethyl)benzamide;

N-((1S,4S)-4-Hydroxycyclohexyl)-3-((4-oxo-7-(5-(trifluoromethyl)-1H-pyrazol-4-yl)quinazolin-3(4H)-yl)methyl)benzamide;

N-((1R,4R)-4-Hydroxycyclohexyl)-3-((4-oxo-7-(5-(trifluoromethyl)-1H-pyrazol-4-yl)quinazolin-3(4H)-yl)methyl)benzamide;

N-(2-Hydroxyethyl)-3-((4-oxo-7-(5-(trifluoromethyl)-1H-pyrazol-4-yl)quinazolin-3(4H)-yl)methyl)benzamide;

N-(4-(Methylsulfonamido)phenyl)-3-((4-oxo-7-(5-(trifluoromethyl)-1H-pyrazol-4-yl)quinazolin-3(4H)-yl)methyl)benzamide;

3-Fluoro-N-methyl-5-((4-oxo-7-(5-(trifluoromethyl)-1H-pyrazol-4-yl)quinazolin-3(4H)-yl)methyl)benzamide;

3-Fluoro-N-(methyl-d3)-5-((4-oxo-7-(5-(trifluoromethyl)-1H-pyrazol-4-yl)quinazolin-3(4H)-yl)methyl)benzamide;

3-Fluoro-N-methyl-5-(1-(4-oxo-7-(5-(trifluoromethyl)-1H-pyrazol-4-yl)quinazolin-3(4H)-yl)ethyl)benzamide;

2-Fluoro-N-methyl-5-((4-oxo-7-(5-(trifluoromethyl)-1H-pyrazol-4-yl)quinazolin-3(4H)-yl)methyl)benzamide;

3-Chloro-N-methyl-5-((4-oxo-7-(5-(trifluoromethyl)-1H-pyrazol-4-yl)quinazolin-3(4H)-yl)methyl)benzamide;

3-((7-(5-(Difluoromethyl)-1H-pyrazol-4-yl)-4-oxoquinazolin-3(4H)-yl)methyl)-N-methylbenzamide;

3-((7-(5-(Difluoromethyl)-1H-pyrazol-4-yl)-4-oxoquinazolin-3(4H)-yl)methyl)-N-(methyl-d3)benzamide;

3-((7-(5-(Difluoromethyl)-1H-pyrazol-4-yl)-4-oxoquinazolin-3(4H)-yl)methyl)-N-(2-hydroxyethyl)benzamide;

3-((7-(5-(Difluoromethyl)-1H-pyrazol-4-yl)-4-oxoquinazolin-3(4H)-yl)methyl)-N-(2-(dimethylamino)ethyl)benzamide;

3-((7-(5-(Difluoromethyl)-1H-pyrazol-4-yl)-4-oxoquinazolin-3(4H)-yl)methyl)-N-((1-methylpiperidin-4-yl)methyl)benzamide;

3-((7-(5-(Difluoromethyl)-1H-pyrazol-4-yl)-4-oxoquinazolin-3(4H)-yl)methyl)-N-((tetrahydro-2H-pyran-4-yl)methyl)benzamide;

3-((7-(5-(Difluoromethyl)-1H-pyrazol-4-yl)-4-oxoquinazolin-3(4H)-yl)methyl)-N-((2-fluoropyridin-4-yl)methyl)benzamide;

3-((7-(5-(Difluoromethyl)-1H-pyrazol-4-yl)-4-oxoquinazolin-3(4H)-yl)methyl)-N-(3-(methylsulfonyl)benzyl)benzamide;

3-((7-(5-(Difluoromethyl)-1H-pyrazol-4-yl)-4-oxoquinazolin-3(4H)-yl)methyl)-N-(3-(methylsulfonamido)benzyl)benzamide;

3-((7-(5-(Difluoromethyl)-1H-pyrazol-4-yl)-4-oxoquinazolin-3(4H)-yl)methyl)-N-(3-(dimethylamino)benzyl)benzamide;

3-((7-(5-(Difluoromethyl)-1H-pyrazol-4-yl)-4-oxoquinazolin-3(4H)-yl)methyl)-5-fluoro-N-methylbenzamide;

3-((7-(5-(Difluoromethyl)-1H-pyrazol-4-yl)-4-oxoquinazolin-3(4H)-yl)methyl)-5-fluoro-N-(methyl-D3)benzamide;

5-((7-(5-Chloro-1H-pyrazol-4-yl)-4-oxoquinazolin-3(4H)-yl)methyl)-N-methylnicotinamide;

3-((7-(5-Chloro-1H-pyrazol-4-yl)-4-oxoquinazolin-3(4H)-yl)methyl)-N-methylbenzamide;

3-((7-(5-Chloro-1H-pyrazol-4-yl)-4-oxoquinazolin-3(4H)-yl)methyl)-N-(methyl-D3)benzamide;

3-(1-(7-(5-Chloro-1H-pyrazol-4-yl)-4-oxoquinazolin-3(4H)-yl)ethyl)-N-methylbenzamide;

3-((7-(5-Chloro-1H-pyrazol-4-yl)-4-oxoquinazolin-3(4H)-yl)methyl)-N-((1S,4S)-4-hydroxycyclohexyl)benzamide;

3-((7-(5-Chloro-1H-pyrazol-4-yl)-4-oxoquinazolin-3(4H)-yl)methyl)-N-(1-methylpiperidin-4-yl)benzamide;

3-((7-(5-Chloro-1H-pyrazol-4-yl)-4-oxoquinazolin-3(4H)-yl)methyl)-N-(piperidin-4-yl)benzamide;

3-((7-(5-Chloro-1H-pyrazol-4-yl)-4-oxoquinazolin-3(4H)-yl)methyl)-N-((1-methylpiperidin-4-yl)methyl)benzamide;

N-Methyl-3-((7-(3-methylisoxazol-4-yl)-4-oxoquinazolin-3(4H)-yl)methyl)benzamide;

N-(Methyl-d3)-3-((7-(3-methylisoxazol-4-yl)-4-oxoquinazolin-3(4H)-yl)methyl)benzamide;

N-methyl-3-(1-(7-(3-methylisoxazol-4-yl)-4-oxoquinazolin-3(4H)-yl)ethyl)benzamide;

N-Isopropyl-3-((7-(3-methylisoxazol-4-yl)-4-oxoquinazolin-3(4H)-yl)methyl)benzamide;

3-((7-(3-Methylisoxazol-4-yl)-4-oxoquinazolin-3(4H)-yl)methyl)-N-(oxetan-3-ylmethyl)benzamide;

3-((7-(3-Methylisoxazol-4-yl)-4-oxoquinazolin-3(4H)-yl)methyl)-N-((tetrahydro-2H-pyran-4-yl)methyl)benzamide;

3-((7-(3-Methylisoxazol-4-yl)-4-oxoquinazolin-3(4H)-yl)methyl)-N-((1-methylpiperidin-4-yl)methyl)benzamide;
3-((7-(3-Methylisoxazol-4-yl)-4-oxoquinazolin-3(4H)-yl)methyl)-N-(piperidin-4-ylmethyl)benzamide;
3-((7-(3-Methylisoxazol-4-yl)-4-oxoquinazolin-3(4H)-yl)methyl)-N-(2-(pyridin-3-yl)ethyl)benzamide;
3-((7-(3-Methylisoxazol-4-yl)-4-oxoquinazolin-3(4H)-yl)methyl)-N-(2-morpholinoethyl)benzamide;
3-((7-(3-Methylisoxazol-4-yl)-4-oxoquinazolin-3(4H)-yl)methyl)-N-(2,2,2-trifluoroethyl)benzamide;
3-Fluoro-N-methyl-5-((7-(3-methylisoxazol-4-yl)-4-oxoquinazolin-3(4H)-yl)methyl)benzamide;
3-Fluoro-N-(methyl-D3)-5-((7-(3-methylisoxazol-4-yl)-4-oxoquinazolin-3(4H)-yl)methyl)benzamide;
N-Methyl-3-((7-(1-methyl-1H-pyrazol-5-yl)-4-oxoquinazolin-3(4H)-yl)methyl)benzamide;
N-(Methyl-D3)-3-((7-(1-methyl-1H-pyrazol-5-yl)-4-oxoquinazolin-3(4H)-yl)methyl)benzamide;
N-Methyl-3-(1-(7-(1-methyl-1H-pyrazol-5-yl)-4-oxoquinazolin-3(4H)-yl)ethyl)benzamide;
N-((1S,3S)-3-Hydroxycyclobutyl)-3-((7-(1-methyl-1H-pyrazol-5-yl)-4-oxoquinazolin-3(4H)-yl)methyl)benzamide;
N-((1R,3R)-3-Hydroxycyclobutyl)-3-((7-(1-methyl-1H-pyrazol-5-yl)-4-oxoquinazolin-3(4H)-yl)methyl)benzamide;
N-((1S,4S)-4-Hydroxycyclohexyl)-3-((7-(1-methyl-1H-pyrazol-5-yl)-4-oxoquinazolin-3(4H)-yl)methyl)benzamide;
3-((7-(1-Methyl-1H-pyrazol-5-yl)-4-oxoquinazolin-3(4H)-yl)methyl)-N-(1-methylpiperidin-4-yl)benzamide;
3-((7-(1-Methyl-1H-pyrazol-5-yl)-4-oxoquinazolin-3(4H)-yl)methyl)-N-(oxetan-3-ylmethyl)benzamide;
N-(2-Hydroxyethyl)-3-((7-(1-methyl-1H-pyrazol-5-yl)-4-oxoquinazolin-3(4H)-yl)methyl)benzamide;
3-((7-(2-Aminopyridin-4-yl)-4-oxoquinazolin-3(4H)-yl)methyl)-N-methylbenzamide;
3-((7-(2-Aminopyridin-4-yl)-4-oxoquinazolin-3(4H)-yl)methyl)-N-(oxetan-3-yl)benzamide;
3-((7-(2-Aminopyridin-4-yl)-4-oxoquinazolin-3(4H)-yl)methyl)-N-(tetrahydro-2H-pyran-4-yl)benzamide;
3-((7-(2-Aminopyridin-4-yl)-4-oxoquinazolin-3(4H)-yl)methyl)-N-(1-methylpiperidin-4-yl)benzamide;
3-((7-(2-Aminopyridin-4-yl)-4-oxoquinazolin-3(4H)-yl)methyl)-N-(2-(pyridin-2-yl)ethyl)benzamide;
3-((7-(2-Aminopyridin-4-yl)-4-oxoquinazolin-3(4H)-yl)methyl)-N-((tetrahydro-2H-pyran-4-yl)methyl)benzamide;
N-Methyl-3-((7-(1-methyl-1H-1,2,3-triazol-5-yl)-4-oxoquinazolin-3(4H)-yl)methyl)benzamide;
(R)—N-Methyl-3-(1-(7-(5-methyl-1H-pyrazol-4-yl)-4-oxoquinazolin-3(4H)-yl)ethyl)benzamide;
(R)—N-Methyl-3-(1-(4-oxo-7-(5-(trifluoromethyl)-1H-pyrazol-4-yl)quinazolin-3(4H)-yl)ethyl)benzamide;
(R)—N-(Methyl-d3)-3-(1-(4-oxo-7-(5-(trifluoromethyl)-1H-pyrazol-4-yl)quinazolin-3(4H)-yl)ethyl)benzamide;
(S)—N-Methyl-3-(1-(4-oxo-7-(5-(trifluoromethyl)-1H-pyrazol-4-yl)quinazolin-3(4H)-yl)ethyl)benzamide;
(R)—N-Isopropyl-3-(1-(4-oxo-7-(5-(trifluoromethyl)-1H-pyrazol-4-yl)quinazolin-3(4H)-yl)ethyl)benzamide;
(R)-3-(1-(4-Oxo-7-(5-(trifluoromethyl)-1H-pyrazol-4-yl)quinazolin-3(4H)-yl)ethyl)-N-(pyridin-4-ylmethyl)benzamide;
(R)—N-(Isoxazol-3-yl)-3-(1-(4-oxo-7-(5-(trifluoromethyl)-1H-pyrazol-4-yl)quinazolin-3(4H)-yl)ethyl)benzamide;
(R)-3-(1-(4-Oxo-7-(5-(trifluoromethyl)-1H-pyrazol-4-yl)quinazolin-3(4H)-yl)ethyl)-N-(tetrahydro-2H-pyran-4-yl)benzamide;
(R)—N-(1-Methylpiperidin-4-yl)-3-(1-(4-oxo-7-(5-(trifluoromethyl)-1H-pyrazol-4-yl)quinazolin-3(4H)-yl)ethyl)benzamide;
(R)-3-(1-(4-Oxo-7-(5-(trifluoromethyl)-1H-pyrazol-4-yl)quinazolin-3(4H)-yl)ethyl)-N-((tetrahydro-2H-pyran-4-yl)methyl)benzamide;
(R)—N-(Oxetan-3-ylmethyl)-3-(1-(4-oxo-7-(5-(trifluoromethyl)-1H-pyrazol-4-yl)quinazolin-3(4H)-yl)ethyl)benzamide;
(R)—N-(2-Hydroxyethyl)-3-(1-(4-oxo-7-(5-(trifluoromethyl)-1H-pyrazol-4-yl)quinazolin-3(4H)-yl)ethyl)benzamide;
(R)-3-Fluoro-N-methyl-5-(1-(4-oxo-7-(5-(trifluoromethyl)-1H-pyrazol-4-yl)quinazolin-3(4H)-yl)ethyl)benzamide;
(R)-3-Fluoro-N-(methyl-d3)-5-(1-(4-oxo-7-(5-(trifluoromethyl)-1H-pyrazol-4-yl)quinazolin-3(4H)-yl)ethyl)benzamide;
(R)-2-Fluoro-N-methyl-5-(1-(4-oxo-7-(5-(trifluoromethyl)-1H-pyrazol-4-yl)quinazolin-3(4H)-yl)ethyl)benzamide;
(R)-3-(1-(7-(5-(Difluoromethyl)-1H-pyrazol-4-yl)-4-oxoquinazolin-3(4H)-yl)ethyl)-N-methylbenzamide;
(R)-3-(1-(7-(5-(Difluoromethyl)-1H-pyrazol-4-yl)-4-oxoquinazolin-3(4H)-yl)ethyl)-N-(methyl-D3)benzamide;
(R)-3-(1-(7-(5-(D)-1H-pyrazol-4-yl)-4-oxoquinazolin-3(4H)-yl)ethyl)-N-(2-hydroxyethyl)benzamide;
(R)-3-(1-(7-(5-(Difluoromethyl)-1H-pyrazol-4-yl)-4-oxoquinazolin-3(4H)-yl)ethyl)-N-(2-(dimethylamino)ethyl)benzamide;
(R)-3-(1-(7-(5-(Difluoromethyl)-1H-pyrazol-4-yl)-4-oxoquinazolin-3(4H)-yl)ethyl)-N-((1-methylpiperidin-4-yl)methyl)benzamide;
(R)-3-(1-(7-(5-(Difluoromethyl)-1H-pyrazol-4-yl)-4-oxoquinazolin-3(4H)-yl)ethyl)-N-((tetrahydro-2H-pyran-4-yl)methyl)benzamide;
(R)-3-(1-(7-(5-(Difluoromethyl)-1H-pyrazol-4-yl)-4-oxoquinazolin-3(4H)-yl)ethyl)-5-fluoro-N-methylbenzamide;
(R)-3-(1-(7-(5-Chloro-1H-pyrazol-4-yl)-4-oxoquinazolin-3(4H)-yl)ethyl)-N-(1-methylpiperidin-4-yl)benzamide;
(R)-3-(1-(7-(5-Chloro-1H-pyrazol-4-yl)-4-oxoquinazolin-3(4H)-yl)ethyl)-N-((1-methylpiperidin-4-yl)methyl)benzamide;
(R)-3-(1-(7-(5-Chloro-1H-pyrazol-4-yl)-4-oxoquinazolin-3(4H)-yl)ethyl)-N-methylbenzamide;
(R)-3-(1-(7-(5-Chloro-1H-pyrazol-4-yl)-4-oxoquinazolin-3(4H)-yl)ethyl)-N-(methyl-d3)benzamide;
(S)-3-(1-(7-(5-Chloro-1H-pyrazol-4-yl)-4-oxoquinazolin-3(4H)-yl)ethyl)-N-methylbenzamide;
(R)—N-Methyl-3-(1-(7-(3-methylisoxazol-4-yl)-4-oxoquinazolin-3(4H)-yl)ethyl)benzamide;
(R)—N-(Methyl-d3)-3-(1-(7-(3-methylisoxazol-4-yl)-4-oxoquinazolin-3(4H)-yl)ethyl)benzamide;
(R)-3-(1-(7-(3-Methylisoxazol-4-yl)-4-oxoquinazolin-3(4H)-yl)ethyl)-N-((1-methylpiperidin-4-yl)methyl)benzamide;
(R)-3-(1-(7-(3-Methylisoxazol-4-yl)-4-oxoquinazolin-3(4H)-yl)ethyl)-N-(piperidin-4-ylmethyl)benzamide;
(R)-3-(1-(7-(3-Methylisoxazol-4-yl)-4-oxoquinazolin-3(4H)-yl)ethyl)-N-(2-morpholinoethyl)benzamide;
(R)-3-(1-(7-(3-Methylisoxazol-4-yl)-4-oxoquinazolin-3(4H)-yl)ethyl)-N-(2,2,2-trifluoroethyl)benzamide;
(R)—N-Methyl-3-(1-(7-(1-methyl-1H-pyrazol-5-yl)-4-oxoquinazolin-3(4H)-yl)ethyl)benzamide;

(R)—N-(Methyl-d3)-3-(1-(7-(1-methyl-1H-pyrazol-5-yl)-4-oxoquinazolin-3(4H)-yl)ethyl)benzamide;
N-((1S,3S)-3-Hydroxycyclobutyl)-3-((R)-1-(7-(1-methyl-1H-pyrazol-5-yl)-4-oxoquinazolin-3(4H)-yl)ethyl)benzamide;
(R)-3-(1-(7-(1-Methyl-1H-pyrazol-5-yl)-4-oxoquinazolin-3(4H)-yl)ethyl)-N-(oxetan-3-ylmethyl)benzamide;
(R)—N-(2-Hydroxyethyl)-3-(1-(7-(1-methyl-1H-pyrazol-5-yl)-4-oxoquinazolin-3(4H)-yl)ethyl)benzamide;
(R)-3-(1-(7-(2-Aminopyridin-4-yl)-4-oxoquinazolin-3(4H)-yl)ethyl)-N-methylbenzamide;
3-(1-(3-Chlorophenyl)-2-hydroxyethyl)-7-(pyridin-4-yl)quinazolin-4(3H)-one;
7-(2-Aminopyridin-4-yl)-3-(1-(3-chlorophenyl)-2-hydroxyethyl)quinazolin-4(3H)-one;
3-(1-(3-Chlorophenyl)-2-hydroxyethyl)-7-(5-methyl-1H-pyrazol-4-yl)quinazolin-4(3H)-one;
3-(1-(3-Chlorophenyl)-2-hydroxyethyl)-7-(5-(trifluoromethyl)-1H-pyrazol-4-yl)quinazolin-4(3H)-one;
7-(5-Chloro-1H-pyrazol-4-yl)-3-(1-(3-chlorophenyl)-2-hydroxyethyl)quinazolin-4(3H)-one;
3-(1-(3-Chlorophenyl)-2-hydroxyethyl)-7-(3-methylisoxazol-4-yl)quinazolin-4(3H)-one;
3-(2-Hydroxy-1-(3-methoxyphenyl)ethyl)-7-(5-methyl-1H-pyrazol-4-yl)quinazolin-4(3H)-one;
3-(2-Hydroxy-1-(3-methoxyphenyl)ethyl)-7-(5-(trifluoromethyl)-1H-pyrazol-4-yl)quinazolin-4(3H)-one;
7-(5-Chloro-1H-pyrazol-4-yl)-3-(2-hydroxy-1-(3-methoxyphenyl)ethyl)quinazolin-4(3H)-one;
3-(2-Amino-1-(3-chlorophenyl)ethyl)-7-(2-aminopyridin-4-yl)quinazolin-4(3H)-one;
3-(2-Amino-1-(3-chlorophenyl)ethyl)-7-(5-methyl-1H-pyrazol-4-yl)quinazolin-4(3H)-one;
3-(2-Amino-1-(3-chlorophenyl)ethyl)-7-(5-(trifluoromethyl)-1H-pyrazol-4-yl)quinazolin-4(3H)-one;
3-(2-Amino-1-(3-chlorophenyl)ethyl)-7-(5-chloro-1H-pyrazol-4-yl)quinazolin-4(3H)-one;
3-(2-Amino-1-(3-chlorophenyl)ethyl)-7-(3-methylisoxazol-4-yl)quinazolin-4(3H)-one;
3-(2-Amino-1-(3-methoxyphenyl)ethyl)-7-(5-methyl-1H-pyrazol-4-yl)quinazolin-4(3H)-one;
3-(2-Amino-1-(3-methoxyphenyl)ethyl)-7-(5-(trifluoromethyl)-1H-pyrazol-4-yl)quinazolin-4(3H)-one;
3-(2-Amino-1-(3-methoxyphenyl)ethyl)-7-(5-chloro-1H-pyrazol-4-yl)quinazolin-4(3H)-one;
3-(2-Amino-1-(7-(2-aminopyridin-4-yl)-4-oxoquinazolin-3(4H)-yl)ethyl)benzonitrile;
3-(2-Amino-1-(7-(2-fluoropyridin-4-yl)-4-oxoquinazolin-3(4H)-yl)ethyl)benzonitrile;
3-(2-Amino-1-(4-oxo-7-(5-(trifluoromethyl)-1H-pyrazol-4-yl)quinazolin-3(4H)-yl)ethyl)benzonitrile;
3-(2-Amino-1-(7-(5-chloro-1H-pyrazol-4-yl)-4-oxoquinazolin-3(4H)-yl)ethyl)benzonitrile;
3-(2-Amino-1-(7-(3-fluoropyridin-4-yl)-4-oxoquinazolin-3(4H)-yl)ethyl)benzamide;
3-(2-Amino-1-(7-(2-aminopyridin-4-yl)-4-oxoquinazolin-3(4H)-yl)ethyl)benzamide;
3-(2-Amino-1-(4-oxo-7-(5-(trifluoromethyl)-1H-pyrazol-4-yl)quinazolin-3(4H)-yl)ethyl)benzamide;
3-(2-Amino-1-(7-(5-chloro-1H-pyrazol-4-yl)-4-oxoquinazolin-3(4H)-yl)ethyl)benzamide;
(R)-3-(1-(7-(5-Bromo-1H-pyrazol-4-yl)-4-oxoquinazolin-3(4H)-yl)ethyl)-N-methylbenzamide;
(R)-3-(1-(7-(5-Bromo-1H-pyrazol-4-yl)-4-oxoquinazolin-3(4H)-yl)ethyl)-N-(methyl-D3)benzamide;
3-((7-(5-Bromo-1H-pyrazol-4-yl)-4-oxoquinazolin-3(4H)-yl)methyl)-N-(methyl-d3)benzamide;
3-((6-(5-Bromo-1H-pyrazol-4-yl)-1-oxoisoquinolin-2(1H)-yl)methyl)-N-methylbenzamide;
3-((6-(5-Bromo-1H-pyrazol-4-yl)-1-oxoisoquinolin-2(1H)-yl)methyl)-N-(methyl-d3)benzamide;
(R)-3-(1-(7-(5-Bromo-1H-pyrazol-4-yl)-4-oxoquinazolin-3(4H)-yl)ethyl)-N-(oxetan-3-yl)benzamide;
(R)-3-(1-(7-(5-Bromo-1H-pyrazol-4-yl)-4-oxoquinazolin-3(4H)-yl)ethyl)-N-cyclopropylbenzamide;
(R)-3-(1-(7-(5-Bromo-1H-pyrazol-4-yl)-4-oxoquinazolin-3(4H)-yl)ethyl)-N-((6-fluoropyridin-3-yl)methyl)benzamide;
(R)-3-(1-(7-(5-Bromo-1H-pyrazol-4-yl)-4-oxoquinazolin-3(4H)-yl)ethyl)-N-(4-fluorophenyl)benzamide;
(R)-3-(1-(7-(5-Amino-1H-pyrazol-4-yl)-4-oxoquinazolin-3(4H)-yl)ethyl)-N-methylbenzamide;
(R)-3-(1-(7-(5-Amino-1H-pyrazol-4-yl)-4-oxoquinazolin-3(4H)-yl)ethyl)-N-(methyl-D3)benzamide;
(R)-3-(1-(7-(5-Amino-1H-pyrazol-4-yl)-4-oxoquinazolin-3(4H)-yl)ethyl)-N-(oxetan-3-yl)benzamide;
(R)-3-(1-(7-(5-Amino-1H-pyrazol-4-yl)-4-oxoquinazolin-3(4H)-yl)ethyl)-N-cyclopropylbenzamide;
(R)-3-(1-(7-(5-Amino-1H-pyrazol-4-yl)-4-oxoquinazolin-3(4H)-yl)ethyl)-N-((6-fluoropyridin-3-yl)methyl)benzamide;
(R)-3-(1-(7-(5-Amino-1H-pyrazol-4-yl)-4-oxoquinazolin-3(4H)-yl)ethyl)-N-methylbenzamide;
(R)-3-(1-(7-(5-Amino-1H-pyrazol-4-yl)-4-oxoquinazolin-3(4H)-yl)ethyl)-N-(methyl-D3)benzamide;
(R)-3-(1-(7-(5-Amino-1H-pyrazol-4-yl)-4-oxoquinazolin-3(4H)-yl)ethyl)-N-(oxetan-3-yl)benzamide;
(R)-3-(1-(7-(5-Amino-1H-pyrazol-4-yl)-4-oxoquinazolin-3(4H)-yl)ethyl)-N-cyclopropylbenzamide;
(R)-3-(1-(7-(5-Amino-1H-pyrazol-4-yl)-4-oxoquinazolin-3(4H)-yl)ethyl)-N-((6-fluoropyridin-3-yl)methyl)benzamide;
(S)-3-(1-(3-Chlorophenyl)-2-hydroxyethyl)-7-(5-methyl-1H-pyrazol-4-yl)-2,3-dihydroquinazolin-4(1H)-one;
(S)-3-(1-(3-Chlorophenyl)-2-hydroxyethyl)-7-(5-(trifluoromethyl)-1H-pyrazol-4-yl)-2,3-dihydroquinazolin-4(1H)-one;
(S)-7-(5-Chloro-1H-pyrazol-4-yl)-3-(1-(3-chlorophenyl)-2-hydroxyethyl)-2,3-dihydroquinazolin-4(1H)-one;
(S)-3-(1-(3-Chlorophenyl)-2-hydroxyethyl)-7-(1-methyl-1H-pyrazol-5-yl)-2,3-dihydroquinazolin-4(1H)-one;
(S)-3-(2-Hydroxy-1-(3-methoxyphenyl)ethyl)-7-(pyridin-4-yl)-2,3-dihydroquinazolin-4(1H)-one;
(S)-3-(2-Hydroxy-1-(3-methoxyphenyl)ethyl)-7-(5-(trifluoromethyl)-1H-pyrazol-4-yl)-2,3-dihydroquinazolin-4(1H)-one;
(S)-3-(2-Hydroxy-1-(3-methoxyphenyl)ethyl)-7-(5-methylisoxazol-4-yl)-2,3-dihydroquinazolin-4(1H)-one;
(S)-7-(5-Chloro-1H-pyrazol-4-yl)-3-(2-hydroxy-1-(3-methoxyphenyl)ethyl)-2,3-dihydroquinazolin-4(1H)-one;
(S)-3-(2-Hydroxy-1-(3-methoxyphenyl)ethyl)-7-(1-methyl-1H-pyrazol-5-yl)-2,3-dihydroquinazolin-4(1H)-one;
3-((4-(1-Hydroxyethyl)-1-oxo-6-(3-(trifluoromethyl)-1l2-pyrazol-4-yl)isoquinolin-2(1H)-yl)methyl)-N-methylbenzamide;
N-Cyclopropyl-3-((4-(1-hydroxyethyl)-1-oxo-6-(3-(trifluoromethyl)-1H-pyrazol-4-yl)isoquinolin-2(1H)-yl)methyl)benzamide;
3-((4-(1-Hydroxyethyl)-1-oxo-6-(3-(trifluoromethyl)-1H-pyrazol-4-yl)isoquinolin-2(1H)-yl)methyl)-N-(oxetan-3-yl)benzamide;
3-((6-(3-(Difluoromethyl)-1H-pyrazol-4-yl)-4-(1-hydroxyethyl)-1-oxoisoquinolin-2(1H)-yl)methyl)-N-methylbenzamide;

3-((6-(3-(Difluoromethyl)-1H-pyrazol-4-yl)-4-(1-hydroxyethyl)-1-oxoisoquinolin-2(1H)-yl)methyl)-N-(tetrahydro-2H-pyran-4-yl)benzamide;
3-((4-(1-Hydroxyethyl)-6-(3-methylisoxazol-4-yl)-1-oxoisoquinolin-2(1H)-yl)methyl)-N-methylbenzamide;
N-((6-Fluoropyridin-3-yl)methyl)-3-((4-(1-hydroxyethyl)-6-(3-methylisoxazol-4-yl)-1-oxoisoquinolin-2(1H)-yl)methyl)benzamide;
N-Benzyl-3-((4-(1-hydroxyethyl)-6-(3-methylisoxazol-4-yl)-1-oxoisoquinolin-2(1H)-yl)methyl)benzamide;
3-((4-(1-Hydroxyethyl)-6-(1-methyl-1H-pyrazol-5-yl)-1-oxoisoquinolin-2(1H)-yl)methyl)-N-methylbenzamide;
3-((6-(3-Chloro-1H-pyrazol-4-yl)-4-(1-hydroxyethyl)-1-oxoisoquinolin-2(1H)-yl)methyl)-N-methylbenzamide;
3-((6-(3-Chloro-1H-pyrazol-4-yl)-4-(1-hydroxyethyl)-1-oxoisoquinolin-2(1H)-yl)methyl)-N-(2-(dimethylamino)ethyl)benzamide;
3-((6-(3-Chloro-1H-pyrazol-4-yl)-4-(1-hydroxyethyl)-1-oxoisoquinolin-2(1H)-yl)methyl)-N-(2-(pyridin-2-yl)ethyl)benzamide;
3-((6-(2-Aminopyridin-4-yl)-4-(1-hydroxyethyl)-1-oxoisoquinolin-2(1H)-yl)methyl)-N-methylbenzamide;
3-((6-(3-(Difluoromethyl)-1H-pyrazol-4-yl)-4-(1-hydroxyethyl)-1-oxoisoquinolin-2(1H)-yl)methyl)-N-(tetrahydro-2H-pyran-4-yl)benzamide;
3-((4-(1-Hydroxyethyl)-6-(3-methylisoxazol-4-yl)-1-oxoisoquinolin-2(1H)-yl)methyl)-N-methylbenzamide;
N-((6-Fluoropyridin-3-yl)methyl)-3-((4-(1-hydroxyethyl)-6-(3-methylisoxazol-4-yl)-1-oxoisoquinolin-2(1H)-yl)methyl)benzamide;
N-Benzyl-3-((4-(1-hydroxyethyl)-6-(3-methylisoxazol-4-yl)-1-oxoisoquinolin-2(1H)-yl)methyl)benzamide;
3-((4-(1-Hydroxyethyl)-6-(1-methyl-1H-pyrazol-5-yl)-1-oxoisoquinolin-2(1H)-yl)methyl)-N-methylbenzamide;
3-((6-(3-Chloro-1H-pyrazol-4-yl)-4-(1-hydroxyethyl)-1-oxoisoquinolin-2(1H)-yl)methyl)-N-methylbenzamide;
3-((6-(3-Chloro-1H-pyrazol-4-yl)-4-(1-hydroxyethyl)-1-oxoisoquinolin-2(1H)-yl)methyl)-N-(2-(dimethylamino)ethyl)benzamide;
3-((6-(3-Chloro-1H-pyrazol-4-yl)-4-(1-hydroxyethyl)-1-oxoisoquinolin-2(1H)-yl)methyl)-N-(2-(pyridin-2-yl)ethyl)benzamide;
3-((6-(2-Aminopyridin-4-yl)-4-(1-hydroxyethyl)-1-oxoisoquinolin-2(1H)-yl)methyl)-N-methylbenzamide;
3-((4-(1-Hydroxyethyl)-1-oxo-6-(3-(trifluoromethyl)-1H-pyrazol-4-yl)isoquinolin-2(1H)-yl)methyl)-N-methylbenzamide;
N-Cyclopropyl-3-((4-(1-hydroxyethyl)-1-oxo-6-(3-(trifluoromethyl)-1H-pyrazol-4-yl)isoquinolin-2(1H)-yl)methyl)benzamide;
3-((4-(1-Hydroxyethyl)-1-oxo-6-(3-(trifluoromethyl)-1H-pyrazol-4-yl)isoquinolin-2(1H)-yl)methyl)-N-(oxetan-3-yl)benzamide;
3-((6-(3-(Difluoromethyl)-1H-pyrazol-4-yl)-4-(1-hydroxyethyl)-1-oxoisoquinolin-2(1H)-yl)methyl)-N-methylbenzamide;
3-((6-(3-(Difluoromethyl)-1H-pyrazol-4-yl)-4-(1-hydroxyethyl)-1-oxoisoquinolin-2(1H)-yl)methyl)-N-methylbenzamide;
3-((6-(3-(Difluoromethyl)-1H-pyrazol-4-yl)-4-(1-hydroxyethyl)-1-oxoisoquinolin-2(1H)-yl)methyl)-N-(tetrahydro-2H-pyran-4-yl)benzamide;
3-((4-(1-Hydroxyethyl)-6-(3-methylisoxazol-4-yl)-1-oxoisoquinolin-2(1H)-yl)methyl)-N-methylbenzamide;
N-((6-Fluoropyridin-3-yl)methyl)-3-((4-(1-hydroxyethyl)-6-(3-methylisoxazol-4-yl)-1-oxoisoquinolin-2(1H)-yl)methyl)benzamide;
N-Benzyl-3-((4-(1-hydroxyethyl)-6-(3-methylisoxazol-4-yl)-1-oxoisoquinolin-2(1H)-yl)methyl)benzamide;
3-((4-(1-Hydroxyethyl)-6-(1-methyl-1H-pyrazol-5-yl)-1-oxoisoquinolin-2(1H)-yl)methyl)-N-methylbenzamide;
3-((6-(3-Chloro-1H-pyrazol-4-yl)-4-(1-hydroxyethyl)-1-oxoisoquinolin-2(1H)-yl)methyl)-N-methylbenzamide;
3-((6-(3-Chloro-1H-pyrazol-4-yl)-4-(1-hydroxyethyl)-1-oxoisoquinolin-2(1H)-yl)methyl)-N-(2-(dimethylamino)ethyl)benzamide;
3-((6-(3-Chloro-1H-pyrazol-4-yl)-4-(1-hydroxyethyl)-1-oxoisoquinolin-2(1H)-yl)methyl)-N-(2-(pyridin-2-yl)ethyl)benzamide;
3-((6-(3-Amino-1H-pyrazol-4-yl)-4-(1-hydroxyethyl)-1-oxoisoquinolin-2(1H)-yl)methyl)-N-methylbenzamide;
3-((6-(2-Aminopyridin-4-yl)-4-(1-hydroxyethyl)-1-oxoisoquinolin-2(1H)-yl)methyl)-N-methylbenzamide;
3-((4-(2-Hydroxyethyl)-1-oxo-6-(5-(trifluoromethyl)-1H-pyrazol-4-yl)isoquinolin-2(1H)-yl)methyl)-N-methylbenzamide;
3-((4-(2-Hydroxypropyl)-1-oxo-6-(5-(trifluoromethyl)-1H-pyrazol-4-yl)isoquinolin-2(1H)-yl)methyl)-N-methylbenzamide;
3-((4-(2-(Dimethylamino)ethyl)-1-oxo-6-(5-(trifluoromethyl)-1H-pyrazol-4-yl)isoquinolin-2(1H)-yl)methyl)-N-methylbenzamide;
3-(1-(4-(2-Hydroxyethyl)-1-oxo-6-(5-(trifluoromethyl)-1H-pyrazol-4-yl)isoquinolin-2(1H)-yl)ethyl)-N-methylbenzamide;
3-((6-(5-Chloro-1H-pyrazol-4-yl)-4-(2-hydroxyethyl)-1-oxoisoquinolin-2(1H)-yl)methyl)-N-methylbenzamide;
3-(1-(6-(5-Chloro-1H-pyrazol-4-yl)-4-(2-hydroxyethyl)-1-oxoisoquinolin-2(1H)-yl)ethyl)-N-methylbenzamide;
3-((4-(2-Hydroxyethyl)-6-(3-methylisoxazol-4-yl)-1-oxoisoquinolin-2(1H)-yl)methyl)-N-methylbenzamide;
3-(1-(4-(2-Hydroxyethyl)-6-(3-methylisoxazol-4-yl)-1-oxoisoquinolin-2(1H)-yl)ethyl)-N-methylbenzamide;
3-(1-(6-(5-Fluoro-1H-pyrazol-4-yl)-4-(2-hydroxyethyl)-1-oxoisoquinolin-2(1H)-yl)ethyl)-N-methylbenzamide;
3-((6-(5-Fluoro-1H-pyrazol-4-yl)-4-(2-hydroxyethyl)-1-oxoisoquinolin-2(1H)-yl)methyl)-N-methylbenzamide;
3-(1-(6-(5-(Difluoromethyl)-1H-pyrazol-4-yl)-4-(2-hydroxyethyl)-1-oxoisoquinolin-2(1H)-yl)ethyl)-N-methylbenzamide;
3-((6-(5-(Difluoromethyl)-1H-pyrazol-4-yl)-4-(2-hydroxyethyl)-1-oxoisoquinolin-2(1H)-yl)methyl)-N-methylbenzamide;
3-(1-(6-(5-(Difluoromethyl)-1H-pyrazol-4-yl)-4-(2-hydroxyethyl)-1-oxoisoquinolin-2(1H)-yl)ethyl)-N-methylbenzamide;
3-((6-(5-(Difluoromethyl)-1H-pyrazol-4-yl)-4-(2-hydroxyethyl)-1-oxoisoquinolin-2(1H)-yl)methyl)-N-methylbenzamide;
3-((6-(2-Aminopyridin-4-yl)-4-(2-hydroxyethyl)-1-oxoisoquinolin-2(1H)-yl)methyl)-N-methylbenzamide;
3-((6-(5-(Difluoromethyl)-1H-pyrazol-4-yl)-4-(2-hydroxypropyl)-1-oxoisoquinolin-2(1H)-yl)methyl)-N-methylbenzamide;
3-((6-(5-Chloro-1H-pyrazol-4-yl)-4-(2-hydroxypropyl)-1-oxoisoquinolin-2(1H)-yl)methyl)-N-methylbenzamide;
3-((6-(2-Fluoro-1H-pyrrol-3-yl)-4-(2-hydroxypropyl)-1-oxoisoquinolin-2(1H)-yl)methyl)-N-methylbenzamide;
3-((4-(2-Hydroxypropyl)-6-(3-methylisoxazol-4-yl)-1-oxoisoquinolin-2(1H)-yl)methyl)-N-methylbenzamide;
3-((6-(3-Amino-1H-pyrazol-4-yl)-4-(2-hydroxypropyl)-1-oxoisoquinolin-2(1H)-yl)methyl)-N-methylbenzamide;

3-(1-(4-(2-(Dimethylamino)ethyl)-1-oxo-6-(5-(trifluoromethyl)-1H-pyrazol-4-yl)isoquinolin-2(1H)-yl)ethyl)-N-methylbenzamide;
3-(1-(4-(2-(Dimethylamino)ethyl)-1-oxo-6-(5-(trifluoromethyl)-1H-pyrazol-4-yl)isoquinolin-2(1H)-yl)ethyl)-N-methylbenzamide;
3-(1-(6-(5-Chloro-1H-pyrazol-4-yl)-4-(2-(dimethylamino)ethyl)-1-oxoisoquinolin-2(1H)-yl)ethyl)-N-methylbenzamide;
3-((4-(2-(Dimethylamino)ethyl)-6-(1-methyl-1H-pyrazol-5-yl)-1-oxoisoquinolin-2(1H)-yl)methyl)-N-methylbenzamide;
3-((6-(3-Amino-1H-pyrazol-4-yl)-4-(2-(dimethylamino)ethyl)-1-oxoisoquinolin-2(1H)-yl)methyl)-N-methylbenzamide;
(R)-3-(1-(7-(5-chloro-1H-pyrazol-4-yl)-4-oxopyrido[4,3-d]pyrimidin-3(4H)-yl)ethyl)-N-methylbenzamide;
(R)-3-(1-(7-(5-fluoro-1H-pyrazol-4-yl)-4-oxopyrido[4,3-d]pyrimidin-3(4H)-yl)ethyl)-N-methylbenzamide;
(R)-3-(1-(7-(5-methoxy-1H-pyrazol-4-yl)-4-oxopyrido[4,3-d]pyrimidin-3(4H)-yl)ethyl)-N-methylbenzamide;
(R)—N-methyl-3-(1-(7-(3-methylisoxazol-4-yl)-4-oxopyrido[4,3-d]pyrimidin-3(4H)-yl)ethyl)benzamide;
(R)-(4-(3-(1-(3-(methylcarbamoyl)phenyl)ethyl)-4-oxo-3,4-dihydroquinazolin-7-yl)-5-(trifluoromethyl)-1H-pyrazol-1-yl)methyl dihydrogen phosphate; and
Disodium (R)-(4-(3-(1-(3-(methylcarbamoyl)phenyl)ethyl)-4-oxo-3,4-dihydroquinazolin-7-yl)-5-(trifluoromethyl)-1H-pyrazol-1-yl)methyl phosphate.

Examples that represent different aspects of the invention follow. Such examples should not be construed as limiting the scope of the disclosure. Alternative mechanistic pathways and analogous structures within the scope of the invention would be apparent to those skilled in the art. Elements and acts in the examples are intended to illustrate the invention for the sake of simplicity and have not necessarily been rendered according to any particular sequence or embodiment.

EXAMPLES

The present invention is further exemplified by the following examples. The examples are for illustrative purpose only and are not intended to limit the invention, nor should they be construed as limiting the invention in any manner. Those skilled in the art will appreciate that variations and modifications can be made without changing the scope of the invention.

Example 1: Preparation of Compounds

Nuclear magnetic resonance (NMR) and mass spectrometry (MS) spectra obtained for compounds described in the examples below and those described herein were consistent with those of the compounds of formulae herein.
Liquid Chromatography-Mass Spectrometry (LC-MS) Method:
1. Samples were run on Agilent Technologies 6120 MSD system with a Zorbax Eclipse XDB-C18 (3.5μ) reverse phase column (4.6×50 mm) run at room temperature with flow rate of 1.5 mL/minute.
2. The mobile phase used solvent A (water/0.1% formic acid) and solvent B (acetonitrile/0.1% formic acid): 95%/5% to 0%/100% (A/B) for 5 minute.
3. The mass spectra (m/z) were recorded using electrospray ionization (ESI).
4. Ionization data was rounded to the nearest integer.

Proton NMR Spectra:
Unless otherwise indicated, all $^1$H NMR spectra were run on a Varian series Mercury 300 or 400 MHz. All observed protons are reported as parts-per-million (ppm) downfield from tetramethylsilane using conventional abbreviations for designation of major peaks: e.g., s (singlet), d (doublet), t (triplet), q (quartet), m (multiplet) and brs (broad singlet).

Compound 1: 2-(3-methoxybenzyl)-6-(1H-pyrazol-4-yl)-3,4-dihydroisoquinolin-1(2H)-one

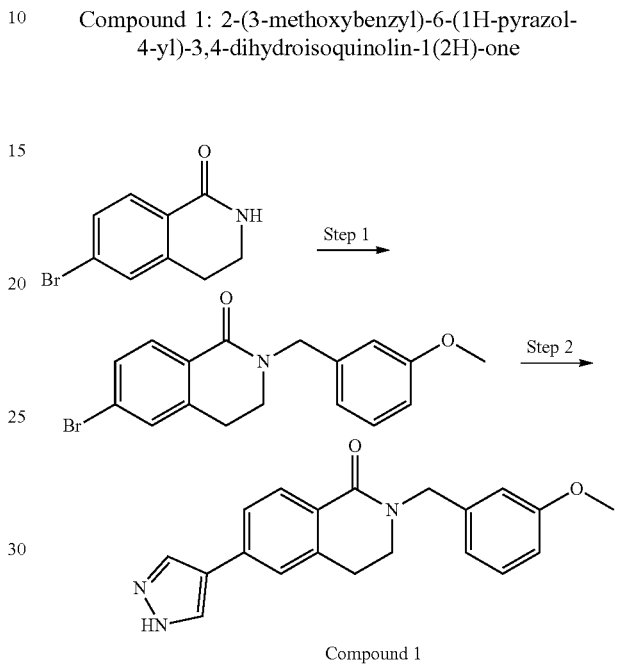

Compound 1

Step 1: A solution of 6-bromo-3,4-dihydroisoquinolin-1(2H)-one (226 mg, 1.0 mmol) in DMF (1.5 mL) was cooled to 0 °C., and 55% NaH (52 mg, 1.2 mmol) was added. The mixture was then stirred for 30 minutes at 0° C. A solution of 3-methoxybenzyl bromide (240 mg, 1.2 mmol) in DMF (0.5 mL) was slowly added to the mixture at 0° C., and then the mixture was warmed to room temperature (RT) and shaken for 1 hour. The reaction was quenched with aq. sat. NH$_4$Cl solution and extracted with EtOAc twice. The combined organic layer was sequentially washed with water and brine, dried (Na$_2$SO$_4$), filtered, concentrated, and purified by silica gel column chromatography to provide 6-bromo-2-(3-methoxybenzyl)-3,4-dihydroisoquinolin-1(2H)-one in 57% yield. LC/MS found 346.0 [M+H]$^+$.

Step 2: A mixture of 6-bromo-2-(3-methoxybenzyl)-3,4-dihydroisoquinolin-1(2H)-one (180 mg, 0.52 mmol) and 4-(4,4,5,5-tetramethyl-1,3,2-dioxaborolan-2-yl)-1H-pyrazole (131 mg, 1.3 equiv), Na$_2$CO$_3$ (175 mg), and Pd(dppf)Cl$_2$·CH$_2$Cl$_2$ (18 mg) in 1,4-dioxane (1.0 mL) and H$_2$O (0.2 mL) was degassed via sparging with argon for 10 minutes and then heated to 100° C. overnight. The mixture was cooled to RT, poured over H$_2$O, and extracted with EtOAc. The combined organic layer was washed with brine, dried over Na$_2$SO$_4$, filtered, and concentrated. The residue was purified by flash column chromatography using a gradient of 0-10% CH$_3$OH in CH$_2$Cl$_2$ to provide Compound 1 as a colorless solid in 60% yield (103 mg). LC/MS found 334.1 [M+H]$^+$.

General Scheme 1

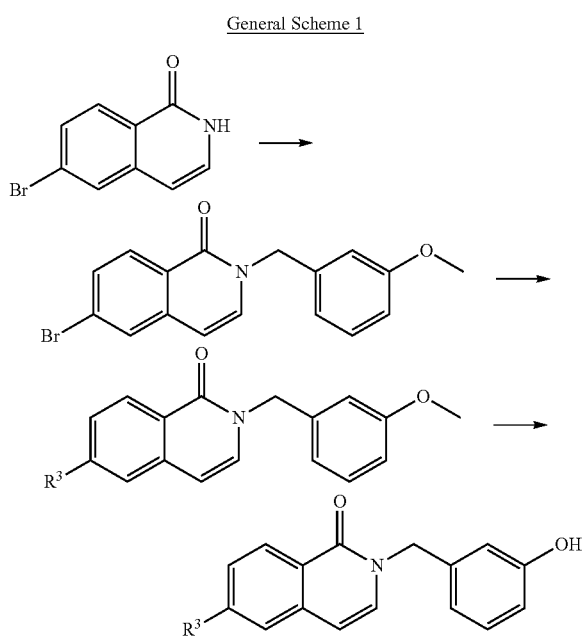

Compound 2: 2-(3-methoxybenzyl)-6-(1H-pyrazol-4-yl)isoquinolin-1(2H)-one

Scheme 1

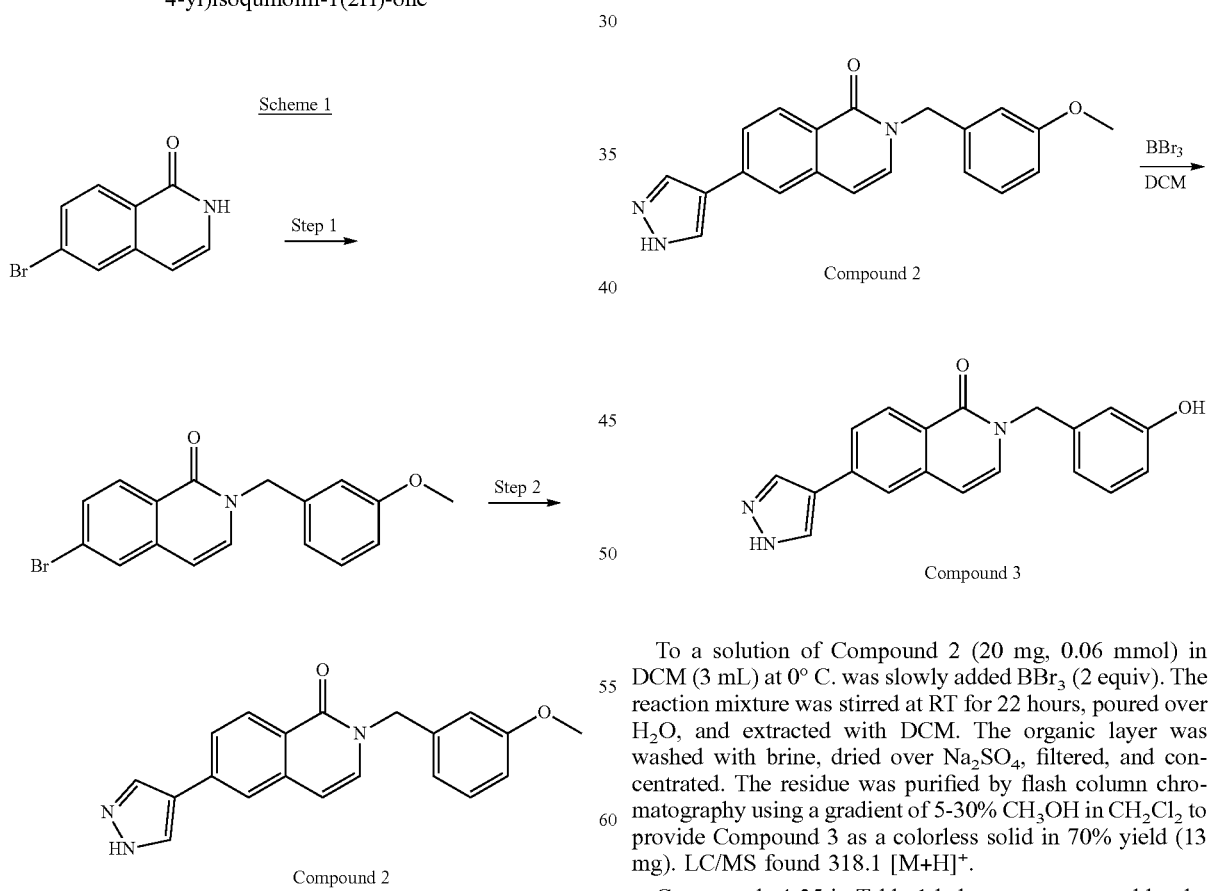

Step 1: 6-Bromoisoquinolin-1(2H)-one (223 mg, 1.00 mmol) in DMF (1.5 mL) was cooled to 0° C., and 55% NaH (1.2 equiv) was added. The mixture was then stirred for 30 minutes at 0° C. A solution of 3-methoxy benzyl bromide (1.2 equivalent) in DMF (0.5 mL) was slowly added to the mixture at 0° C., and then the mixture was warmed to RT and shaken for 1 hour. The reaction was quenched with aq. sat. NH$_4$Cl solution and extracted with EtOAc twice. The combined organic layer was sequentially washed with water and brine, dried over Na$_2$SO$_4$, filtered, concentrated, and purified by silica gel column chromatography to provide 6-bromo-2-(3-methoxybenzyl)-isoquinolin-1(2H)-one in 80% yield (275 mg). LC/MS found 344.0 [M+H]$^+$.

Step 2: A mixture of 6-bromo-2-(3-methoxybenzyl)-isoquinolin-1(2H)-one (68 mg, 0.2 mmol) and 4-(4,4,5,5-tetramethyl-1,3,2-dioxaborolan-2-yl)-1H-pyrazole (50 mg, 1.3 equiv), Na$_2$CO$_3$ (65 mg), and Pd(dppf)Cl$_2$·CH$_2$Cl$_2$ (8 mg) in 1,4-dioxane (1.0 mL) and H$_2$O (0.2 mL) was degassed via sparging with argon for 10 minutes and then heated to 100° C. overnight. The mixture was cooled to RT, poured over H$_2$O, and extracted with EtOAc. The organic layer was washed with brine, dried over Na$_2$SO$_4$, filtered, and concentrated. The residue was purified by flash column chromatography using a gradient of 0-10% CH$_3$OH in CH$_2$Cl$_2$ to provide Compound 2 as a colorless solid in 53% yield (35 mg). LC/MS found 332.1 [M+H]$^+$.

Compound 3: 2-(3-hydroxybenzyl)-6-(1H-pyrazol-4-yl)isoquinolin-1(2H)-one

To a solution of Compound 2 (20 mg, 0.06 mmol) in DCM (3 mL) at 0° C. was slowly added BBr$_3$ (2 equiv). The reaction mixture was stirred at RT for 22 hours, poured over H$_2$O, and extracted with DCM. The organic layer was washed with brine, dried over Na$_2$SO$_4$, filtered, and concentrated. The residue was purified by flash column chromatography using a gradient of 5-30% CH$_3$OH in CH$_2$Cl$_2$ to provide Compound 3 as a colorless solid in 70% yield (13 mg). LC/MS found 318.1 [M+H]$^+$.

Compounds 4-25 in Table 1 below were prepared by the method (General Scheme 1) similar to that described above for the preparation of Compound 2 and Compound 3 using an appropriate boronic acid and appropriate 6-bromo-2-(3-methoxybenzyl)-isoquinolin-1(2H)-one.

TABLE 1

| Compd | Boronic acid | Structure | MS found [M + H]+ |
|---|---|---|---|
| 4 | 3-methyl-1H-pyrazol-4-yl B(OH)₂ | 2-(3-methoxybenzyl)-6-(3-methyl-1H-pyrazol-4-yl)isoquinolin-1(2H)-one | 346.3 |
| 5 | 3-methyl-1H-pyrazol-4-yl B(OH)₂ | 2-(3-hydroxybenzyl)-6-(3-methyl-1H-pyrazol-4-yl)isoquinolin-1(2H)-one | 332.2 |
| 6 | 3-(trifluoromethyl)-1H-pyrazol-4-yl Bpin | 2-(3-methoxybenzyl)-6-(3-(trifluoromethyl)-1H-pyrazol-4-yl)isoquinolin-1(2H)-one | 400.2 |
| 7 | 3-(trifluoromethyl)-1H-pyrazol-4-yl Bpin | 2-(3-hydroxybenzyl)-6-(3-(trifluoromethyl)-1H-pyrazol-4-yl)isoquinolin-1(2H)-one | 386.1 |
| 8 | 3-(trifluoromethyl)-1H-pyrazol-4-yl Bpin | 2-(1-(3-hydroxyphenyl)ethyl)-6-(3-(trifluoromethyl)-1H-pyrazol-4-yl)isoquinolin-1(2H)-one | 400.1 |
| 9 | 3-methylisoxazol-4-yl B(OH)₂ | 2-(3-methoxybenzyl)-6-(3-methylisoxazol-4-yl)isoquinolin-1(2H)-one | 347.3 |
| 10 | 3-methylisoxazol-4-yl B(OH)₂ | 2-(3-hydroxybenzyl)-6-(3-methylisoxazol-4-yl)isoquinolin-1(2H)-one | 333.2 |

TABLE 1-continued

| Compd | Boronic acid | Structure | MS found [M + H]+ |
|---|---|---|---|
| 11 | | 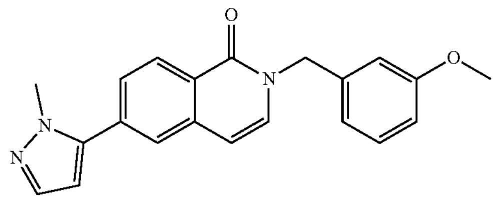 [SMILES: COc1cccc(Cn2ccc3cc(-c4ccnn4C)ccc3c2=O)c1] | 346.1 |
| 12 | | 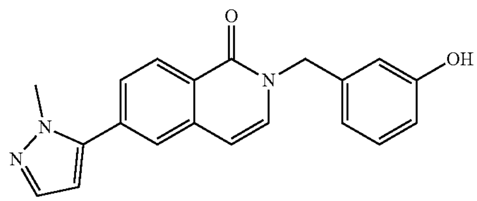 [SMILES: Cn1nccc1-c1ccc2c(=O)n(Cc3cccc(O)c3)ccc2c1] | 332.1 |
| 13 | | 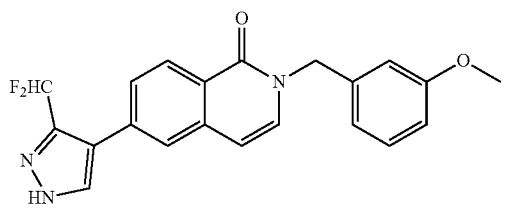 [SMILES: COc1cccc(Cn2ccc3cc(-c4c[nH]nc4C(F)F)ccc3c2=O)c1] | 382.2 |
| 14 | | 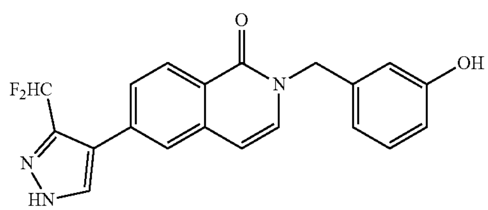 [SMILES: O=c1c2ccc(-c3c[nH]nc3C(F)F)cc2ccn1Cc1cccc(O)c1] | 368.2 |
| 15 | | 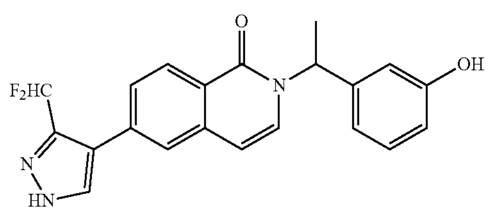 [SMILES: CC(c1cccc(O)c1)n1ccc2cc(-c3c[nH]nc3C(F)F)ccc2c1=O] | 382.4 |
| 16 | | 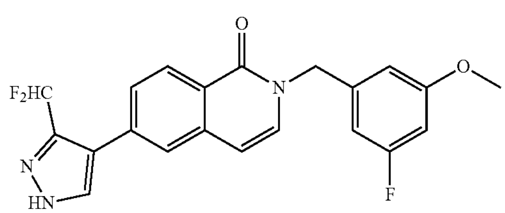 [SMILES: COc1cc(F)cc(Cn2ccc3cc(-c4c[nH]nc4C(F)F)ccc3c2=O)c1] | 382.1 |

TABLE 1-continued

| Compd | Boronic acid | Structure | MS found [M + H]+ |
|---|---|---|---|
| 17 | 3-chloro-1H-pyrazol-4-yl pinacol boronate | 6-(3-chloro-1H-pyrazol-4-yl)-2-(3-fluoro-5-methoxybenzyl)isoquinolin-1(2H)-one | 384. |
| 18 | 3-chloro-1H-pyrazol-4-yl pinacol boronate | 6-(3-chloro-1H-pyrazol-4-yl)-2-(3-methoxybenzyl)isoquinolin-1(2H)-one | 366.2 |
| 19 | 3-chloro-1H-pyrazol-4-yl pinacol boronate | 6-(3-chloro-1H-pyrazol-4-yl)-2-(1-(3-methoxyphenyl)ethyl)isoquinolin-1(2H)-one | 380.1 |
| 20 | 3-chloro-1H-pyrazol-4-yl pinacol boronate | 6-(3-chloro-1H-pyrazol-4-yl)-2-(3-hydroxybenzyl)isoquinolin-1(2H)-one | 352.3 |
| 21 | 3-chloro-1H-pyrazol-4-yl pinacol boronate | 6-(3-chloro-1H-pyrazol-4-yl)-2-(1-(3-hydroxyphenyl)ethyl)isoquinolin-1(2H)-one | 366.2 |
| 22 | pyridin-4-yl boronic acid | 2-(3-methoxybenzyl)-6-(pyridin-4-yl)isoquinolin-1(2H)-one | 343.0 |

TABLE 1-continued
| Compd | Boronic acid | Structure | MS found [M + H]+ |
|---|---|---|---|
| 23 | | 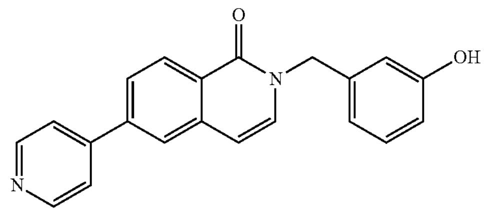 [SMILES: O=c1c2ccc(-c3ccncc3)cc2ccn1Cc1cccc(O)c1] | 329.1 |
| 24 | | 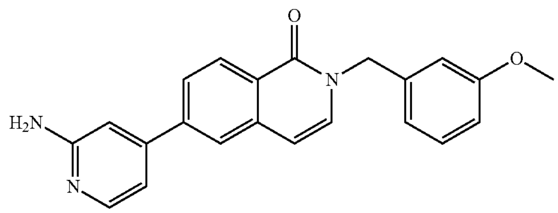 [SMILES: COc1cccc(Cn2ccc3cc(-c4ccnc(N)c4)ccc3c2=O)c1] | 358.2 |
| 25 | | 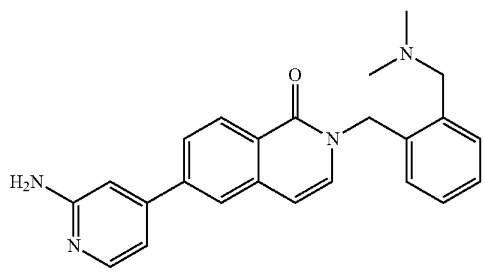 [SMILES: CN(C)Cc1ccccc1Cn1ccc2cc(-c3ccnc(N)c3)ccc2c1=O] | 385.1 |
| 26 | | 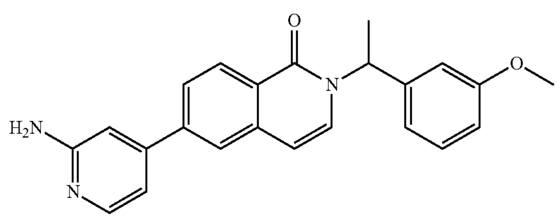 [SMILES: COc1cccc(C(C)n2ccc3cc(-c4ccnc(N)c4)ccc3c2=O)c1] | 372.2 |
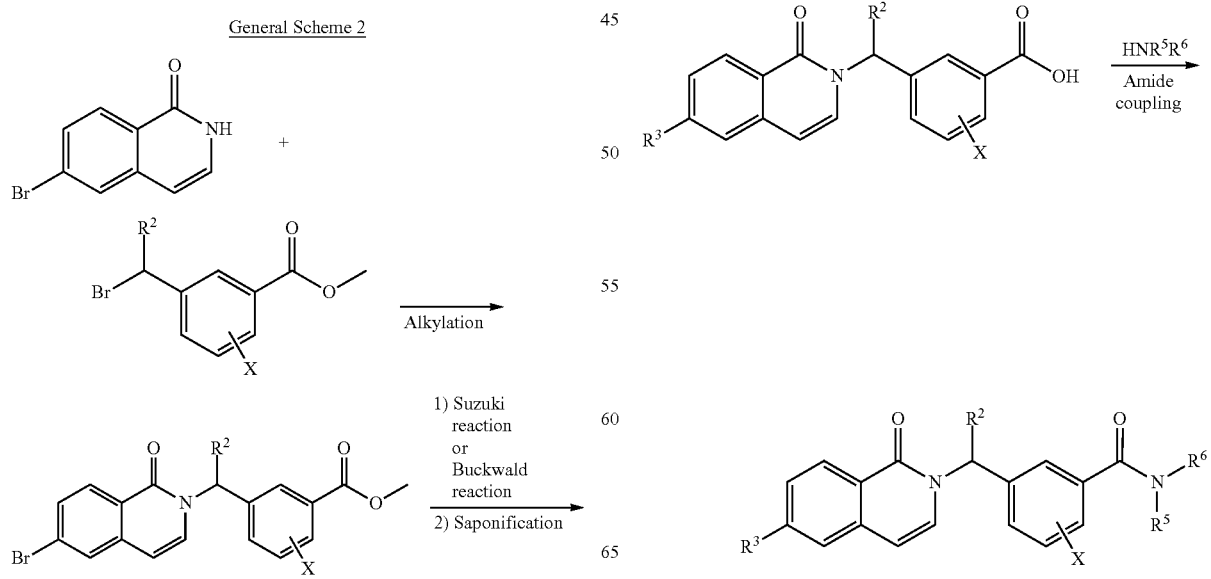
General Scheme 2

Compound 27: (3-((1-oxo-6-(1H-pyrazol-4-yl)isoquinolin-2(1H)-yl)methyl)-N-(2-(pyridin-2-yl)ethyl)benzamide)

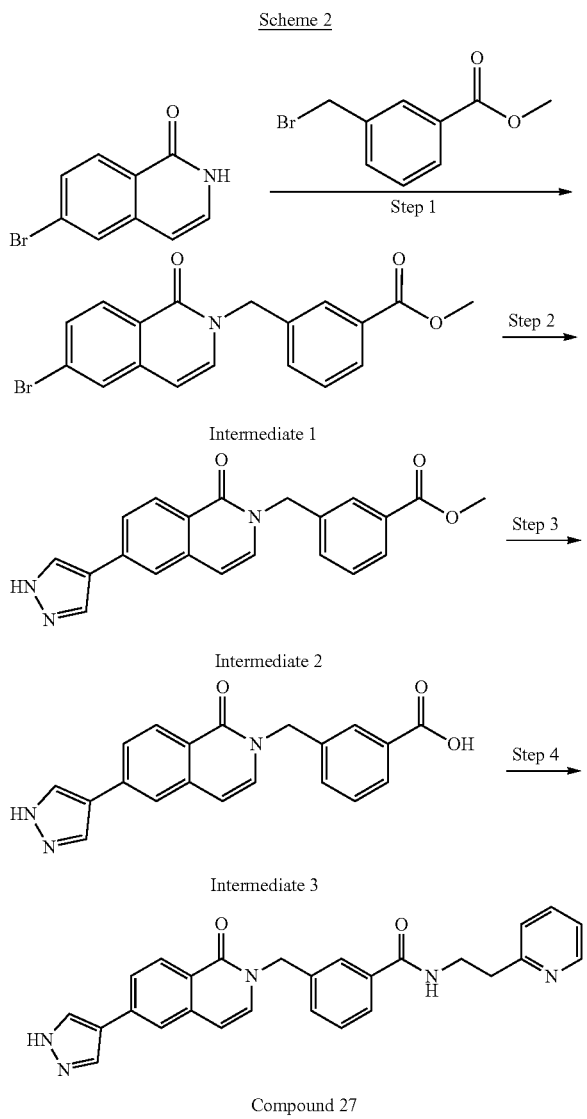

Scheme 2

Intermediate 1

Intermediate 2

Intermediate 3

Compound 27

Step 1: A mixture of 6-bromoisoquinolin-1(2H)-one (674 mg, 3.00 mmol), methyl 3-(bromomethyl)benzoate (1.05 g, 4.60 mmol), Na$_2$CO$_3$ (1.59 g, 15.0 mmol), and NaI (97 mg, 0.65 mmol) in acetone (30 mL) was heated to reflux with stirring overnight. The mixture was cooled to RT, poured over H$_2$O, and extracted with EtOAc. The organic layer was washed with brine, dried over Na$_2$SO$_4$, filtered, and concentrated. The residue was purified by flash column chromatography on SiO$_2$ using a gradient of 10-40% EtOAc in heptanes to provide methyl 3-((6-bromo-1-oxoisoquinolin-2(1H)-yl)methyl)benzoate, Intermediate 1 as dull yellow solid in 79% yield (928 mg, 2.49 mmol). LC/MS found 372.0 [M+H]$^+$.

Step 2: A mixture of Intermediate 1 (740 mg, 2.0 mmol), 4-pyrazoleboronic acid, pinacol ester (630 mg, 3.0 mmol), Na$_2$CO$_3$ (700 mg, 0.66 mmol), and Pd(PPh$_3$)$_2$Cl$_2$ (57 mg, 81 μmol) in 1,4-dioxane (15 mL) and H$_2$O (5 mL) was degassed via sparging with argon for 10 minutes and then heated to 100° C. overnight. The mixture was cooled to RT, poured over H$_2$O, and extracted with CH$_2$Cl$_2$. The organic layer was washed with H$_2$O, washed with brine, dried over MgSO$_4$, filtered, and concentrated. The residue was purified by flash column chromatography using a gradient of 1-10% CH$_3$OH in CH$_2$Cl$_2$ to provide Intermediate 2 as a white solid in 53% yield (380 mg). LC/MS found 360.3 [M+H]$^+$.

Step 3: A mixture of Intermediate 2 (380 mg, 1.1 mmol) and LiOH·H$_2$O (480 mg, 11 mmol) in CH$_3$OH (40 mL) and H$_2$O (10 mL) was stirred at RT overnight. The mixture was acidified to pH 2 with 1N HCl. The resulting precipitate was vacuum filtered, washed with H$_2$O, and dried under a vacuum overnight to give 3-((1-oxo-6-(1H-pyrazol-4-yl)isoquinolin-2(1H)-yl)methyl)benzoic acid (Intermediate 3) as a white solid in 80% yield (303 mg). LC/MS found 346.2 [M+H]$^+$.

Step 4: Intermediate 3 (35 mg, 0.1 mmol), HBTU (57.2 mg, 0.15 mmol), i-Pr$_2$NEt (0.52 mL, 0.3 mmol), and 2-(pyridin-2-yl)ethan-1-amine (0.16 mL) in CH$_2$Cl$_2$ (3 mL) was stirred at RT overnight. The mixture was poured over H$_2$O and extracted with CH$_2$Cl$_2$. The organic layer was washed with brine, dried over MgSO$_4$, filtered, and concentrated. The residue was purified by flash column chromatography on SiO$_2$ using a gradient of 5-30% MeOH in CH$_2$Cl$_2$ to provide 3-((1-oxo-6-(1H-pyrazol-4-yl)isoquinolin-2(1H)-yl)methyl)-N-(2-(pyridin-2-yl)ethyl)benzamide, Compound 27 as a white solid in 90% yield (40.5 mg). LC/MS found 450.3 [M+H]$^+$.

Compounds 28-230 in Table 2 below were prepared by the method (General Scheme 2) similar to that described for the preparation of Compound 27 using methyl 3-(bromomethyl)benzoate, an appropriate boronic acid/ester, and an appropriate amine.

TABLE 2

| Compd | R$^1$ | R2HN$^5$R$^6$ | Structure | MS found [M + H]$^+$ |
|---|---|---|---|---|
| 28 | ![pyrazole boronate] | i-PrNH2 | ![structure] | 387.2 |

TABLE 2-continued

| Compd | R¹ | R2HN⁵R⁶ | Structure | MS found [M + H]⁺ |
|---|---|---|---|---|
| 29 | pyrazole-Bpin | Aniline | (structure) | 421.01 |
| 30 | pyrazole-Bpin | Benzylamine | (structure) | 435.0 |
| 31 | methylpyrazole-B(OH)₂ | 2-(pyridin-2-yl)ethylamine | (structure) | 464.1 |
| 32 | methylpyrazole-B(OH)₂ | 3-amino-1-methylpyrazole | (structure) | 439.1 |
| 33 | methylpyrazole-B(OH)₂ | 3-(methylsulfonamido)benzylamine | (structure) | 542.3 |
| 34 | methylpyrazole-B(OH)₂ | 3-aminobenzenesulfonamide | (structure) | 514.3 |
| 35 | methylpyrazole-B(OH)₂ | 3-(trifluoromethoxy)aniline | (structure) | 519.2 |
| 36 | methylpyrazole-B(OH)₂ | 4-aminobenzenesulfonamide | (structure) | 514.2 |
| 37 | methylpyrazole-B(OH)₂ | 4-aminobenzenesulfonamide | (structure) | 528.1 |
| 38 | methylpyrazole-B(OH)₂ | 2-(trifluoromethoxy)aniline | (structure) | 519.3 |

TABLE 2-continued
| Compd | R¹ | R2HN⁵R⁶ | Structure | MS found [M + H]⁺ |
|---|---|---|---|---|
| 39 | 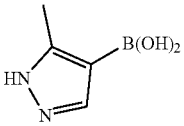 | 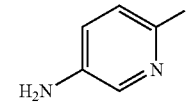 | 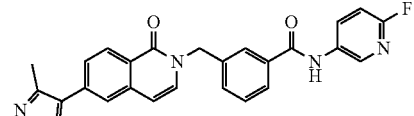 | 454.2 |
| 40 | 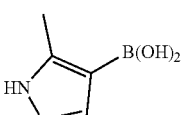 | 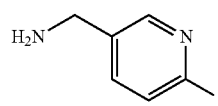 | 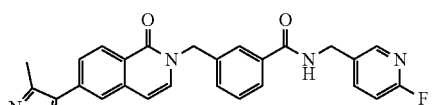 | 454.1 |
| 41 | 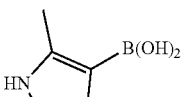 | 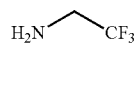 | 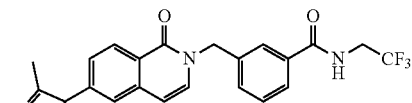 | 441.0 |
| 42 | 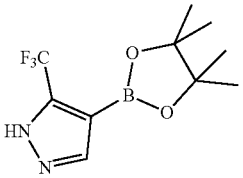 | 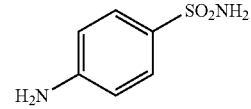 | 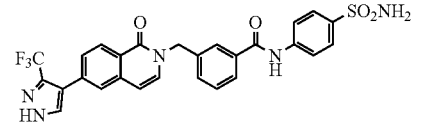 [SMILES: NS(=O)(=O)c1ccc(NC(=O)c2cccc(Cn3ccc4cc(-c5c[nH]nc5C(F)(F)F)ccc4c3=O)c2)cc1] | 568.4 |
| 43 | 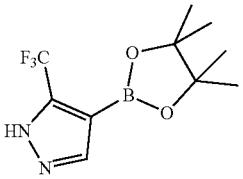 | 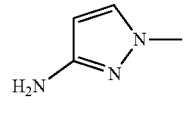 | 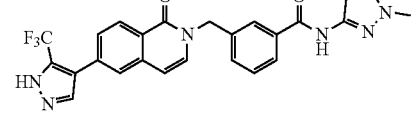 | 493.2 |
| 44 | 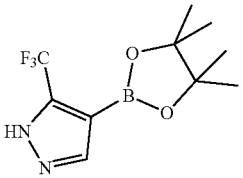 | 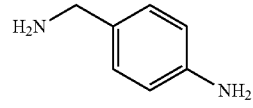 | 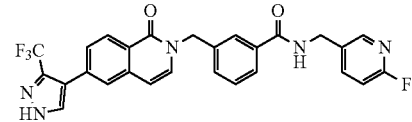 [SMILES: O=C(NCc1ccc(F)nc1)c1cccc(Cn2ccc3cc(-c4c[nH]nc4C(F)(F)F)ccc3c2=O)c1] | 522.3 |
| 45 | 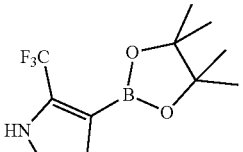 | 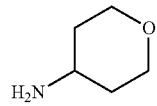 | 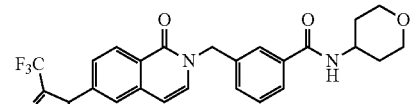 | 497.2 |
| 46 | 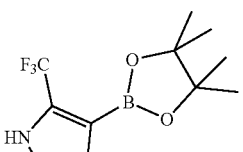 | 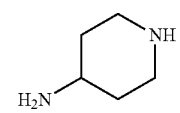 | 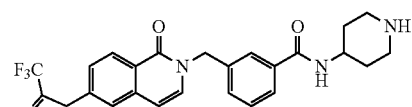 | 496.2 |

TABLE 2-continued

| Compd | R¹ | R2HN⁵R⁶ | Structure | MS found [M + H]⁺ |
|---|---|---|---|---|
| 47 | 3-(trifluoromethyl)-1H-pyrazole-4-boronic acid pinacol ester | 1-methyl-4-aminopiperidine | 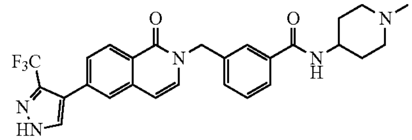 [SMILES: CN1CCC(NC(=O)c2cccc(Cn3ccc4cc(-c5c[nH]nc5C(F)(F)F)ccc4c3=O)c2)CC1] | 510.3 |
| 48 | 3-(trifluoromethyl)-1H-pyrazole-4-boronic acid pinacol ester | 1-(oxetan-3-yl)piperidin-4-amine | 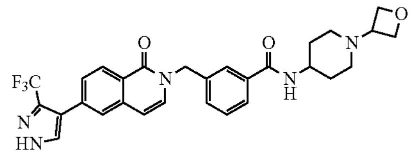 [SMILES: O=C(NC1CCN(C2COC2)CC1)c1cccc(Cn2ccc3cc(-c4c[nH]nc4C(F)(F)F)ccc3c2=O)c1] | 552.3 |
| 49 | 3-(trifluoromethyl)-1H-pyrazole-4-boronic acid pinacol ester | 1-(2,2-difluoroethyl)piperidin-4-amine | 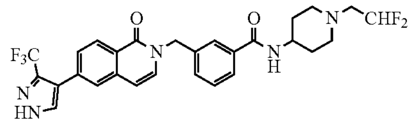 [SMILES: O=C(NC1CCN(CC(F)F)CC1)c1cccc(Cn2ccc3cc(-c4c[nH]nc4C(F)(F)F)ccc3c2=O)c1] | 560.5 |
| 50 | 3-(trifluoromethyl)-1H-pyrazole-4-boronic acid pinacol ester | cyclopropylamine | 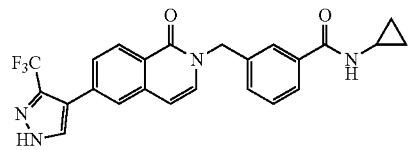 [SMILES: O=C(NC1CC1)c1cccc(Cn2ccc3cc(-c4c[nH]nc4C(F)(F)F)ccc3c2=O)c1] | 453.2 |
| 51 | 3-(trifluoromethyl)-1H-pyrazole-4-boronic acid pinacol ester | (1-methylpiperidin-4-yl)methanamine | 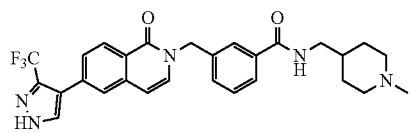 | 524.1 |
| 52 | 3-(trifluoromethyl)-1H-pyrazole-4-boronic acid pinacol ester | (tetrahydro-2H-pyran-4-yl)methanamine | 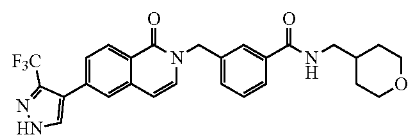 [SMILES: O=C(NCC1CCOCC1)c1cccc(Cn2ccc3cc(-c4c[nH]nc4C(F)(F)F)ccc3c2=O)c1] | 511.3 |
| 53 | 3-(trifluoromethyl)-1H-pyrazole-4-boronic acid pinacol ester | oxetan-3-ylmethanamine | 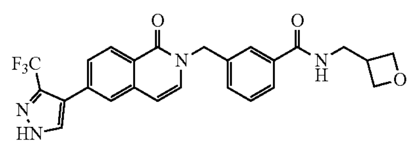 | 483.2 |
| 54 | 3-(trifluoromethyl)-1H-pyrazole-4-boronic acid pinacol ester | 2-(6-fluoropyridin-2-yl)ethan-1-amine | 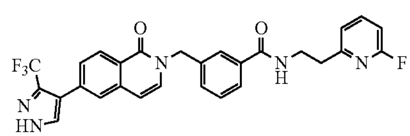 [SMILES: O=C(NCCc1cccc(F)n1)c1cccc(Cn2ccc3cc(-c4c[nH]nc4C(F)(F)F)ccc3c2=O)c1] | 536.2 |

TABLE 2-continued

| Compd | R¹ | R2HN⁵R⁶ | Structure | MS found [M + H]⁺ |
|---|---|---|---|---|
| 55 | | | 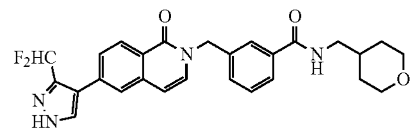 [SMILES: O=C(NCC1CCOCC1)c1cccc(Cn2ccc3cc(-c4c[nH]nc4C(F)F)ccc3c2=O)c1] | 493.2 |
| 56 | | | 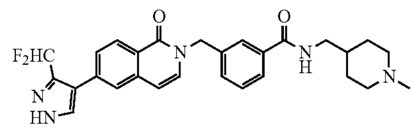 [SMILES: CN1CCC(CNC(=O)c2cccc(Cn3ccc4cc(-c5c[nH]nc5C(F)F)ccc4c3=O)c2)CC1] | 506.2 |
| 57 | | | 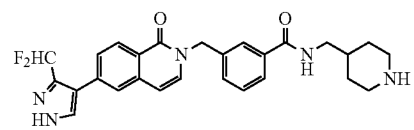 | 492.3 |
| 58 | | | 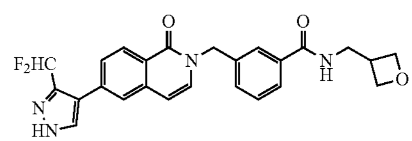 [SMILES: O=C(NCC1COC1)c1cccc(Cn2ccc3cc(-c4c[nH]nc4C(F)F)ccc3c2=O)c1] | 465.3 |
| 59 | | | 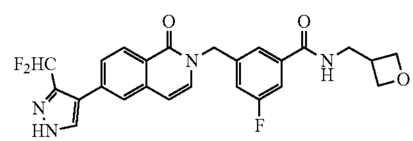 [SMILES: O=C(NCC1COC1)c1cc(F)cc(Cn2ccc3cc(-c4c[nH]nc4C(F)F)ccc3c2=O)c1] | 483.3 |
| 60 | | | 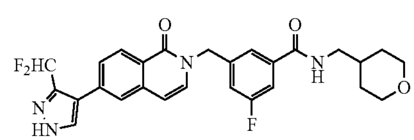 [SMILES: O=C(NCC1CCOCC1)c1cc(F)cc(Cn2ccc3cc(-c4c[nH]nc4C(F)F)ccc3c2=O)c1] | 511.3 |
| 61 | | | 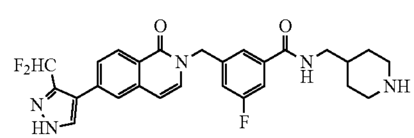 [SMILES: O=C(NCC1CCNCC1)c1cc(F)cc(Cn2ccc3cc(-c4c[nH]nc4C(F)F)ccc3c2=O)c1] | 510.4 |
| 62 | | | 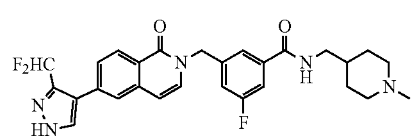 [SMILES: CN1CCC(CNC(=O)c2cc(F)cc(Cn3ccc4cc(-c5c[nH]nc5C(F)F)ccc4c3=O)c2)CC1] | 524.2 |

TABLE 2-continued
| Compd | R¹ | R2HN⁵R⁶ | Structure | MS found [M + H]⁺ |
|---|---|---|---|---|
| 63 | 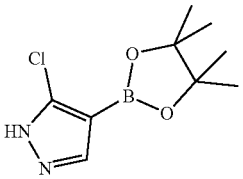 | 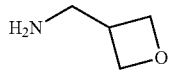 | 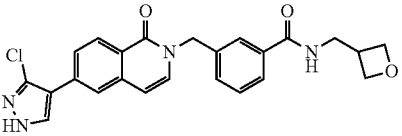 [SMILES: O=C(NCC1COC1)c1cccc(Cn2ccc3cc(-c4c[nH]nc4Cl)ccc3c2=O)c1] | 449.2 |
| 64 | 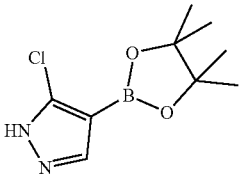 | 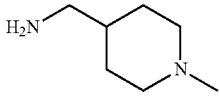 | 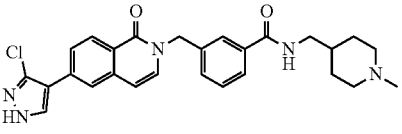 [SMILES: CN1CCC(CNC(=O)c2cccc(Cn3ccc4cc(-c5c[nH]nc5Cl)ccc4c3=O)c2)CC1] | 491.1 |
| 65 | 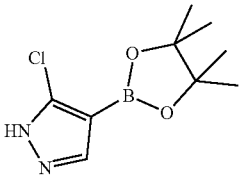 | 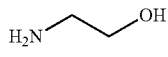 | 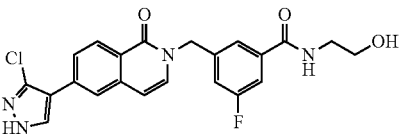 [SMILES: O=C(NCCO)c1cc(F)cc(Cn2ccc3cc(-c4c[nH]nc4Cl)ccc3c2=O)c1] | 441.3 |
| 66 | 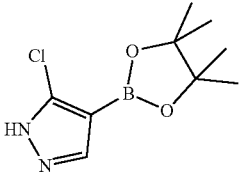 | 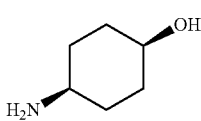 | 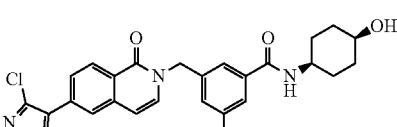 | 495.5 |
| 67 | 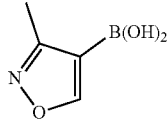 | 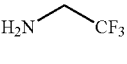 | 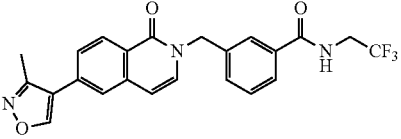 [SMILES: Cc1nocc1-c1ccc2c(=O)n(Cc3cccc(C(=O)NCC(F)(F)F)c3)ccc2c1] | 442.3 |
| 68 | 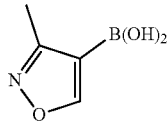 | 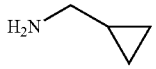 | 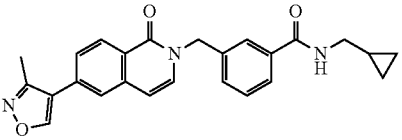 [SMILES: Cc1nocc1-c1ccc2c(=O)n(Cc3cccc(C(=O)NCC4CC4)c3)ccc2c1] | 414.1 |
| 69 | 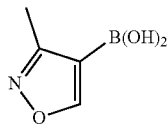 |  | 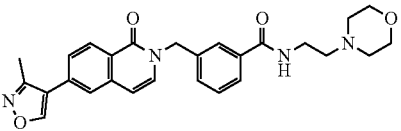 [SMILES: Cc1nocc1-c1ccc2c(=O)n(Cc3cccc(C(=O)NCCN4CCOCC4)c3)ccc2c1] | 473.2 |
| 70 | 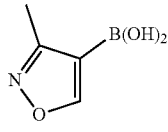 |  | 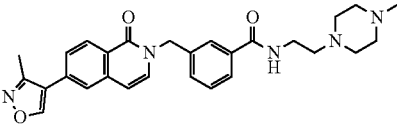 [SMILES: Cc1nocc1-c1ccc2c(=O)n(Cc3cccc(C(=O)NCCN4CCN(C)CC4)c3)ccc2c1] | 486.5 |
| 71 | 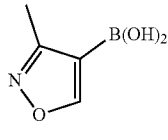 | 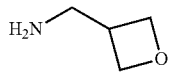 | 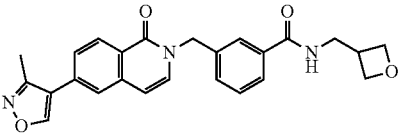 [SMILES: Cc1nocc1-c1ccc2c(=O)n(Cc3cccc(C(=O)NCC4COC4)c3)ccc2c1] | 430.2 |

TABLE 2-continued

| Compd | R¹ | R2HN⁵R⁶ | Structure | MS found [M + H]⁺ |
|---|---|---|---|---|
| 72 | 3-methylisoxazol-4-yl B(OH)₂ | cis-4-aminocyclobutanol | 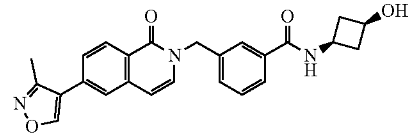 [SMILES: Cc1nocc1-c1ccc2c(=O)n(Cc3cccc(C(=O)N[C@H]4C[C@@H](O)C4)c3)ccc2c1] | 430.1 |
| 73 | 3-methylisoxazol-4-yl B(OH)₂ | trans-4-aminocyclobutanol | 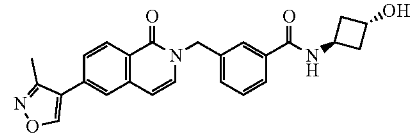 [SMILES: Cc1nocc1-c1ccc2c(=O)n(Cc3cccc(C(=O)N[C@H]4C[C@H](O)C4)c3)ccc2c1] | 430.2 |
| 74 | 3-methylisoxazol-4-yl B(OH)₂ | cis-4-aminocyclohexanol | 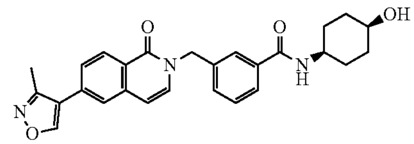 [SMILES: Cc1nocc1-c1ccc2c(=O)n(Cc3cccc(C(=O)N[C@H]4CC[C@@H](O)CC4)c3)ccc2c1] | 458.3 |
| 75 | 3-methylisoxazol-4-yl B(OH)₂ | trans-4-aminocyclohexanol | 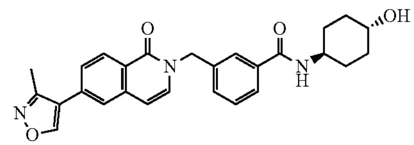 [SMILES: Cc1nocc1-c1ccc2c(=O)n(Cc3cccc(C(=O)N[C@H]4CC[C@H](O)CC4)c3)ccc2c1] | 458.4 |
| 76 | 3-methylisoxazol-4-yl B(OH)₂ | (6-fluoropyridin-3-yl)methanamine | 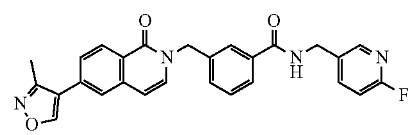 [SMILES: Cc1nocc1-c1ccc2c(=O)n(Cc3cccc(C(=O)NCc4ccc(F)nc4)c3)ccc2c1] | 469.5 |
| 77 | 3-methylisoxazol-4-yl B(OH)₂ | tetrahydro-2H-pyran-4-amine | 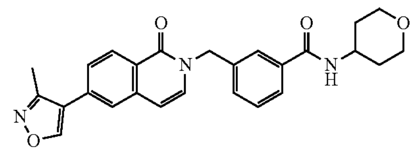 [SMILES: Cc1nocc1-c1ccc2c(=O)n(Cc3cccc(C(=O)NC4CCOCC4)c3)ccc2c1] | 444.2 |
| 78 | 3-methylisoxazol-4-yl B(OH)₂ | (1-methylpiperidin-4-yl)methanamine | 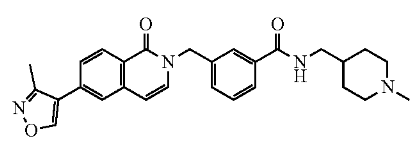 [SMILES: Cc1nocc1-c1ccc2c(=O)n(Cc3cccc(C(=O)NCC4CCN(C)CC4)c3)ccc2c1] | 471.2 |
| 79 | 3-methylisoxazol-4-yl B(OH)₂ | piperidin-4-ylmethanamine | HCl | 457.2 |
| 80 | 3-methylisoxazol-4-yl B(OH)₂ | (1-cyclopropylpiperidin-4-yl)methanamine | 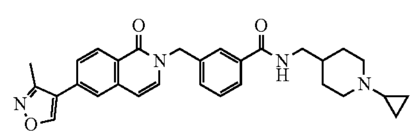 [SMILES: Cc1nocc1-c1ccc2c(=O)n(Cc3cccc(C(=O)NCC4CCN(C5CC5)CC4)c3)ccc2c1] | 497.2 |
| 81 | 3-methylisoxazol-4-yl B(OH)₂ | (1-isopropylpiperidin-4-yl)methanamine | 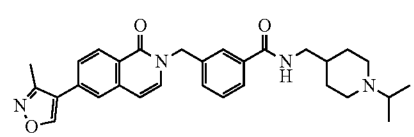 [SMILES: Cc1nocc1-c1ccc2c(=O)n(Cc3cccc(C(=O)NCC4CCN(C(C)C)CC4)c3)ccc2c1] | 499.5 |

TABLE 2-continued
| Compd | R¹ | R2HN⁵R⁶ | Structure | MS found [M + H]⁺ |
|---|---|---|---|---|
| 82 | 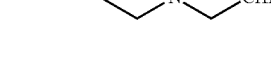 |  | 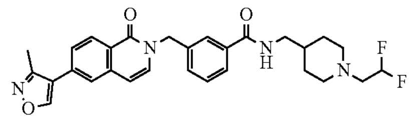 [SMILES: Cc1nocc1-c1ccc2c(=O)n(Cc3cccc(C(=O)NCC4CCN(CC(F)F)CC4)c3)ccc2c1] | 521.2 |
| 83 | 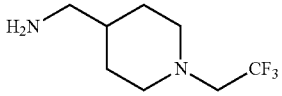 | 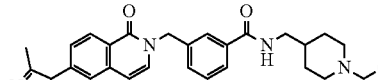 | 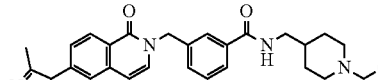 | 539.4 |
| 84 | 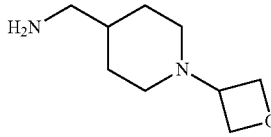 | 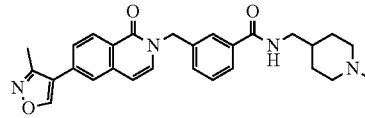 | 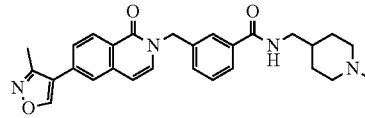 | 513.2 |
| 85 | 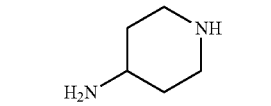 | 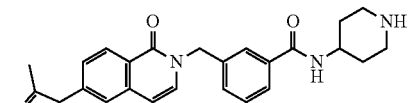 | 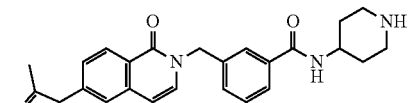 HCl | 443.6 |
| 86 | 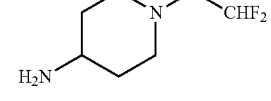 | 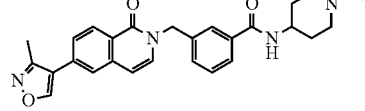 | 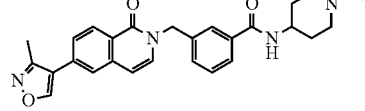 | 507.2 |
| 87 | 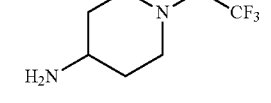 | 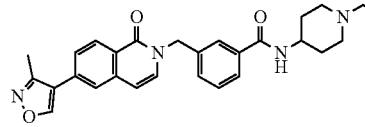 | 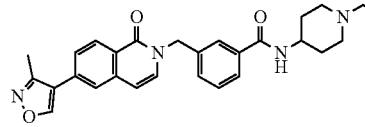 | 525.3 |
| 88 | 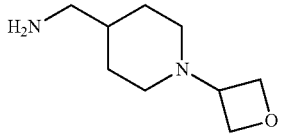 | 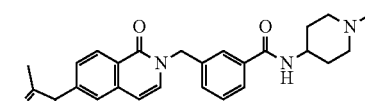 | 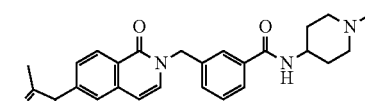 | 499.1 |
| 89 | 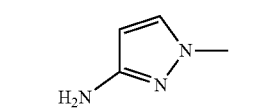 | 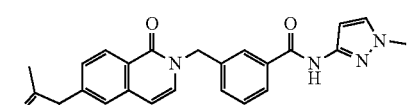 | 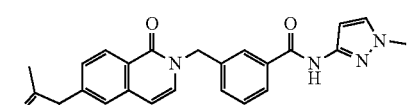 | 440.2 |
| 90 | 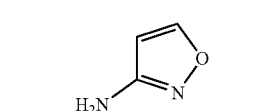 | 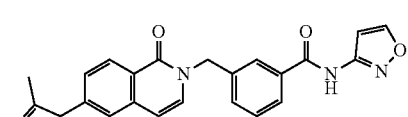 | 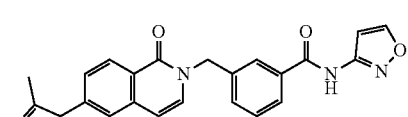 | 427.4 |
| 91 | 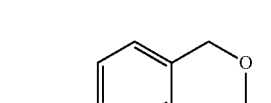 | 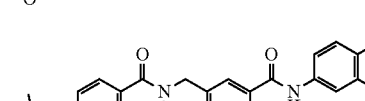 | 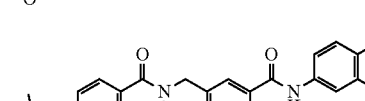 | 492.1 |

TABLE 2-continued
| Compd | R¹ | R2HN⁵R⁶ | Structure | MS found [M + H]⁺ |
|---|---|---|---|---|
| 92 | 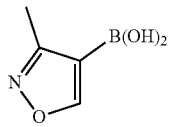 | 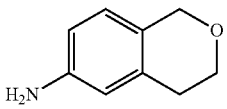 | 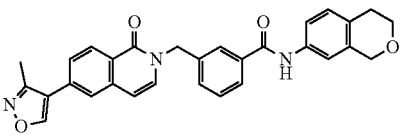 [SMILES: Cc1nocc1-c1ccc2c(=O)n(Cc3cccc(C(=O)Nc4ccc5c(c4)COCC5)c3)ccc2c1] | 492.1 |
| 93 | 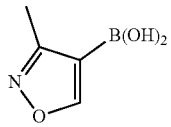 | 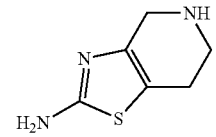 | 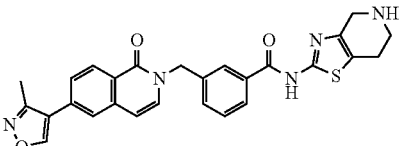 | 498.5 |
| 94 | 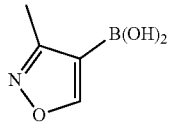 | 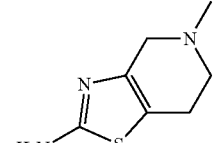 | 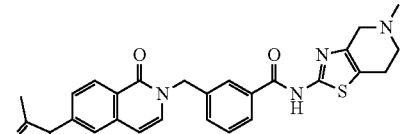 | 512.3 |
| 95 | 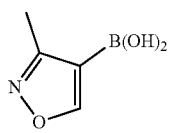 | 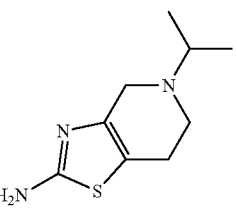 | 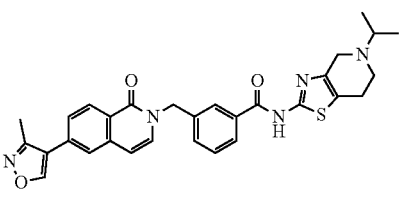 [SMILES: Cc1nocc1-c1ccc2c(=O)n(Cc3cccc(C(=O)Nc4nc5c(s4)CCN(C(C)C)C5)c3)ccc2c1] | 540.2 |
| 96 | 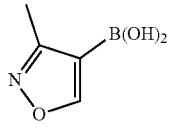 | 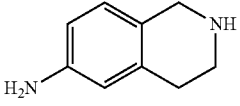 | 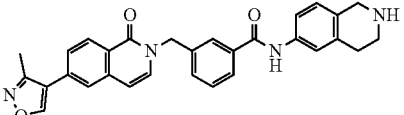 | 491.2 |
| 97 | 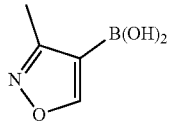 | 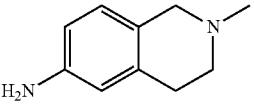 | 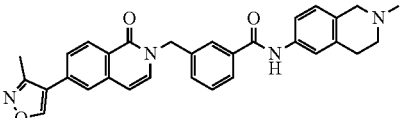 | 505.2 |
| 98 | 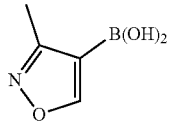 | 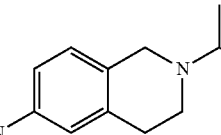 | 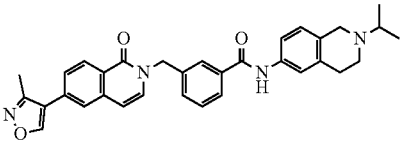 [SMILES: Cc1nocc1-c1ccc2c(=O)n(Cc3cccc(C(=O)Nc4ccc5c(c4)CCN(C(C)C)C5)c3)ccc2c1] | 533.3 |
| 99 | 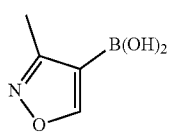 | 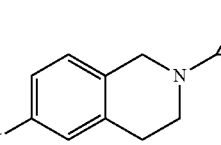 | 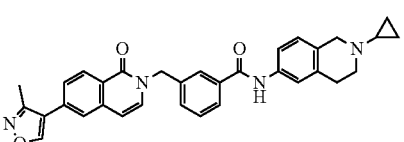 | 531.4 |
| 100 | 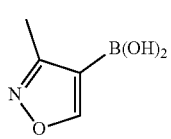 | 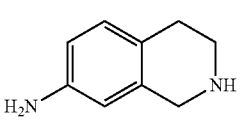 | 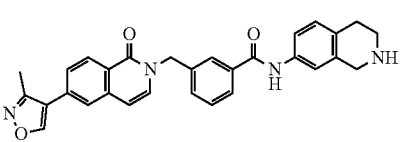 [SMILES: Cc1nocc1-c1ccc2c(=O)n(Cc3cccc(C(=O)Nc4ccc5c(c4)CN(C)CC5)c3)ccc2c1] | 491.2 |

TABLE 2-continued
| Compd | R¹ | R2HN⁵R⁶ | Structure | MS found [M + H]⁺ |
|---|---|---|---|---|
| 101 | 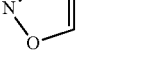 | 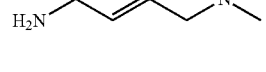 | 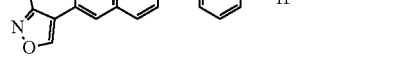 | 505.3 |
| 102 | 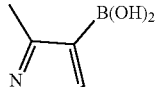 | 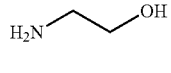 | 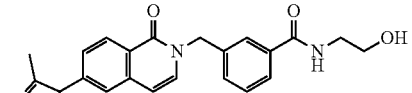 | 404.2 |
| 103 | 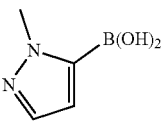 | 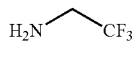 | 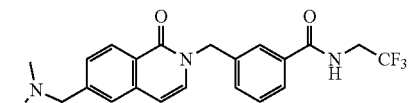 | 441.3 |
| 104 | 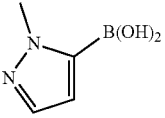 | 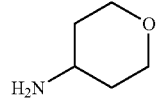 | 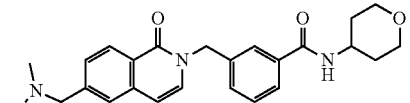 | 443.1 |
| 105 | 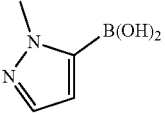 | 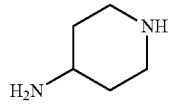 | 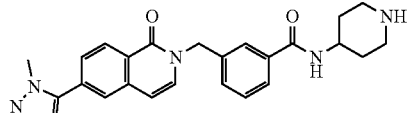 | 442.4 |
| 106 | 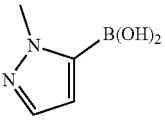 | 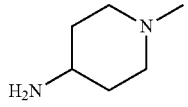 | 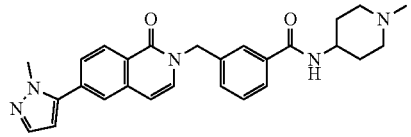 [SMILES: CN1CCC(NC(=O)c2cccc(Cn3ccc4cc(-c5ccnn5C)ccc4c3=O)c2)CC1] | 456.3 |
| 107 | 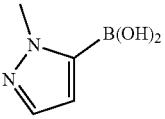 | 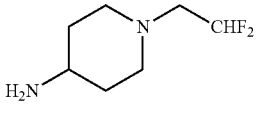 | 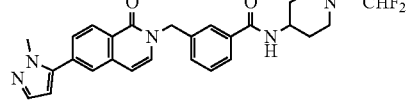 | 506.2 |
| 108 | 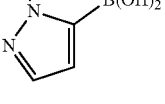 | 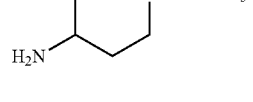 | 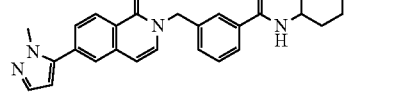 | 524.2 |
| 109 |  | 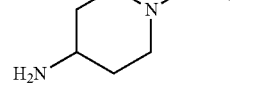 | 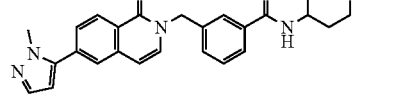 | 498.3 |
| 110 | 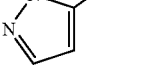 | 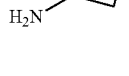 | 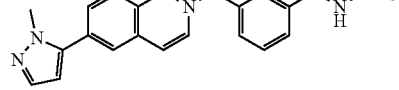 | 415.2 |

US 12,064,426 B2
TABLE 2-continued
| Compd | R¹ | R2HN⁵R⁶ | Structure | MS found [M + H]⁺ |
|---|---|---|---|---|
| 111 | 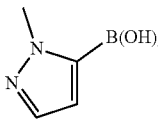 | 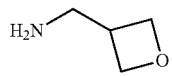 | 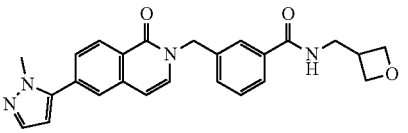 [SMILES: Cn1nccc1-c1ccc2c(=O)n(Cc3cccc(C(=O)NCC4COC4)c3)ccc2c1] | 429.4 |
| 112 | 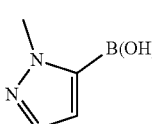 | 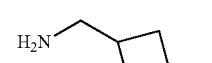 | 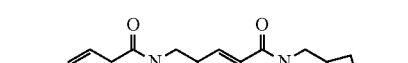 | 443.2 |
| 113 | 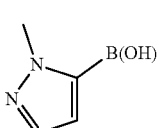 | 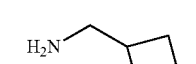 | 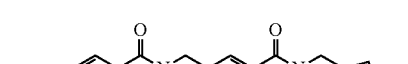 | 442.1 |
| 114 | 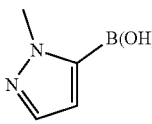 | 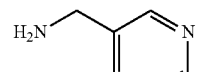 | 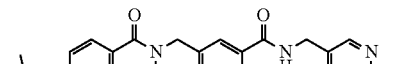 | 468.1 |
| 115 | 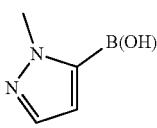 | 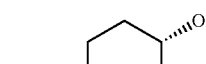 | 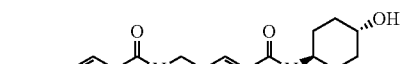 | 457.2 |
| 116 | 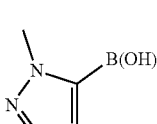 | 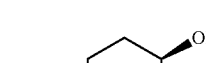 | 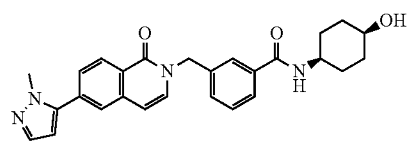 [SMILES: Cn1nccc1-c1ccc2c(=O)n(Cc3cccc(C(=O)N[C@H]4CC[C@@H](O)CC4)c3)ccc2c1] | 457.1 |
| 117 | 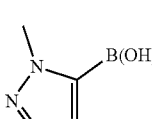 | 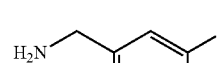 | 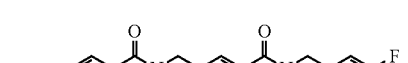 | 468.2 |
| 118 | 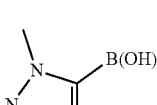 |  | 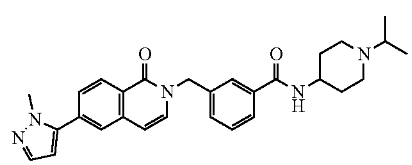 [SMILES: CC(C)N1CCC(NC(=O)c2cccc(Cn3ccc4cc(-c5ccnn5C)ccc4c3=O)c2)CC1] | 484.3 |
| 119 | 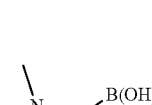 | 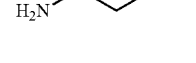 | 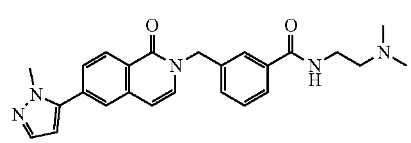 [SMILES: CN(C)CCNC(=O)c1cccc(Cn2ccc3cc(-c4ccnn4C)ccc3c2=O)c1] | 430.2 |
| 120 | 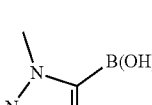 | 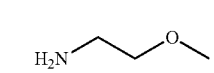 | 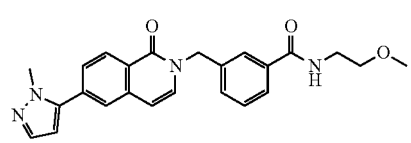 [SMILES: COCCNC(=O)c1cccc(Cn2ccc3cc(-c4ccnn4C)ccc3c2=O)c1] | 417.3 |

TABLE 2-continued

| Compd | R¹ | R2HN⁵R⁶ | Structure | MS found [M + H]⁺ |
|---|---|---|---|---|
| 121 | | | 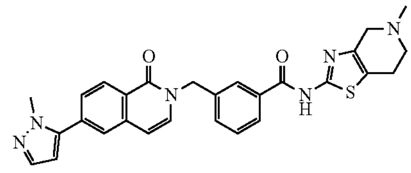 [SMILES: CN1CCc2sc(NC(=O)c3cccc(Cn4ccc5cc(-c6ccnn6C)ccc5c4=O)c3)nc2C1] | 511.5 |
| 122 | | | 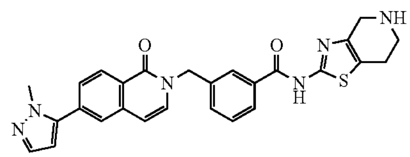 [SMILES: Cn1nccc1-c1ccc2c(=O)n(Cc3cccc(C(=O)Nc4nc5c(s4)CCNC5)c3)ccc2c1] | 497.4 |
| 123 | | | 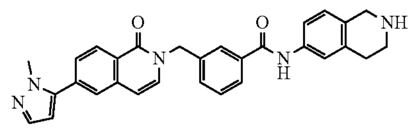 | 483.2 |
| 124 | | | 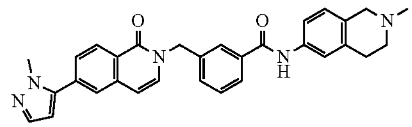 [SMILES: CN1CCc2cc(NC(=O)c3cccc(Cn4ccc5cc(-c6ccnn6C)ccc5c4=O)c3)ccc2C1] | 504.2 |
| 125 | | | 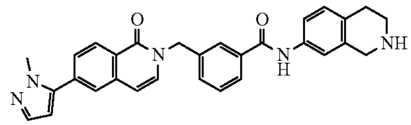 [SMILES: Cn1nccc1-c1ccc2c(=O)n(Cc3cccc(C(=O)Nc4ccc5c(c4)CNCC5)c3)ccc2c1] | 490.4 |
| 126 | | | 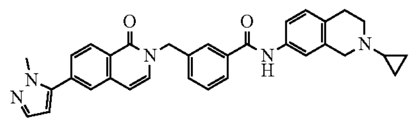 [SMILES: Cn1nccc1-c1ccc2c(=O)n(Cc3cccc(C(=O)Nc4ccc5c(c4)CN(C4CC4)CC5)c3)ccc2c1] | 530.4 |
| 127 | | | 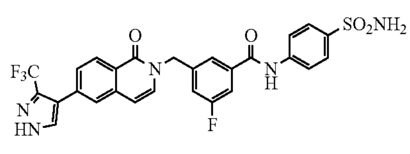 [SMILES: NS(=O)(=O)c1ccc(NC(=O)c2cc(F)cc(Cn3ccc4cc(-c5c[nH]nc5C(F)(F)F)ccc4c3=O)c2)cc1] | 586.2 |
| 128 | | | 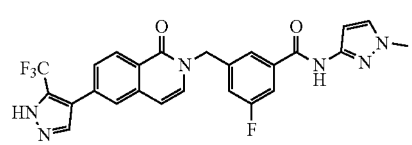 [SMILES: Cn1ccc(NC(=O)c2cc(F)cc(Cn3ccc4cc(-c5cn[nH]c5C(F)(F)F)ccc4c3=O)c2)n1] | 511.1 |
| 129 | | | 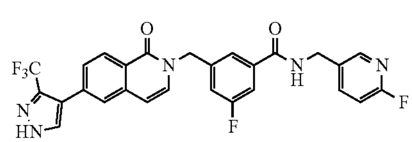 [SMILES: O=C(NCc1ccc(F)nc1)c1cc(F)cc(Cn2ccc3cc(-c4c[nH]nc4C(F)(F)F)ccc3c2=O)c1] | 540.3 |

TABLE 2-continued

| Compd | R¹ | R2HN⁵R⁶ | Structure | MS found [M + H]⁺ |
|---|---|---|---|---|
| 130 | F₃C-pyrazole-Bpin | 4-aminotetrahydropyran | 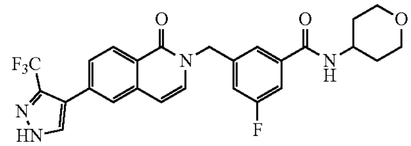 [SMILES: O=C(NC1CCOCC1)c1cc(F)cc(Cn2ccc3cc(-c4c[nH]nc4C(F)(F)F)ccc3c2=O)c1] | 515.3 |
| 131 | F₃C-pyrazole-Bpin | 4-aminopiperidine | 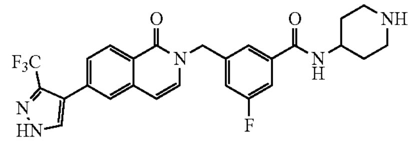 [SMILES: O=C(NC1CCNCC1)c1cc(F)cc(Cn2ccc3cc(-c4c[nH]nc4C(F)(F)F)ccc3c2=O)c1] | 514.3 |
| 132 | F₃C-pyrazole-Bpin | 4-amino-1-methylpiperidine | 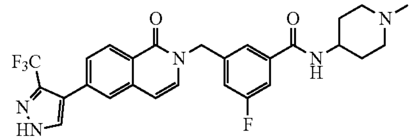 | 528.1 |
| 133 | F₃C-pyrazole-Bpin | cyclopropylamine | 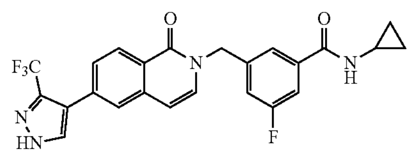 [SMILES: O=C(NC1CC1)c1cc(F)cc(Cn2ccc3cc(-c4c[nH]nc4C(F)(F)F)ccc3c2=O)c1] | 471.2 |
| 134 | F₃C-pyrazole-Bpin | (1-methylpiperidin-4-yl)methanamine | 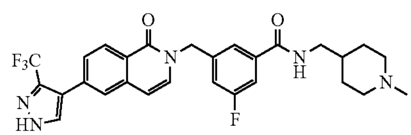 [SMILES: CN1CCC(CNC(=O)c2cc(F)cc(Cn3ccc4cc(-c5c[nH]nc5C(F)(F)F)ccc4c3=O)c2)CC1] | 542.3 |
| 135 | F₃C-pyrazole-Bpin | (tetrahydropyran-4-yl)methanamine | 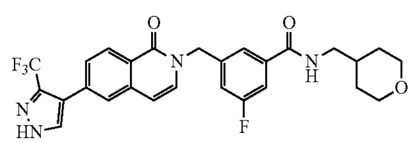 [SMILES: O=C(NCC1CCOCC1)c1cc(F)cc(Cn2ccc3cc(-c4c[nH]nc4C(F)(F)F)ccc3c2=O)c1] | 529.4 |
| 136 | F₃C-pyrazole-Bpin | oxetan-3-ylmethanamine | 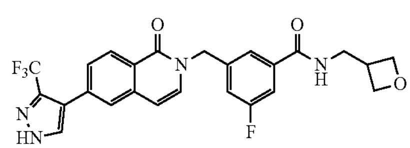 [SMILES: O=C(NCC1COC1)c1cc(F)cc(Cn2ccc3cc(-c4c[nH]nc4C(F)(F)F)ccc3c2=O)c1] | 501.2 |
| 137 | 3-methylisoxazole-B(OH)₂ | cis-3-aminocyclobutanol | 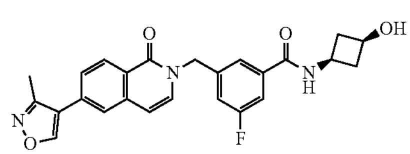 [SMILES: Cc1nocc1-c1ccc2c(=O)n(Cc3cc(F)cc(C(=O)N[C@H]4C[C@@H](O)C4)c3)ccc2c1] | 448.2 |

TABLE 2-continued
| Compd | R¹ | R2HN⁵R⁶ | Structure | MS found [M + H]⁺ |
|---|---|---|---|---|
| 138 | 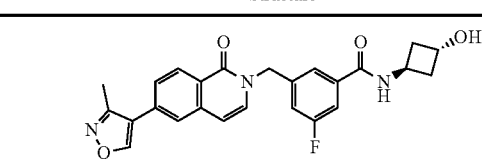 | 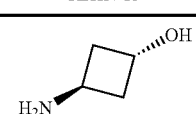 | 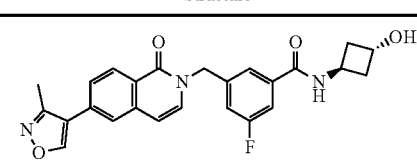 | 448.1 |
| 139 | 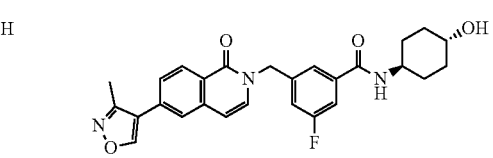 | 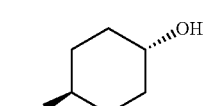 | 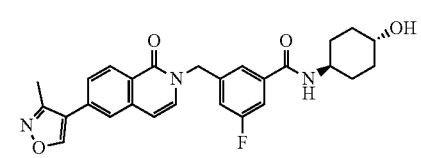 | 476.5 |
| 140 | 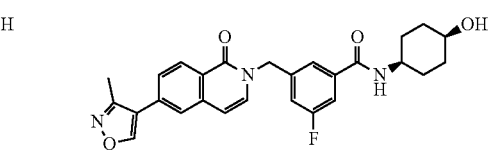 | 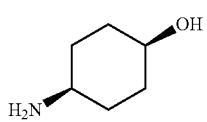 | 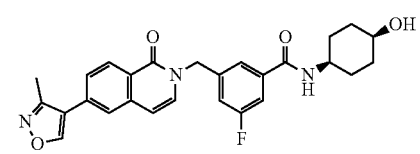 [SMILES: Cc1nocc1-c1ccc2c(=O)n(Cc3cc(F)cc(C(=O)N[C@H]4CC[C@@H](O)CC4)c3)ccc2c1] | 476.1 |
| 141 | 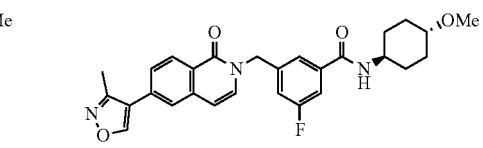 | 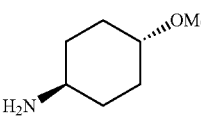 | 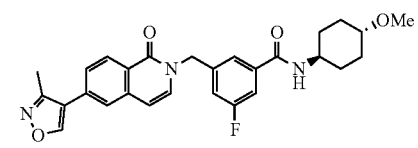 | 490.2 |
| 142 | 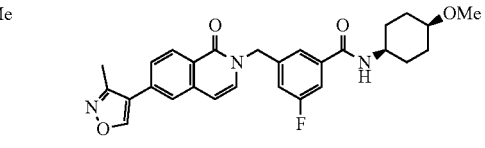 | 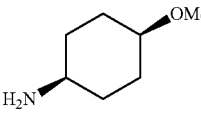 | 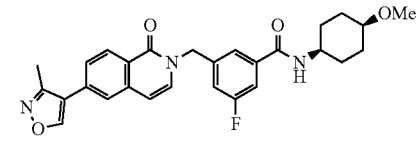 [SMILES: CO[C@H]1CC[C@H](NC(=O)c2cc(F)cc(Cn3ccc4cc(-c5conc5C)ccc4c3=O)c2)CC1] | 490.3 |
| 143 | 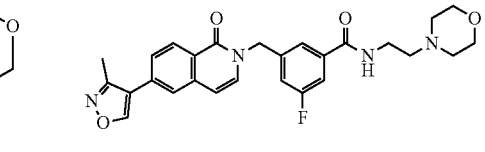 | 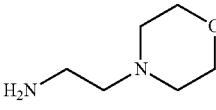 | 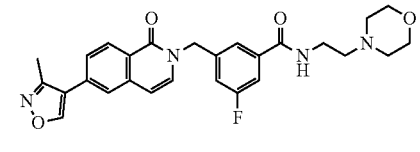 [SMILES: Cc1nocc1-c1ccc2c(=O)n(Cc3cc(F)cc(C(=O)NCCN4CCOCC4)c3)ccc2c1] | 491.4 |
| 144 | 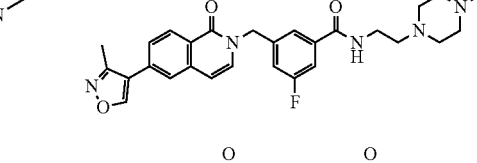 | 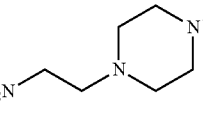 | 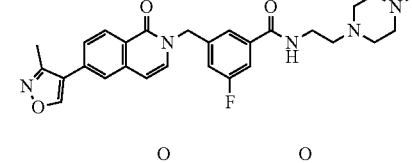 | 504.3 |
| 145 | 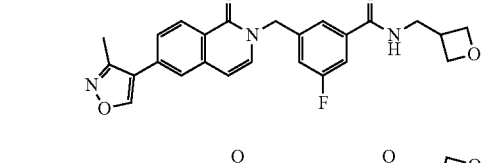 |  | 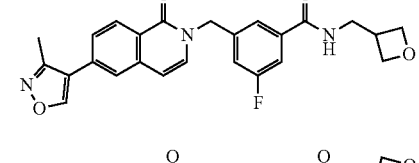 | 447.1 |
| 146 | 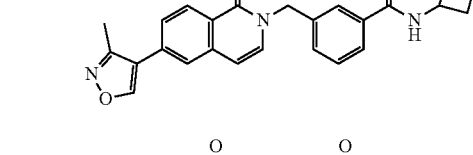 | 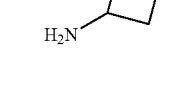 | 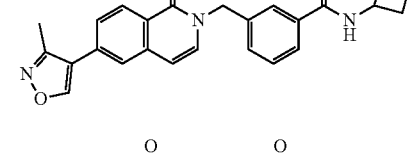 | 416.2 |
| 147 | 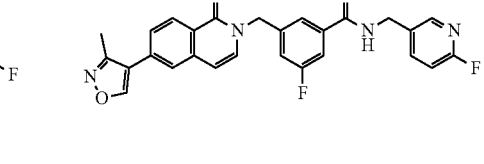 | 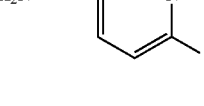 | 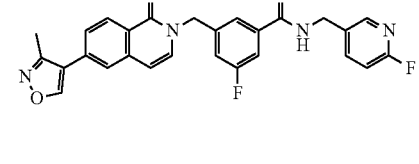 | 487.4 |

TABLE 2-continued

| Compd | R¹ | R2HN⁵R⁶ | Structure | MS found [M + H]⁺ |
|---|---|---|---|---|
| 148 | 3-methylisoxazol-4-yl-B(OH)₂ | 4-aminotetrahydropyran | 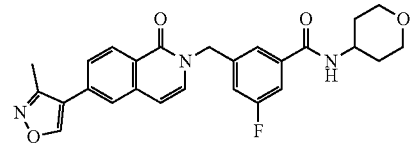 [SMILES: Cc1nocc1-c1ccc2c(=O)n(Cc3cc(F)cc(C(=O)NC4CCOCC4)c3)ccc2c1] | 462.5 |
| 149 | 3-methylisoxazol-4-yl-B(OH)₂ | (1-methylpiperidin-4-yl)methanamine | 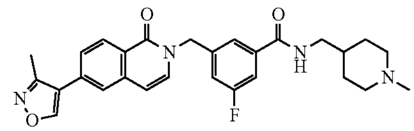 [SMILES: Cc1nocc1-c1ccc2c(=O)n(Cc3cc(F)cc(C(=O)NCC4CCN(C)CC4)c3)ccc2c1] | 489.4 |
| 150 | 3-methylisoxazol-4-yl-B(OH)₂ | piperidin-4-ylmethanamine | 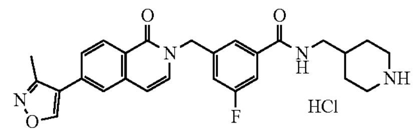 [SMILES: Cc1nocc1-c1ccc2c(=O)n(Cc3cc(F)cc(C(=O)NCC4CCNCC4)c3)ccc2c1 ; Cl] | 475.2 (HCl) |
| 151 | 3-methylisoxazol-4-yl-B(OH)₂ | (1-cyclopropylpiperidin-4-yl)methanamine | 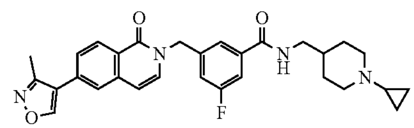 [SMILES: Cc1nocc1-c1ccc2c(=O)n(Cc3cc(F)cc(C(=O)NCC4CCN(C5CC5)CC4)c3)ccc2c1] | 515.2 |
| 152 | 3-methylisoxazol-4-yl-B(OH)₂ | (1-isopropylpiperidin-4-yl)methanamine | 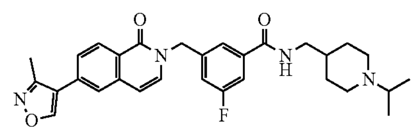 [SMILES: Cc1nocc1-c1ccc2c(=O)n(Cc3cc(F)cc(C(=O)NCC4CCN(C(C)C)CC4)c3)ccc2c1] | 517.3 |
| 153 | 3-methylisoxazol-4-yl-B(OH)₂ | (1-(2,2,2-trifluoroethyl)piperidin-4-yl)methanamine | 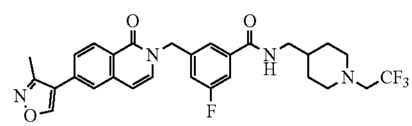 [SMILES: Cc1nocc1-c1ccc2c(=O)n(Cc3cc(F)cc(C(=O)NCC4CCN(CC(F)(F)F)CC4)c3)ccc2c1] | 557.2 |
| 154 | 3-methylisoxazol-4-yl-B(OH)₂ | (1-(oxetan-3-yl)piperidin-4-yl)methanamine | 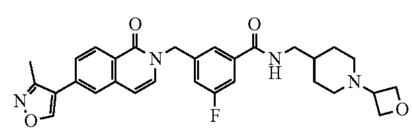 [SMILES: Cc1nocc1-c1ccc2c(=O)n(Cc3cc(F)cc(C(=O)NCC4CCN(C5COC5)CC4)c3)ccc2c1] | 531.4 |
| 155 | 3-methylisoxazol-4-yl-B(OH)₂ | 1-methylpiperidin-4-amine | 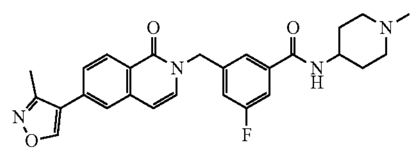 [SMILES: Cc1nocc1-c1ccc2c(=O)n(Cc3cc(F)cc(C(=O)NC4CCN(C)CC4)c3)ccc2c1] | 545.3 |
| 156 | 3-methylisoxazol-4-yl-B(OH)₂ | 1-methyl-1H-pyrazol-3-amine | 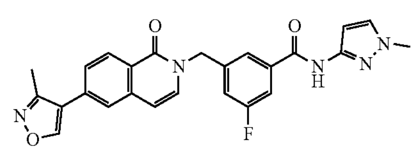 [SMILES: Cc1nocc1-c1ccc2c(=O)n(Cc3cc(F)cc(C(=O)Nc4ccn(C)n4)c3)ccc2c1] | 458.3 |
| 157 | 3-methylisoxazol-4-yl-B(OH)₂ | 4,5,6,7-tetrahydrothiazolo[5,4-c]pyridin-2-amine | 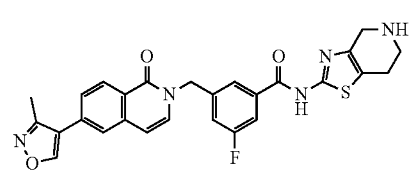 [SMILES: Cc1nocc1-c1ccc2c(=O)n(Cc3cc(F)cc(C(=O)Nc4nc5c(s4)CCNC5)c3)ccc2c1] | 516.2 |

TABLE 2-continued

| Compd | R¹ | R2HN⁵R⁶ | Structure | MS found [M + H]⁺ |
|---|---|---|---|---|
| 158 | 3-methylisoxazol-4-yl B(OH)₂ | 5-methyl-4,5,6,7-tetrahydrothiazolo[5,4-c]pyridin-2-amine | (structure) | 530.2 |
| 159 | 3-methylisoxazol-4-yl B(OH)₂ | 5-isopropyl-4,5,6,7-tetrahydrothiazolo[5,4-c]pyridin-2-amine | (structure) | 558.2 |
| 160 | 3-methylisoxazol-4-yl B(OH)₂ | 1,2,3,4-tetrahydroisoquinolin-6-amine | (structure) | 509.4 |
| 161 | 3-methylisoxazol-4-yl B(OH)₂ | 2-cyclopropyl-1,2,3,4-tetrahydroisoquinolin-7-amine | (structure) | 549.2 |
| 162 | 3-methylisoxazol-4-yl B(OH)₂ | 1,2,3,4-tetrahydroisoquinolin-6-amine | (structure) | 509.5 |
| 163 | 3-methylisoxazol-4-yl B(OH)₂ | 2-methyl-1,2,3,4-tetrahydroisoquinolin-6-amine | (structure) | 523.3 |
| 164 | 1-methyl-1H-pyrazol-5-yl B(OH)₂ | trans-4-aminocyclohexan-1-ol | (structure) | 475.2 |
| 165 | 1-methyl-1H-pyrazol-5-yl B(OH)₂ | cis-4-aminocyclohexan-1-ol | (structure) | 475.1 |
| 166 | 1-methyl-1H-pyrazol-5-yl B(OH)₂ | tetrahydro-2H-pyran-4-amine | (structure) | 461.1 |
| 167 | 1-methyl-1H-pyrazol-5-yl B(OH)₂ | 3-(aminomethyl)cyclobutan-1-ol | (structure) | 443.2 |

TABLE 2-continued

| Compd | R¹ | R2HN⁵R⁶ | Structure | MS found [M + H]⁺ |
|---|---|---|---|---|
| 168 | 1-methylpyrazol-5-yl-B(OH)₂ | H₂N-CH₂-(1-methylazetidin-3-yl) | 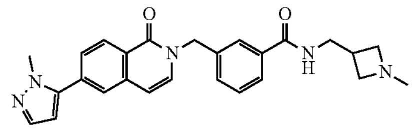 [SMILES: CN1CC(CNC(=O)c2cccc(Cn3ccc4cc(-c5ccnn5C)ccc4c3=O)c2)C1] | 442.2 |
| 169 | 1-methylpyrazol-5-yl-B(OH)₂ | H₂N-CH₂-(piperidin-4-yl) | 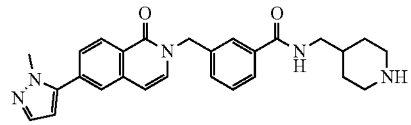 | 456.2 |
| 170 | 1-methylpyrazol-5-yl-B(OH)₂ | H₂N-CH₂-[1-(2,2-difluoroethyl)piperidin-4-yl] | 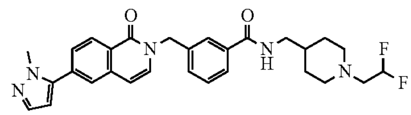 [SMILES: Cn1nccc1-c1ccc2c(=O)n(Cc3cccc(C(=O)NCC4CCN(CC(F)F)CC4)c3)ccc2c1] | 520.3 |
| 171 | 1-methylpyrazol-5-yl-B(OH)₂ | H₂N-CH₂-(1-methylpiperidin-4-yl) | 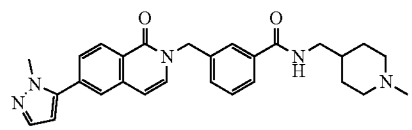 [SMILES: CN1CCC(CNC(=O)c2cccc(Cn3ccc4cc(-c5ccnn5C)ccc4c3=O)c2)CC1] | 470.2 |
| 172 | 1-methylpyrazol-5-yl-B(OH)₂ | H₂N-CH₂-(1-methylpiperidin-4-yl) | 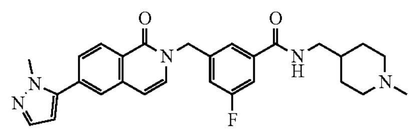 [SMILES: CN1CCC(CNC(=O)c2cc(F)cc(Cn3ccc4cc(-c5ccnn5C)ccc4c3=O)c2)CC1] | 488.3 |
| 173 | 1-methylpyrazol-5-yl-B(OH)₂ | H₂N-CH₂-(piperidin-4-yl) | HCl | 474.2 |
| 174 | 1-methylpyrazol-5-yl-B(OH)₂ | H₂N-CH₂-(6-fluoropyridin-3-yl) | 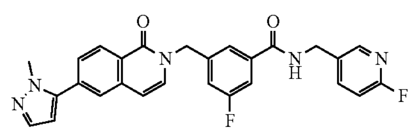 | 486.3 |
| 175 | 1-methylpyrazol-5-yl-B(OH)₂ | 1-isopropyl-4-aminopiperidine | 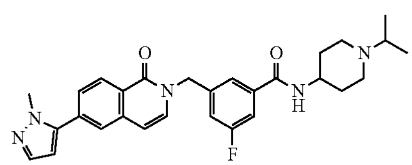 [SMILES: CC(C)N1CCC(NC(=O)c2cc(F)cc(Cn3ccc4cc(-c5ccnn5C)ccc4c3=O)c2)CC1] | 502.4 |
| 176 | 1-methylpyrazol-5-yl-B(OH)₂ | 1-methyl-4-aminopiperidine | 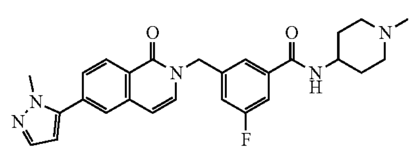 [SMILES: CN1CCC(NC(=O)c2cc(F)cc(Cn3ccc4cc(-c5ccnn5C)ccc4c3=O)c2)CC1] | 474.3 |
| 177 | 1-methylpyrazol-5-yl-B(OH)₂ | 4-aminopiperidine | HCl | 460.2 |

TABLE 2-continued

| Compd | R¹ | R2HN⁵R⁶ | Structure | MS found [M + H]⁺ |
|---|---|---|---|---|
| 178 | 1-methyl-pyrazole-5-boronic acid | N,N-dimethylethylenediamine | (structure) | 478.3 |
| 179 | 1-methyl-pyrazole-5-boronic acid | 3-amino-1-methylpyrazole | (structure) | 457.2 |
| 180 | pyridine-4-boronic acid | 2-(2-methylpyridin-4-yl)ethylamine | (structure) | 478.2 |
| 181 | 2-aminopyridine-4-boronic acid | benzylamine | (structure) | 461.2 |
| 182 | 2-aminopyridine-4-boronic acid | 2-naphthylmethylamine | (structure) | 511.4 |
| 183 | 2-aminopyridine-4-boronic acid | 1,2-bis(aminomethyl)benzene | (structure) | 490.2 |
| 184 | 2-aminopyridine-4-boronic acid | 2-(aminomethyl)benzyl alcohol | (structure) | 491.3 |
| 185 | 2-aminopyridine-4-boronic acid | 2-phenylethylamine | (structure) | 475.4 |
| 186 | 2-aminopyridine-4-boronic acid | 2-(pyridin-2-yl)ethylamine | (structure) | 476.2 |

TABLE 2-continued

| Compd | R¹ | R2HN⁵R⁶ | Structure | MS found [M + H]⁺ |
|---|---|---|---|---|
| 187 | 2-aminopyridin-4-yl boronic acid | 7-amino-1,2,3,4-tetrahydroisoquinoline | 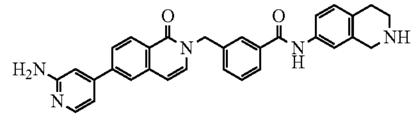 [SMILES: Nc1cc(-c2ccc3c(=O)n(Cc4cccc(C(=O)Nc5ccc6c(c5)CNCC6)c4)ccc3c2)ccn1] | 502.3 |
| 188 | 2-aminopyridin-4-yl boronic acid | 6-amino-1,2,3,4-tetrahydroisoquinoline | 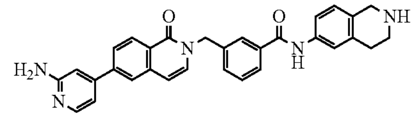 [SMILES: Nc1cc(-c2ccc3c(=O)n(Cc4cccc(C(=O)Nc5ccc6c(c5)CCNC6)c4)ccc3c2)ccn1] | 502.4 |
| 189 | 2-aminopyridin-4-yl boronic acid | 6-amino-2-methyl-1,2,3,4-tetrahydroisoquinoline | 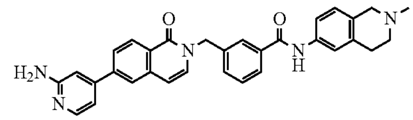 [SMILES: CN1CCc2cc(NC(=O)c3cccc(Cn4ccc5cc(-c6ccnc(N)c6)ccc5c4=O)c3)ccc2C1] | 516.4 |
| 190 | 2-aminopyridin-4-yl boronic acid | 2-amino-4,5,6,7-tetrahydrothiazolo[5,4-c]pyridine | 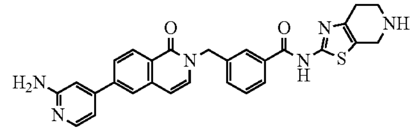 | 508.4 |
| 191 | 2-aminopyridin-4-yl boronic acid | 2-amino-5-methyl-4,5,6,7-tetrahydrothiazolo[5,4-c]pyridine | 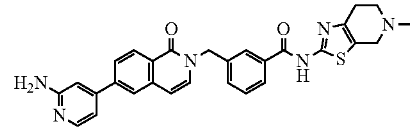 [SMILES: CN1CCc2nc(NC(=O)c3cccc(Cn4ccc5cc(-c6ccnc(N)c6)ccc5c4=O)c3)sc2C1] | 512.4 |
| 192 | 2-aminopyridin-4-yl boronic acid | trans-4-aminocyclohexanol | 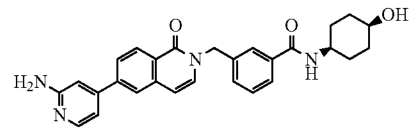 [SMILES: Nc1cc(-c2ccc3c(=O)n(Cc4cccc(C(=O)N[C@H]5CC[C@@H](O)CC5)c4)ccc3c2)ccn1] | 469.4 |
| 193 | 2-aminopyridin-4-yl boronic acid | cis-4-aminocyclohexanol | 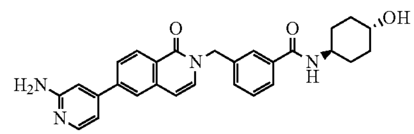 [SMILES: Nc1cc(-c2ccc3c(=O)n(Cc4cccc(C(=O)N[C@H]5CC[C@H](O)CC5)c4)ccc3c2)ccn1] | 469.3 |
| 194 | 2-aminopyridin-4-yl boronic acid | 4-aminotetrahydropyran | 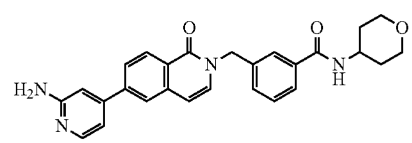 [SMILES: Nc1cc(-c2ccc3c(=O)n(Cc4cccc(C(=O)NC5CCOCC5)c4)ccc3c2)ccn1] | 455.1 |
| 195 | 2-aminopyridin-4-yl boronic acid | 3-aminooxetane | 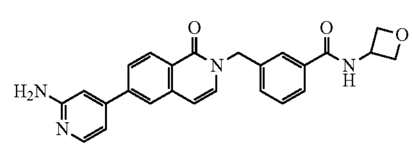 [SMILES: Nc1cc(-c2ccc3c(=O)n(Cc4cccc(C(=O)NC5COC5)c4)ccc3c2)ccn1] | 427.3 |

TABLE 2-continued

| Compd | R¹ | R2HN5R6 | Structure | MS found [M + H]⁺ |
|---|---|---|---|---|
| 196 | H₂N-pyridine-B(OH)₂ | 6-amino-isochroman | [structure] | 503.4 |
| 197 | H₂N-pyridine-B(OH)₂ | 7-amino-isochroman | [structure] | 503.5 |
| 198 | H₂N-pyridine-B(OH)₂ | cyclopentylamine | [structure] | 439.2 |
| 199 | H₂N-pyridine-B(OH)₂ | 2-amino-imidazole | [structure] | 437.2 |
| 200 | H₂N-pyridine-B(OH)₂ | 3-amino-1-methylpyrazole | [structure] | 451.3 |
| 201 | H₂N-pyridine-B(OH)₂ | 3-amino-1-methylpyrazole | [structure] | 469.5 |
| 202 | H₂N-pyridine-B(OH)₂ | 3-aminooxetane | [structure] | 445.2 |
| 203 | H₂N-pyridine-B(OH)₂ | 5-aminoisoxazole | [structure] | 438.3 |
| 204 | H₂N-pyridine-B(OH)₂ | 3-aminoisoxazole | [structure] | 438.4 |

TABLE 2-continued

| Compd | R¹ | R2HN⁵R⁶ | Structure | MS found [M + H]⁺ |
|---|---|---|---|---|
| 205 | 2-aminopyridin-4-yl boronic acid | 3-aminoisoxazole | (structure) | 156.3 |
| 206 | morpholine | 3-aminoisoxazole | (structure) | 431.2 |
| 207 | morpholine | 3-aminooxetane | (structure) | 420.1 |
| 208 | morpholine | 3-aminooxetane | (structure) | 438.3 |
| 209 | morpholine | cis-3-aminocyclobutanol | (structure) | 452.2 |
| 210 | morpholine | trans-3-aminocyclobutanol | (structure) | 452.2 |
| 211 | morpholine | 4-aminotetrahydropyran | (structure) | 466.3 |
| 212 | morpholine | 4-aminotetrahydropyran | (structure) | 448.3 |
| 213 | morpholine | trans-4-aminocyclohexanol | (structure) | 462.2 |

TABLE 2-continued

| Compd | R¹ | R2HN⁵R⁶ | Structure | MS found [M + H]⁺ |
|---|---|---|---|---|
| 214 | morpholine-NH | trans-4-aminocyclohexanol | (structure) | 462.3 |
| 215 | morpholine-NH | trans-4-aminocyclohexanol | (structure with F) | 480.5 |
| 216 | morpholine-NH | 2-morpholinoethylamine | (structure) | 477.4 |
| 217 | morpholine-NH | (piperidin-4-yl)methanamine | (structure) HCl | 461.5 |
| 218 | morpholine-NH | (1-methylpiperidin-4-yl)methanamine | (structure) | 474.3 |
| 219 | morpholine-NH | (1-(2,2-difluoroethyl)piperidin-4-yl)methanamine | (structure) | 525.3 |
| 220 | morpholine-NH | (1-(2,2,2-trifluoroethyl)piperidin-4-yl)methanamine | (structure) | 543.2 |
| 221 | morpholine-NH | (1-(2,2,2-trifluoroethyl)piperidin-4-yl)methanamine | (structure with F) | 561.4 |
| 222 | morpholine-NH | (1-methylpiperidin-4-yl)methanamine | (structure with F) | 493.4 |
| 223 | morpholine-NH | (1-isopropylpiperidin-4-yl)methanamine | (structure) | 503.2 |
| 224 | morpholine-NH | (1-isopropylpiperidin-4-yl)methanamine | (structure with F) | 521.3 |

TABLE 2-continued
| Compd | R¹ | R2HN⁵R⁶ | Structure | MS found [M + H]⁺ |
|---|---|---|---|---|
| 225 |  | 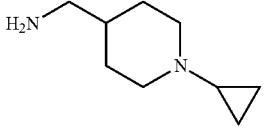 | 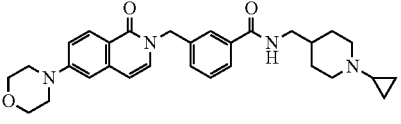 [SMILES: O=C(NCC1CCN(C2CC2)CC1)c1cccc(Cn2ccc3cc(N4CCOCC4)ccc3c2=O)c1] | 501.2 |
| 226 |  | 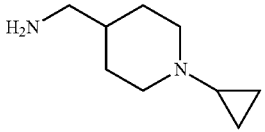 | 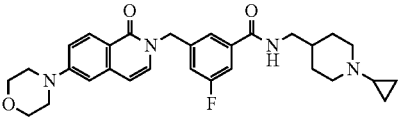 [SMILES: O=C(NCC1CCN(C2CC2)CC1)c1cc(F)cc(Cn2ccc3cc(N4CCOCC4)ccc3c2=O)c1] | 519.4 |
| 227 |  | 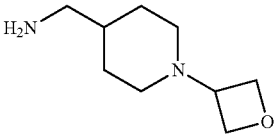 | 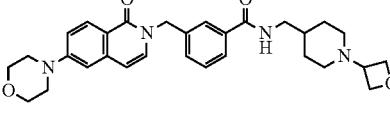 | 517.4 |
| 228 |  | 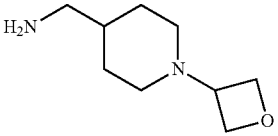 | 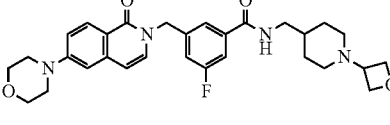 | 535.4 |
| 229 |  | 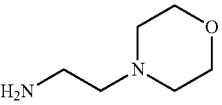 | 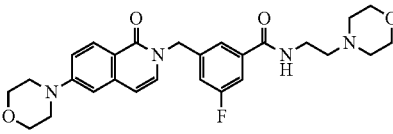 | 495.5 |
| 230 |  | 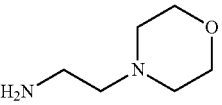 | 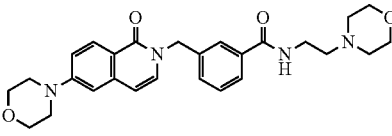 [SMILES: O=C(NCCN1CCOCC1)c1cccc(Cn2ccc3cc(N4CCOCC4)ccc3c2=O)c1] | 477.4 |
General Scheme 3
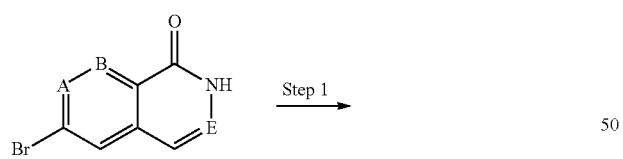
Step 1
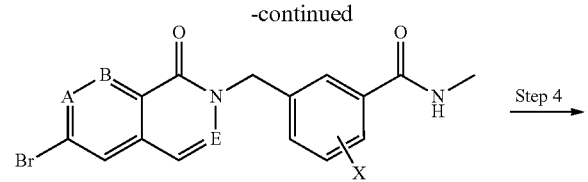
Step 4
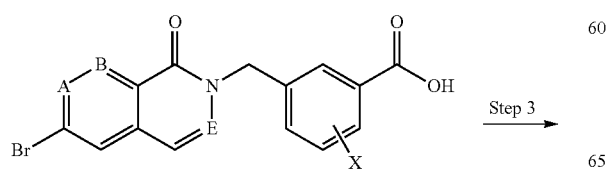
Step 2
Step 3
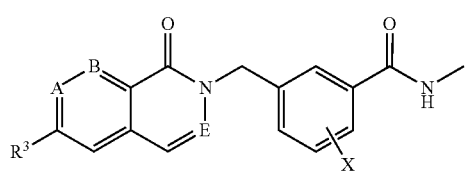

Compound 231: N-methyl-3-((6-(2-methyl-1H-pyrrol-3-yl)-1-oxo-2,7-naphthyridin-2(1H)-yl)methyl)benzamide

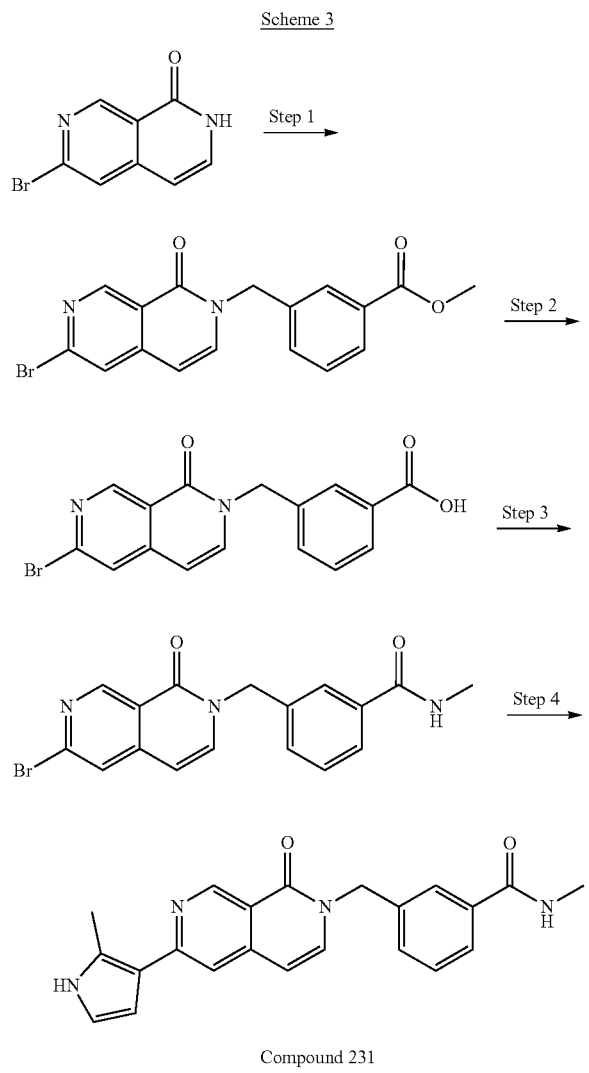

Scheme 3

Compound 231

Step 1: A mixture of 6-bromo-2,7-naphthyridin-1(2H)-one (674 mg, 3.00 mmol), methyl 3-(bromomethyl)benzoate (1.05 g, 4.60 mmol), Na₂CO₃ (1.59 g, 15.0 mmol), and NaI (97 mg, 0.65 mmol) in acetone (30 mL) was heated to reflux with stirring overnight. The mixture was cooled to RT, poured over H₂O, and extracted with EtOAc. The organic layer was washed with brine, dried over Na₂SO₄, filtered, and concentrated. The residue was purified by flash column chromatography on SiO₂ using a gradient of 1040 EtOAc in heptanes to give methyl 3-((6-bromo-1-oxo-2,7-naphthyridin-2(1H)-yl)methyl)benzoate as yellow solid in 95% yield (1.06 g). LC/MS found 374.2 [M+H]⁺.

Step 2: A mixture of methyl 3-((6-bromo-1-oxo-2,7-naphthyridin-2(1H)-yl)methyl)benzoate (380 mg, 1.1 mmol) and LiOH·H₂O (480 mg, 11 mmol) in CH₃OH (40 mL) and H₂O (10 mL) was stirred at RT overnight. The mixture was acidified to pH 2 with 1N HCl. The resulting precipitate was vacuum filtered, washed with H₂O, and dried under a vacuum overnight to give 3-((1-oxo-6-(1H-pyrazol-4-yl)isoquinolin-2(1H)-yl)methyl)benzoic acid as a white solid in 85% yield (336 mg). LC/MS found 359.2 [M+H]⁺.

Step 3: A mixture of 3-((1-Oxo-6-(1H-pyrazol-4-yl)isoquinolin-2(1H)-yl)methyl)benzoic acid (72 mg, 0.2 mmol), HBTU (120 mg, 0.30 mmol), i-Pr₂NEt (1.0 mL, 0.6 mmol), and 1M solution of methylamine in THF (1 mL) in CH₂Cl₂ (3 mL) was stirred at RT overnight. The mixture was poured over H₂O and extracted with CH₂Cl₂. The organic layer was washed with brine, dried over MgSO₄, filtered, and concentrated. The residue was purified by flash column chromatography on SiO₂ using a gradient of 0-30% MeOH in CH₂Cl₂ to provide 3-((6-bromo-1-oxo-2,7-naphthyridin-2(1H)-yl)methyl)-N-methylbenzamide as a white solid in 80% yield (59.5 mg). LC/MS found 372.3 [M+H]⁺.

Step 4: A mixture of methyl 3-((6-bromo-1-oxo-2,7-naphthyridin-2(1H)-yl)methyl)-N-methylbenzamide (37 mg, 0.1 mmol), 42-methyl-3-(4,4,5,5-tetramethyl-1,3,2-dioxaborolan-2-yl)-1H-pyrrole (31 mg, 0.15 mmol), Na₂CO₃ (32 mg, 0.3 mmol), and Pd(PPh₃)₂Cl₂ (6 mg) in 1,4-dioxane (2 mL) and H₂O (0.4 mL) was degassed via sparging with argon for 10 minutes and then heated to 100° C. overnight. The mixture was cooled to RT, poured over H₂O, and extracted with CH₂Cl₂. The organic layer was washed with H₂O, washed with brine, dried over MgSO₄, filtered, and concentrated. The residue was purified by flash column chromatography using a gradient of 0-10% CH₃OH in CH₂Cl₂ to provide Compound 231 as a white solid in 60% yield (22.3 mg). LC/MS found 373.3 [M+H]⁺.

Compounds 232-252 in Table 3 below were prepared by the method (General Scheme 3) similar to that described for the preparation of Compound 231 using methyl 3-(bromomethyl)benzoate, an appropriate boronic acid/ester, and an appropriate amine.

TABLE 3

| Compd | Boronic acid | structure | MS found [M + H]⁺ |
|---|---|---|---|
| 232 | ![structure] | ![structure] | 376.1 |

TABLE 3-continued

| Compd | Boronic acid | structure | MS found [M + H]+ |
|---|---|---|---|
| 233 | | 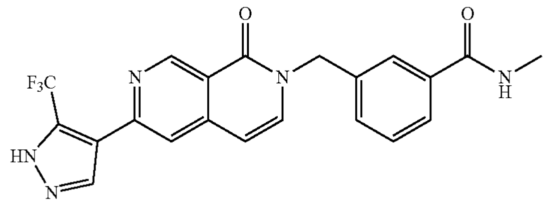 [SMILES: CNC(=O)c1cccc(Cn2ccc3cc(-c4cn[nH]c4C(F)(F)F)ncc3c2=O)c1] | 428.3 |
| 234 | | 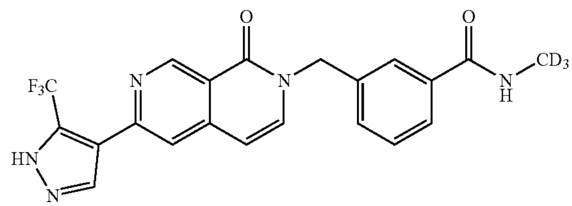 [SMILES: [2H]C([2H])([2H])NC(=O)c1cccc(Cn2ccc3cc(-c4cn[nH]c4C(F)(F)F)ncc3c2=O)c1] | 431.2 |
| 235 | | 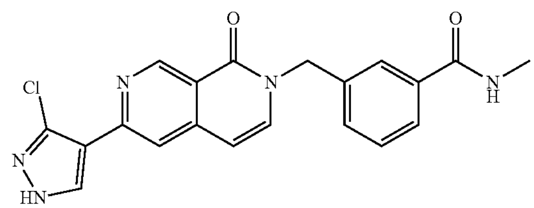 [SMILES: CNC(=O)c1cccc(Cn2ccc3cc(-c4c[nH]nc4Cl)ncc3c2=O)c1] | 394.1 |
| 236 | | 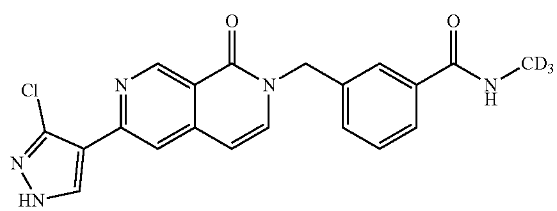 [SMILES: [2H]C([2H])([2H])NC(=O)c1cccc(Cn2ccc3cc(-c4c[nH]nc4Cl)ncc3c2=O)c1] | 397.2 |
| 237 | | 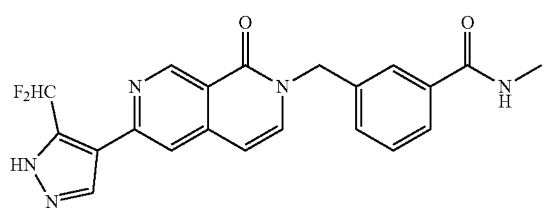 [SMILES: CNC(=O)c1cccc(Cn2ccc3cc(-c4cn[nH]c4C(F)F)ncc3c2=O)c1] | 410.2 |
| 238 | | 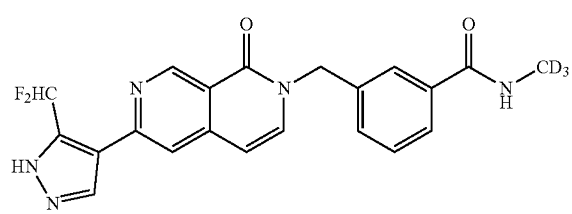 [SMILES: [2H]C([2H])([2H])NC(=O)c1cccc(Cn2ccc3cc(-c4cn[nH]c4C(F)F)ncc3c2=O)c1] | 413.1 |
| 239 | | 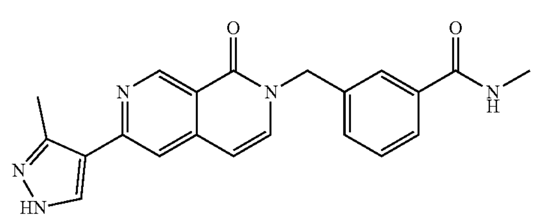 [SMILES: CNC(=O)c1cccc(Cn2ccc3cc(-c4c[nH]nc4C)ncc3c2=O)c1] | 374.2 |

TABLE 3-continued

| Compd | Boronic acid | structure | MS found [M + H]+ |
|---|---|---|---|
| 240 | | 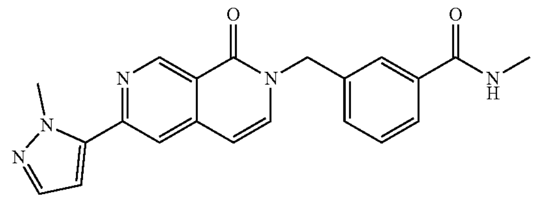 [SMILES: CNC(=O)c1cccc(Cn2ccc3cc(-c4ccnn4C)ncc3c2=O)c1] | 374.1 |
| 241 | | 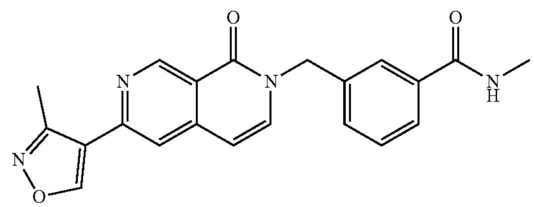 [SMILES: CNC(=O)c1cccc(Cn2ccc3cc(-c4conc4C)ncc3c2=O)c1] | 375.3 |
| 242 | | 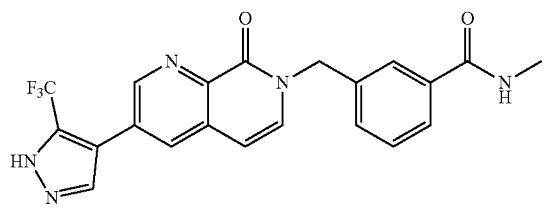 [SMILES: CNC(=O)c1cccc(Cn2ccc3cc(-c4cn[nH]c4C(F)(F)F)cnc3c2=O)c1] | 428.2 |
| 243 | | 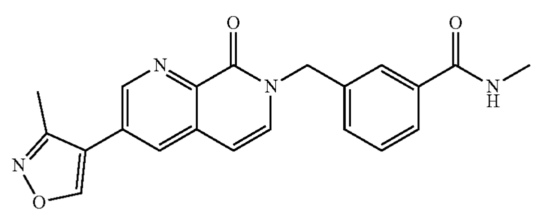 [SMILES: CNC(=O)c1cccc(Cn2ccc3cc(-c4conc4C)cnc3c2=O)c1] | 375.3 |
| 244 | | 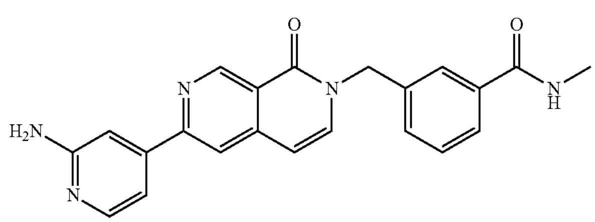 [SMILES: CNC(=O)c1cccc(Cn2ccc3cc(-c4ccnc(N)c4)ncc3c2=O)c1] | 386.1 |
| 245 | | 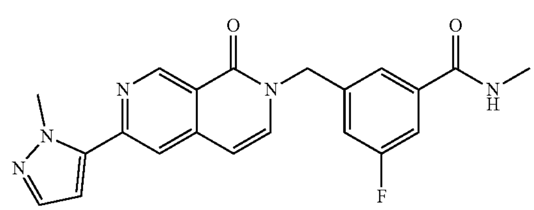 [SMILES: CNC(=O)c1cc(F)cc(Cn2ccc3cc(-c4ccnn4C)ncc3c2=O)c1] | 392.2 |
| 246 | | 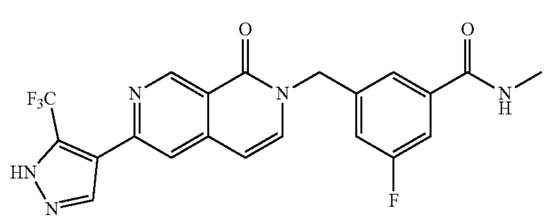 [SMILES: CNC(=O)c1cc(F)cc(Cn2ccc3cc(-c4cn[nH]c4C(F)(F)F)ncc3c2=O)c1] | 446.4 |

TABLE 3-continued

| Compd | Boronic acid | structure | MS found [M + H]+ |
|---|---|---|---|
| 247 | | 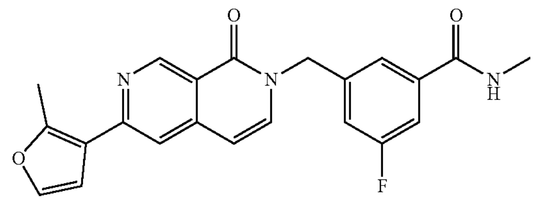 [SMILES: CNC(=O)c1cc(F)cc(Cn2ccc3cc(-c4ccoc4C)ncc3c2=O)c1] | 392.1 |
| 248 | | 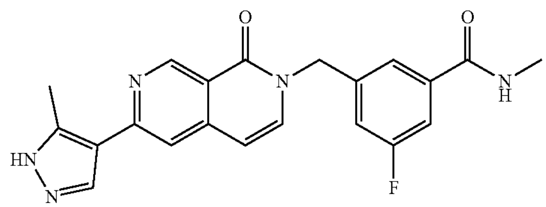 [SMILES: CNC(=O)c1cc(F)cc(Cn2ccc3cc(-c4cn[nH]c4C)ncc3c2=O)c1] | 392.3 |
| 249 | | 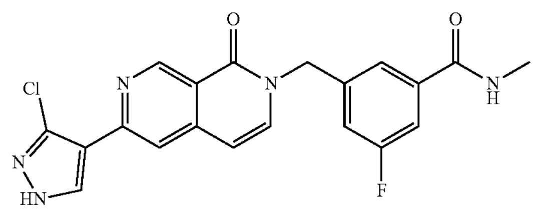 [SMILES: CNC(=O)c1cc(F)cc(Cn2ccc3cc(-c4c[nH]nc4Cl)ncc3c2=O)c1] | 412.4 |
| 250 | | 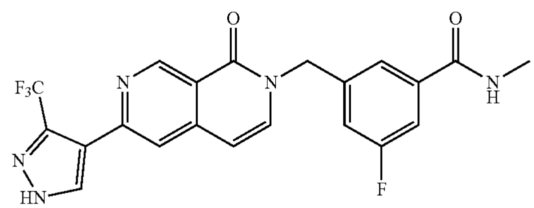 [SMILES: CNC(=O)c1cc(F)cc(Cn2ccc3cc(-c4c[nH]nc4C(F)(F)F)ncc3c2=O)c1] | 446.2 |
| 251 | | 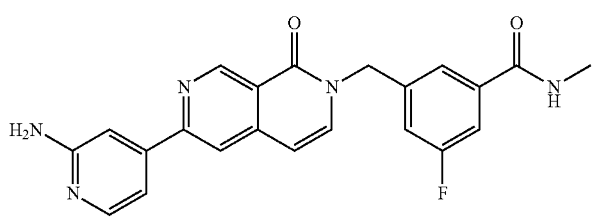 [SMILES: CNC(=O)c1cc(F)cc(Cn2ccc3cc(-c4ccnc(N)c4)ncc3c2=O)c1] | 404.3 |
| 252 | | 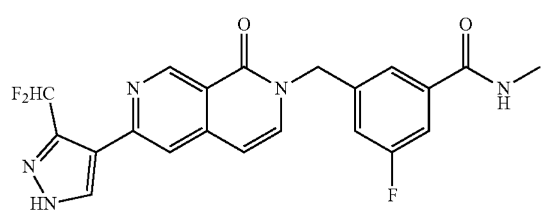 [SMILES: CNC(=O)c1cc(F)cc(Cn2ccc3cc(-c4c[nH]nc4C(F)F)ncc3c2=O)c1] | 428.2 |

General Scheme 4
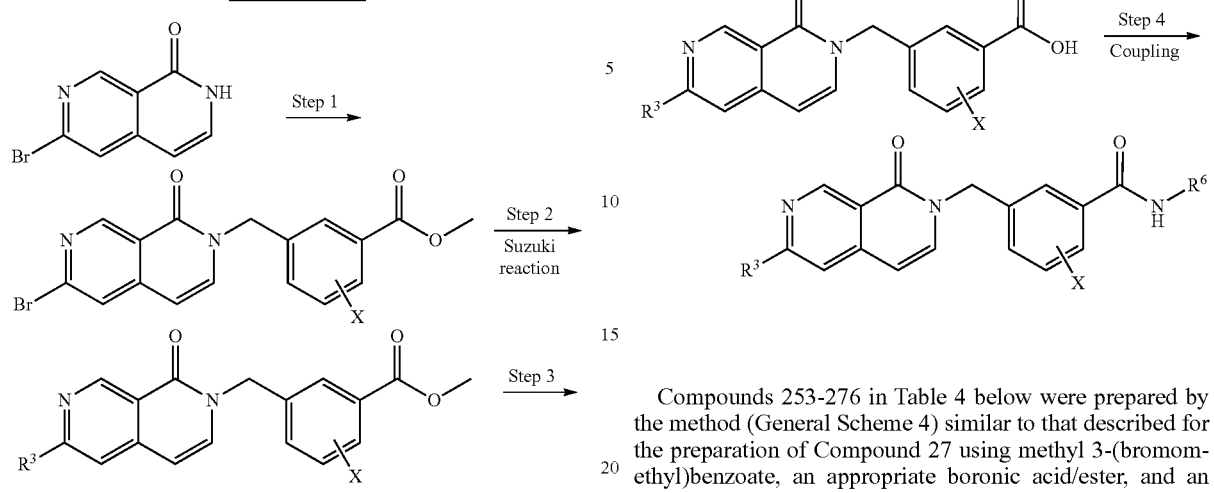
Compounds 253-276 in Table 4 below were prepared by the method (General Scheme 4) similar to that described for the preparation of Compound 27 using methyl 3-(bromomethyl)benzoate, an appropriate boronic acid/ester, and an appropriate amine.
TABLE 4
| Compd | Boronic acid/ester | Amine | Structure | MS found [M + H]+ |
|---|---|---|---|---|
| 253 | 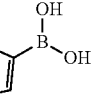 | 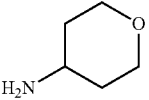 | 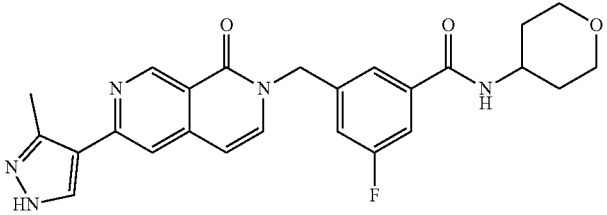 [SMILES: Cc1n[nH]cc1-c1cc2ccn(Cc3cc(F)cc(C(=O)NC4CCOCC4)c3)c(=O)c2cn1] | 462.1 |
| 254 | 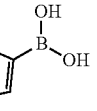 | EtNH₂ | 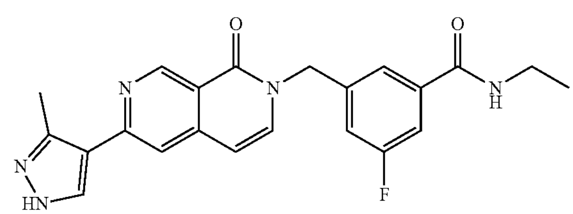 [SMILES: CCNC(=O)c1cc(F)cc(Cn2ccc3cc(-c4c[nH]nc4C)ncc3c2=O)c1] | 406.2 |
| 255 | 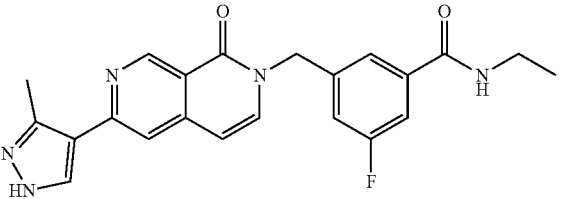 | 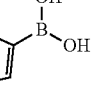 | 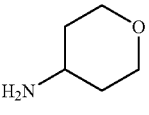 | 462.3 |
| 256 | 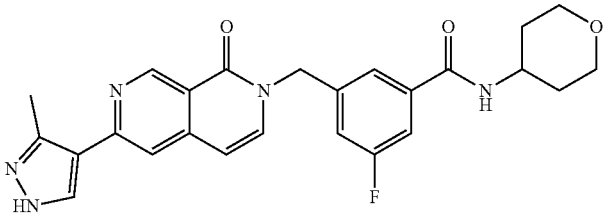 [SMILES: Cc1n[nH]cc1-c1cc2ccn(Cc3cc(F)cc(C(=O)NC4CCOCC4)c3)c(=O)c2cn1] | 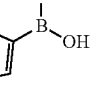 | 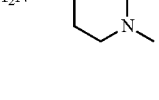 | 489.4 |

TABLE 4-continued

| Compd | Boronic acid/ester | Amine | Structure | MS found [M + H]+ |
|---|---|---|---|---|
| 257 | F3C, pinacol boronate pyrazole | H2N-CH2-(N-methylpiperidine) | (structure) | 543.2 |
| 258 | F3C, pinacol boronate pyrazole | H2N-CH2-oxetane | (structure) | 502.3 |
| 259 | F3C, pinacol boronate pyrazole | H2N-(N-methylpiperidin-4-yl) | (structure) | 529.2 |
| 260 | F3C, pinacol boronate pyrazole | trans-4-aminocyclohexanol | (structure) | 530.3 |
| 261 | Cl, pinacol boronate pyrazole | H2N-(N-methylpiperidin-4-yl) | (structure) | 495.3 |
| 262 | Cl, pinacol boronate pyrazole | cis-4-aminocyclohexanol | (structure) | 496.1 |
| 263 | Cl, pinacol boronate pyrazole | trans-4-aminocyclohexanol | (structure) | 496.2 |

TABLE 4-continued

| Compd | Boronic acid/ester | Amine | Structure | MS found [M + H]+ |
|---|---|---|---|---|
| 264 | | | 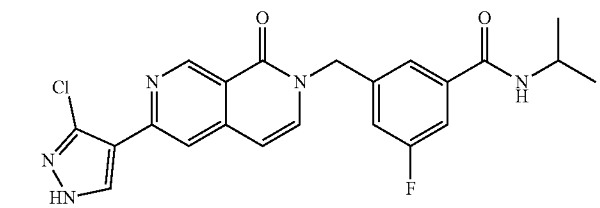 [SMILES: CC(C)NC(=O)c1cc(F)cc(Cn2ccc3cc(-c4c[nH]nc4Cl)ncc3c2=O)c1] | 440.2 |
| 265 | | | 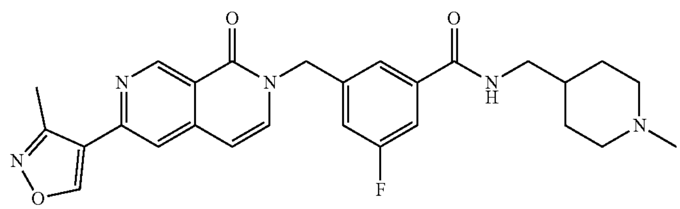 [SMILES: Cc1nocc1-c1cc2ccn(Cc3cc(F)cc(C(=O)NCC4CCN(C)CC4)c3)c(=O)c2cn1] | 490.2 |
| 266 | | | 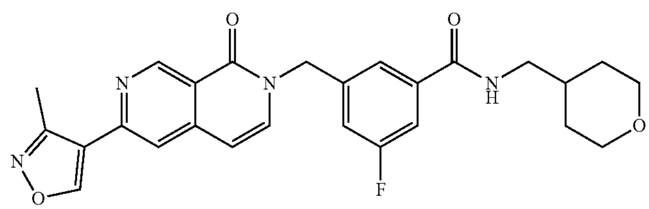 [SMILES: Cc1nocc1-c1cc2ccn(Cc3cc(F)cc(C(=O)NCC4CCOCC4)c3)c(=O)c2cn1] | 477.3 |
| 267 | | | 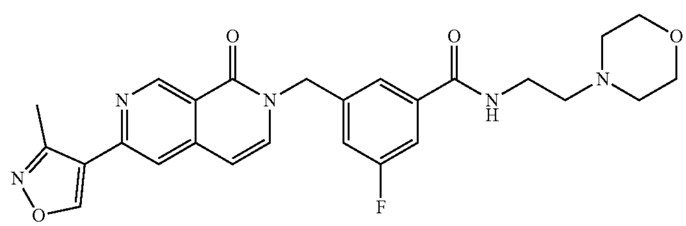 [SMILES: Cc1nocc1-c1cc2ccn(Cc3cc(F)cc(C(=O)NCCN4CCOCC4)c3)c(=O)c2cn1] | 492.3 |
| 268 | | | 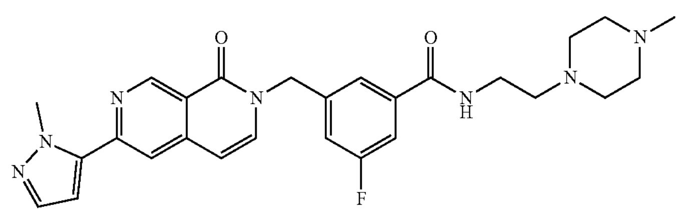 [SMILES: CN1CCN(CCNC(=O)c2cc(F)cc(Cn3ccc4cc(-c5ccnn5C)ncc4c3=O)c2)CC1] | 504.4 |
| 269 | | | 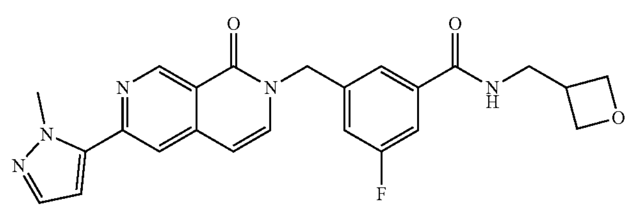 [SMILES: Cn1nccc1-c1cc2ccn(Cc3cc(F)cc(C(=O)NCC4COC4)c3)c(=O)c2cn1] | 448.2 |
| 270 | | | 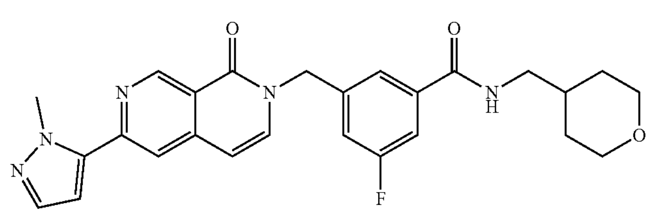 [SMILES: Cn1nccc1-c1cc2ccn(Cc3cc(F)cc(C(=O)NCC4CCOCC4)c3)c(=O)c2cn1] | 476.2 |

TABLE 4-continued

| Compd | Boronic acid/ester | Amine | Structure | MS found [M + H]+ |
|---|---|---|---|---|
| 271 | | | 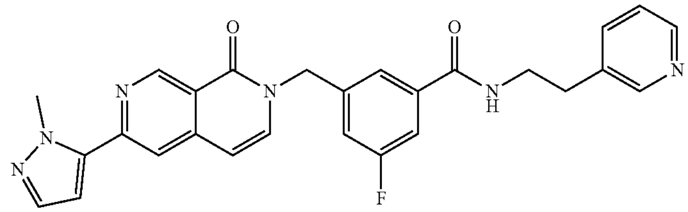 [SMILES: Cn1nccc1-c1cc2ccn(Cc3cc(F)cc(C(=O)NCCc4cccnc4)c3)c(=O)c2cn1] | 483.1 |
| 272 | | | 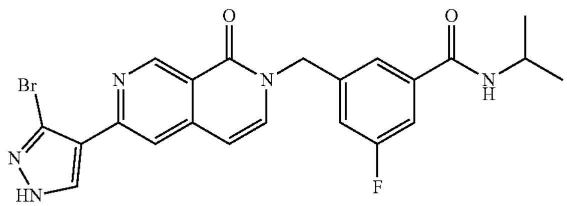 [SMILES: CC(C)NC(=O)c1cc(F)cc(Cn2ccc3cc(-c4c[nH]nc4Br)ncc3c2=O)c1] | 485.3 |
| 273 | | | 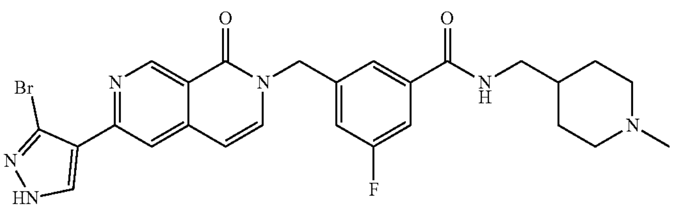 | 554.3 |
| 274 | | | 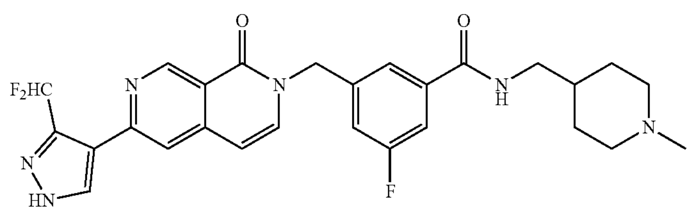 [SMILES: CN1CCC(CNC(=O)c2cc(F)cc(Cn3ccc4cc(-c5c[nH]nc5C(F)F)ncc4c3=O)c2)CC1] | 525.1 |
| 275 | | | 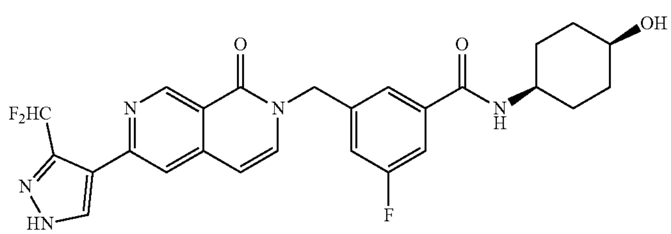 [SMILES: O=C(N[C@H]1CC[C@@H](O)CC1)c1cc(F)cc(Cn2ccc3cc(-c4c[nH]nc4C(F)F)ncc3c2=O)c1] | 512.3 |
| 276 | | | 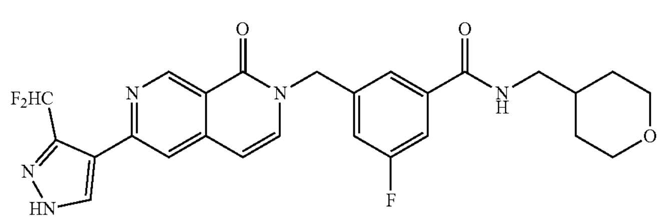 [SMILES: O=C(NCC1CCOCC1)c1cc(F)cc(Cn2ccc3cc(-c4c[nH]nc4C(F)F)ncc3c2=O)c1] | 512.3 |

General Scheme 5

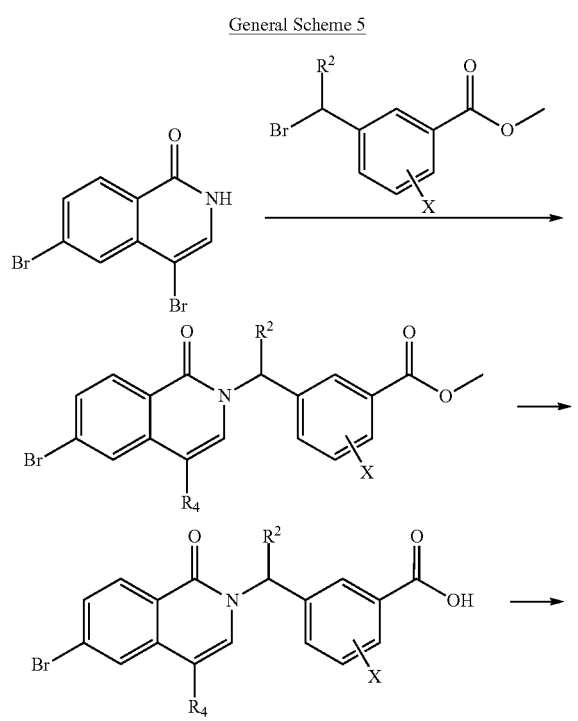

Compound 277: N-methyl-3-((1-oxo-6-(1H-pyrazol-4-yl)isoquinolin-2(1H)-yl)methyl)benzamide

Scheme 4

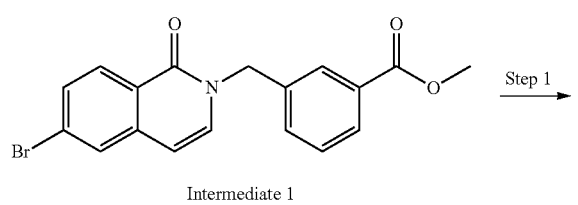

Intermediate 1

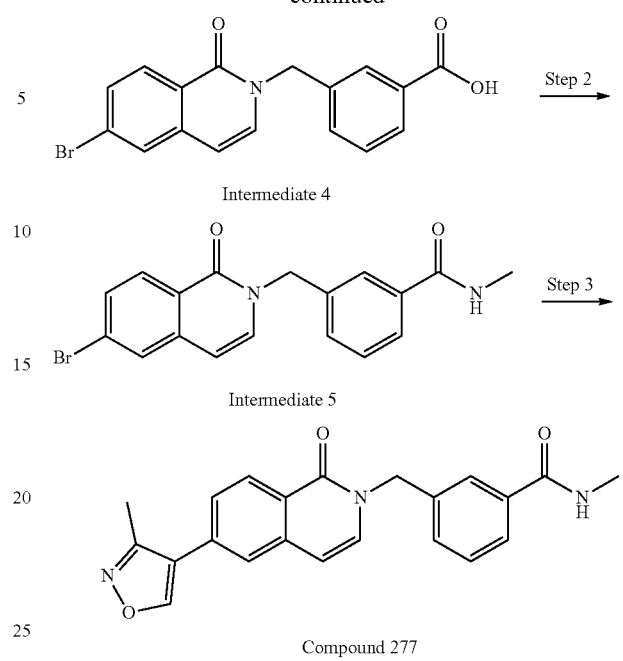

Step 1: A mixture of Intermediate 1 (450 mg, 1.1 mmol) from Scheme 2 and LiOH·H$_2$O (480 mg, 11 mmol) in CH$_3$OH (8 mL) and H$_2$O (4 mL) was stirred at RT overnight. The mixture was acidified to pH 2 with 1M HCl. The resulting precipitate was vacuum filtered, washed with H$_2$O, and dried under a vacuum overnight to give 3-((6-bromo-1-oxoisoquinolin-2(1H)-yl)methyl)benzoic acid (Intermediate 4) as a pale-yellow solid in 69% yield (285 mg). LC/MS found 358.1 [M+H]$^+$.

Step 2: A mixture of 3-((6-bromo-1-oxoisoquinolin-2(1H)-yl)methyl)benzoic acid (366 mg, 1.02 mmol), HBTU (572 mg, 1.50 mmol), i-Pr$_2$NEt (0.52 mL, 3.0 mmol), and CH$_3$NH$_2$ (2.0M in THF, 1.0 mL, 2.0 mmol) in CH$_2$Cl$_2$ (10 mL) was stirred at RT overnight. The mixture was poured over H$_2$O and extracted with CH$_2$Cl$_2$. The combined organic layer was washed with brine, dried over MgSO$_4$, filtered, and concentrated. The residue was purified by flash column chromatography on SiO$_2$ using a gradient of 50-100% EtOAc in heptanes to provide 3-((6-bromo-1-oxoisoquinolin-2(1H)-yl)methyl)-N-methylbenzamide (Intermediate 5) as a white solid in quantitative yield (379 mg). LC/MS found 370.9 [M+H]$^+$.

Step 3: A mixture of 3-((6-bromo-1-oxoisoquinolin-2(1H)-yl)methyl)-N-methylbenzamide (77 mg, 0.2 mmol), (3-methylisoxazol-4-yl)boronic acid (39 mg, 0.30 mmol), Na$_2$CO$_3$ (70 mg, 0.66 mmol), and PdCl$_2$(PPh$_3$)$_2$ (5.7 mg, 8.1 μmol) in 1,4-dioxane (1.5 mL) and H$_2$O (0.5 mL) was degassed via sparging with argon for 10 minutes and then heated to 100° C. overnight. The mixture was cooled to RT, poured over H$_2$O, and extracted with 10% i-PrOH in CH$_2$Cl$_2$. The combined organic layer was washed sequentially with H$_2$O and brine, dried over MgSO$_4$, filtered, and concentrated. The residue was purified by flash column chromatography using a gradient of 1-10% CH$_3$OH in CH$_2$C$_2$ to provide Compound 277 as a white solid in 70% yield (52.1 mg). LC/MS found 374.2 [M+H]$^+$. Compound 277 was prepared using an alternative method below.

General Scheme 6

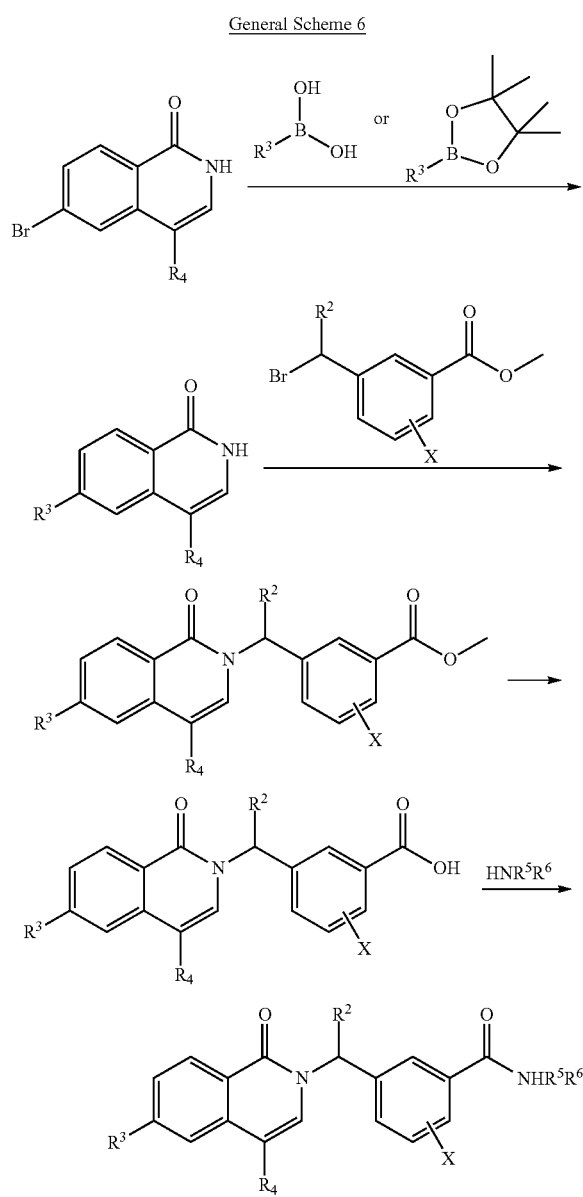

Scheme 5

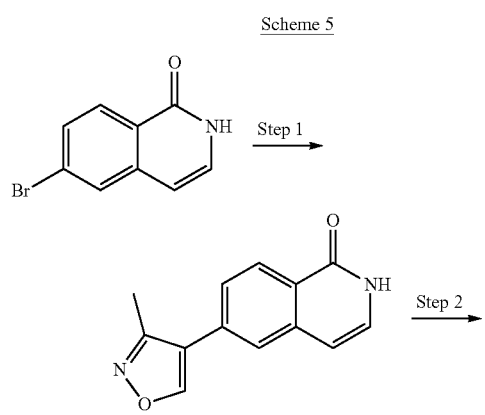

Step 1: A mixture of 6-bromoisoquinolin-1(2H)-one (4.48 g, 20 mmol), (3-methylisoxazol-4-yl)boronic acid (7.86 g, 30 mmol), $Na_2CO_3$ (6.3 g, 60 mmol), and $PdCl_2(PPh_3)_2$ (700 mg, 1.0 mol) in 1,4-dioxane (30 mL) and $H_2O$ (6.0 mL) was degassed via sparging with argon for 10 minutes and then heated to 100° C. overnight. The mixture was cooled to RT and poured over $H_2O$ to form precipitates. The resulted precipitates were collected by filtration, washed with water, and then dried with high vacuum to provide 6-(5-(trifluoromethyl)-1H-pyrazol-4-yl)isoquinolin-1(2H)-one as a pale yellow solid (3.34 g, 73%) LC/MS found 227.1 $[M+H]^+$.

Step 2: A mixture of 6-(3-Methylisoxazol-4-yl)isoquinolin-1(2H)-one (228.0 mg, 1.0 mmol), methyl 3-(bromomethyl)benzoate (0.34 g, 1.5 mmol), $Na_2CO_3$ (0.53 g, 3.0 mmol), and NaI (30 mg, 0.2 mmol) in acetone (10 mL) was heated to reflux with stirring overnight. The mixture was cooled to RT, poured over $H_2O$, and extracted with EtOAc. The organic layer was washed with brine, dried over $Na_2SO_4$, filtered, and concentrated. The residue was purified by silica gel column chromatography using a gradient of 10-40% EtOAc in heptanes to give methyl 3-((6-(3-methylisoxazol-4-yl)-1-oxoisoquinolin-2(1H)-yl)methyl)benzoate as yellow solid in 90% yield (337 mg). LC/MS found 375.2 $[M+H]^+$.

Step 3: A mixture of methyl 3-((6-(3-methylisoxazol-4-yl)-1-oxoisoquinolin-2(1H)-yl)methyl)benzoate (337, 0.9 mmol) and $LiOH·H_2O$ (380 mg, 9.0 mmol) in $CH_3OH$ (40 mL) and $H_2O$ (10 mL) was stirred at RT overnight. The mixture was acidified to pH 2 with 1N HCl. The resulting precipitate was vacuum filtered, washed with $H_2O$, and dried under a vacuum overnight to give 3-((6-(3-methylisoxazol-4-yl)-1-oxoisoquinolin-2(1H)-yl)methyl)benzoic acid in 85% yield (276 mg). LC/MS found 361.1 $[M+H]^+$.

Step 4: A mixture of 3-((6-(3-methylisoxazol-4-yl)-1-oxoisoquinolin-2(1H)-yl)methyl)benzoic acid (82 mg, 0.2 mmol), HBTU (108 mg, 0.30 mmol), i-$Pr_2NEt$ (1.0 mL, 0.6 mmol), and 1M solution of methylamine in THF (1 mL) in $CH_2Cl_2$ (3 mL) was stirred at RT overnight. The mixture was poured over $H_2O$ and extracted with $CH_2Cl_2$. The organic layer was washed with brine, dried over $MgSO_4$, filtered, and concentrated. The residue was purified by flash column chromatography on SiO$_2$ using a gradient of 0-30% MeOH in CH$_2$Cl$_2$ to provide N-methyl-3-((6-(3-methylisoxazol-4-yl)-1-oxoisoquinolin-2(1H)-yl)methyl)benzamide, Compound 277, as a white solid in 90% yield (100.8 mg). LC/MS found 374.2.1 [M+H]$^+$.

$^1$H NMR (400 MHz, DMSO-d6) δ 9.30 (s, 1H), 8.42 (m, 1H), 8.27 (d, 1H, J=8.4 Hz), 7.84 (d, 1H, J=1.5 Hz), 7.78 (s, 1H), 7.72 (dt, 1H, J=7.3, 1.5 Hz), 7.68 (dd, 1H, J=8.4, 1.8 Hz), 7.63 (d, 1H, J=7.3 Hz), 7.43 (m, 2H), 6.71 (d, 1H, J=7.4 Hz), 5.24 (s, 2H), 2.75 (d, 3H, J=4.5 Hz), 2.47 (s, 3H).

Compounds 278-327 in Table 5 below were prepared by the above methods (Scheme 4 or 5) using reaction condition described preparation Compound 277.

TABLE 5

| Compd | Boronic acid/ester | Structure | MS found [M + H]$^+$ |
|---|---|---|---|
| 278 | | 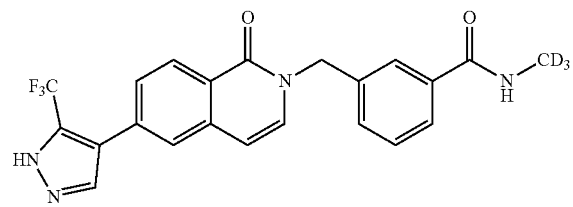 [SMILES: [2H]C([2H])([2H])NC(=O)c1cccc(Cn2ccc3cc(-c4cn[nH]c4C(F)(F)F)ccc3c2=O)c1] | 430.1 |
| 279 | | 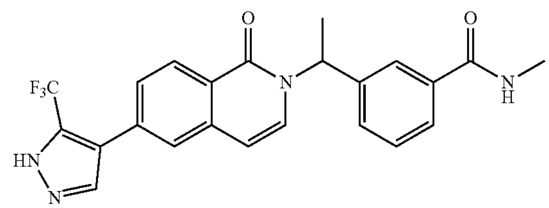 [SMILES: CNC(=O)c1cccc(C(C)n2ccc3cc(-c4cn[nH]c4C(F)(F)F)ccc3c2=O)c1] | 441.3 |
| 280 | | 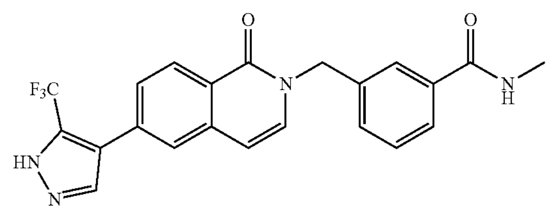 | 427.1 |
| 281 | | 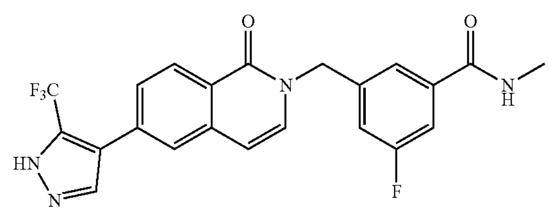 [SMILES: CNC(=O)c1cc(F)cc(Cn2ccc3cc(-c4cn[nH]c4C(F)(F)F)ccc3c2=O)c1] | 445.3 |
| 282 | | 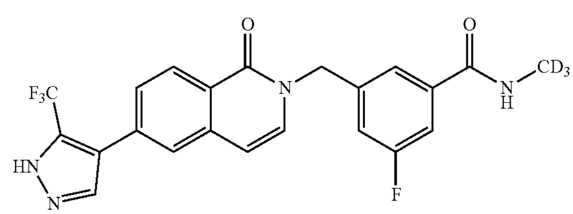 [SMILES: [2H]C([2H])([2H])NC(=O)c1cc(F)cc(Cn2ccc3cc(-c4cn[nH]c4C(F)(F)F)ccc3c2=O)c1] | 448.2 |
| 283 | | 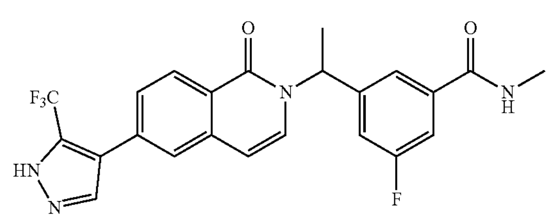 [SMILES: CNC(=O)c1cc(F)cc(C(C)n2ccc3cc(-c4cn[nH]c4C(F)(F)F)ccc3c2=O)c1] | 459.1 |

TABLE 5-continued

| Compd | Boronic acid/ester | Structure | MS found [M + H]+ |
|---|---|---|---|
| 284 | | 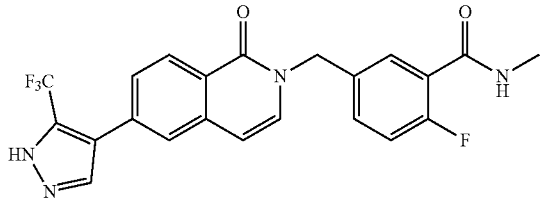 [SMILES: CNC(=O)c1cc(Cn2ccc3cc(-c4cn[nH]c4C(F)(F)F)ccc3c2=O)ccc1F] | 445.2 |
| 285 | | 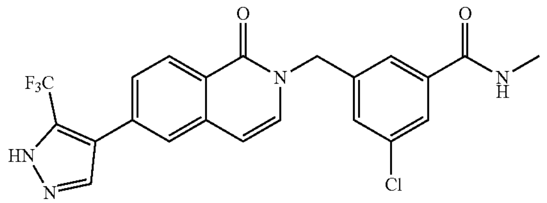 [SMILES: CNC(=O)c1cc(Cl)cc(Cn2ccc3cc(-c4cn[nH]c4C(F)(F)F)ccc3c2=O)c1] | 461.4 |
| 286 | | 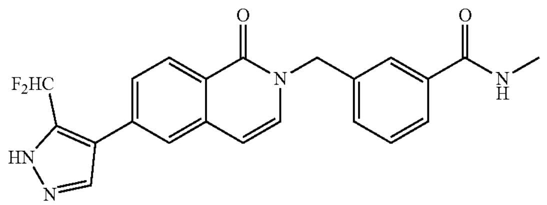 [SMILES: CNC(=O)c1cccc(Cn2ccc3cc(-c4cn[nH]c4C(F)F)ccc3c2=O)c1] | 409.2 |
| 287 | | 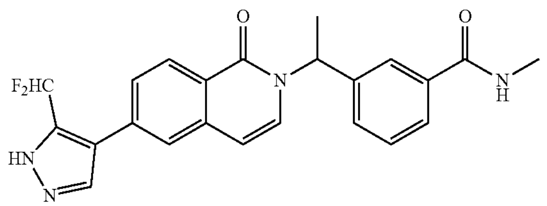 [SMILES: CNC(=O)c1cccc(C(C)n2ccc3cc(-c4cn[nH]c4C(F)F)ccc3c2=O)c1] | 423.2 |
| 288 | | 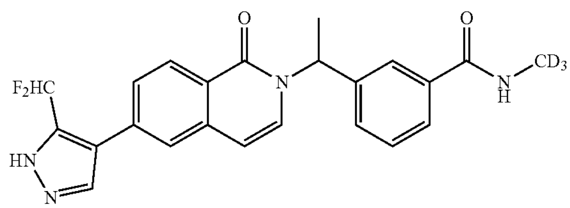 [SMILES: [2H]C([2H])([2H])NC(=O)c1cccc(C(C)n2ccc3cc(-c4cn[nH]c4C(F)F)ccc3c2=O)c1] | 426.1 |
| 289 | | 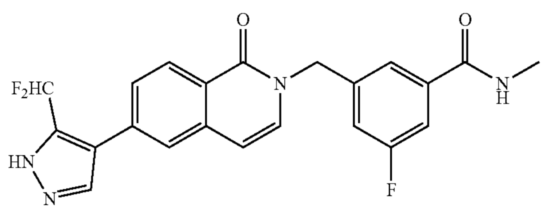 [SMILES: CNC(=O)c1cc(F)cc(Cn2ccc3cc(-c4cn[nH]c4C(F)F)ccc3c2=O)c1] | 427.4 |
| 290 | | 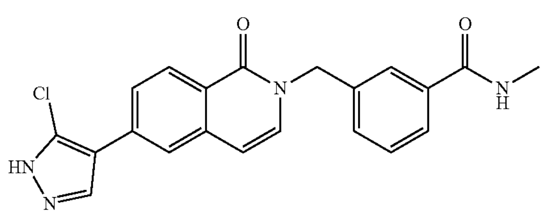 [SMILES: CNC(=O)c1cccc(Cn2ccc3cc(-c4cn[nH]c4Cl)ccc3c2=O)c1] | 393.2 |

TABLE 5-continued

| Compd | Boronic acid/ester | Structure | MS found [M + H]+ |
|---|---|---|---|
| 291 | | 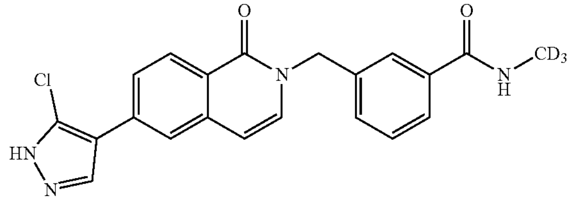 [SMILES: [2H]C([2H])([2H])NC(=O)c1cccc(Cn2ccc3cc(-c4cn[nH]c4Cl)ccc3c2=O)c1] | 396.1 |
| 292 | | 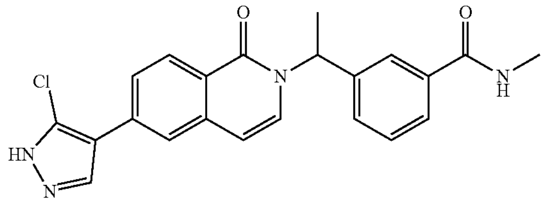 [SMILES: CNC(=O)c1cccc(C(C)n2ccc3cc(-c4cn[nH]c4Cl)ccc3c2=O)c1] | 407.4 |
| 293 | | 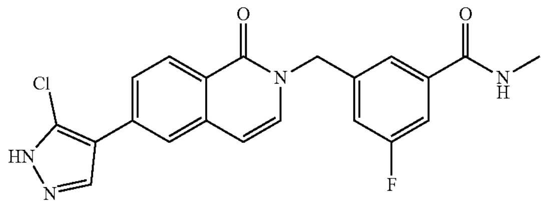 [SMILES: CNC(=O)c1cc(F)cc(Cn2ccc3cc(-c4cn[nH]c4Cl)ccc3c2=O)c1] | 411.1 |
| 294 | | 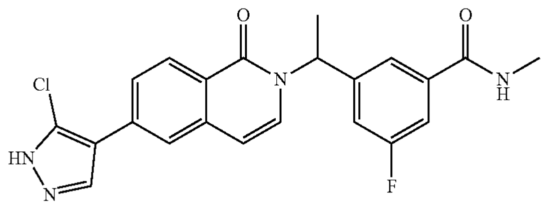 [SMILES: CNC(=O)c1cc(F)cc(C(C)n2ccc3cc(-c4cn[nH]c4Cl)ccc3c2=O)c1] | 425.3 |
| 295 | | 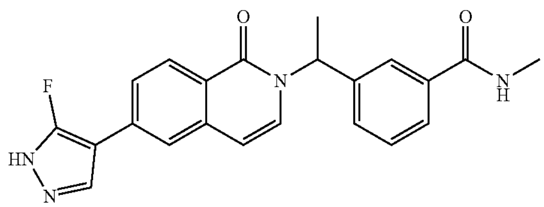 [SMILES: CNC(=O)c1cccc(C(C)n2ccc3cc(-c4cn[nH]c4F)ccc3c2=O)c1] | 395.2 |
| 296 | | 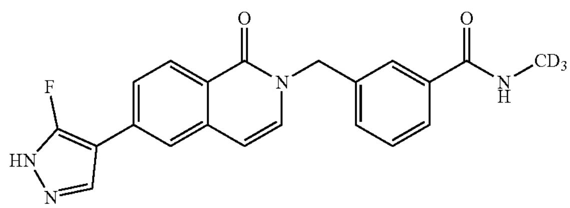 [SMILES: [2H]C([2H])([2H])NC(=O)c1cccc(Cn2ccc3cc(-c4cn[nH]c4F)ccc3c2=O)c1] | 380.2 |
| 297 | | 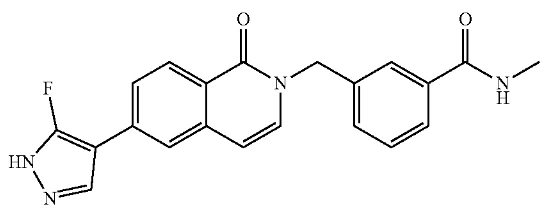 [SMILES: CNC(=O)c1cccc(Cn2ccc3cc(-c4cn[nH]c4F)ccc3c2=O)c1] | 377.1 |

TABLE 5-continued

| Compd | Boronic acid/ester | Structure | MS found [M + H]+ |
|---|---|---|---|
| 298 | | 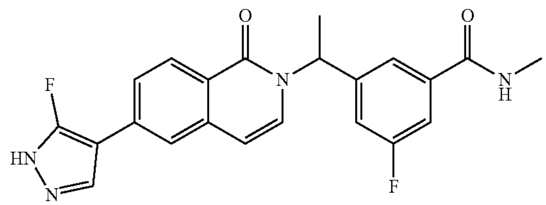 [SMILES: CNC(=O)c1cc(F)cc(C(C)n2ccc3cc(-c4cn[nH]c4F)ccc3c2=O)c1] | 409.3 |
| 299 | | 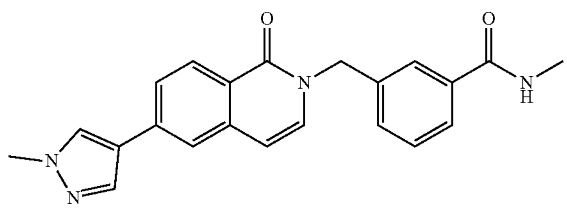 | 373.2 |
| 300 | | 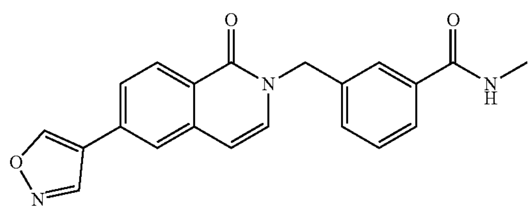 [SMILES: CNC(=O)c1cccc(Cn2ccc3cc(-c4cnoc4)ccc3c2=O)c1] | 360.1 |
| 301 | | 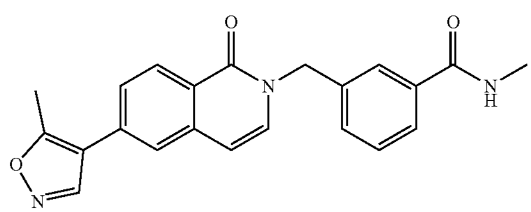 [SMILES: CNC(=O)c1cccc(Cn2ccc3cc(-c4cnoc4C)ccc3c2=O)c1] | 374.3 |
| 302 | | 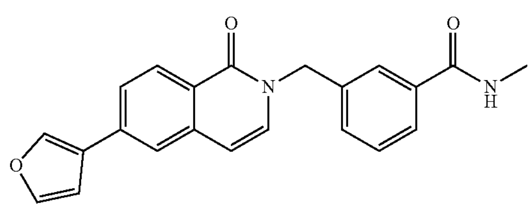 [SMILES: CNC(=O)c1cccc(Cn2ccc3cc(-c4ccoc4)ccc3c2=O)c1] | 359.2 |
| 303 | | 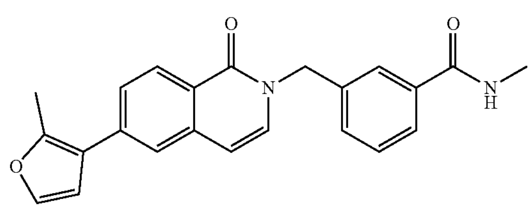 [SMILES: CNC(=O)c1cccc(Cn2ccc3cc(-c4ccoc4C)ccc3c2=O)c1] | 373.2 |
| 304 | | 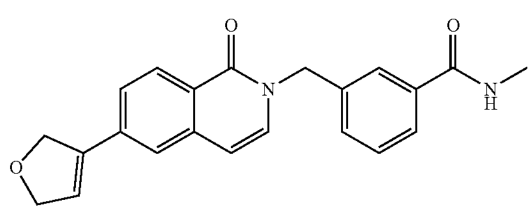 [SMILES: CNC(=O)c1cccc(Cn2ccc3cc(C4=CCOC4)ccc3c2=O)c1] | 361.3 |

TABLE 5-continued

| Compd | Boronic acid/ester | Structure | MS found [M + H]+ |
|---|---|---|---|
| 305 | | 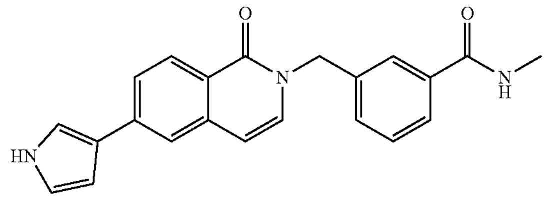 [SMILES: CNC(=O)c1cccc(Cn2ccc3cc(-c4cc[nH]c4)ccc3c2=O)c1] | 358.4 |
| 306 | | 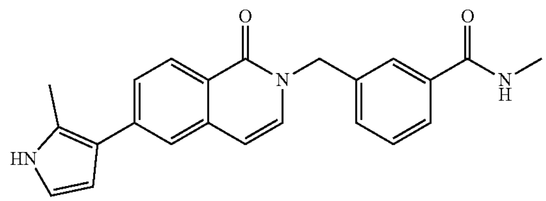 [SMILES: CNC(=O)c1cccc(Cn2ccc3cc(-c4cc[nH]c4C)ccc3c2=O)c1] | 372.4 |
| 307 | | 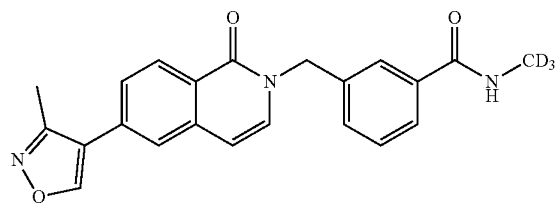 [SMILES: [2H]C([2H])([2H])NC(=O)c1cccc(Cn2ccc3cc(-c4conc4C)ccc3c2=O)c1] | 377.1 |
| 308 | | 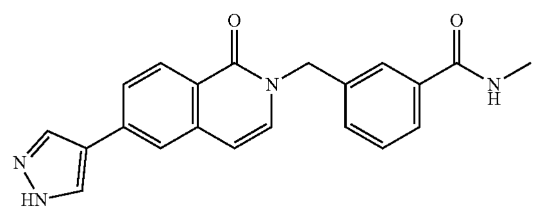 [SMILES: CNC(=O)c1cccc(Cn2ccc3cc(-c4cn[nH]c4)ccc3c2=O)c1] | 359.1 |
| 309 | | 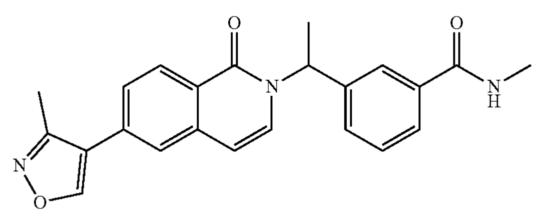 [SMILES: CNC(=O)c1cccc(C(C)n2ccc3cc(-c4conc4C)ccc3c2=O)c1] | 388.2 |
| 310 | | 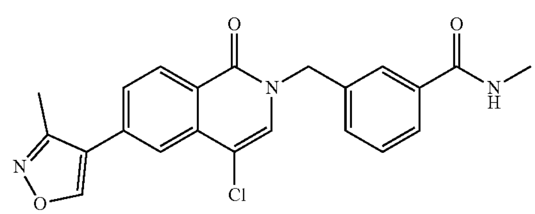 [SMILES: CNC(=O)c1cccc(Cn2cc(Cl)c3cc(-c4conc4C)ccc3c2=O)c1] | 408.7 |
| 311 | | 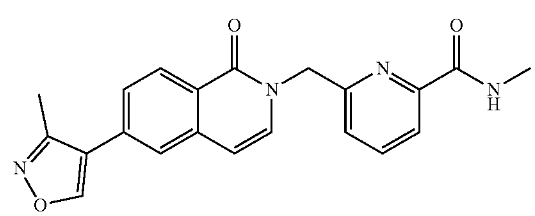 [SMILES: CNC(=O)c1cccc(Cn2ccc3cc(-c4conc4C)ccc3c2=O)n1] | 375.3 |

TABLE 5-continued
| Compd | Boronic acid/ester | Structure | MS found [M + H]+ |
|---|---|---|---|
| 312 | 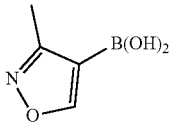 | 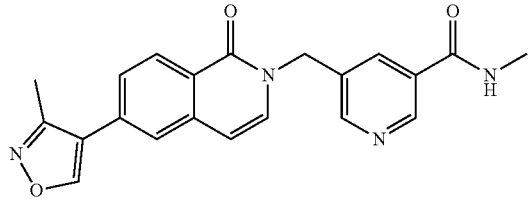 [SMILES: CNC(=O)c1cncc(Cn2ccc3cc(-c4conc4C)ccc3c2=O)c1] | 375.2 |
| 313 | 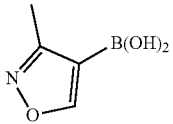 | 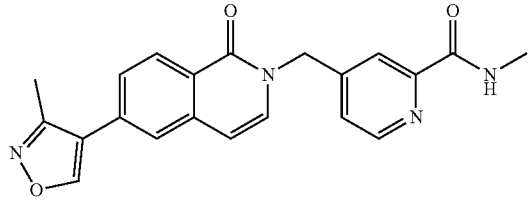 [SMILES: CNC(=O)c1cc(Cn2ccc3cc(-c4conc4C)ccc3c2=O)ccn1] | 375.2 |
| 314 | 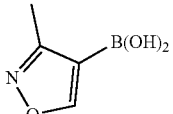 | 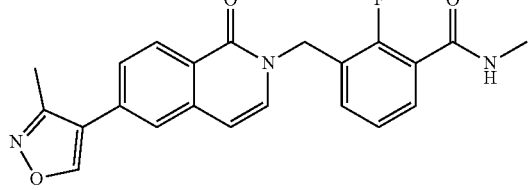 | 392.1 |
| 315 | 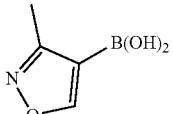 | 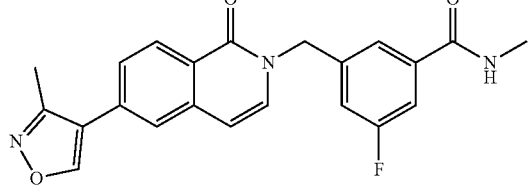 | 392.3 |
| 316 | 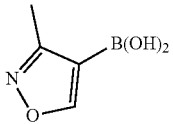 | 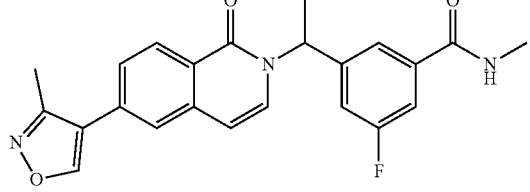 | 406.3 |
| 317 | 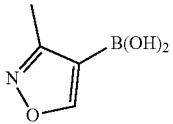 | 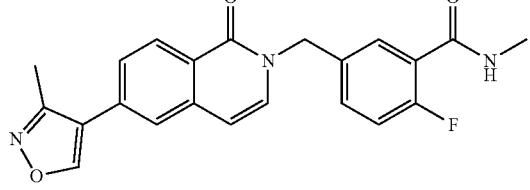 | 392.3 |
| 318 | 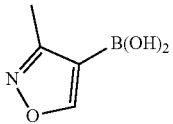 | 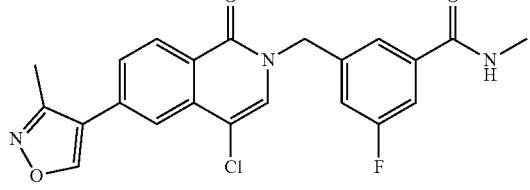 | 426.8 |

TABLE 5-continued
| Compd | Boronic acid/ester | Structure | MS found [M + H]+ |
|---|---|---|---|
| 319 | 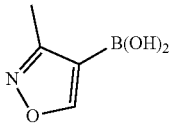 | 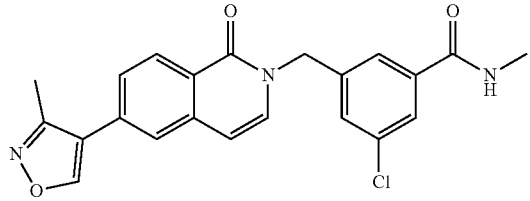 [SMILES: CNC(=O)c1cc(Cl)cc(Cn2ccc3cc(-c4conc4C)ccc3c2=O)c1] | 408.6 |
| 320 | 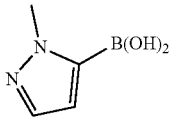 | 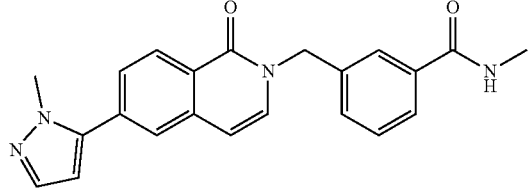 [SMILES: CNC(=O)c1cccc(Cn2ccc3cc(-c4ccnn4C)ccc3c2=O)c1] | 373.2 |
| 321 | 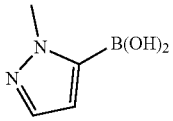 | 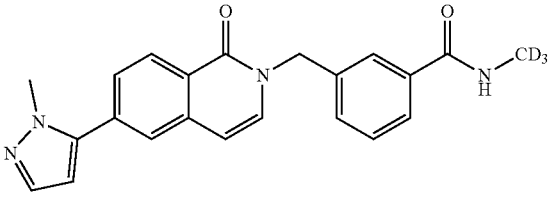 [SMILES: [2H]C([2H])([2H])NC(=O)c1cccc(Cn2ccc3cc(-c4ccnn4C)ccc3c2=O)c1] | 376.2 |
| 322 | 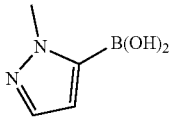 | 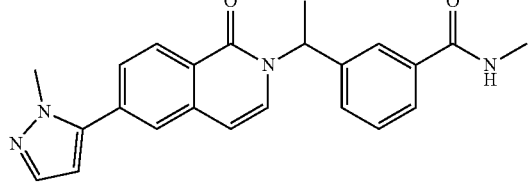 | 388.4 |
| 323 | 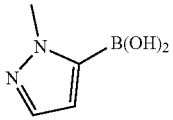 | 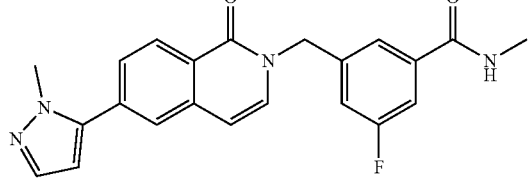 | 391.2 |
| 324 | 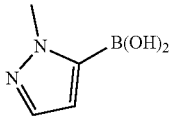 | 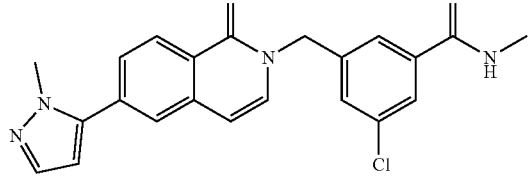 | 407.6 |
| 325 | 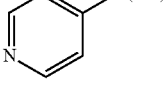 | 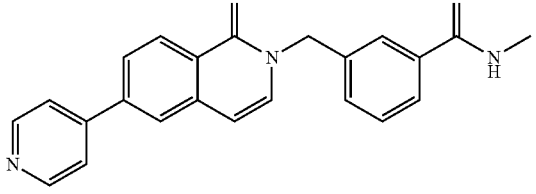 | 370.2 |

TABLE 5-continued

| Compd | Boronic acid/ester | Structure | MS found [M + H]+ |
|---|---|---|---|
| 326 | H2N-pyridine-B(OH)2 | 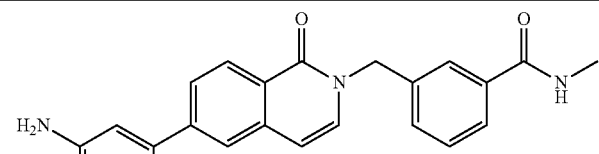 | 384.1 |
| 327 | N-methyl-triazole-B(OH)2 | 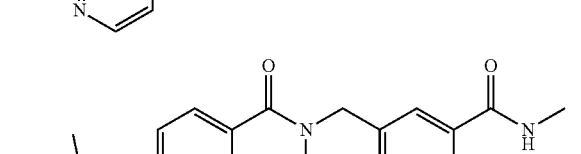 | 374.2 |

General Scheme 7

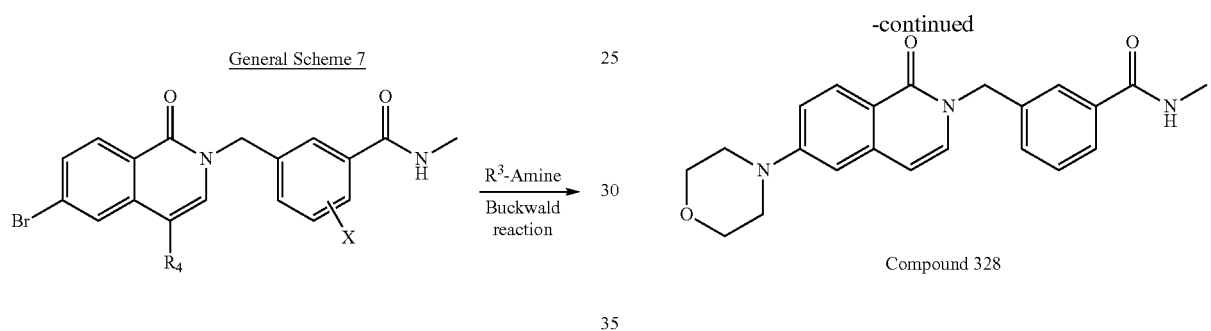

Compound 328

Compound 328: N-methyl-3-((6-morpholino-1-oxoisoquinolin-2(1H)-yl)methyl)benzamide A mixture of Intermediate 5 (Scheme 5), 3-((6-bromo-1-oxoisoquinolin-2(1H)-yl)methyl)-N-methylbenzamide (75 mg, 0.2 mmol), morpholine (26 mg, 0.3 mmol), NaOBu$^t$(58 mg, 0.6 mmol), Binap (10 mol %) and Pd$_2$(bda)$_3$ (5 mol %) in toluene (3 mL) was degassed via sparging with argon for 10 minutes and then heated to 100° C. overnight. The mixture was cooled to RT, poured over H$_2$O, and extracted with EtOAc. The combined organic layer was washed with H$_2$O, washed with brine, dried over MgSO$_4$, filtered, and concentrated. The residue was purified by flash column chromatography using a gradient of 1-10% CH$_3$OH in CH$_2$Cl$_2$ to provide Compound 328 as a white solid in 85% yield (64 mg). LC/MS found 378.2 [M+H]$^+$.

Scheme 6

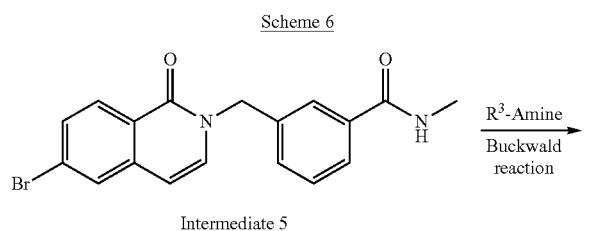

Intermediate 5

Compounds 329-331 in Table 6 below were prepared using intermediate 5 and an appropriate amine by Buckwald reaction condition described preparation of Compound 328.

TABLE 6
| Compd | Amine | Structure | MS found [M + H]+ |
|---|---|---|---|
| 329 | morpholine | 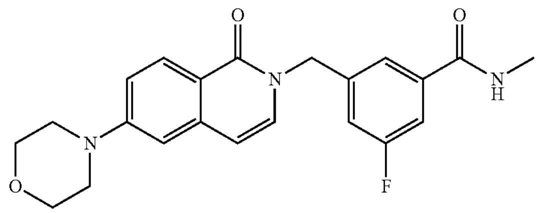 [SMILES: CNC(=O)c1cc(F)cc(Cn2ccc3cc(N4CCOCC4)ccc3c2=O)c1] | 396.2 |
| 330 | 2-oxa-5-azabicyclo[2.2.1]heptane | 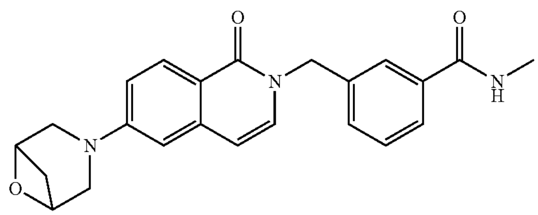 [SMILES: CNC(=O)c1cccc(Cn2ccc3cc(N4CC5CC(C4)O5)ccc3c2=O)c1] | 390.4 |
| 331 | (S)-2-methylmorpholine | 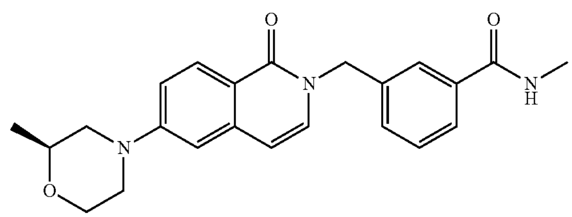 | 392.2 |
Compound 332: N-(3-((6-(2-methylfuran-3-yl)-1-oxoisoquinolin-2(1H)-yl)methyl)phenyl)acetamide
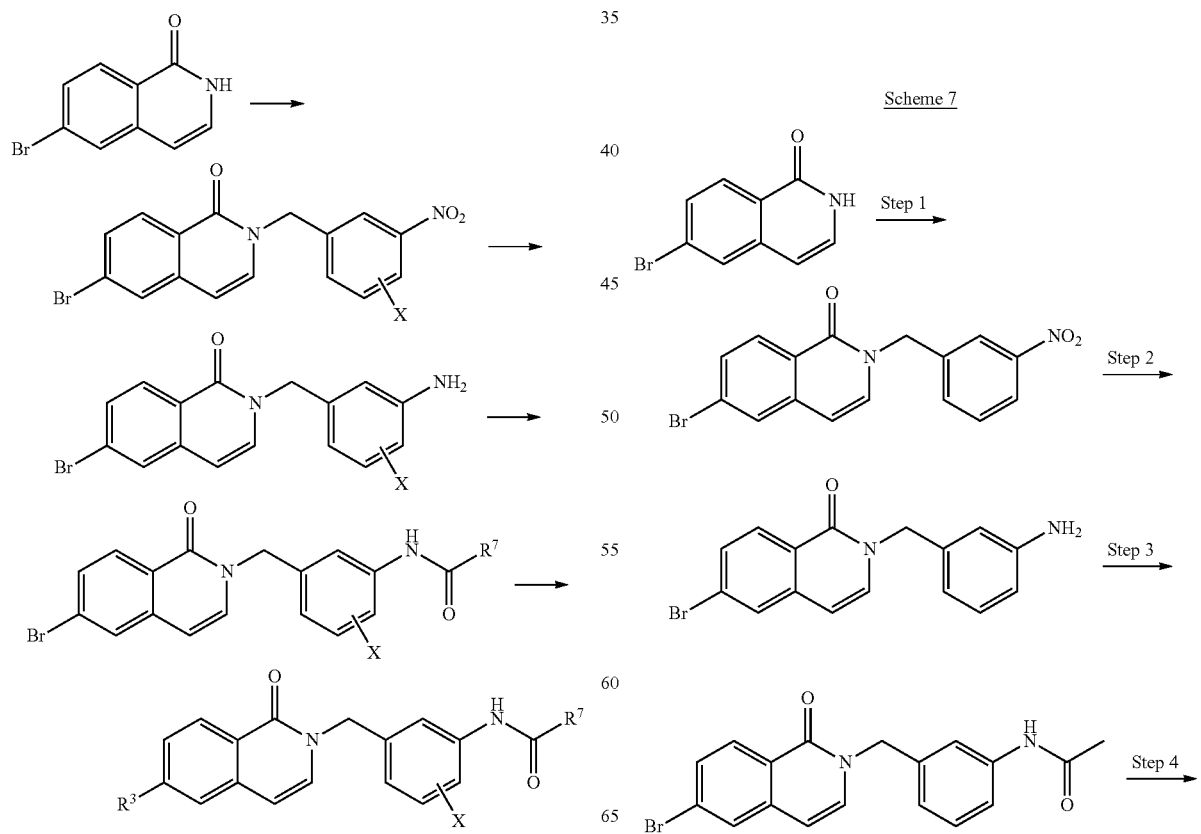
General Scheme 8
Scheme 7

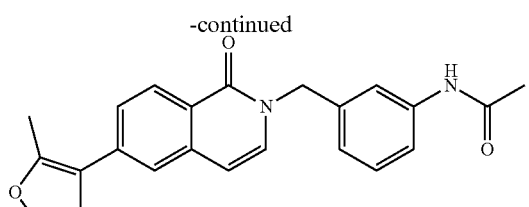

Compound 332

Step 1: Starting with 1-(bromomethyl)-3-nitrobenzene (1.2 g, 5.5 mmol) and 6-bromoisoquinolin-1(2H)-one (1.12 g, 5 mmol), and using Step 1 of the preparation of Intermediate 1, 6-bromo-2-(3-nitrobenzyl)isoquinolin-1(2H)-one was obtained (1.6 g, 95%). LC/MS found 359.0 [M+H]⁺.

Step 2: A suspension of 6-bromo-2-(3-nitrobenzyl)isoquinolin-1(2H)-one (530 mg, 1.48 mmol) and SnCl₂ (839 mg, 4.5 mmol) in EtOH (20 mL) was shaken at 70° C. for 3 hours. The mixture was cooled with ice bath and diluted with water. The mixture was neutralized with a solution of 1N NaOH at 0° C. and was then stirred for 30 min. The suspension was filtered, and then the crude was re-suspended in CH₂Cl₂. The mixture was dried over MgSO₄, filtered, and concentrated to provide 2-(3-aminobenzyl)-6-bromoisoquinolin-1(2H)-one. LC/MS found 329.1 [M+H]⁺.

Step 3: A mixture of 2-(3-aminobenzyl)-6-bromoisoquinolin-1(2H)-one (330 mg, 1.0 mmol), HBTU (572 mg, 1.50 mmol), i-Pr₂NEt (0.52 mL, 3.0 mmol), and acetic acid (140 mg, 2.0 mmol) in CH₂Cl₂ (10 mL) was stirred at RT overnight. The mixture was poured over H₂O and extracted with CH₂Cl₂. The organic layer was washed with brine, dried over MgSO₄, filtered, and concentrated. The residue was purified by flash column chromatography on SiO₂ using a gradient of 50-100% EtOAc in heptanes to provide N-(3-((6-bromo-1-oxoisoquinolin-2(1H)-yl)methyl)phenyl)acetamide as a white solid in 90% yield (340 mg). LC/MS found 371.5 [M+H]⁺.

Step 4: Starting with N-(3-((6-bromo-1-oxoisoquinolin-2(1H)-yl)methyl)phenyl)acetamide (170 mg, 0.45 mmol) and 4,4,5,5-tetramethyl-2-(2-methylfuran-3-yl)-1,3,2-dioxaborolane and using Step 4 of the preparation of Compound 27, Compound 332 (65 mg, 35% yield) was synthesized as a white solid. LCMS found 373.2 [M+H]⁺.

Compounds 333-353 in Table 7 below were prepared by the method (General Scheme 8) similar to that described for the preparation of Compound 332 using an appropriate 2-(3-aminobenzyl)-6-bromoisoquinolin-1(2H)-one, an appropriate boronic acid/ester, and an appropriate acid.

TABLE 7

| Compd | Boronic acid/ester | Structure | MS found [M + H]⁺ |
|---|---|---|---|
| 333 | | 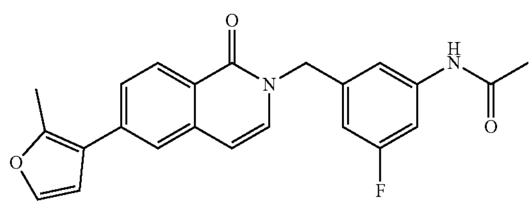 [SMILES: CC(=O)Nc1cc(F)cc(Cn2ccc3cc(-c4ccoc4C)ccc3c2=O)c1] | 391.3 |
| 334 | | 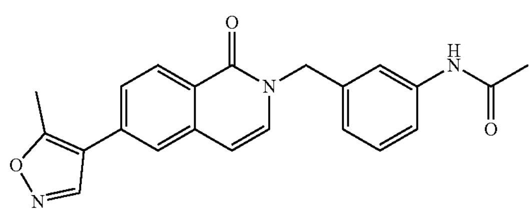 [SMILES: CC(=O)Nc1cccc(Cn2ccc3cc(-c4cnoc4C)ccc3c2=O)c1] | 374.3 |
| 335 | | 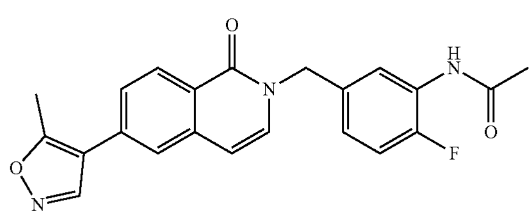 [SMILES: CC(=O)Nc1cc(Cn2ccc3cc(-c4cnoc4C)ccc3c2=O)ccc1F] | 392.3 |
| 336 | | 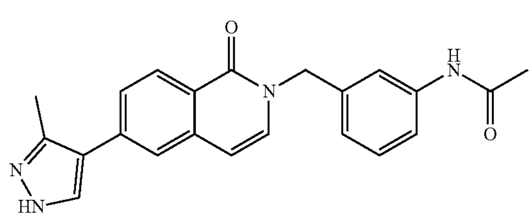 [SMILES: CC(=O)Nc1cccc(Cn2ccc3cc(-c4c[nH]nc4C)ccc3c2=O)c1] | 373.3 |

TABLE 7-continued
| Compd | Boronic acid/ester | Structure | MS found [M + H]+ |
|---|---|---|---|
| 337 | 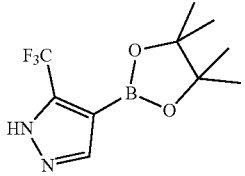 [SMILES: CC1(C)OB(c2cn[nH]c2C(F)(F)F)OC1(C)C] | 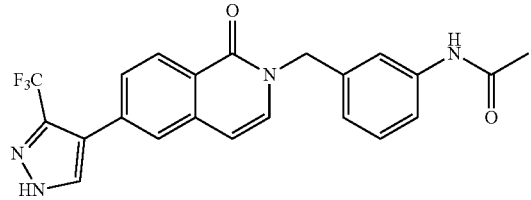 [SMILES: CC(=O)Nc1cccc(Cn2ccc3cc(-c4c[nH]nc4C(F)(F)F)ccc3c2=O)c1] | 427.3 |
| 338 | 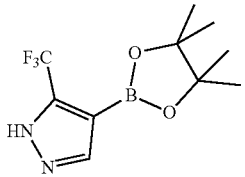 [SMILES: CC1(C)OB(c2cn[nH]c2C(F)(F)F)OC1(C)C] | 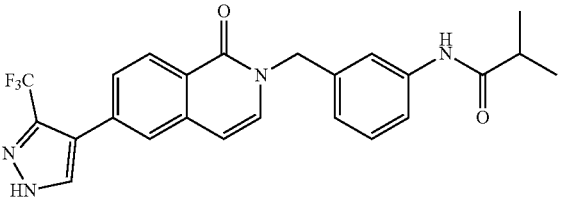 [SMILES: CC(C)C(=O)Nc1cccc(Cn2ccc3cc(-c4c[nH]nc4C(F)(F)F)ccc3c2=O)c1] | 455.3 |
| 339 | 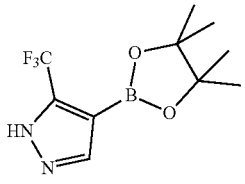 [SMILES: CC1(C)OB(c2cn[nH]c2C(F)(F)F)OC1(C)C] | 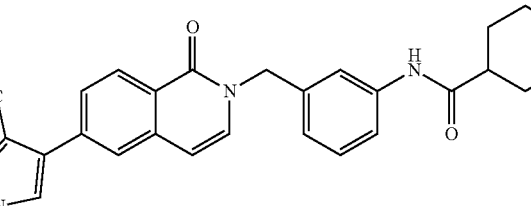 | 497.4 |
| 340 | 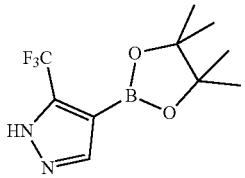 [SMILES: CC1(C)OB(c2cn[nH]c2C(F)(F)F)OC1(C)C] | 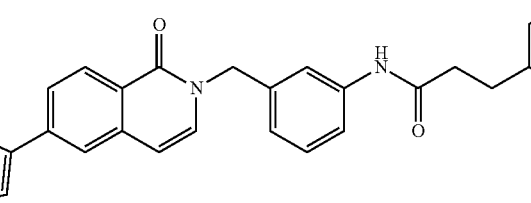 | 518.3 |
| 341 | 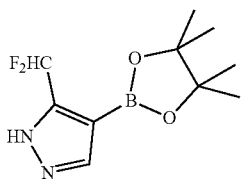 [SMILES: CC1(C)OB(c2cn[nH]c2C(F)F)OC1(C)C] | 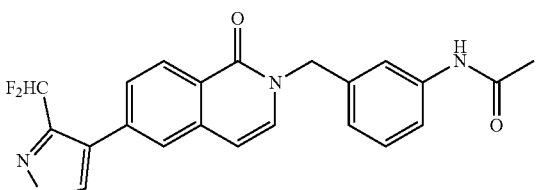 | 409.1 |
| 342 | 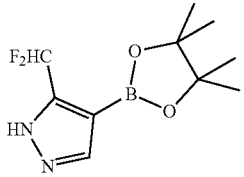 | 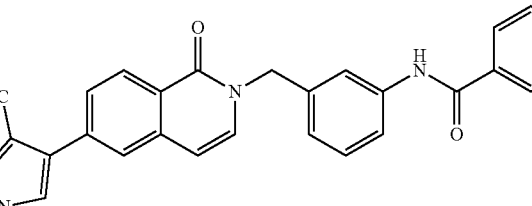 | 472.4 |
| 343 | 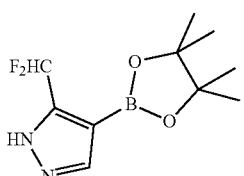 | 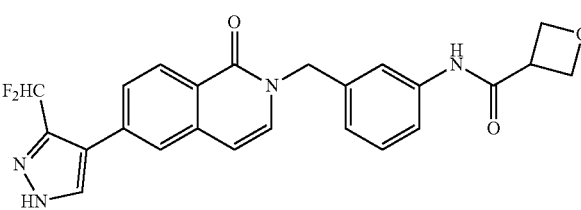 | 451.2 |

TABLE 7-continued

| Compd | Boronic acid/ester | Structure | MS found [M + H]+ |
|---|---|---|---|
| 344 | | 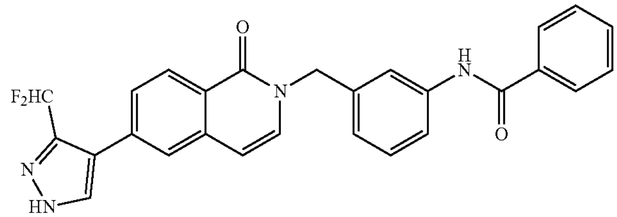 [SMILES: O=C(Nc1cccc(Cn2ccc3cc(-c4c[nH]nc4C(F)F)ccc3c2=O)c1)c1ccccc1] | 471.2 |
| 345 | | 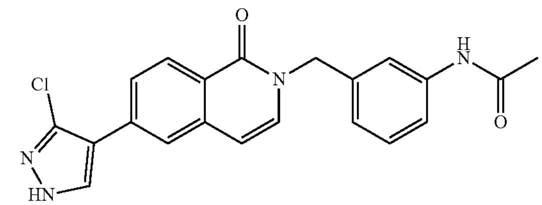 [SMILES: CC(=O)Nc1cccc(Cn2ccc3cc(-c4c[nH]nc4Cl)ccc3c2=O)c1] | 393.4 |
| 346 | | 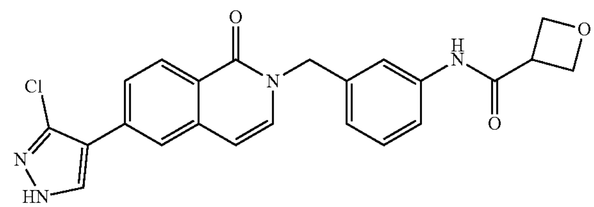 [SMILES: O=C(Nc1cccc(Cn2ccc3cc(-c4c[nH]nc4Cl)ccc3c2=O)c1)C1COC1] | 435.6 |
| 347 | | 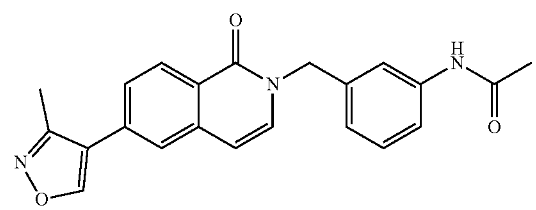 [SMILES: CC(=O)Nc1cccc(Cn2ccc3cc(-c4conc4C)ccc3c2=O)c1] | 374.2 |
| 348 | | 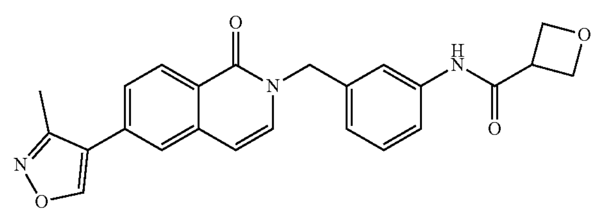 [SMILES: Cc1nocc1-c1ccc2c(=O)n(Cc3cccc(NC(=O)C4COC4)c3)ccc2c1] | 416.2 |
| 349 | | 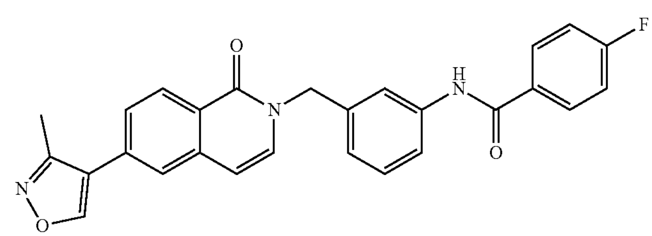 [SMILES: Cc1nocc1-c1ccc2c(=O)n(Cc3cccc(NC(=O)c4ccc(F)cc4)c3)ccc2c1] | 454.4 |
| 350 | | 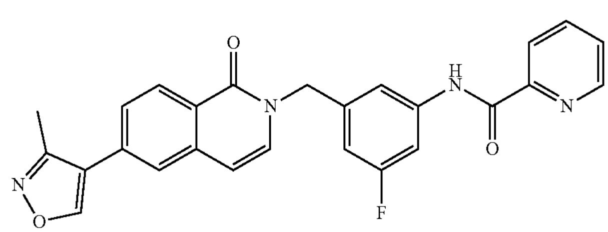 [SMILES: Cc1nocc1-c1ccc2c(=O)n(Cc3cc(F)cc(NC(=O)c4ccccn4)c3)ccc2c1] | 455.4 |

TABLE 7-continued

| Compd | Boronic acid/ester | Structure | MS found [M + H]+ |
|---|---|---|---|
| 351 | 3-methylisoxazol-4-yl boronic acid | 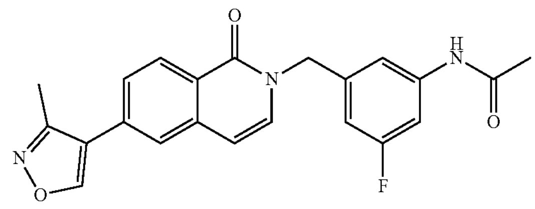 [SMILES: CC(=O)Nc1cc(F)cc(Cn2ccc3cc(-c4conc4C)ccc3c2=O)c1] | 392.2 |
| 352 | 1H-pyrazol-4-yl pinacol boronate | 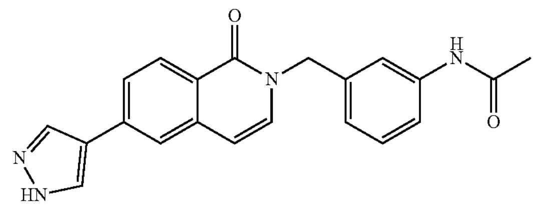 [SMILES: CC(=O)Nc1cccc(Cn2ccc3cc(-c4cn[nH]c4)ccc3c2=O)c1] | 359.3 |
| 353 | 2-aminopyridin-4-yl boronic acid | 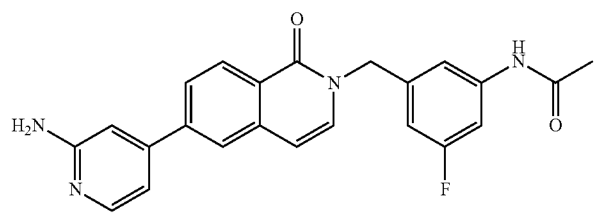 [SMILES: CC(=O)Nc1cc(F)cc(Cn2ccc3cc(-c4ccnc(N)c4)ccc3c2=O)c1] | 403.3 |

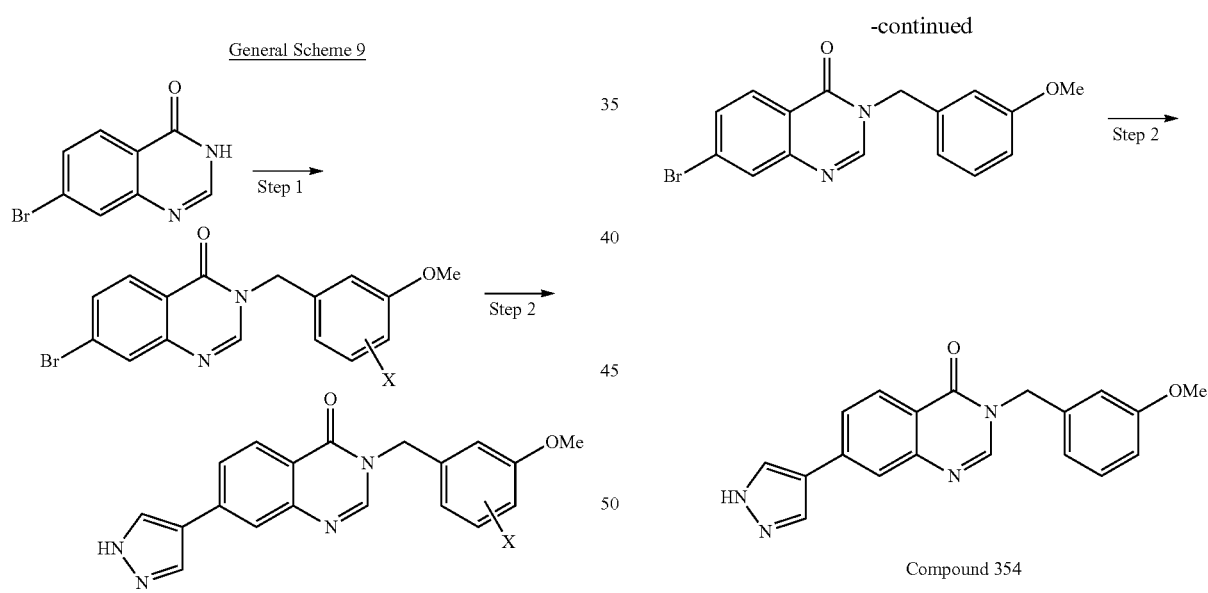

-continued

General Scheme 9

Compound 354: 3-(3-methoxybenzyl)-7-(1H-pyrazol-4-yl)quinazolin-4(3H)-one

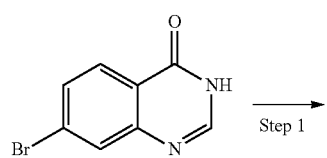

Step 1: A mixture of 7-bromoquinazolin-4(3H)-one (224 mg, 1.0 mmol), 3-methoxybenzyl bromide (300 mg, 1.5 mmol), K$_2$CO$_3$ (530 mg, 5.0 mmol), and NaI (30 mg, 0.20 mmol) in acetone (10 mL) was heated to reflux with stirring overnight. The mixture was cooled to RT, poured over H$_2$O, and extracted with EtOAc. The organic layer was washed with brine, dried over Na$_2$SO$_4$, filtered, and concentrated. The residue was purified by flash column chromatography on SiO$_2$ using a gradient of 10-50% EtOAc in heptanes to provide 7-bromo-3-(3-methoxybenzyl)quinazolin-4(3H)-one as white solid in 80% yield (276 mg). LC/MS found 345.0 [M+H]+.

Step 2: A mixture of 7-bromo-3-(3-methoxybenzyl)quinazolin-4(3H)-one (41 mg, 0.12 mmol), 4-pyrazoleboronic acid, pinacol ester (35 mg, 0.18 mmol), Na$_2$CO$_3$ (43 mg, 0.41 mmol), and Pd(dppf)Cl$_2$·CH$_2$Cl$_2$ (4.8 mg, 6.0 μmol) in 1,4-dioxane (1.0 mL) and H$_2$O (0.2 mL) was degassed via sparging with argon for 10 minutes and then heated to 100° C. overnight. The mixture was cooled to RT, poured over H$_2$O, and extracted with EtOAc. The organic layer was washed with brine, dried over Na$_2$SO$_4$, filtered, and concentrated. The residue was purified by flash column chromatography using a gradient of 5-10% CH$_3$OH in CH$_2$Cl$_2$ to provide Compound 354 as a colorless solid in 54% yield (21 mg). LC/MS found 333.1 [M+H]$^+$.

Compounds 355-365 in Table 8 below were prepared by the method (General Scheme 9) similar to that described for the preparation of Compound 355 using an appropriate 7-bromo-3-(3-methoxybenzyl)quinazolin-4(3H)-one and an appropriate boronic acid/ester.

TABLE 8

| Compd | Boronic acid/ester | Structure | MS found [M + H]$^+$ |
|---|---|---|---|
| 355 | | 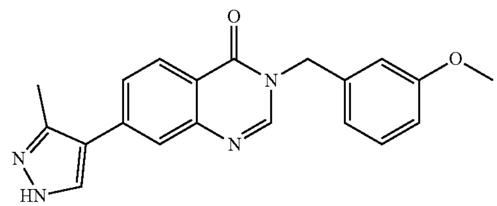 | 346.3 |
| 356 | | 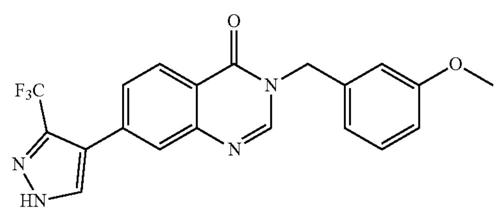 [SMILES: COc1cccc(Cn2cnc3cc(-c4c[nH]nc4C(F)(F)F)ccc3c2=O)c1] | 400.2 |
| 357 | | 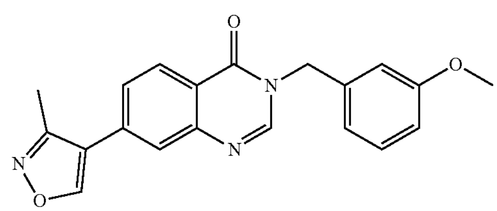 | 347.4 |
| 358 | | 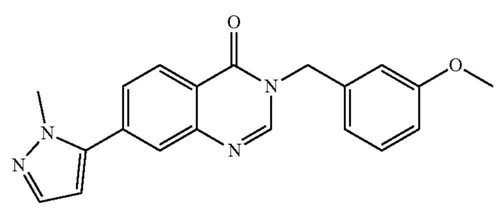 [SMILES: COc1cccc(Cn2cnc3cc(-c4ccnn4C)ccc3c2=O)c1] | 346.1 |
| 359 | | 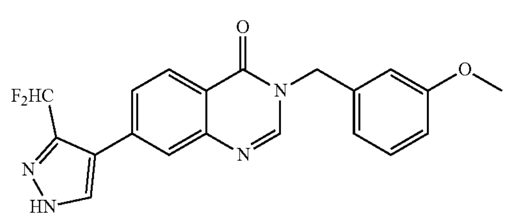 | 383.3 |
| 360 | | 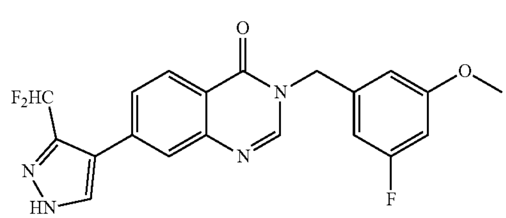 [SMILES: COc1cc(F)cc(Cn2cnc3cc(-c4c[nH]nc4C(F)F)ccc3c2=O)c1] | 401.2 |

TABLE 8-continued
| Compd | Boronic acid/ester | Structure | MS found [M + H]+ |
|---|---|---|---|
| 361 | | 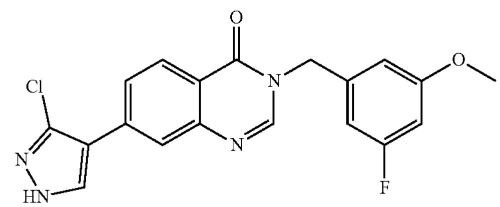 | 385.4 |
| 362 | | 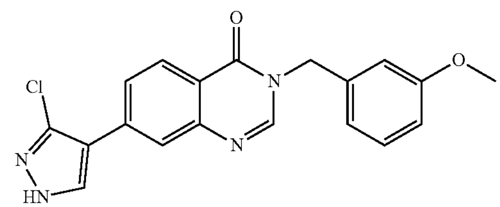 | 367.2 |
| 363 | | 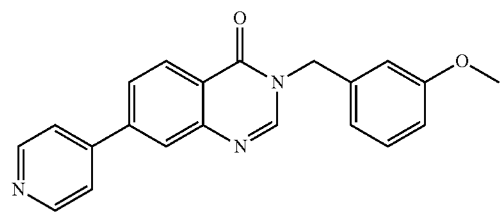 [SMILES: COc1cccc(Cn2cnc3cc(-c4ccncc4)ccc3c2=O)c1] | 344.2 |
| 364 | | 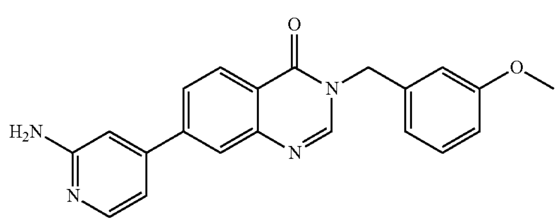 [SMILES: COc1cccc(Cn2cnc3cc(-c4ccnc(N)c4)ccc3c2=O)c1] | 359.4 |
| 365 | | 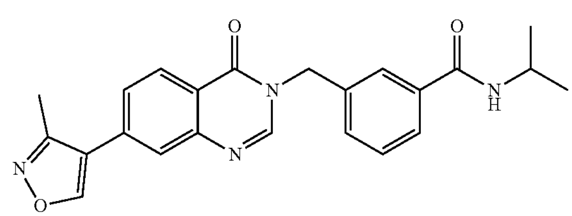 [SMILES: Cc1nocc1-c1ccc2c(=O)n(Cc3cccc(C(=O)NC(C)C)c3)cnc2c1] | 373.2 |
General Scheme 10
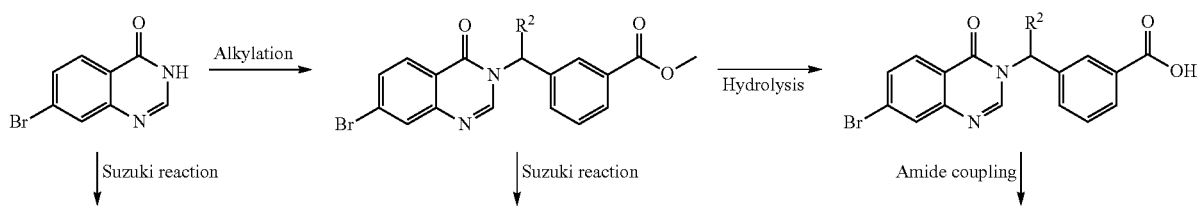

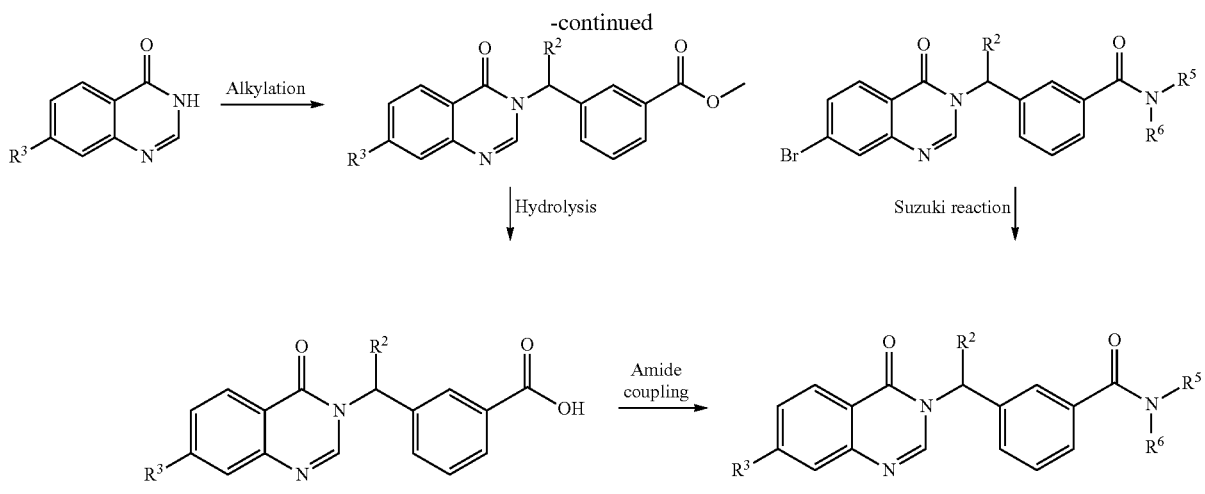

Compound 366: N-methyl-3-((4-oxo-7-(1H-pyrazol-4-yl)quinazolin-3(4H)-yl)methyl)benzamide Scheme 8

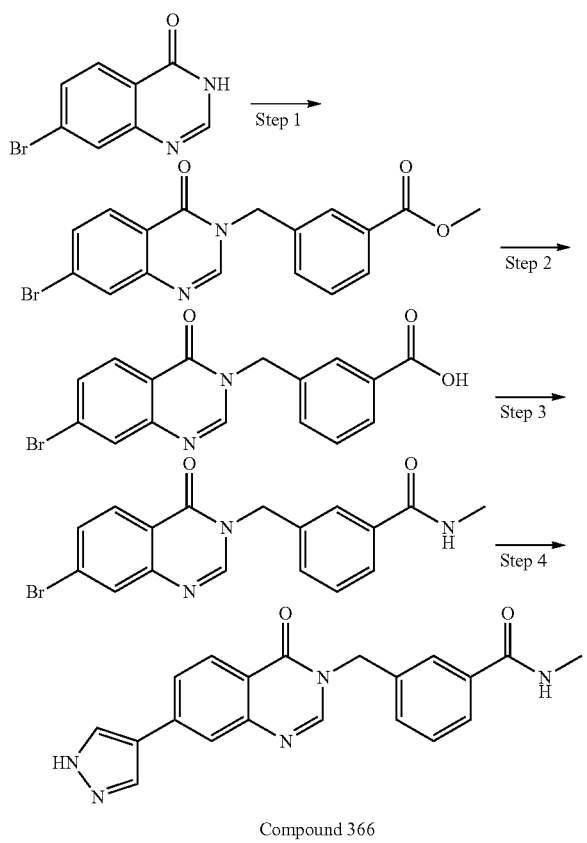

Compound 366

Step 1: Two 40-mL vials were each charged with 7-bromoquinazolin-4(3H)-one (450 mg, 2.0 mmol), methyl 3-(bromomethyl)benzoate (687 mg, 3.0 mmol), potassium carbonate (1.38 g, 10 mmol), sodium iodide (45 mg, 0.30 mmol), and acetone (9.0 mL). The vials were shaken at 45° C. overnight. The mixtures were combined, diluted with EtOAc (250 mL), washed sequentially with water and brine (250 mL each), dried ($Na_2SO_4$), treated with silica gel, and evaporated under reduced pressure. The resulting material was purified by silica gel column chromatography to provide methyl 3-((7-bromo-4-oxoquinazolin-3(4H)-yl)methyl)benzoate (1.23 g, 82% yield). LC/MS found 373.0 $[M+H]^+$.

Step 2: A mixture of Intermediate 2 (1.23 g, 3.3 mmol) and $LiOH \cdot H_2O$ (33 mmol) in $CH_3OH$ (20 mL) and $H_2O$ (10 mL) was stirred at RT overnight. The mixture was acidified to 15 pH 2 with 1M HCl. The resulting precipitate was vacuum filtered, washed with $H_2O$, and dried under a vacuum overnight to give 3-((7-bromo-4-oxoquinazolin-3(4H)-yl)methyl)benzoic acid as a pale-yellow solid in 85% yield (1.01 g). LC/MS found 359.1 $[M+H]^+$.

Step 3: A mixture of 3-((7-bromo-4-oxoquinazolin-3(4H)-yl)methyl)benzoic acid (366 mg, 1.0 mmol), HBTU (572 mg, 1.5 mmol), i-$Pr_2NEt$ (0.52 mL, 3.0 mmol), and $CH_3NH_2$ (2.0M in THF, 1.0 mL, 2.0 mmol) in $CH_2Cl_2$ (10 mL) was stirred at RT overnight. The mixture was poured over $H_2O$ and extracted with $CH_2Cl_2$. The organic layer was washed with brine, dried over $MgSO_4$, filtered, and concentrated. The residue was purified by flash column chromatography on $SiO_2$ using a gradient of 50-100% EtOAc in heptanes to provide 3-((7-bromo-4-oxoquinazolin-3(4H)-yl)methyl)-N-methylbenzamide as a white solid in quantitative yield (379 mg). LC/MS found 372.2 $[M+H]^+$.

Step 4: A mixture of 3-((7-Bromo-4-oxoquinazolin-3(4H)-yl)methyl)-N-methylbenzamide (74 mg, 0.20 mmol), 4-pyrazoleboronic acid pinacol ester (57 mg, 0.30 mmol), $Na_2CO_3$ (65 mg, 0.6 mmol), and $Pd(dppf)Cl_2$—$CH_2Cl_2$ (8.0 mg, 10.0 mmol) in 1,4-dioxane (1.0 mL) and $H_2O$ (0.2 mL) was degassed via sparging with argon for 10 minutes and then heated to 100° C. overnight. The mixture was cooled to RT, poured over $H_2O$, and extracted with EtOAc twice. The combined organic layer was washed with brine, dried over $Na_2SO_4$, filtered, and concentrated. The residue was purified by flash column chromatography using a gradient of 5-10% $CH_3OH$ in $CH_2Cl_2$ to provide N-methyl-3-((4-oxo-7-(1H-pyrazol-4-yl)quinazolin-3(4H)-yl)methyl)benzamide, Compound 366, as a colorless solid in 60% yield (43 mg). LC/MS found 360.1 $[M+H]^+$.

Compound 367-439 in Table 9 below were prepared by the method (General Scheme 10) similar to that described for the preparation of Compound 366 using an appropriate boronic acid/ester and an appropriate amine.

TABLE 9

| Compd | Boronic acid/ester | Structure | MS found [M + H]+ |
|---|---|---|---|
| 367 | (pinacol boronate of 3-CF3-1H-pyrazole) | 7-(3-CF3-1H-pyrazol-4-yl)-3-[[3-(methylcarbamoyl)phenyl]methyl]quinazolin-4-one | 427.3 |
| 368 | (pinacol boronate of 3-CF3-1H-pyrazole) | 7-(3-CF3-1H-pyrazol-4-yl)-3-[[3-(CD3-methylcarbamoyl)phenyl]methyl]quinazolin-4-one | 430.1 |
| 369 | (pinacol boronate of 3-CF3-1H-pyrazole) | 7-(3-CF3-1H-pyrazol-4-yl)-3-[[3-(isopropylcarbamoyl)phenyl]methyl]quinazolin-4-one | 456.4 |
| 370 | (pinacol boronate of 3-CF3-1H-pyrazole) | 7-(3-CF3-1H-pyrazol-4-yl)-3-[[3-[[2-(pyridin-4-yl)ethyl]carbamoyl]phenyl]methyl]quinazolin-4-one | 519.3 |
| 371 | (pinacol boronate of 3-CF3-1H-pyrazole) | 7-(3-CF3-1H-pyrazol-4-yl)-3-[[3-(benzylcarbamoyl)phenyl]methyl]quinazolin-4-one | 504.2 |
| 372 | (pinacol boronate of 3-CF3-1H-pyrazole) | 7-(3-CF3-1H-pyrazol-4-yl)-3-[[3-[(pyridin-4-ylmethyl)carbamoyl]phenyl]methyl]quinazolin-4-one | 505.4 |
| 373 | (pinacol boronate of 3-CF3-1H-pyrazole) | 7-(3-CF3-1H-pyrazol-4-yl)-3-[[3-[[4-(NHSO2Me)benzyl]carbamoyl]phenyl]methyl]quinazolin-4-one | 597.4 |

TABLE 9-continued

| Compd | Boronic acid/ester | Structure | MS found [M + H]+ |
|---|---|---|---|
| 374 | | 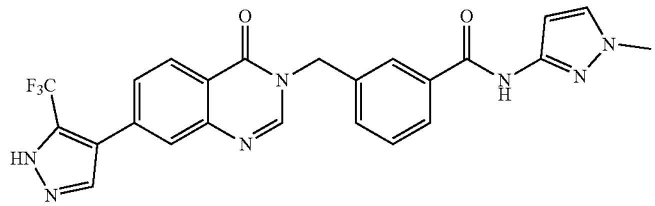 [SMILES: Cn1ccc(NC(=O)c2cccc(Cn3cnc4cc(-c5cn[nH]c5C(F)(F)F)ccc4c3=O)c2)n1] | 494.3 |
| 375 | | 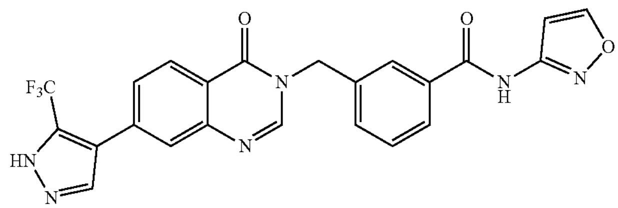 [SMILES: O=C(Nc1ccon1)c1cccc(Cn2cnc3cc(-c4cn[nH]c4C(F)(F)F)ccc3c2=O)c1] | 481.5 |
| 376 | | 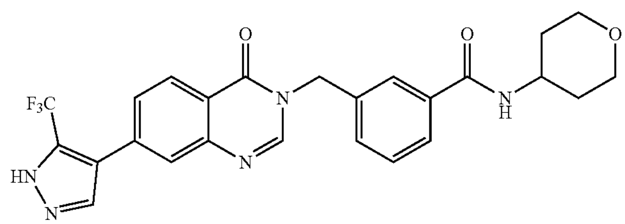 [SMILES: O=C(NC1CCOCC1)c1cccc(Cn2cnc3cc(-c4cn[nH]c4C(F)(F)F)ccc3c2=O)c1] | 498.3 |
| 377 | | 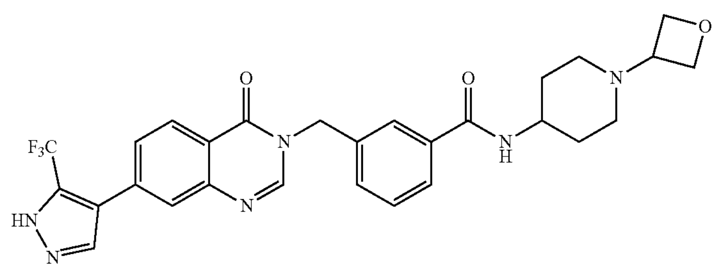 [SMILES: O=C(NC1CCN(C2COC2)CC1)c1cccc(Cn2cnc3cc(-c4cn[nH]c4C(F)(F)F)ccc3c2=O)c1] | 553.1 |
| 378 | | 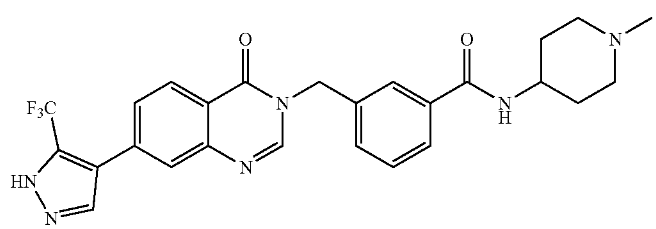 [SMILES: CN1CCC(NC(=O)c2cccc(Cn3cnc4cc(-c5cn[nH]c5C(F)(F)F)ccc4c3=O)c2)CC1] | 511.4 |
| 379 | | 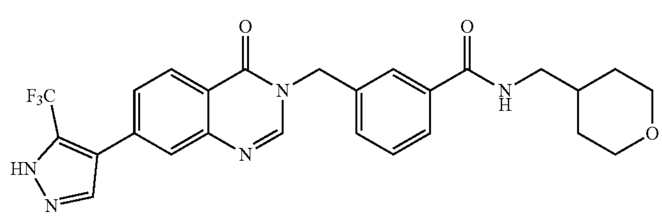 [SMILES: O=C(NCC1CCOCC1)c1cccc(Cn2cnc3cc(-c4cn[nH]c4C(F)(F)F)ccc3c2=O)c1] | 512.3 |

TABLE 9-continued

| Compd | Boronic acid/ester | Structure | MS found [M + H]+ |
|---|---|---|---|
| 380 | | 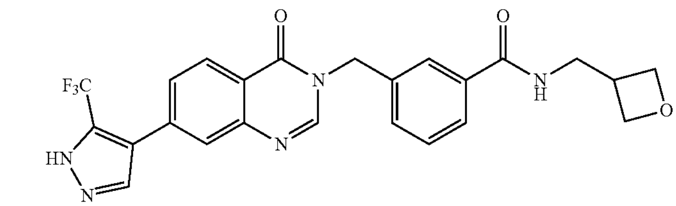 [SMILES: O=C(NCC1COC1)c1cccc(Cn2cnc3cc(-c4cn[nH]c4C(F)(F)F)ccc3c2=O)c1] | 484.3 |
| 381 | | 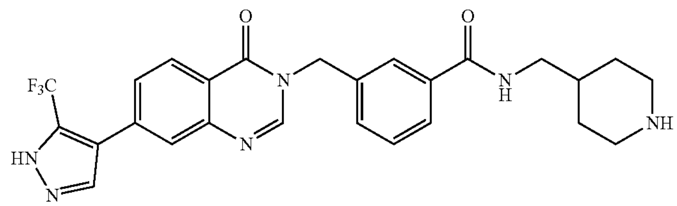 [SMILES: O=C(NCC1CCNCC1)c1cccc(Cn2cnc3cc(-c4cn[nH]c4C(F)(F)F)ccc3c2=O)c1] | 511.3 |
| 382 | | 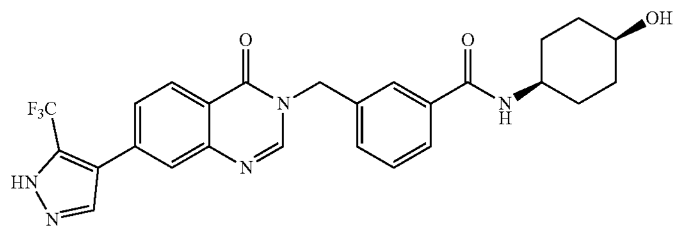 [SMILES: O=C(N[C@H]1CC[C@@H](O)CC1)c1cccc(Cn2cnc3cc(-c4cn[nH]c4C(F)(F)F)ccc3c2=O)c1] | 512.4 |
| 383 | | 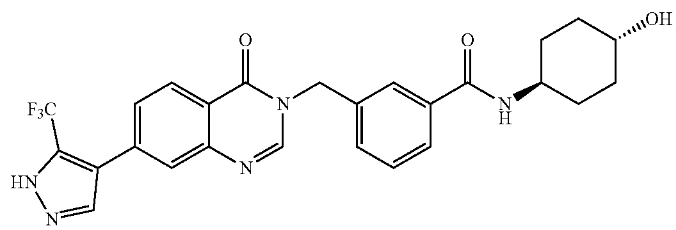 [SMILES: O=C(N[C@H]1CC[C@H](O)CC1)c1cccc(Cn2cnc3cc(-c4cn[nH]c4C(F)(F)F)ccc3c2=O)c1] | 512.3 |
| 384 | | 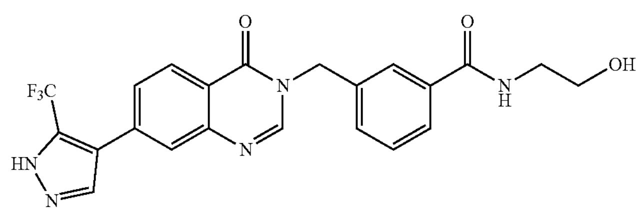 [SMILES: O=C(NCCO)c1cccc(Cn2cnc3cc(-c4cn[nH]c4C(F)(F)F)ccc3c2=O)c1] | 458.4 |
| 385 | | 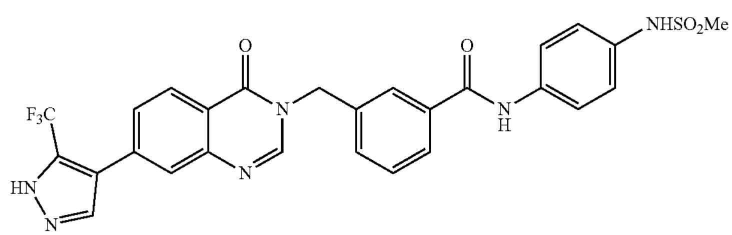 | 583.4 |
| 386 | | 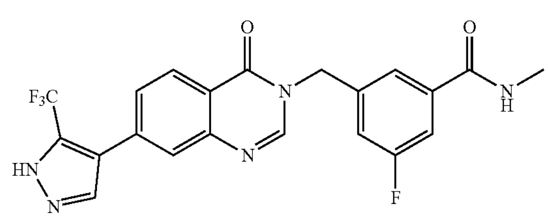 [SMILES: CNC(=O)c1cc(F)cc(Cn2cnc3cc(-c4cn[nH]c4C(F)(F)F)ccc3c2=O)c1] | 446.3 |

TABLE 9-continued

| Compd | Boronic acid/ester | Structure | MS found [M + H]+ |
|---|---|---|---|
| 387 | (3-CF3-pyrazole pinacol boronate) | 7-(3-CF3-1H-pyrazol-4-yl)-3-[[3-fluoro-5-(N-CD3-carbamoyl)phenyl]methyl]quinazolin-4(3H)-one | 449.3 |
| 388 | (3-CF3-pyrazole pinacol boronate) | 7-(3-CF3-1H-pyrazol-4-yl)-3-[1-[3-fluoro-5-(N-methylcarbamoyl)phenyl]ethyl]quinazolin-4(3H)-one | 460.2 |
| 389 | (3-CF3-pyrazole pinacol boronate) | 7-(3-CF3-1H-pyrazol-4-yl)-3-[[4-fluoro-3-(N-methylcarbamoyl)phenyl]methyl]quinazolin-4(3H)-one | 446.3 |
| 390 | (3-CF3-pyrazole pinacol boronate) | 7-(3-CF3-1H-pyrazol-4-yl)-3-[[3-chloro-5-(N-methylcarbamoyl)phenyl]methyl]quinazolin-4(3H)-one | 465.4 |
| 391 | (3-CHF2-pyrazole pinacol boronate) | 7-(3-CHF2-1H-pyrazol-4-yl)-3-[[3-(N-methylcarbamoyl)phenyl]methyl]quinazolin-4(3H)-one | 410.2 |
| 392 | (3-CHF2-pyrazole pinacol boronate) | 7-(3-CHF2-1H-pyrazol-4-yl)-3-[[3-(N-CD3-carbamoyl)phenyl]methyl]quinazolin-4(3H)-one | 413.1 |
| 393 | (3-CHF2-pyrazole pinacol boronate) | 7-(3-CHF2-1H-pyrazol-4-yl)-3-[[3-(N-(2-hydroxyethyl)carbamoyl)phenyl]methyl]quinazolin-4(3H)-one | 440.3 |

TABLE 9-continued

| Compd | Boronic acid/ester | Structure | MS found [M + H]+ |
|---|---|---|---|
| 394 | | 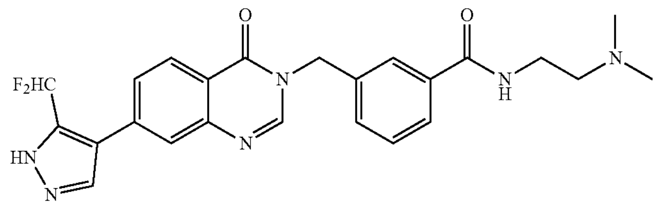 [SMILES: CN(C)CCNC(=O)c1cccc(Cn2cnc3cc(-c4cn[nH]c4C(F)F)ccc3c2=O)c1] | 467.4 |
| 395 | | 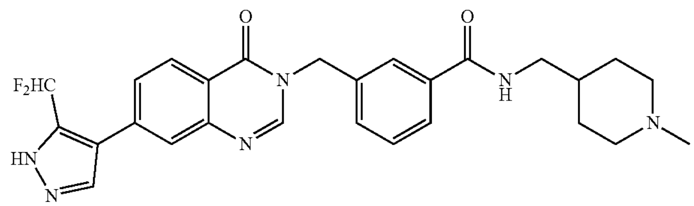 [SMILES: CN1CCC(CNC(=O)c2cccc(Cn3cnc4cc(-c5cn[nH]c5C(F)F)ccc4c3=O)c2)CC1] | 507.2 |
| 396 | | 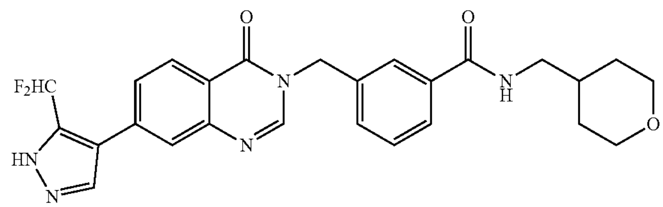 [SMILES: O=C(NCC1CCOCC1)c1cccc(Cn2cnc3cc(-c4cn[nH]c4C(F)F)ccc3c2=O)c1] | 494.4 |
| 397 | | 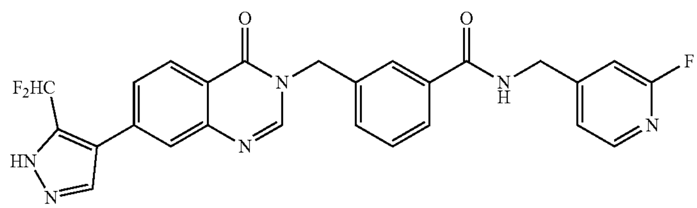 [SMILES: O=C(NCc1ccnc(F)c1)c1cccc(Cn2cnc3cc(-c4cn[nH]c4C(F)F)ccc3c2=O)c1] | 505.3 |
| 398 | | 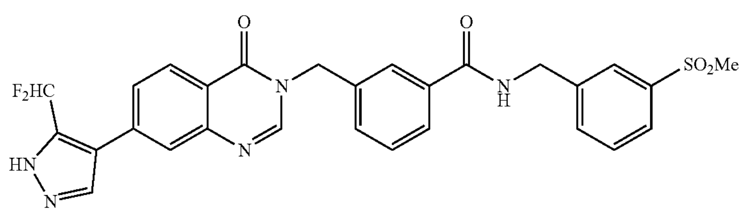 [SMILES: CS(=O)(=O)c1cccc(CNC(=O)c2cccc(Cn3cnc4cc(-c5cn[nH]c5C(F)F)ccc4c3=O)c2)c1] | 564.2 |
| 399 | | 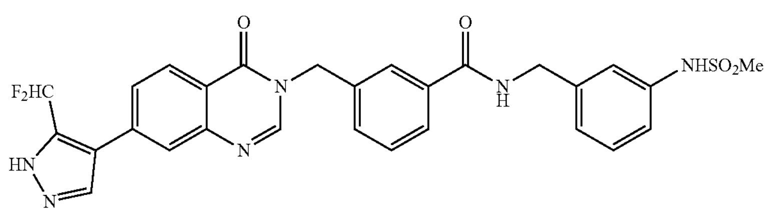 | 579.2 |
| 400 | | 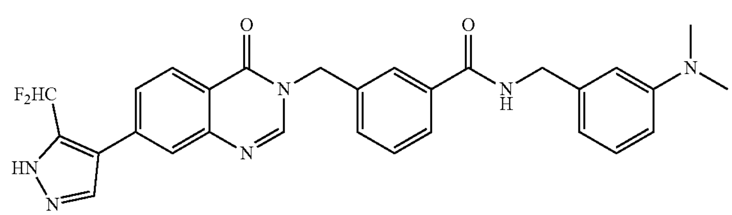 [SMILES: CN(C)c1cccc(CNC(=O)c2cccc(Cn3cnc4cc(-c5cn[nH]c5C(F)F)ccc4c3=O)c2)c1] | 529.4 |

TABLE 9-continued

| Compd | Boronic acid/ester | Structure | MS found [M + H]+ |
|---|---|---|---|
| 401 | | 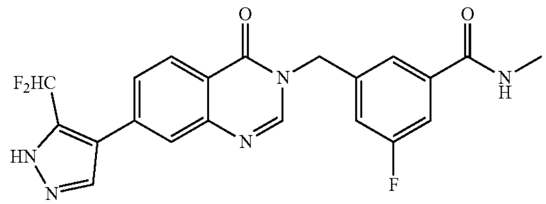 [SMILES: CNC(=O)c1cc(F)cc(Cn2cnc3cc(-c4cn[nH]c4C(F)F)ccc3c2=O)c1] | 428.4 |
| 402 | | 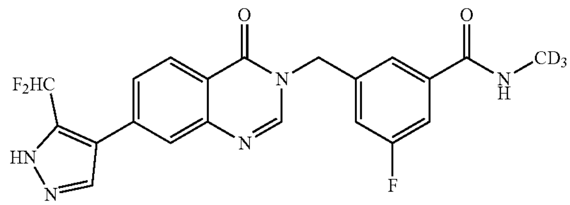 [SMILES: [2H]C([2H])([2H])NC(=O)c1cc(F)cc(Cn2cnc3cc(-c4cn[nH]c4C(F)F)ccc3c2=O)c1] | 431.1 |
| 403 | | 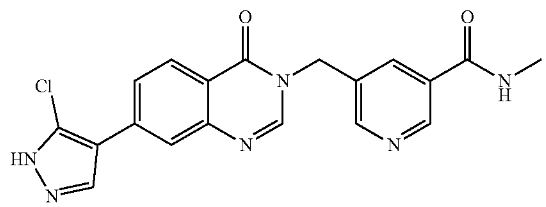 [SMILES: CNC(=O)c1cncc(Cn2cnc3cc(-c4cn[nH]c4Cl)ccc3c2=O)c1] | 395.2 |
| 404 | | 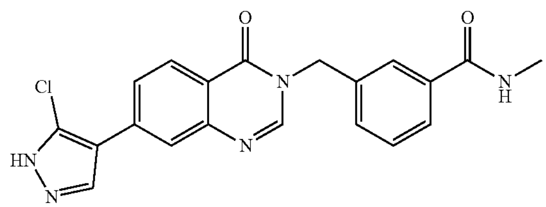 | 394.3 |
| 405 | | 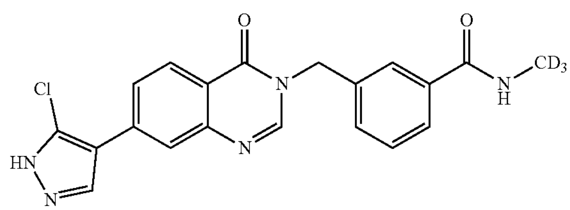 [SMILES: [2H]C([2H])([2H])NC(=O)c1cccc(Cn2cnc3cc(-c4cn[nH]c4Cl)ccc3c2=O)c1] | 397.2 |
| 406 | | 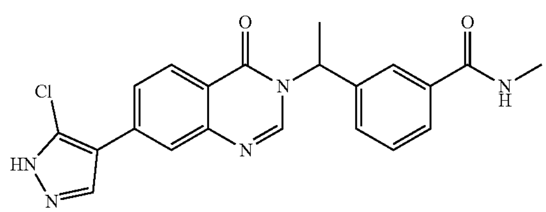 [SMILES: CNC(=O)c1cccc(C(C)n2cnc3cc(-c4cn[nH]c4Cl)ccc3c2=O)c1] | 407.3 |
| 407 | | 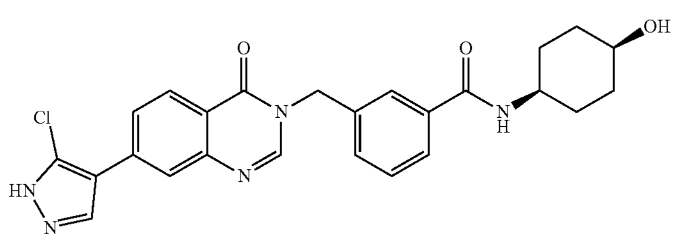 | 478.4 |

TABLE 9-continued

| Compd | Boronic acid/ester | Structure | MS found [M + H]+ |
|---|---|---|---|
| 408 | | 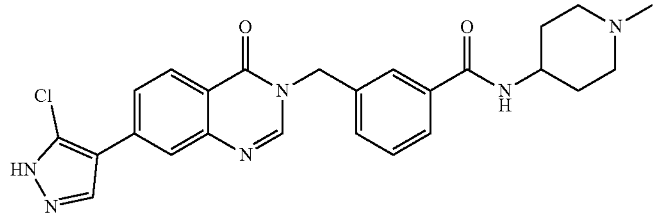 [SMILES: CN1CCC(NC(=O)c2cccc(Cn3cnc4cc(-c5cn[nH]c5Cl)ccc4c3=O)c2)CC1] | 477.3 |
| 409 | | 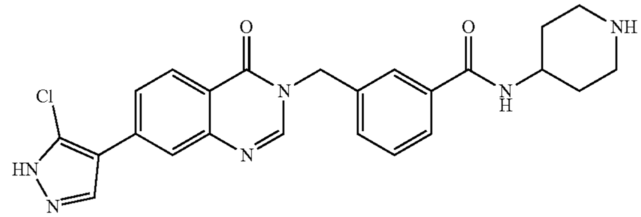 [SMILES: O=C(NC1CCNCC1)c1cccc(Cn2cnc3cc(-c4cn[nH]c4Cl)ccc3c2=O)c1] | 463.1 |
| 410 | | 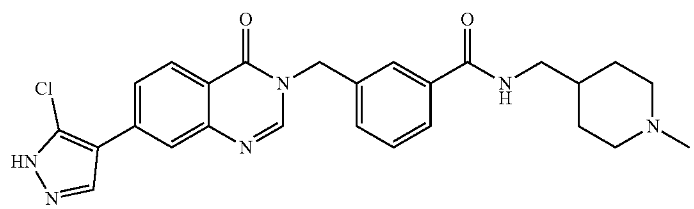 [SMILES: CN1CCC(CNC(=O)c2cccc(Cn3cnc4cc(-c5cn[nH]c5Cl)ccc4c3=O)c2)CC1] | 491.4 |
| 411 | | 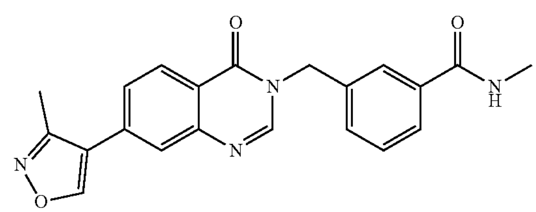 [SMILES: CNC(=O)c1cccc(Cn2cnc3cc(-c4conc4C)ccc3c2=O)c1] | 375.1 |
| 412 | | 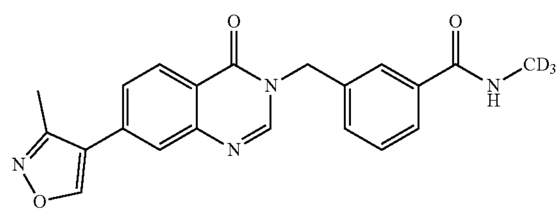 [SMILES: [2H]C([2H])([2H])NC(=O)c1cccc(Cn2cnc3cc(-c4conc4C)ccc3c2=O)c1] | 378.1 |
| 413 | | 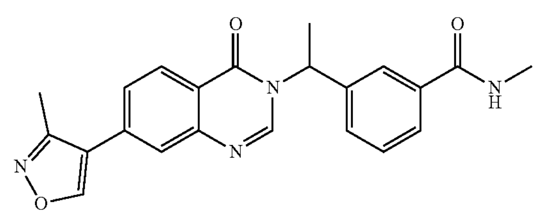 [SMILES: CNC(=O)c1cccc(C(C)n2cnc3cc(-c4conc4C)ccc3c2=O)c1] | 489.3 |
| 414 | | 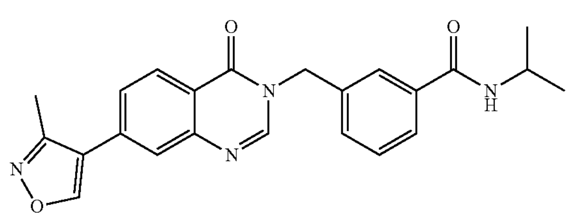 [SMILES: Cc1nocc1-c1ccc2c(=O)n(Cc3cccc(C(=O)NC(C)C)c3)cnc2c1] | 403.2 |

TABLE 9-continued

| Compd | Boronic acid/ester | Structure | MS found [M + H]+ |
|---|---|---|---|
| 415 | 3-methylisoxazol-4-yl B(OH)₂ | 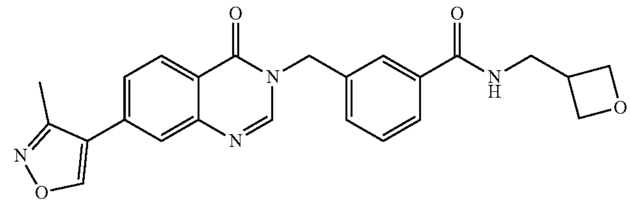 [SMILES: Cc1nocc1-c1ccc2c(=O)n(Cc3cccc(C(=O)NCC4COC4)c3)cnc2c1] | 431.2 |
| 416 | 3-methylisoxazol-4-yl B(OH)₂ | 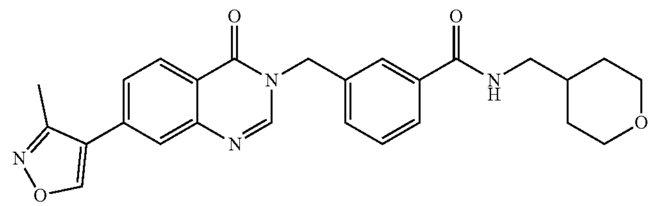 [SMILES: Cc1nocc1-c1ccc2c(=O)n(Cc3cccc(C(=O)NCC4CCOCC4)c3)cnc2c1] | 459.2 |
| 417 | 3-methylisoxazol-4-yl B(OH)₂ | 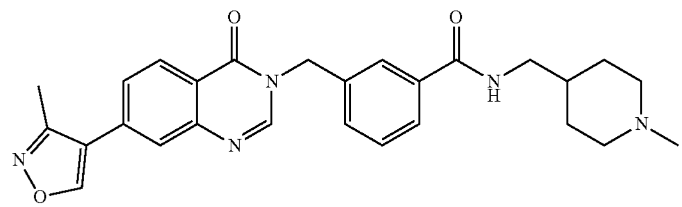 [SMILES: Cc1nocc1-c1ccc2c(=O)n(Cc3cccc(C(=O)NCC4CCN(C)CC4)c3)cnc2c1] | 472.4 |
| 418 | 3-methylisoxazol-4-yl B(OH)₂ | 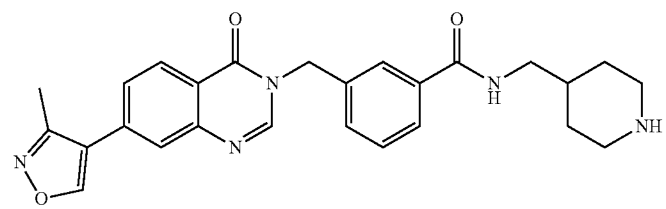 [SMILES: Cc1nocc1-c1ccc2c(=O)n(Cc3cccc(C(=O)NCC4CCNCC4)c3)cnc2c1] | 458.3 |
| 419 | 3-methylisoxazol-4-yl B(OH)₂ | 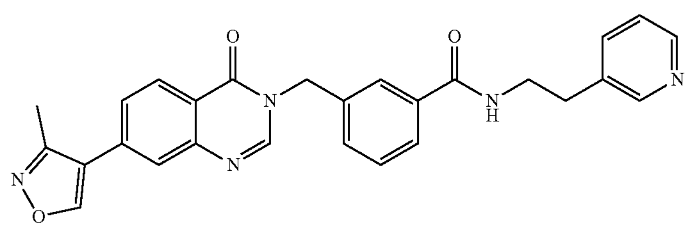 [SMILES: Cc1nocc1-c1ccc2c(=O)n(Cc3cccc(C(=O)NCCc4cccnc4)c3)cnc2c1] | 466.3 |
| 420 | 3-methylisoxazol-4-yl B(OH)₂ | 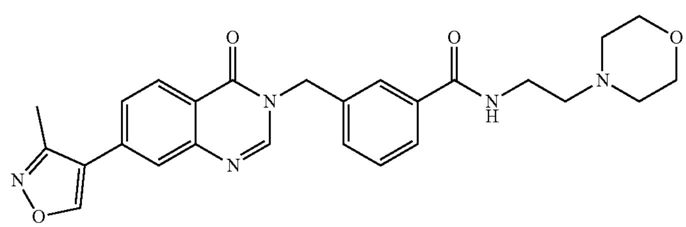 [SMILES: Cc1nocc1-c1ccc2c(=O)n(Cc3cccc(C(=O)NCCN4CCOCC4)c3)cnc2c1] | 474.3 |
| 421 | 3-methylisoxazol-4-yl B(OH)₂ | 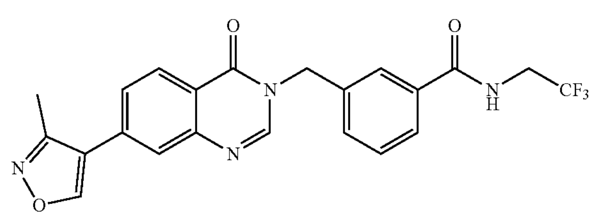 [SMILES: Cc1nocc1-c1ccc2c(=O)n(Cc3cccc(C(=O)NCC(F)(F)F)c3)cnc2c1] | 443.2 |

TABLE 9-continued

| Compd | Boronic acid/ester | Structure | MS found [M + H]+ |
|---|---|---|---|
| 422 | 3-methylisoxazole-4-B(OH)₂ | [structure] | 393.4 |
| 423 | 3-methylisoxazole-4-B(OH)₂ | [structure with CD₃] | 396.1 |
| 424 | 1-methylpyrazole-5-B(OH)₂ | [structure] | 373.2 |
| 425 | 1-methylpyrazole-5-B(OH)₂ | [structure with CD₃] | 376.2 |
| 426 | 1-methylpyrazole-5-B(OH)₂ | [structure] | 388.4 |
| 427 | 1-methylpyrazole-5-B(OH)₂ | [structure with cis-3-hydroxycyclobutyl] | 430.3 |
| 428 | 1-methylpyrazole-5-B(OH)₂ | [structure with trans-3-hydroxycyclobutyl] | 430.1 |

TABLE 9-continued

| Compd | Boronic acid/ester | Structure | MS found [M + H]+ |
|---|---|---|---|
| 429 | 1-methyl-pyrazole-5-B(OH)₂ | [quinazolinone with 1-methylpyrazole, benzamide, N-(4-hydroxycyclohexyl)] | 458.4 |
| 430 | 1-methyl-pyrazole-5-B(OH)₂ | [quinazolinone with 1-methylpyrazole, benzamide, N-(1-methylpiperidin-4-yl)] | 457.3 |
| 431 | 1-methyl-pyrazole-5-B(OH)₂ | [quinazolinone with 1-methylpyrazole, benzamide, N-(oxetan-3-ylmethyl)] | 430.4 |
| 432 | 1-methyl-pyrazole-5-B(OH)₂ | [quinazolinone with 1-methylpyrazole, benzamide, N-(2-hydroxyethyl)] | 404.4 |
| 433 | 2-aminopyridine-4-B(OH)₂ | [quinazolinone with 2-aminopyridine, benzamide, N-methyl] | 386.2 |
| 434 | 2-aminopyridine-4-B(OH)₂ | [quinazolinone with 2-aminopyridine, benzamide, N-(oxetan-3-yl)] | 428.3 |
| 435 | 2-aminopyridine-4-B(OH)₂ | [quinazolinone with 2-aminopyridine, benzamide, N-(tetrahydropyran-4-yl)] | 456.1 |

TABLE 9-continued
| Compd | Boronic acid/ester | Structure | MS found [M + H]+ |
|---|---|---|---|
| 436 | | 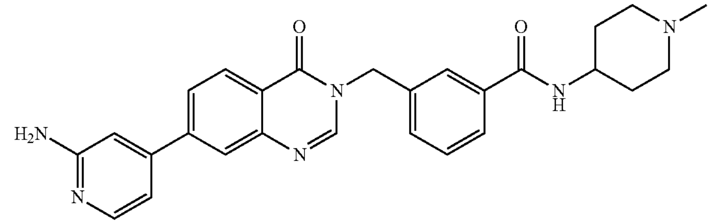 [SMILES: CN1CCC(NC(=O)c2cccc(Cn3cnc4cc(-c5ccnc(N)c5)ccc4c3=O)c2)CC1] | 469.3 |
| 437 | | 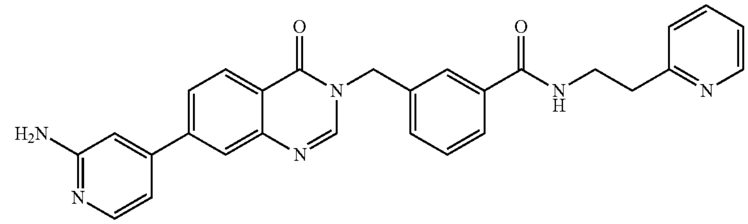 [SMILES: Nc1cc(-c2ccc3c(=O)n(Cc4cccc(C(=O)NCCc5ccccn5)c4)cnc3c2)ccn1] | 477.1 |
| 438 | | 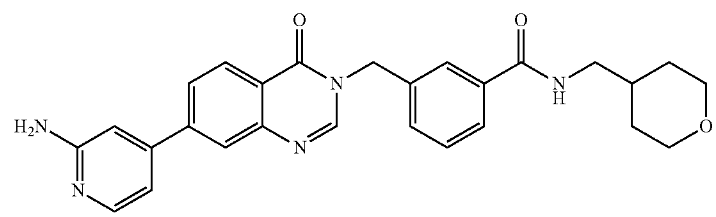 [SMILES: Nc1cc(-c2ccc3c(=O)n(Cc4cccc(C(=O)NCC5CCOCC5)c4)cnc3c2)ccn1] | 470.3 |
| 439 | | 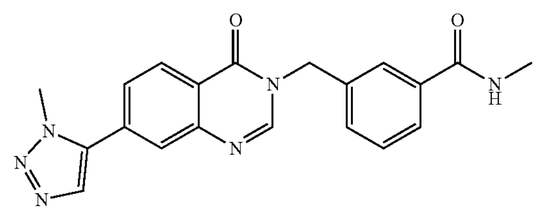 [SMILES: CNC(=O)c1cccc(Cn2cnc3cc(-c4cnnn4C)ccc3c2=O)c1] | 375.2 |
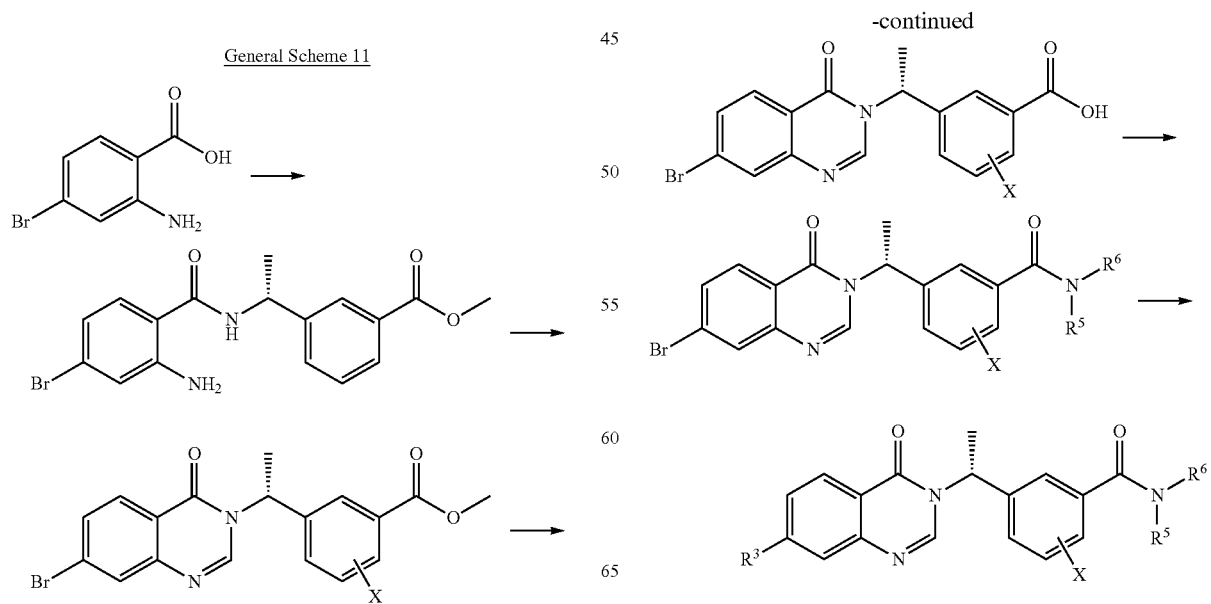
General Scheme 11

Compound 440: (R)—N-methyl-3-(1-(7-(5-methyl-1H-pyrazol-4-yl)-4-oxoquinazolin-3(4H)-yl)ethyl)benzamide

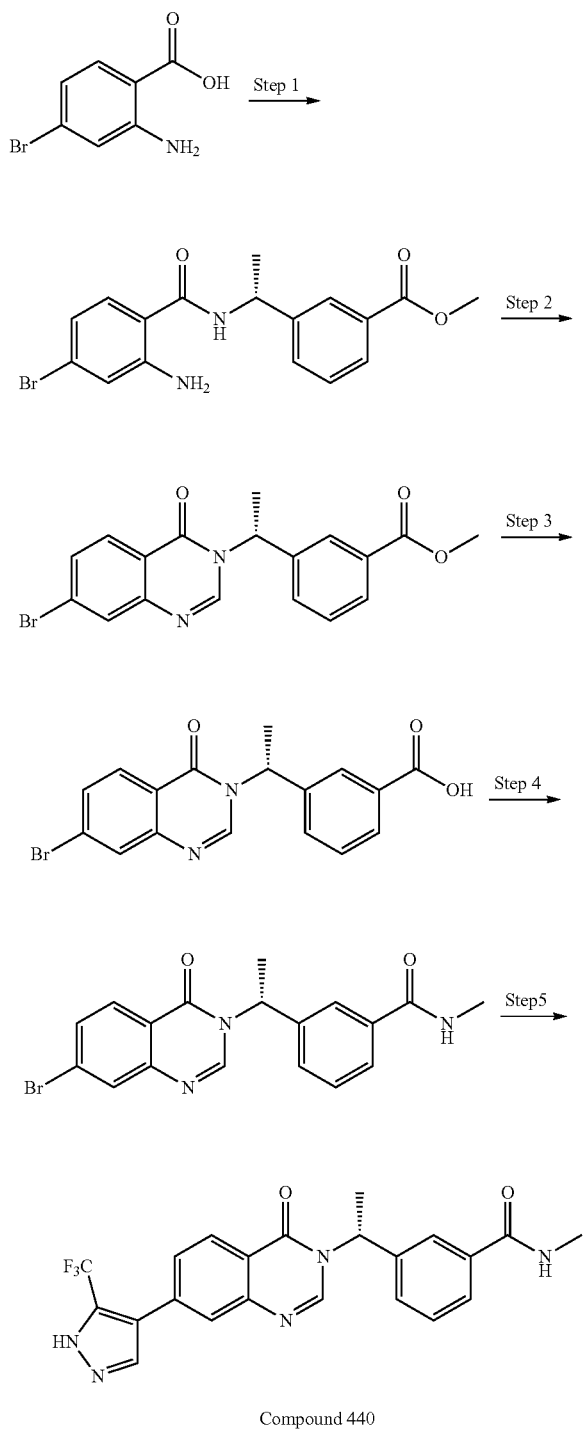

Compound 440

Step 1: A mixture of 2-amino-4-bromobenzoic acid (2.40 g, 11 mmol), HBTU (4.94 g, 13 mmol), and DIEA (6.8 mL) in DMF (30 mL) was shaken at ambient temperature for 30 minutes. The mixture was treated with methyl (R)-3-(1-aminoethyl)benzoate (1.80 g, 10 mmol) and shaken overnight at RT. The reaction mixture was diluted with EtOAc and brine. The organic later was separated, washed sequentially with water and brine, dried (MgSO$_4$), concentrated, and purified by silica gel column chromatography to provide methyl (R)-3-(1-(2-amino-4-bromobenzamido)ethyl)benzoate (3.31 g, 88% yield). LC/MS found 377.0 [M+H]$^+$.

Step 2: A suspension of (R)-3-(1-(2-amino-4-bromobenzamido)ethyl)benzoate (3.31 g, 8.8 mmol) and p-TsOH—H$_2$O (23 mg, 1.3 mmol) in neat triethyl orthoformate (30 mL) was shaken at 80° C. overnight. The mixture was diluted with EtOAc, washed sequentially with saturated aqueous NaHCO$_3$ and brine, dried (Na$_2$SO$_4$), filtered, concentrated, and purified by silica gel column chromatography to provide methyl (R)-3-(1-(4-bromo-N-methyl-2-(methyleneamino)benzamido)ethyl)benzoate (2.8 g, 82% yield). LC/MS found [M+H]$^+$.

Step 3: aq. 2M LiOH solution (36 mL, 72 mmol) was added to a suspension of methyl (R)-3-(1-(4-bromo-N-methyl-2-(methyleneamino)benzamido)ethyl)benzoate (2.8 g, 7.2 mmol) in MeOH (70 mL), and then the mixture was shaken overnight at RT. The mixture was acidified with aq. 1N HCl solution to pH 2~4, extracted with DCM. The organic layer was dried (Na$_2$SO$_4$), concentrated, and purified by silica gel column chromatography to provide (R)-3-(1-(7-bromo-4-oxoquinazolin-3(4H)-yl)ethyl)benzoic acid (2.06 g, 77% yield). LC/MS found 373.0 [M+H]$^+$.

Step 4: A mixture of (R)-3-(1-(7-bromo-4-oxoquinazolin-3(4H)-yl)ethyl)benzoic acid (373 mg, 1 mmol), HBTU (1.5 equiv), and DIEA (2.0 equiv) in DMF (3 mL) was shaken at ambient temperature 30 minutes. The mixture was treated with a 2M solution of methyl amine (1 mL) in THF and shaken overnight at room temperature. The reaction mixture was diluted with EtOAc and brine. The organic later was separated, washed sequentially with water and brine, dried Na$_2$SO$_4$, concentrated, and purified by silica gel column chromatography to provide methyl (R)-3-(1-(7-bromo-4-oxoquinazolin-3(4H)-yl)ethyl)-N-methylbenzamide (193 mg, 50% yield). LCMS found 386.1 [M+H]$^+$.

Step 5: A mixture of (R)-3-(1-(7-bromo-4-oxoquinazolin-3(4H)-yl)ethyl)-N-methylbenzamide (39 mg, 0.1 mmol), 4-(4,4,5,5-tetramethyl-1,3,2-dioxaborolan-2-yl)-5-(trifluoromethyl)-1H-pyrazole (39 mg, 1.5 mmol), aq. 2M sodium carbonate solution (150 uL, 3.0 equiv), and PdCl$_2$(PPh$_3$)$_2$ (10.5 mg, 0.1 equiv) in dioxane (2 mL) was purged with argon for 5 minutes. The mixture was shaken at 70° C. overnight. The sample was filtered, then the filtrate was evaporated under reduced pressure. The material was purified by silica gel column chromatography to provide (R)—N-methyl-3-(1-(4-oxo-7-(5-(trifluoromethyl)-1H-pyrazol-4-yl)quinazolin-3(4H)-yl)ethyl)benzamide, Compound 440, as a pale yellow solid (21.1 mg, 48%). LC/MS found 442.2 [M+H]$^+$.

$^1$H NMR (400 MHz, DMSO-d6) δ 13.94 (br. s, 1H), 8.45 (m, 3H), 8.20 (d, 1H, J=8.30 Hz), 7.85 (m, 1H), 7.76 (d, 1H, J=7.7 Hz), 7.73 (d, 1H, J=1.6 Hz), 7.63 (dd, 1H, J=8.3, 1.6 Hz), 7.56 (d, 1H, J=7.9 Hz), 7.46 (t, 1H, J=7.7 Hz), 6.13 (q, 1H, J=7.2 Hz), 2.77 (d, 3H, J=4.6 Hz), 1.88 (d, 3H, J=7.2 Hz).

Compounds 441-482 in Table 10 below were prepared by the method (General Scheme 11) similar to that described for the preparation of Compound 440 using 3-(1-(6-bromo-1-oxoisoquinolin-2(1H)-yl)ethyl)benzoic acid, an appropriate boronic acid/ester, and an appropriate amine.

TABLE 10

| Compd | Boronic acid/ester | Structure | MS found [M + H]+ |
|---|---|---|---|
| 441 | | 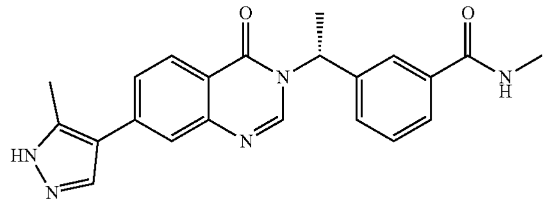 [SMILES: CNC(=O)c1cccc([C@@H](C)n2cnc3cc(-c4cn[nH]c4C)ccc3c2=O)c1] | 388.3 |
| 442 | | 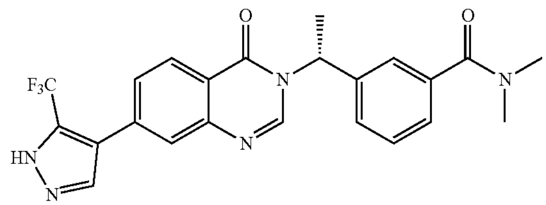 [SMILES: C[C@H](c1cccc(C(=O)N(C)C)c1)n1cnc2cc(-c3cn[nH]c3C(F)(F)F)ccc2c1=O] | 456.1 |
| 443 | | 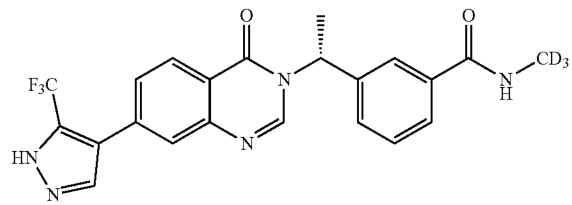 [SMILES: [2H]C([2H])([2H])NC(=O)c1cccc([C@@H](C)n2cnc3cc(-c4cn[nH]c4C(F)(F)F)ccc3c2=O)c1] | 445.2 |
| 444 | | 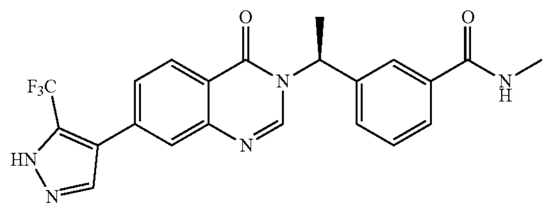 [SMILES: CNC(=O)c1cccc([C@H](C)n2cnc3cc(-c4cn[nH]c4C(F)(F)F)ccc3c2=O)c1] | 442.1 |
| 445 | | 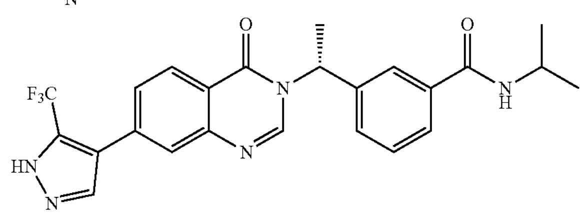 | 470.3 |
| 446 | | 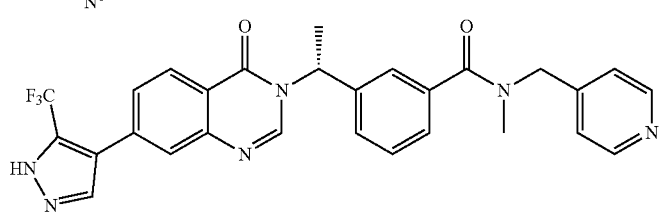 | 533.2 |
| 447 | | 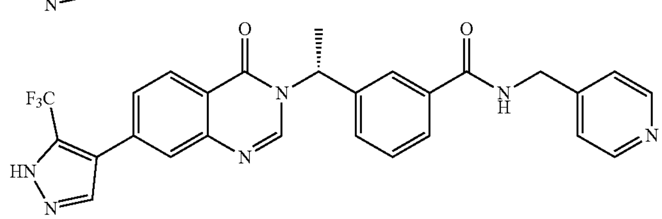 | 519.3 |
| 448 | | 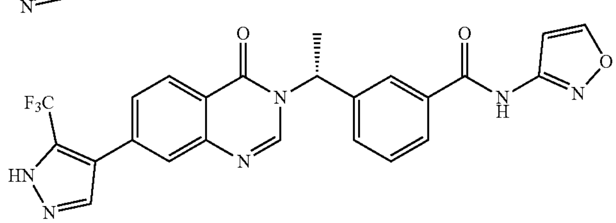 | 495.3 |

TABLE 10-continued

| Compd | Boronic acid/ester | Structure | MS found [M + H]+ |
|---|---|---|---|
| 449 | | 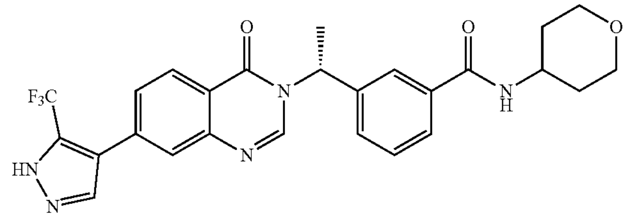 [SMILES: C[C@H](c1cccc(C(=O)NC2CCOCC2)c1)n1cnc2cc(-c3cn[nH]c3C(F)(F)F)ccc2c1=O] | 512.4 |
| 450 | | 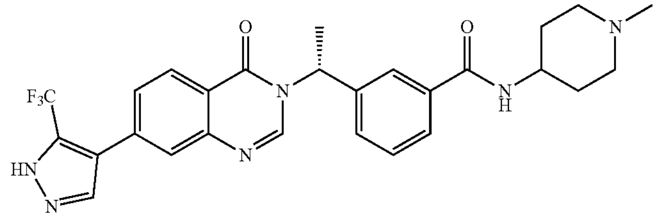 [SMILES: C[C@H](c1cccc(C(=O)NC2CCN(C)CC2)c1)n1cnc2cc(-c3cn[nH]c3C(F)(F)F)ccc2c1=O] | 525.4 |
| 451 | | 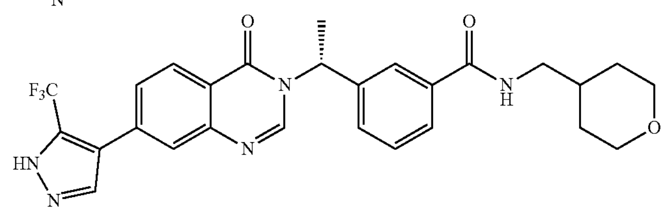 | 526.1 |
| 452 | | 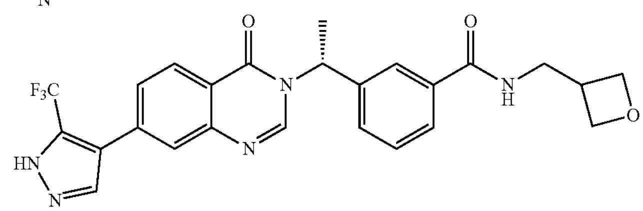 | 498.2 |
| 453 | | 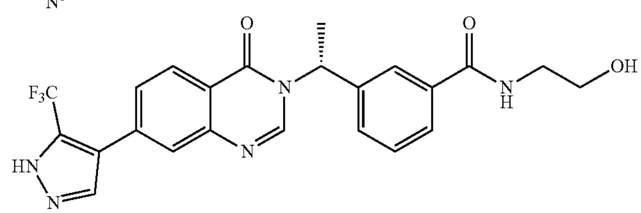 | 472.4 |
| 454 | | 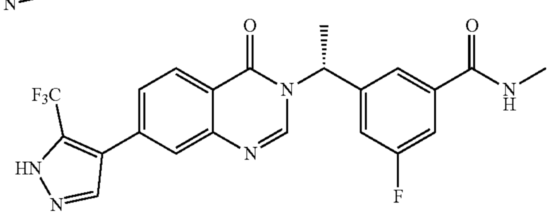 | 460.2 |
| 455 | | 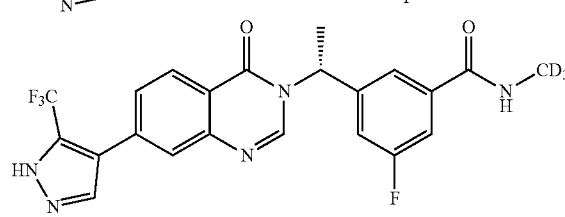 | 463.1 |
| 456 | | 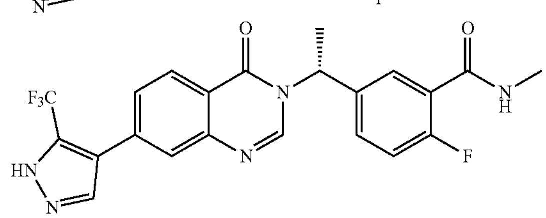 | 460.1 |

TABLE 10-continued

| Compd | Boronic acid/ester | Structure | MS found [M + H]+ |
|---|---|---|---|
| 457 | F₂HC-pyrazole-Bpin | F₂HC-pyrazole-quinazolinone-CH(CH₃)-phenyl-C(O)NHCH₃ | 424.3 |
| 458 | F₂HC-pyrazole-Bpin | F₂HC-pyrazole-quinazolinone-CH(CH₃)-phenyl-C(O)NH-CD₃ | 427.1 |
| 459 | F₂HC-pyrazole-Bpin | F₂HC-pyrazole-quinazolinone-CH(CH₃)-phenyl-C(O)NHCH₂CH₂OH | 454.3 |
| 460 | F₂HC-pyrazole-Bpin | F₂HC-pyrazole-quinazolinone-CH(CH₃)-phenyl-C(O)NHCH₂CH₂N(CH₃)₂ | 481.4 |
| 461 | F₂HC-pyrazole-Bpin | F₂HC-pyrazole-quinazolinone-CH(CH₃)-phenyl-C(O)NH-CH₂-(N-methylpiperidine) | 521.3 |
| 462 | F₂HC-pyrazole-Bpin | F₂HC-pyrazole-quinazolinone-CH(CH₃)-phenyl-C(O)NH-CH₂-(tetrahydropyran) | 508.4 |
| 463 | F₂HC-pyrazole-Bpin | F₂HC-pyrazole-quinazolinone-CH(CH₃)-(3-F-phenyl)-C(O)NHCH₃ | 442.3 |
| 464 | Cl-pyrazole-Bpin | Cl-pyrazole-quinazolinone-CH(CH₃)-phenyl-C(O)NH-(N-methylpiperidin-4-yl) | 491.5 |

TABLE 10-continued

| Compd | Boronic acid/ester | Structure | MS found [M + H]+ |
|---|---|---|---|
| 465 | | 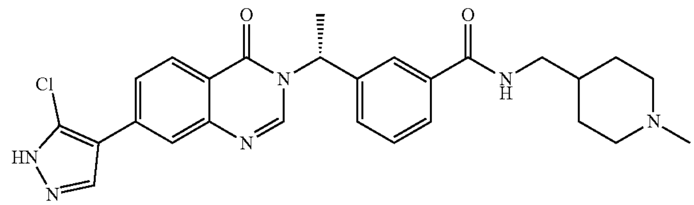 [SMILES: C[C@H](c1cccc(C(=O)NCC2CCN(C)CC2)c1)n1cnc2cc(-c3cn[nH]c3Cl)ccc2c1=O] | 505.4 |
| 466 | | 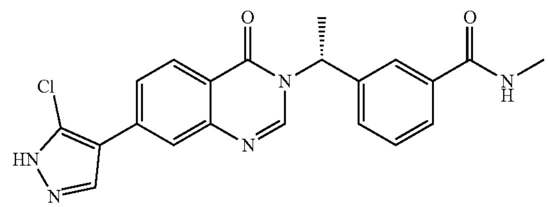 [SMILES: CNC(=O)c1cccc([C@@H](C)n2cnc3cc(-c4cn[nH]c4Cl)ccc3c2=O)c1] | 408.2 |
| 467 | | 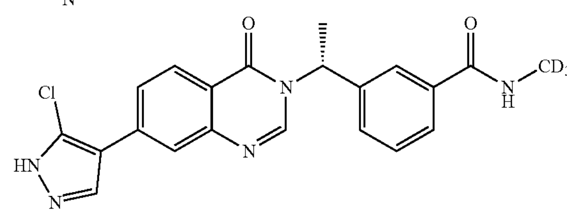 | 411.3 |
| 468 | | 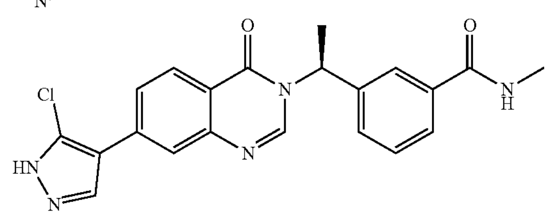 | 408.5 |
| 469 | | 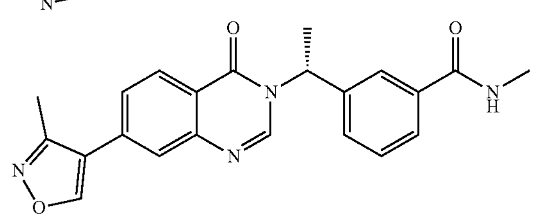 | 389.4 |
| 470 | | 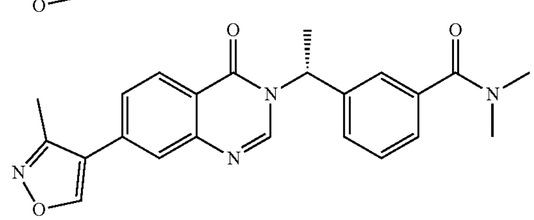 | 403.2 |
| 471 | | 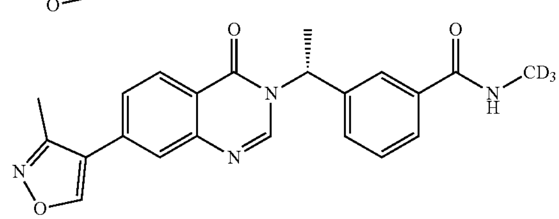 | 393.1 |
| 472 | | 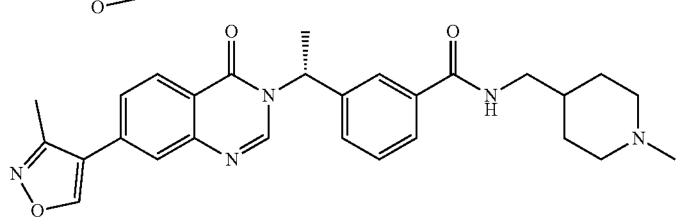 | 486.4 |

TABLE 10-continued

| Compd | Boronic acid/ester | Structure | MS found [M + H]+ |
|---|---|---|---|
| 473 | 3-methylisoxazole-4-B(OH)2 | 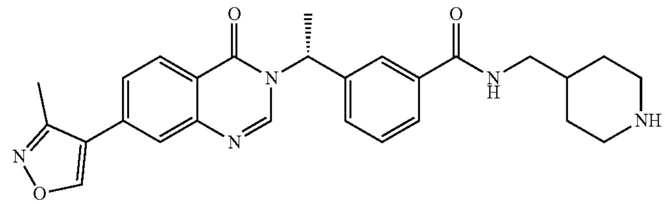 [SMILES: Cc1nocc1-c1ccc2c(=O)n([C@H](C)c3cccc(C(=O)NCC4CCNCC4)c3)cnc2c1] | 472.3 |
| 474 | 3-methylisoxazole-4-B(OH)2 | 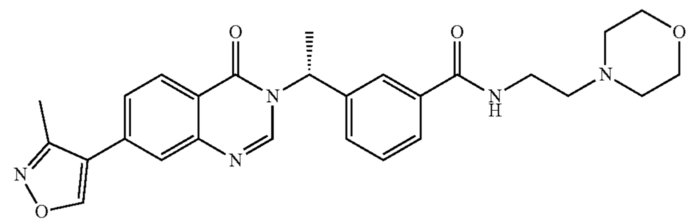 [SMILES: Cc1nocc1-c1ccc2c(=O)n([C@H](C)c3cccc(C(=O)NCCN4CCOCC4)c3)cnc2c1] | 488.2 |
| 475 | 3-methylisoxazole-4-B(OH)2 | 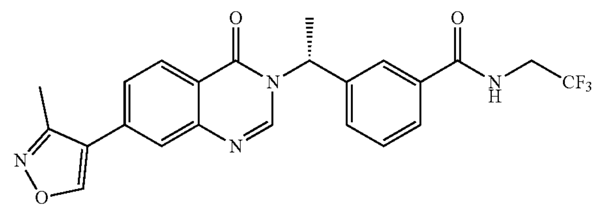 [SMILES: Cc1nocc1-c1ccc2c(=O)n([C@H](C)c3cccc(C(=O)NCC(F)(F)F)c3)cnc2c1] | 457.3 |
| 476 | 1-methylpyrazole-5-B(OH)2 | 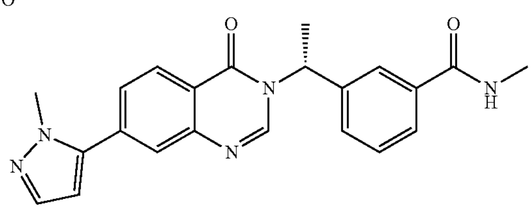 | 388.4 |
| 477 | 1-methylpyrazole-5-B(OH)2 | 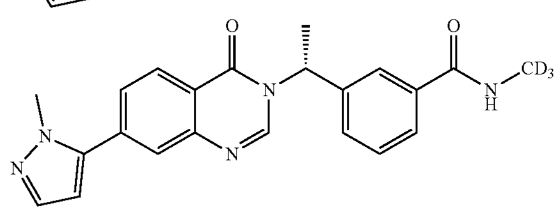 | 391.2 |
| 478 | 1-methylpyrazole-5-B(OH)2 | 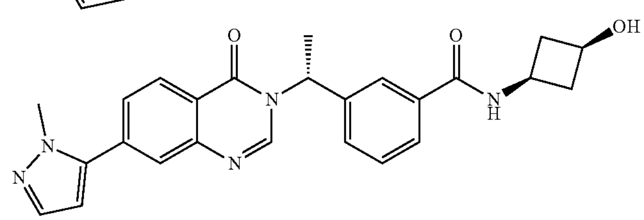 | 444.1 |
| 479 | 1-methylpyrazole-5-B(OH)2 | 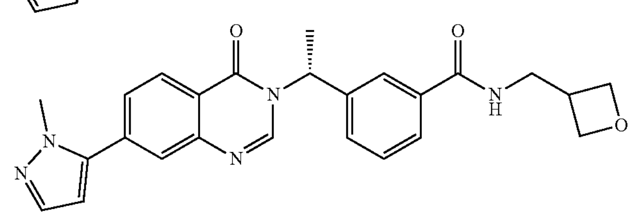 | 444.3 |
| 480 | 1-methylpyrazole-5-B(OH)2 | 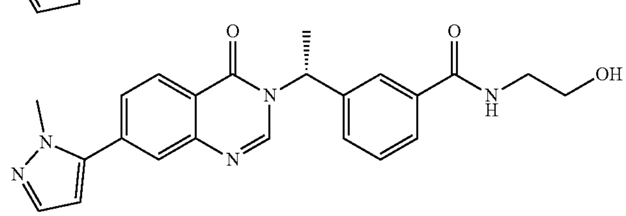 | 418.3 |

TABLE 10-continued

| Compd | Boronic acid/ester | Structure | MS found [M + H]+ |
|---|---|---|---|
| 481 | 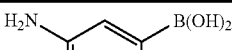 | 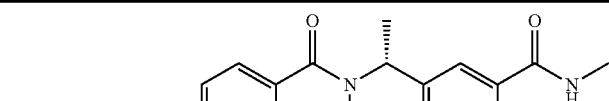 | 400.4 |
| 482 |  | 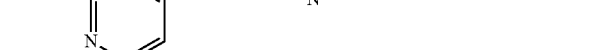 | 414.2 |

General Scheme 12

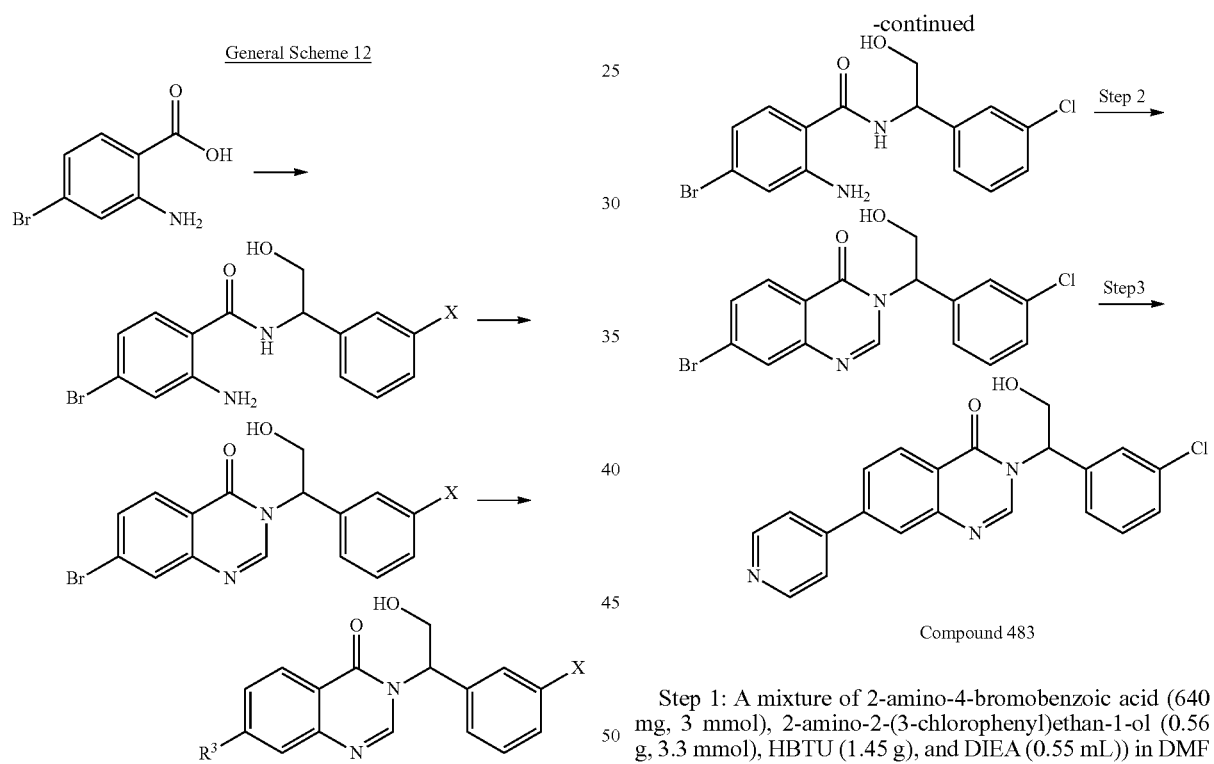

Compound 483: 3-(1-(3-chlorophenyl)-2-hydroxyethyl)-7-(pyridin-4-yl)quinazolin-4(3H)-one Step 1: A mixture of 2-amino-4-bromobenzoic acid (640 mg, 3 mmol), 2-amino-2-(3-chlorophenyl)ethan-1-ol (0.56 g, 3.3 mmol), HBTU (1.45 g), and DIEA (0.55 mL)) in DMF (20 mL) was shaken at ambient temperature for 2 hours. The reaction mixture was diluted with EtOAc and brine. The organic layer was separated, washed sequentially with water and brine, dried (MgSO$_4$), concentrated, and purified by silica gel column chromatography to provide methyl 2-amino-4-bromo-N-(1-(3-chlorophenyl)-2-hydroxyethyl) benzamide (943 mg, 85%). LC/MS found 369.5 [M+H]+.

Step 2: 2-Amino-4-bromo-N-(1-(3-chlorophenyl)-2-hydroxyethyl)benzamide (900 mg, 2.4 mmol)) and p-TsOH—H$_2$O (0.15 equiv) in neat triethyl orthoformate (20 mL) was shaken at 80° C. overnight. The reaction mixture was diluted with EtOAc, washed sequentially with saturated aqueous NaHCO$_3$ and brine, dried with MgSO$_4$, filtered, concentrated, and purified by silica gel column chromatography to provide 7-bromo-3-(1-(3-chlorophenyl)-2-hydroxyethyl) quinazolin-4(3H)-one (684 mg, 75%). LC/MS found 379 [M+H]+.

Scheme 9

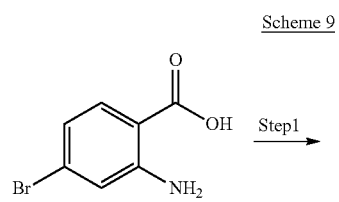

Step1

Step 3: A mixture of 7-bromo-3-(1-(3-chlorophenyl)-2-hydroxyethyl)quinazolin-4(3H)-one (80 mg, 0.2 mmol), pyridin-4-ylboronic acid (37 mg, 0.3 mmol), aq. 2M sodium carbonate solution (3.0 equiv), and PdCl$_2$(PPh$_3$)$_2$ (0.1 equiv) in dioxane (3 mL) was purged with argon for 5 minutes. The mixture was shaken at 70° C. overnight. The reaction mixture was diluted with EtOAc, washed sequentially with saturated aqueous NaHCO$_3$ and brine, dried with MgSO$_4$, filtered, concentrated, and purified by silica gel column chromatography to provide 3-(1-(3-chlorophenyl)-2-hydroxyethyl)-7-(pyridin-4-yl)quinazolin-4(3H)-one, Compound 483, (34 mg, 45%). LC/MS found 378.4 [M+H]$^+$.

Compounds 484-491 in Table 11 below were prepared by the method (General Scheme 12) similar to that described for the preparation of Compound 483 using an appropriate 7-bromo-(2-hydroxyethyl)quinazolin-4(3H)-one and an appropriate boronic acid/ester.

TABLE 11

| Compd | Boronic acid/ester | Structure | MS found [M + H]$^+$ |
|---|---|---|---|
| 484 | 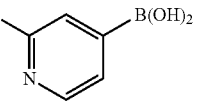 | 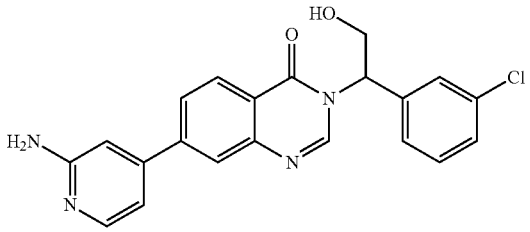 [SMILES: Nc1cc(-c2ccc3c(=O)n(C(CO)c4cccc(Cl)c4)cnc3c2)ccn1] | 393.1 |
| 485 | 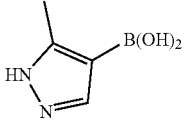 | 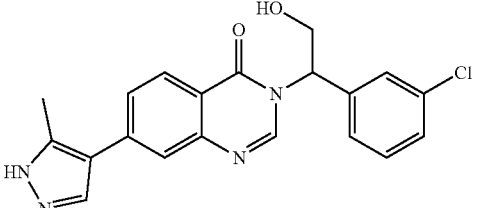 | 381.3 |
| 486 | 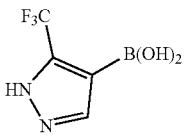 | 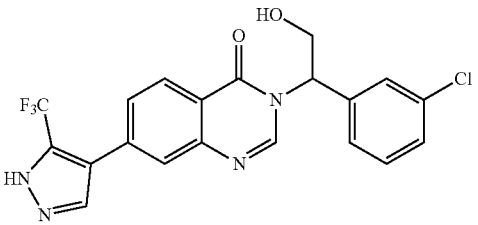 [SMILES: O=c1c2ccc(-c3cn[nH]c3C(F)(F)F)cc2ncn1C(CO)c1cccc(Cl)c1] | 344.1 |
| 487 | 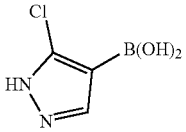 | 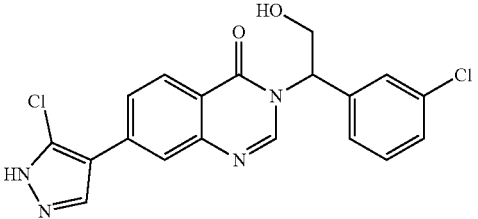 [SMILES: O=c1c2ccc(-c3cn[nH]c3Cl)cc2ncn1C(CO)c1cccc(Cl)c1] | 401.4 |
| 488 | 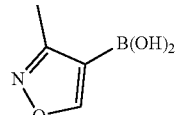 | 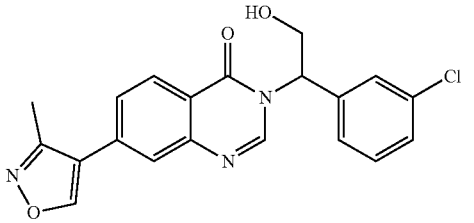 [SMILES: Cc1nocc1-c1ccc2c(=O)n(C(CO)c3cccc(Cl)c3)cnc2c1] | 382.2 |

TABLE 11-continued
| Compd | Boronic acid/ester | Structure | MS found [M + H]+ |
|---|---|---|---|
| 489 | 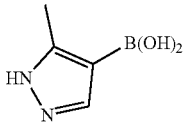 | 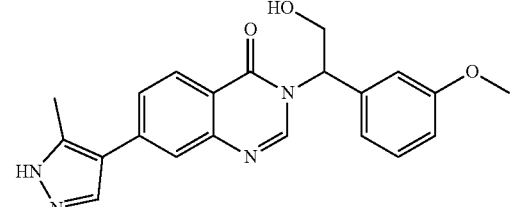 | 377.1 |
| 490 | 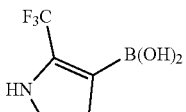 | 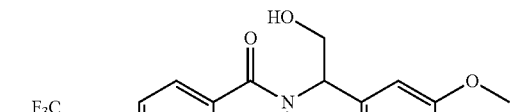 | 431.2 |
| 491 | 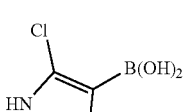 | 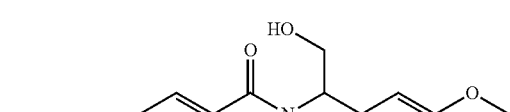 | 397.1 |
General Scheme 13
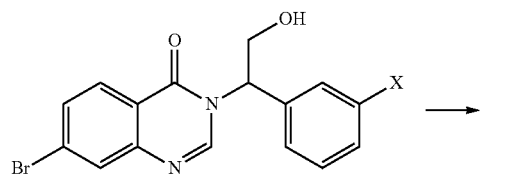
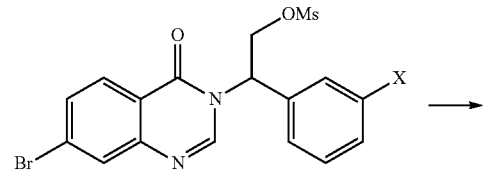
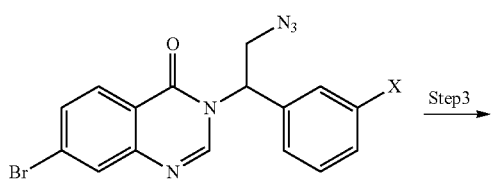
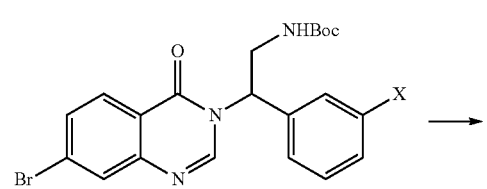 Step 3
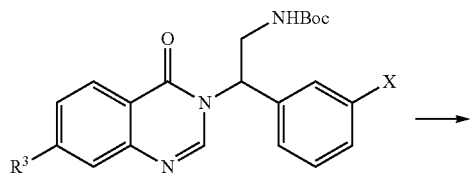
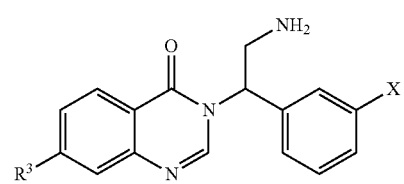
-continued
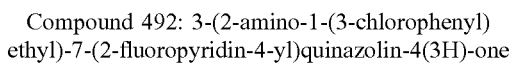
Compound 492: 3-(2-amino-1-(3-chlorophenyl)ethyl)-7-(2-fluoropyridin-4-yl)quinazolin-4(3H)-one
Scheme 11
 Step 1

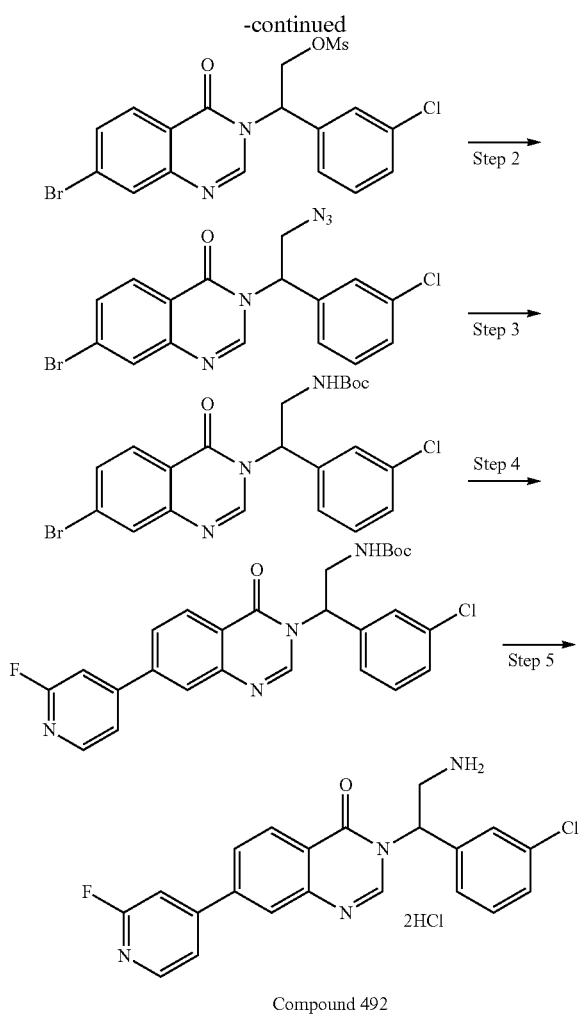

Compound 492

Step 1: A solution of 7-bromo-3-(1-(3-chlorophenyl)-2-hydroxyethyl)quinazolin-4(3H)-one (381 mg, 1.0 mmol) in DCM (10 mL) was cooled to 0° C., and then TEA (2.0 equiv) and methanesulfonyl chloride (1.2 equiv) were added to the mixture at 0° C. After 3 hours at 0° C., the mixture was quenched with aq. sat. NH$_4$Cl solution and then extracted with CH$_2$Cl$_2$ twice. The combined organic layer was dried over MgSO$_4$, filtered, concentrated, and purified by silica gel column chromatography to provide 2-(7-bromo-4-oxoquinazolin-3(4H)-yl)-2-(3-chlorophenyl)ethyl methanesulfonate as a pale brownish solid (434 mg, 95%). LC/MS found 457.0 [M+H]$^+$.

Step 2: A mixture of 2-(7-bromo-4-oxoquinazolin-3(4H)-yl)-2-(3-chlorophenyl)ethyl methanesulfonate (292 mg, 0.64 mmol) and sodium azide (127 mg, 1.92 mmol) in DMF (3 mL) was shaken for 3 days at RT. The mixture was diluted with EtOAc and sequentially washed with water and brine. The organic layer was dried over MgSO$_4$, filtered, concentrated, and purified by silica gel column chromatography to provide 3-(2-azido-1-(3-chlorophenyl)ethyl)-7-bromoquinazolin-4(3H)-one (200 mg, 61%). LC/MS found 404.0 [M+H]$^+$.

Step 3: A suspension of 3-(2-azido-1-(3-chlorophenyl)ethyl)-7-bromoquinazolin-4(3H)-one (110 mg, 0.27 mmol) and 10% Pd/C (10 mg) in methanol (3 mL) was shaken under hydrogen gas at ambient temperature overnight. The mixture was filtered through Celite, and the Celite was washed with MeOH. The filtrate was evaporated under reduced pressure. The residue was suspended in CH$_2$Cl$_2$ (3 mL) and cooled to 0° C. The mixture was treated with TEA (74 μL) and Boc$_2$O (68 mg, 0.32 mmol) and stirred for 2 hours at 0° C. The mixture was diluted with CH$_2$Cl$_2$ and brine. Organic layer was separated, dried over MgSO$_4$, filtered, concentrated, and purified by silica gel column chromatography to provide tert-butyl (2-(7-bromo-4-oxoquinazolin-3(4H)-yl)-2-(3-chlorophenyl)ethyl)carbamate (39 mg, 30%). LC/MS found 378.0 [M−99 (Boc)]$^+$.

Step 4: Starting with tert-butyl (2-(7-bromo-4-oxoquinazolin-3(4H)-yl)-2-(3-chlorophenyl)ethyl)carbamate (38 mg, 0.10 mmol) and 3-fluoro-4-(4,4,5,5-tetramethyl-1,3,2-dioxaborolan-2-yl)pyridine (36 mg, 0.16 mmol), and using Suzuki reaction condition, tert-butyl (2-(3-chlorophenyl)-2-(7-(2-fluoropyridin-4-yl)-4-oxoquinazolin-3(4H)-yl)ethyl)carbamate (41 mg, 83%) was synthesized. LC/MS found 395.1 [M−99 (Boc)]$^+$.

Step 5: To the solution of tert-butyl (2-(3-chlorophenyl)-2-(7-(2-fluoropyridin-4-yl)-4-oxoquinazolin-3(4H)-yl)ethyl)carbamate (41 mg, 0.08 mmol)) in DCM (3 mL), was added 4M HCl solution (0.2 mL) in dioxane. After 3 hours at room temperature, volatiles were removed to give 3-(2-amino-1-(3-chlorophenyl)ethyl)-7-(2-fluoropyridin-4-yl)quinazolin-4(3H)-one hydrochloride, Compound 492, as a pale brown solid. LC/MS found 395.1 [M+H]$^+$.

Compounds 493-504 in Table 12 below were prepared by the method (General Scheme 13) similar to that described for the preparation of Compound 492 using an appropriate 7-bromo-(2-hydroxyethyl)quinazolin-4(3H)-one and an appropriate boronic acid/ester.

TABLE 12

| Compd | Boronic acid/ester | Structure | MS found [M + H]$^+$ |
|---|---|---|---|
| 493 | ![H$_2$N-pyridine-B(OH)$_2$] | ![structure] | 392.4 |

TABLE 12-continued

| Compd | Boronic acid/ester | Structure | MS found [M + H]+ |
|---|---|---|---|
| 494 | | 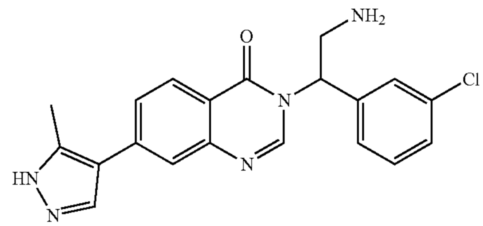 [SMILES: Cc1[nH]ncc1-c1ccc2c(=O)n(C(CN)c3cccc(Cl)c3)cnc2c1] | 380.3 |
| 495 | | 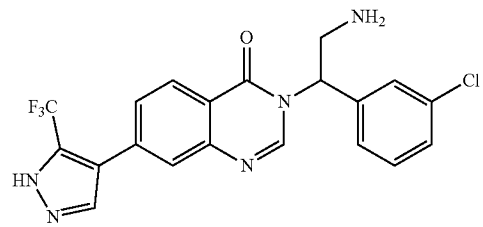 [SMILES: NCC(c1cccc(Cl)c1)n1cnc2cc(-c3cn[nH]c3C(F)(F)F)ccc2c1=O] | 334.5 |
| 496 | | 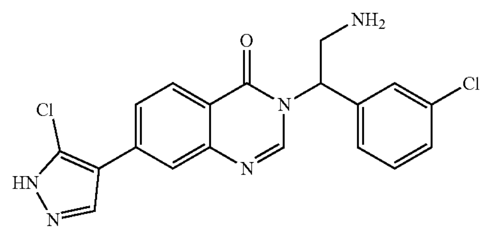 [SMILES: NCC(c1cccc(Cl)c1)n1cnc2cc(-c3cn[nH]c3Cl)ccc2c1=O] | 400.1 |
| 497 | | 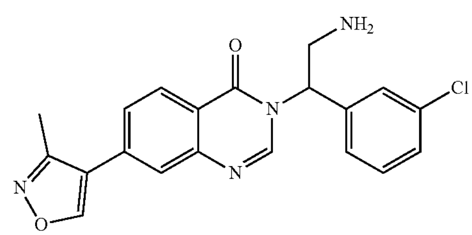 [SMILES: Cc1nocc1-c1ccc2c(=O)n(C(CN)c3cccc(Cl)c3)cnc2c1] | 381.4 |
| 498 | | 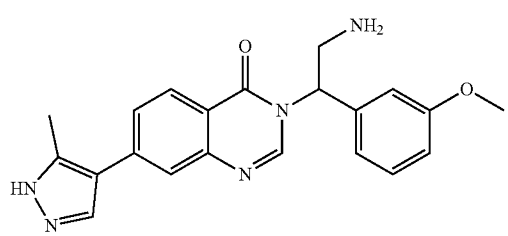 [SMILES: COc1cccc(C(CN)n2cnc3cc(-c4cn[nH]c4C)ccc3c2=O)c1] | 376.2 |
| 499 | | 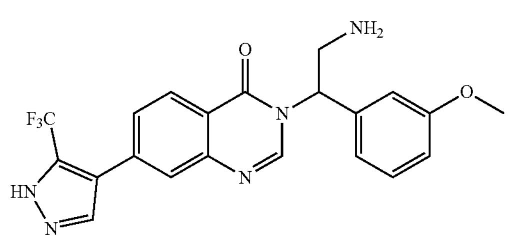 [SMILES: COc1cccc(C(CN)n2cnc3cc(-c4cn[nH]c4C(F)(F)F)ccc3c2=O)c1] | 430.2 |

TABLE 12-continued
| Compd | Boronic acid/ester | Structure | MS found [M + H]+ |
|---|---|---|---|
| 500 | 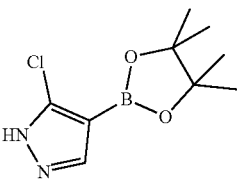 | 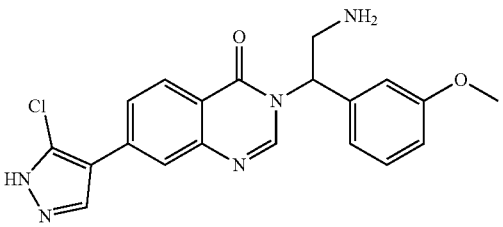 [SMILES: COc1cccc(C(CN)n2cnc3cc(-c4cn[nH]c4Cl)ccc3c2=O)c1] | 396.4 |
| 501 | 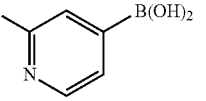 | 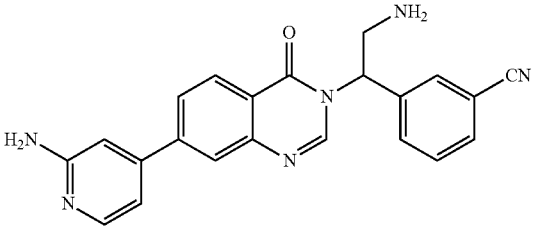 [SMILES: N#Cc1cccc(C(CN)n2cnc3cc(-c4ccnc(N)c4)ccc3c2=O)c1] | 383.2 |
| 502 | 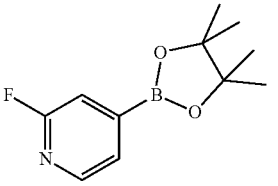 [SMILES: CC1(C)OB(c2ccnc(F)c2)OC1(C)C] | 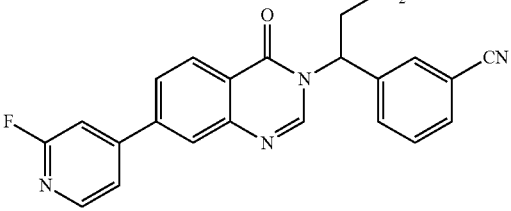 | 386.4 |
| 503 | 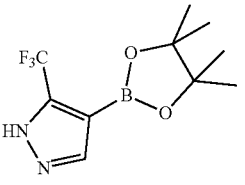 | 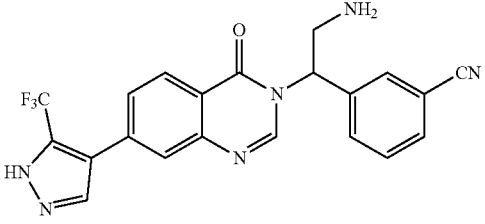 [SMILES: N#Cc1cccc(C(CN)n2cnc3cc(-c4cn[nH]c4C(F)(F)F)ccc3c2=O)c1] | 425.4 |
| 504 | 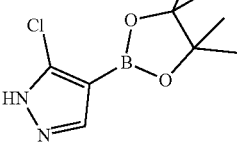 | 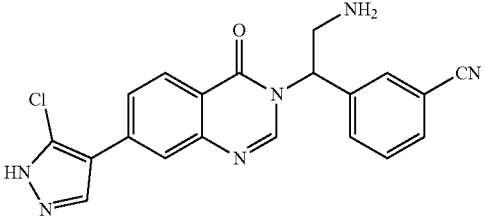 [SMILES: N#Cc1cccc(C(CN)n2cnc3cc(-c4cn[nH]c4Cl)ccc3c2=O)c1] | 391.2 |

General Scheme 14

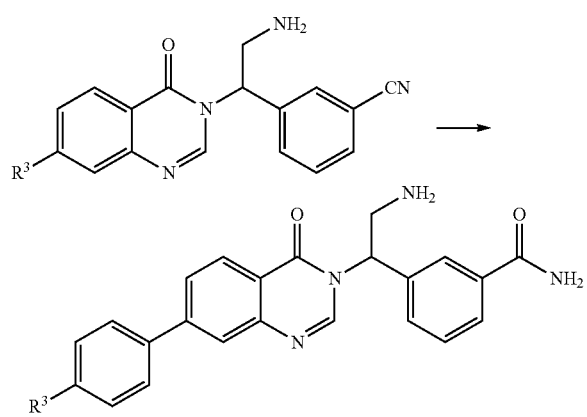

Compound 505: 3-(2-amino-1-(7-(3-fluoropyridin-4-yl)-4-oxoquinazolin-3(4H)-yl)ethyl)benzamide

Scheme 12

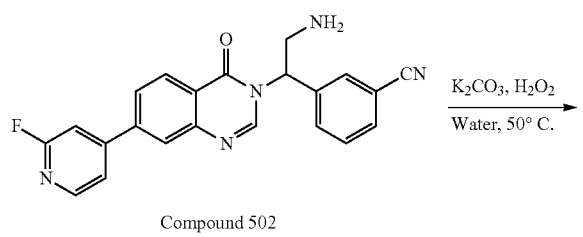

Compound 502

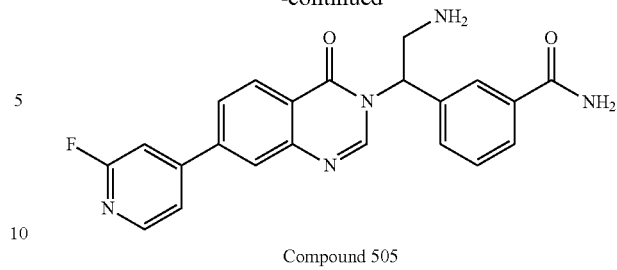

Compound 505

A suspension of 3-(2-amino-1-(7-(2-fluoropyridin-4-yl)-4-oxoquinazolin-3(4H)-yl)ethyl)benzonitrile, Compound 502, (12 mg, 0.03 mmol) in MeOH (2 mL) was treated with aq. 2N potassium carbonate solution (0.2 equiv) and 30% $H_2O_2$ (3.0 equiv). The mixture was shaken for 2 hours at 50° C. The mixture was concentrated, re-suspended in water, and extracted with DCM twice. The combined organic layer was dried over $MgSO_4$, filtered, concentrated, and purified by silica gel column chromatography to provide 3-(2-amino-1-(7-(3-fluorophenyl)-4-oxoquinazolin-3(4H)-yl)ethyl)benzamide, Compound 505, as a transparent oil (4.4 mg, 35%). LC/MS found 404.1 [M+H]$^+$.

Compounds 506-508 in Table 13 below were prepared by the reaction condition described preparation of Compound 505 using Compounds 501, 503, and 504, respectively.

TABLE 13

| Compd | Structure | MS found [M + H]$^+$ |
|---|---|---|
| 506 | 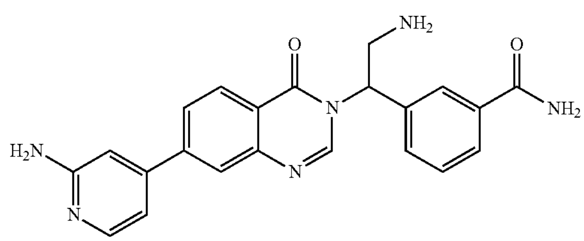 [SMILES: NCC(c1cccc(C(N)=O)c1)n1cnc2cc(-c3ccnc(N)c3)ccc2c1=O] | 401.4 |
| 507 | 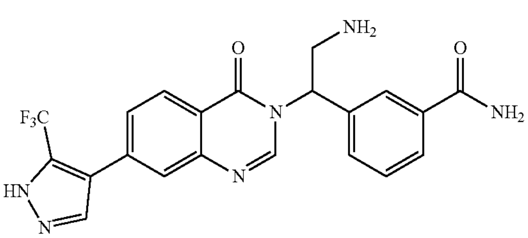 [SMILES: NCC(c1cccc(C(N)=O)c1)n1cnc2cc(-c3cn[nH]c3C(F)(F)F)ccc2c1=O] | 443.4 |

TABLE 13-continued
| Compd | Structure | MS found [M + H]+ |
|---|---|---|
| 508 | 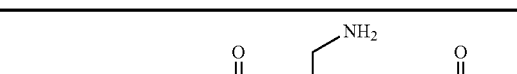 | 409.2 |
General Scheme 15
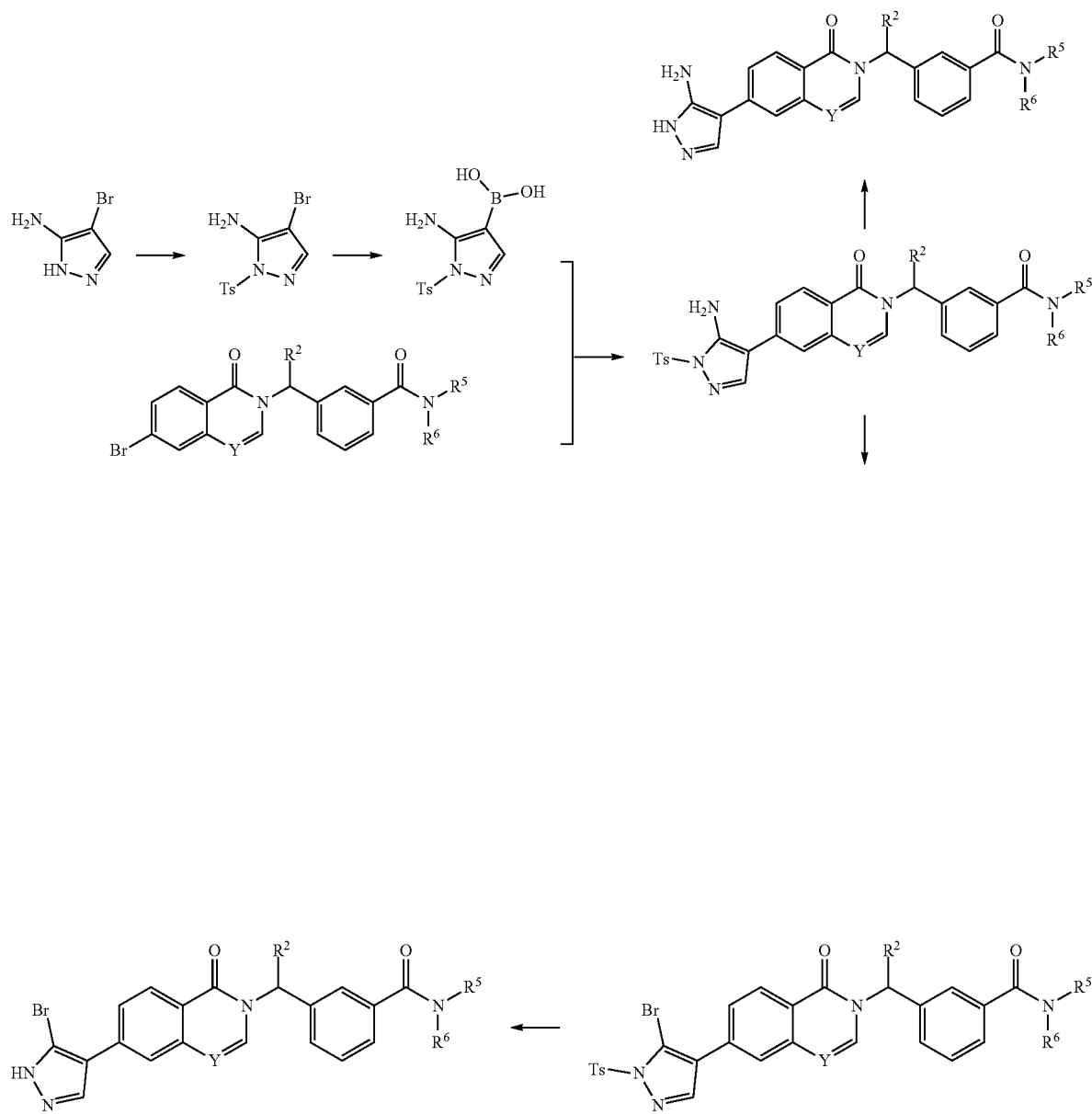

Compound 509: (R)-3-(1-(7-(5-bromo-1H-pyrazol-4-yl)-4-oxoquinazolin-3(4H)-yl)ethyl)-N-methylbenzamide Scheme 13

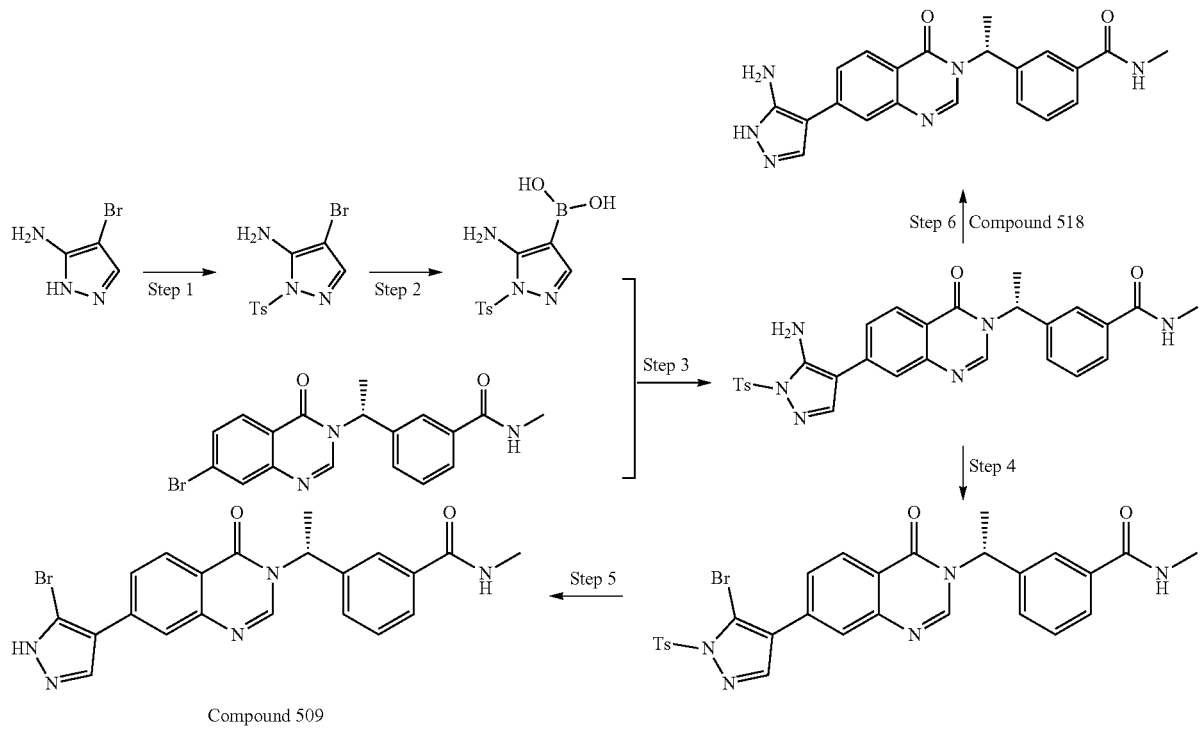

Compound 509

Step 1: 4-Toluenesulfonyl chloride (9.38 g, 53.7 mmol) was added to a mixture of 4-bromo-1H-pyrazol-5-amine (4.35 g, 26.9 mmol) in $CH_2Cl_2$ (50 mL) and pyridine (0.5 mL) at RT. After being stirred for 3 hours, the mixture was diluted with DCM and washed with aq. sat. $NH_4Cl$ solution. The combined organic layer was dried over $Na_2SO_4$, concentrated, and purified by column chromatography to provide target compound 4-bromo-1-tosyl-1H-pyrazol-5-amine (12.02 g, 69%) was synthesized. LC/MS found 316.1/318.1 $[M+H]^+$.

Step 2: 4-Bromo-1-tosyl-1H-pyrazol-5-amine (5.95 g, 18.8 mmol), bis(pinacolato) diboron (7.17 g, 28.2 mmol), potassium acetate (4.62 g, 47.05 mmol) were suspended in anhydrous dioxane (30 mL). The mixture was vacuumed and charged with argon gas three times. Dichloro[1,1'-bis(diphenylphosphino)ferrocene] palladium(II)$CH_2Cl_2$ (922.08 mg, 1.13 mmol) was added. The mixture was heated to 100° C. overnight. The mixture was diluted with EtOAc filtered through a Celite pad, concentrated, and purified by silica gel column to provide target compound (5-amino-1-tosyl-1H-pyrazol-4-yl)boronic acid (2.83 g, 41%). LC/MS found 364.2 $[M+H]^+$.

Step 3: (5-Amino-1-tosyl-1H-pyrazol-4-yl)boronic acid (727.8 mg, 2.59 mmol), (R)-3-(1-(7-(5-bromo-1H-pyrazol-4-yl)-4-oxoquinazolin-3(4H)-yl)ethyl)-N-methylbenzamide (500 mg, 1.3 mmol), 2M $K_2CO_3$ solution (1.62 mL) were added in dioxane (7 mL). The mixture was purged with nitrogen gas for 3 minutes. Tetrakis(triphenylphosphine) palladium (74.8 mg, 64.7 mol) was added to the mixture, and then the mixture was purged with nitrogen gas for 3 minutes. After being stirred for 16 hours at 70° C., volatiles were removed in vacuum. The mixture was diluted with $CH_2Cl_2$, washed with brine, dried over $Na_2SO_4$, concentrated, and then purified by silica gel column to provide target compound (R)-3-(1-(7-(5-amino-1-tosyl-1H-pyrazol-4-yl)-4-oxoquinazolin-3(4H)-yl)ethyl)-N-methylbenzamide (81%). LC/MS found 543.1 $[M+H]^+$.

Step 4: A solution of (R)-3-(1-(7-(5-amino-1-tosyl-1H-pyrazol-4-yl)-4-oxoquinazolin-3(4H)-yl)ethyl)-N-methylbenzamide (500 mg, 0.9 mmol) in acetonitrile (15 mL) was slowly added to a suspension of tert-butyl nitrite (1.84 mmol, 243 µL) and copper(II) bromide (411.6 mg, 1.8 mmol) in acetonitrile (15 mL) at 0° C. The mixture was stirred at 0° C., warmed to RT, and then stirred for additional 40 minutes. The mixture was filtered through a Celite pad and then washed with EtOAc. The filtrate was extracted with EtOAc and then washed with sat-$NaHCO_3$ solution. The organic layer was separated, washed with aq. ~10% $NH_4OH$ solution, dried over $Na_2SO_4$, concentrated, and purified by silica gel column to provide the target compound (R)-3-(1-(7-(5-bromo-1-tosyl-1H-pyrazol-4-yl)-4-oxoquinazolin-3(4H)-yl)ethyl)-N-methylbenzamide (354 mg, 65%) was synthesized. LC/MS found 606.1, 608.1 $[M+H]^+$.

Step 5: To a suspension of (R)-3-(1-(7-(5-bromo-1-tosyl-1H-pyrazol-4-yl)-4-oxoquinazolin-3(4H)-yl)ethyl)-N-methylbenzamide (354 mg, 0.58 mmol) in MeOH (8 mL) was added 5N aq, NaOH (1.2 mL, 6.0 mmol). After being stirred for 1 hour at RT, volatiles were removed in vacuum. The resulting residue was extracted (×2) with EtOAc and washed with brine. The combined organic layer was dried over Na$_2$SO$_4$, concentrated, and purified by silica gel column to provide Compound 509 as a white solid (183.5 mg, 69%). LCMS found 452.1/454.1 [M+H]$^+$. $^1$H NMR (400 MHz, DMSO-d6) δ 13.44 (br. S, 1H), 8.45 (m, 3H), 8.18 (d, 1H, J=8.4 Hz), 7.97 (d, 1H, J=1.4 Hz), 7.84 (m, 2H), 7.76 (dt 1H, J=7.8, 1.2 Hz), 7.56 (d, 1H, 7.8 Hz), 7.46 (t, 1H, 7.7 Hz), 6.13 (q, 1H, 7.1 Hz), 2.77 (d, 3H, J=4.4 Hz), 1.88 (d, 3H, J=7.3 Hz).

Step 6: To a suspension of (R)-3-(1-(7-(5-amino-1-tosyl-1H-pyrazol-4-yl)-4-oxoquinazolin-3(4H)-yl)ethyl)-N-methylbenzamide (39 mg, 0.1 mmol) from Step 3 in MeOH (2 mL) was added 5N aq, NaOH (0.2 mL, 1.0 mmol). After being stirred for 1 hour at RT, volatiles were removed in vacuum. The resulting residue was extracted (×2) with DCM and washed with brine. The combined organic layer was dried over Na$_2$SO$_4$, concentrated, and purified by silica gel column to provide Compound 518 as a white solid (31.1 mg, 82%). LCMS found 389.1 [M+H]$^+$.

Compounds 510-522 in Table 14 below were prepared by the method (General Scheme 15) similar to that described for the preparation of Compound 509.

TABLE 14

| Compound # | Structure | MS found [M + H]$^+$ |
|---|---|---|
| 510 | 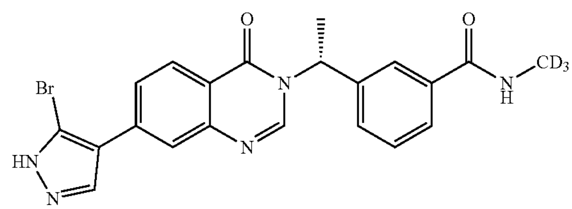 [SMILES: [2H]C([2H])([2H])NC(=O)c1cccc([C@@H](C)n2cnc3cc(-c4cn[nH]c4Br)ccc3c2=O)c1] | 405.1, 407.2 |
| 511 | 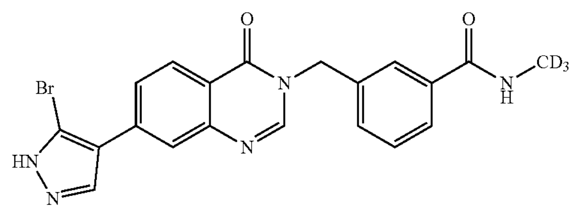 [SMILES: [2H]C([2H])([2H])NC(=O)c1cccc(Cn2cnc3cc(-c4cn[nH]c4Br)ccc3c2=O)c1] | 441.2, 443.3 |
| 512 | 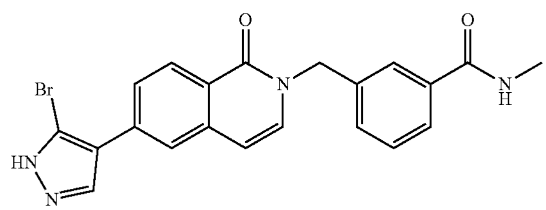 [SMILES: CNC(=O)c1cccc(Cn2ccc3cc(-c4cn[nH]c4Br)ccc3c2=O)c1] | 438.2, 440.1 |
| 513 | 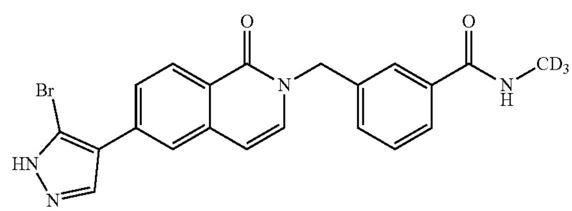 | 441.1, 443.2 |
| 514 | 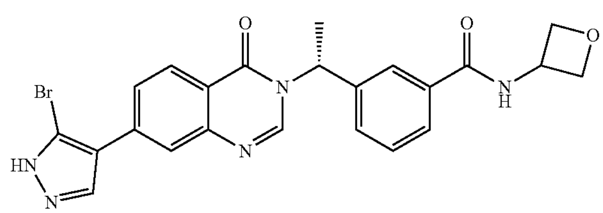 [SMILES: C[C@H](c1cccc(C(=O)NC2COC2)c1)n1cnc2cc(-c3cn[nH]c3Br)ccc2c1=O] | 494.1, 496.1 |
| 515 | 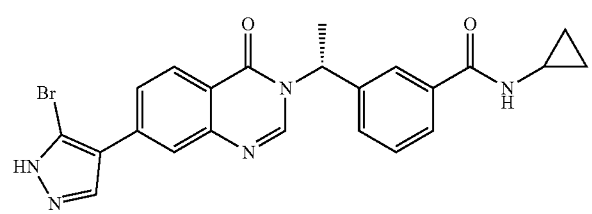 [SMILES: C[C@H](c1cccc(C(=O)NC2CC2)c1)n1cnc2cc(-c3cn[nH]c3Br)ccc2c1=O] | 478.0, 480.1 |

TABLE 14-continued

| Compound # | Structure | MS found [M + H]+ |
|---|---|---|
| 516 | 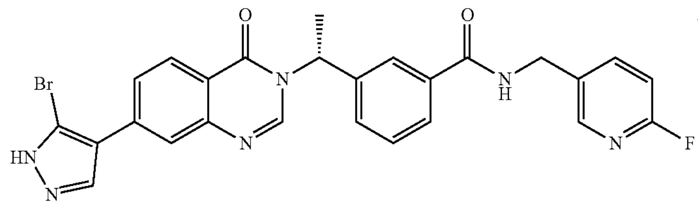 [SMILES: C[C@H](c1cccc(C(=O)NCc2ccc(F)nc2)c1)n1cnc2cc(-c3cn[nH]c3Br)ccc2c1=O] | 547.2, 549.0 |
| 517 | 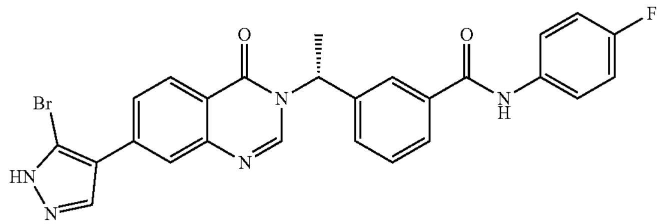 [SMILES: C[C@H](c1cccc(C(=O)Nc2ccc(F)cc2)c1)n1cnc2cc(-c3cn[nH]c3Br)ccc2c1=O] | 532.0, 534.1 |
| 518 | 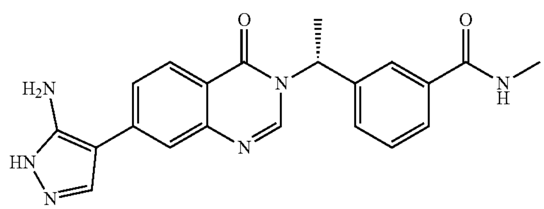 [SMILES: CNC(=O)c1cccc([C@@H](C)n2cnc3cc(-c4cn[nH]c4N)ccc3c2=O)c1] | 389.1 |
| 519 | 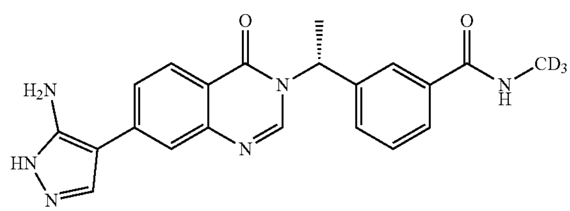 | 392.1 |
| 520 | 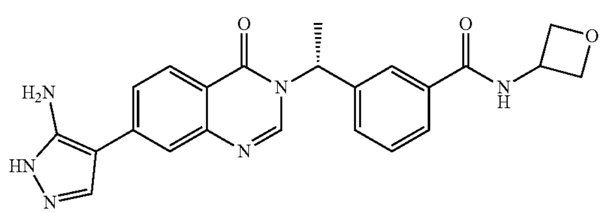 [SMILES: C[C@H](c1cccc(C(=O)NC2COC2)c1)n1cnc2cc(-c3cn[nH]c3N)ccc2c1=O] | 431.0 |
| 521 | 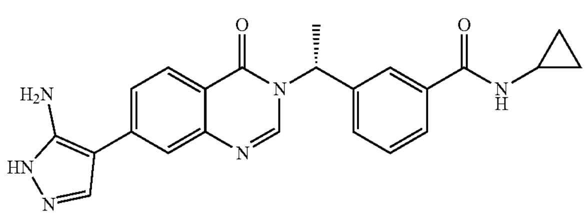 [SMILES: C[C@H](c1cccc(C(=O)NC2CC2)c1)n1cnc2cc(-c3cn[nH]c3N)ccc2c1=O] | 415.2 |
| 522 | 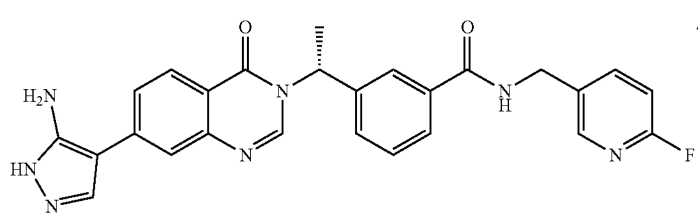 [SMILES: C[C@H](c1cccc(C(=O)NCc2ccc(F)nc2)c1)n1cnc2cc(-c3cn[nH]c3N)ccc2c1=O] | 484.2 |

General Scheme 16

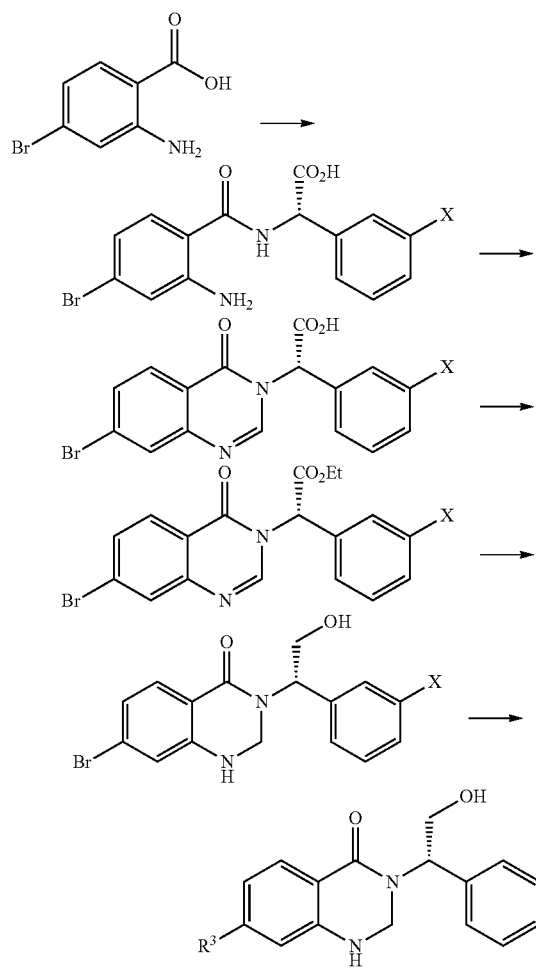

Compound 523: (S)-3-(1-(3-chlorophenyl)-2-hydroxyethyl)-7-(5-methyl-11H-pyrazol-4-yl)-2,3-dihydroquinazolin-4(1H)-one Scheme 14

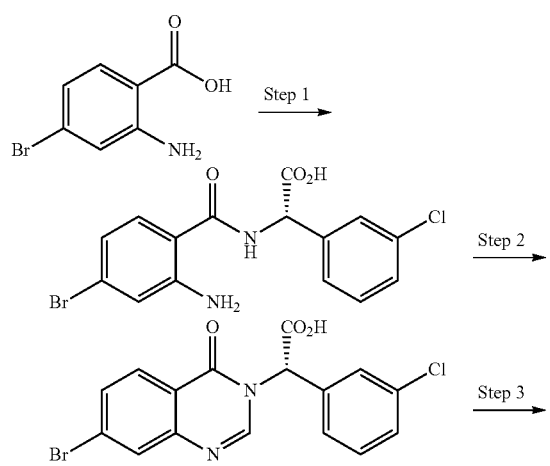

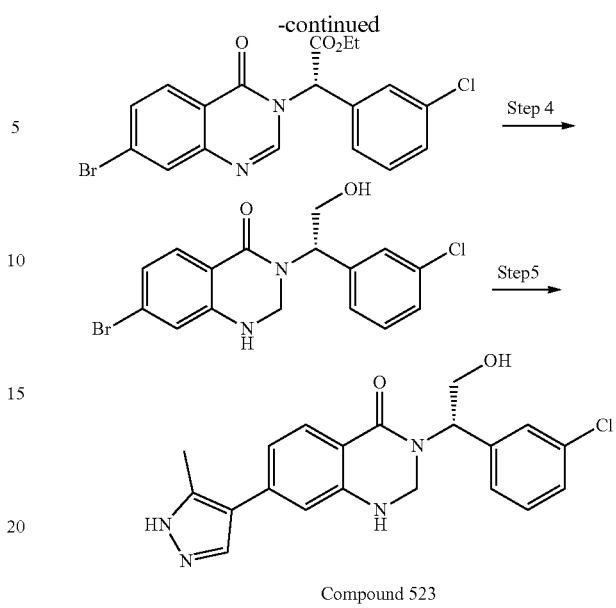

Compound 523

Step 1: A mixture of 2-amino-4-bromobenzoic acid (460 mg, 4 mmol), (S)-2-amino-2-(3-chlorophenyl)acetic acid (880 mg, 4.8 mmol), HBTU (2.2 g, 63 mmol), and DIEA (2.0 mL) in DMF (20 mL) was shaken at ambient temperature for 3 hours. The reaction mixture was diluted with EtOAc and brine. The organic layer was separated, washed sequentially with water and brine, dried over MgSO$_4$, concentrated, and purified by silica gel column chromatography to provide (S)-2-(2-amino-4-bromobenzamido)-2-(3-chlorophenyl)acetic acid (1.46 g, 95%). LC/MS found 383.1 [M−H]$^-$.

Step 2: A suspension of (S)-2-(2-amino-4-bromobenzamido)-2-(3-chlorophenyl)acetic acid (1.46 mg, 3.8 mmol) and p-TsOH—H$_2$O (115 mg, 0.6 mmol) in neat triethyl orthoformate (30 mL) was shaken at 80° C. overnight. The reaction mixture was diluted with EtOAc, washed sequentially with saturated aq. NaHCO$_3$ and brine, dried (MgSO$_4$), filtered, concentrated, and purified by silica gel column chromatography to provide (S)-2-(7-bromo-4-oxoquinazolin-3(4H)-yl)-2-(3-chlorophenyl)acetic acid (1.05 g, 70%). LC/MS found 393.1 [M+H]$^+$.

Step 3: A suspension of (S)-2-(7-bromo-4-oxoquinazolin-3(4H)-yl)-2-(3-chlorophenyl)acetic acid (1.05 g, 2.6 mmol) in EtOH (10 mL) was cooled to 0° C. and then treated with DMF (4-5 drops) and oxalyl chloride (2.2 mL, 10 equiv). The mixture was warmed to RT and shaken overnight. The mixture was concentrated and purified by silica gel column chromatography to provide ethyl (S)-2-(7-bromo-4-oxoquinazolin-3(4H)-yl)-2-(3-chlorophenyl)acetate (0.96 g, 86% yield). LC/MS found 420.8 [M+H]$^+$.

Step 4: A suspension of ethyl (S)-2-(7-bromo-4-oxoquinazolin-3(4H)-yl)-2-(3-chlorophenyl)acetate (3.7 g) in THF (40 mL) was treated with sodium borohydride (9.3 g, 10 equiv.) and then shaken overnight at RT. The mixture was quenched with aq. sat. NH$_4$Cl solution (~50 mL) and stirred for 30 minutes. The suspension was extracted with EtOAc twice, and then the combined organic layer was dried over MgSO$_4$, concentrated, and purified by silica gel column chromatography to provide (S)-7-bromo-3-(1-(3-chlorophenyl)-2-hydroxyethyl)-2,3-dihydroquinazolin-4(1H)-one (1.0 g, 38%). LC/MS found 382.1 [M+H]$^+$.

Step 5: A mixture of (S)-7-bromo-3-(1-(3-chlorophenyl)-2-hydroxyethyl)-2,3-dihydroquinazolin-4(1H)-one (300 mg, 0.78 mmol), 3-methyl-4-(4,4,5,5-tetramethyl-1,3,2-dioxaborolan-2-yl)-1H-pyrazole (246 mg, 1.5 equiv), aq. 2M potassium carbonate solution (1.2 mL, 3.0 equiv), and Pd(PPh$_3$)$_4$ (91 mg, 0.1 equiv) in dioxane (5 mL) was purged with argon for 5 minutes. The mixture was shaken at 70° C. overnight. The reaction mixture was filtered, and the filtrate was evaporated under reduced pressure. The resulting material was dissolved in CH$_2$Cl$_2$/MeOH, treated with silica gel, and evaporated under reduced pressure. The resulting material was purified by silica gel column chromatography to provide (S)-3-(1-(3-chlorophenyl)-2-hydroxyethyl)-7-(5-methyl-1H-pyrazol-4-yl)-2,3-dihydroquinazolin-4(1H)-one Compound 523 as an yellowish gel (175 mg, 58%). LC/MS found 383.0 [M+H]$^+$.

Compounds 524-531 in Table 15 below were prepared by the method (General Scheme 16) similar to that described for the preparation of Compound 523 using an appropriate boronic acid by Suzuki reaction condition.

TABLE 15

| Compd | Boronic acid/ester | Structure | MS found [M + H]$^+$ |
|---|---|---|---|
| 524 | | 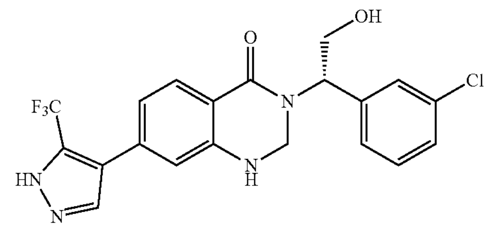 [SMILES: O=C1c2ccc(-c3cn[nH]c3C(F)(F)F)cc2NCN1[C@H](CO)c1cccc(Cl)c1] | 437.2 |
| 525 | | 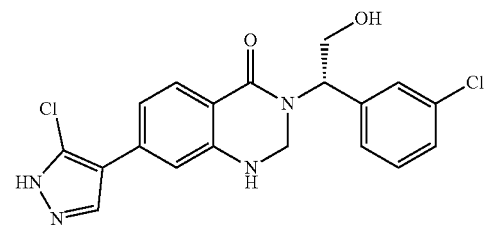 [SMILES: O=C1c2ccc(-c3cn[nH]c3Cl)cc2NCN1[C@H](CO)c1cccc(Cl)c1] | 403.4 |
| 526 | | 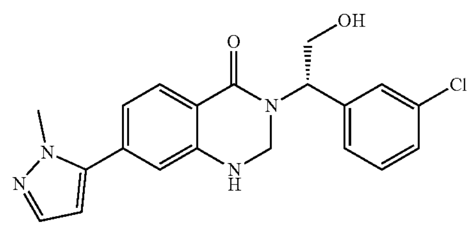 [SMILES: Cn1nccc1-c1ccc2c(c1)NCN([C@H](CO)c1cccc(Cl)c1)C2=O] | 383.3 |
| 527 | | 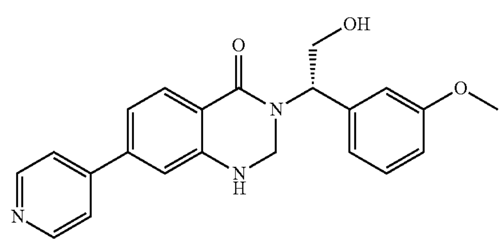 [SMILES: COc1cccc([C@@H](CO)N2CNc3cc(-c4ccncc4)ccc3C2=O)c1] | 376.2 |
| 528 | | 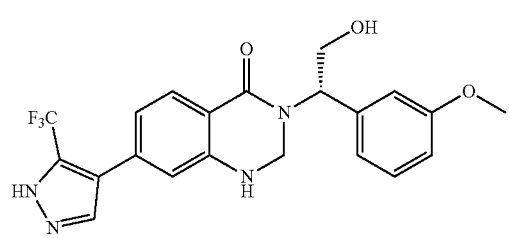 [SMILES: COc1cccc([C@@H](CO)N2CNc3cc(-c4cn[nH]c4C(F)(F)F)ccc3C2=O)c1] | 433.2 |

TABLE 15-continued
| Compd | Boronic acid/ester | Structure | MS found [M + H]+ |
|---|---|---|---|
| 529 | | 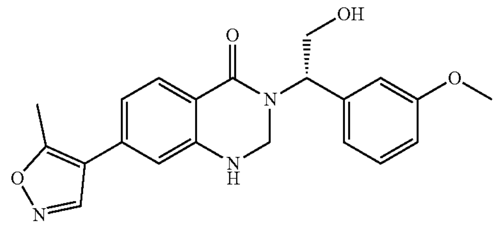 [SMILES: COc1cccc([C@@H](CO)N2CNc3cc(-c4cnoc4C)ccc3C2=O)c1] | 380.4 |
| 530 | | 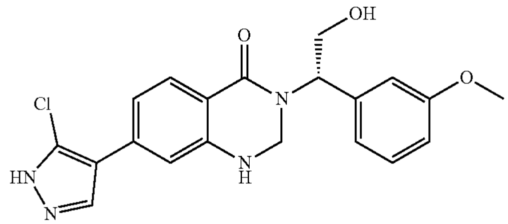 [SMILES: COc1cccc([C@@H](CO)N2CNc3cc(-c4cn[nH]c4Cl)ccc3C2=O)c1] | 399.2 |
| 531 | | 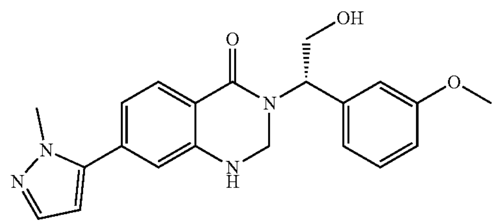 [SMILES: COc1cccc([C@@H](CO)N2CNc3cc(-c4ccnn4C)ccc3C2=O)c1] | 379.4 |
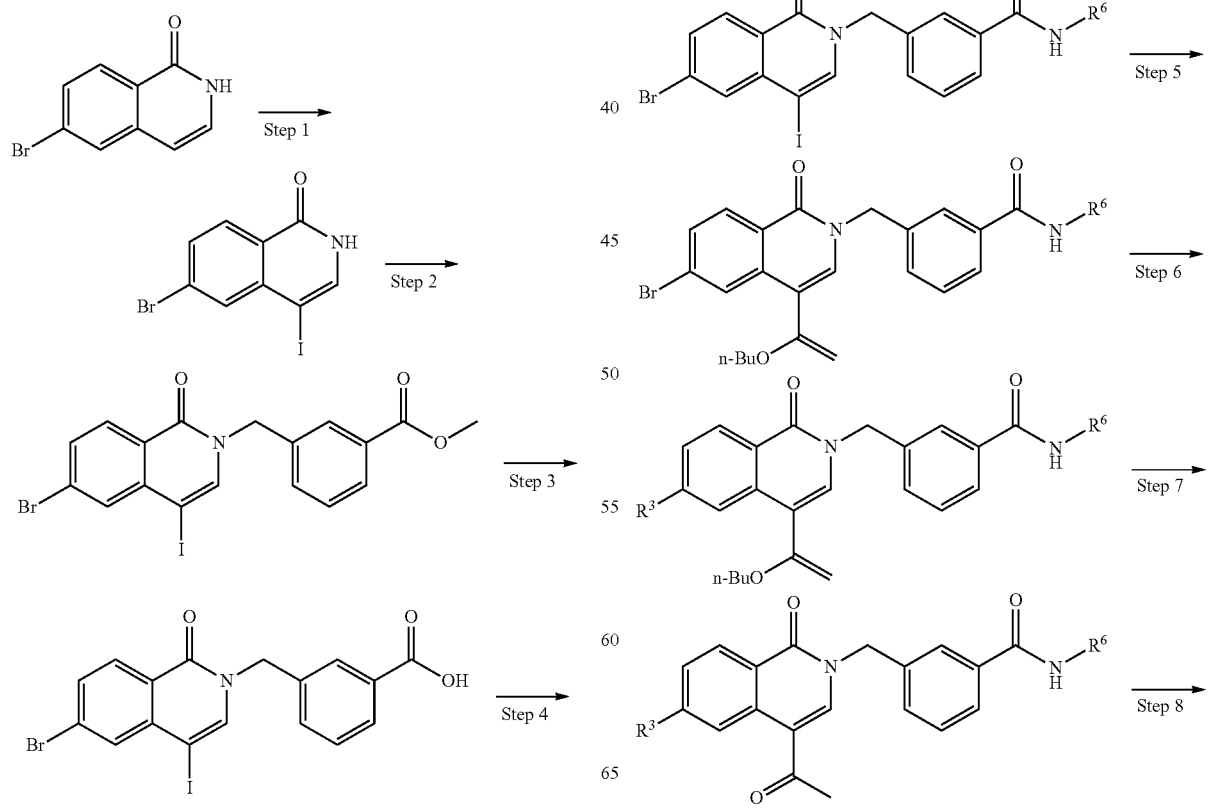

-continued

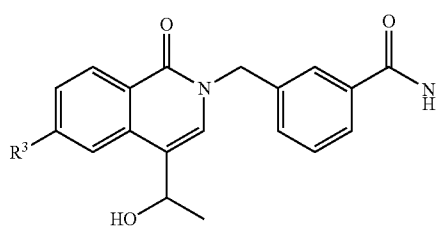

Compound 532: 3-((4-(1-hydroxyethyl)-1-oxo-6-(3-(trifluoromethyl)-1H-pyrazol-4-yl)isoquinolin-2(1H)-yl)methyl)-N-methylbenzamide Scheme 15

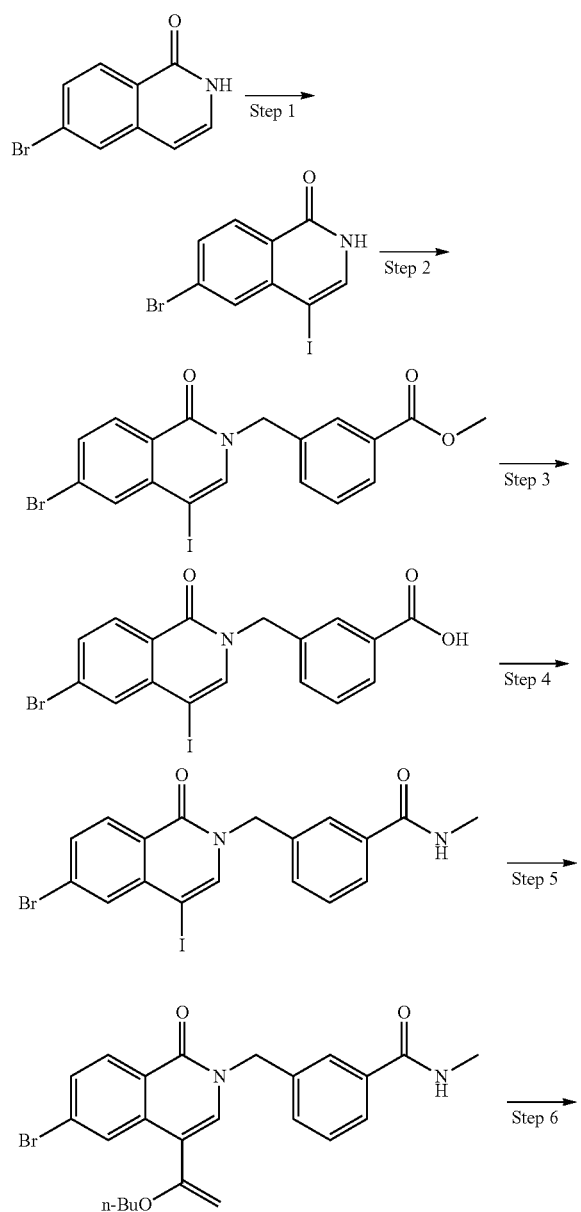

-continued

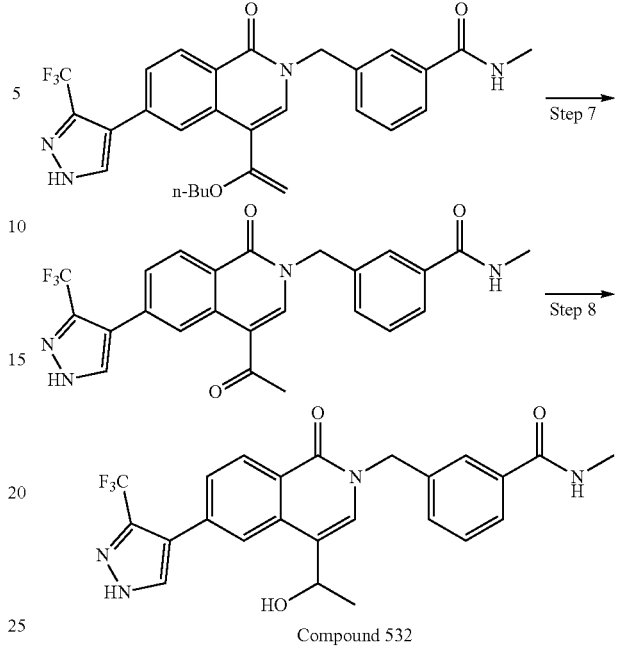

Compound 532

Step 1: To a mixture of 6-bromo-2H-isoquinolin-1-one (4.48 g, 20.0 mmol) in acetonitrile (80 mL) was added N-iodosuccinimide (4.72 g, 21.0 mmol), and the mixture was heated to reflux with stirring for 7 hours. The mixture was cooled to RT, poured over ice-H₂O, and stirred for 5 minutes. NaHSO₃ was added, and the mixture was stirred for another 10 minutes. The remaining solid was vacuum filtered, washed with H₂O, and dried under a vacuum overnight to provide 6-bromo-4-iodoisoquinolin-1(2H)-one as a tan colored solid in 95% yield (6.64 g). LC/MS found 350.0 [M+H]⁺.

Step 2: To a mixture of 6-bromo-4-iodo-2H-isoquinolin-1-one (2.10 g, 6.0 mmol), potassium carbonate (1.66 g, 12.0 mmol), and sodium iodide (180 mg, 1.20 mmol) in acetone (60 mL) was added methyl 3-(bromomethyl)benzoate (1.51 g, 6.6 mmol). The mixture was heated to reflux with stirring overnight, cooled to RT, poured over H₂O, and extracted with EtOAc. The organic layer was washed with brine, dried over Na₂SO₄, filtered, and concentrated. Crude methyl 3-((6-bromo-4-iodo-1-oxoisoquinolin-2(1H)-yl)methyl)benzoate was collected as a pale off-white solid in 82% yield (2.46 g, 4.94 mmol) and used without further purification. LC/MS found 498.0 [M+H]⁺.

Step 3: To a mixture of methyl 3-((6-bromo-4-iodo-1-oxoisoquinolin-2(1H)-yl)methyl)benzoate (2.46 g, 4.94 mmol) in methanol (25 mL) was added 1M aq. NaOH (25 mL), and the resulting mixture was heated to 60° C. with stirring for 2 hours. The mixture was cooled to RT, poured over ice-H₂O, and acidified to ~pH 2 with 1M aq. HCl. The mixture was stirred for 10 minutes. The precipitate was vacuum filtered, washed with H₂O, and dried under a vacuum overnight to give 3-((6-bromo-4-iodo-1-oxoisoquinolin-2(1H)-yl)methyl)benzoic acid as a white solid in 99% yield (2.37 g, 4.9 mmol). LC/MS found 484.0 [M+H]⁺.

Step 4: A mixture of 3-((6-bromo-4-iodo-1-oxoisoquinolin-2(1H)-yl)methyl)benzoic acid (2.37 g, 4.90 mmol), methylamine hydrochloride (666 mg, 9.86 mmol), HBTU (2.05 g, 5.41 mmol), and triethylamine (4.1 mL, 29 mmol) in THF (50 mL) was stirred at RT for 2 hours. The mixture was poured over ice-H₂O and stirred for 5 minutes. The precipitate was vacuum filtered, washed with H₂O, and dried under a vacuum overnight to provide 3-((6-bromo-4-iodo-1-oxoisoquinolin-2(1H)-yl)methyl)-N-methylbenzamide as a white solid in 96% yield (2.34 g, 4.71 mmol). LC/MS found 497.0 [M+H]⁺.

Step 5: To a mixture of 3-((6-bromo-4-iodo-1-oxoisoquinolin-2(1H)-yl)methyl)-N-methylbenzamide (500 mg, 1.01 mmol) and bis(triphenylphosphine)palladium (II) chloride (14 mg, 20 µmol) in dry acetonitrile (10 mL) was added triethylamine (0.42 mL, 3.0 mmol) and butyl vinyl ether (0.16 mL, 1.2 mmol). The mixture was degassed via sparging with N₂ for 5 minutes and then heated to 80° C. with stirring overnight. The mixture was cooled to RT and concentrated. The residue was purified by flash column chromatography on SiO₂ using a gradient of 50-100% EtOAc in CH₂Cl₂ to provide 3-((6-bromo-4-(1-butoxyvinyl)-1-oxoisoquinolin-2(1H)-yl)methyl)-N-methylbenzamide as a foamy yellow solid in 50% yield (238 mg). LC/MS found 469.2 [M+H]⁺.

Step 6: A mixture of 3-((6-bromo-4-(1-butoxyvinyl)-1-oxoisoquinolin-2(1H)-yl)methyl)-N-methylbenzamide (70 mg, 0.15 mmol), [3-(trifluoromethyl)-1H-pyrazol-4-yl]boronic acid (44 mg, 0.24 mmol), Na₂CO₃ (34 mg, 0.32 mmol), and PdCl₂(PPh₃)₂ (2.4 mg, 3.4 µmol) in 1,4-dioxane (3 mL) and H₂O (1 mL) was degassed via sparging with N₂ for 10 minutes then heated to 100° C. with stirring overnight. The mixture was cooled to room temperature, poured over H₂O, and extracted with 10% i-PrOH in CH₂Cl₂. The organic layer was washed with brine, dried over MgSO₄, filtered, and concentrated. The residue was purified by silica gel column using a gradient of 50-100% EtOAc in CH₂Cl₂ to provide 3-((4-(1-butoxyvinyl)-1-oxo-6-(3-(trifluoromethyl)-1H-pyrazol-4-yl)isoquinolin-2(1H)-yl)methyl)-N-methylbenzamide, as a white solid in 88% yield (69 mg, 0.13 mmol). LC/MS found 469.2 [M+H−BuOH+H₂O]⁺.

Step 7: To a solution of 3-((4-(1-butoxyvinyl)-1-oxo-6-(3-(trifluoromethyl)-1H-pyrazol-4-yl)isoquinolin-2(1H)-yl)methyl)-N-methylbenzamide (69 mg, 0.13 mmol) in THF (2 mL) was added aq. HCl (1 M, 2 mL), and the mixture was stirred at RT for 1 hour. The mixture was quenched with aq. NaHCO₃ and extracted with EtOAc. The collected organic layer was washed with brine, dried over MgSO₄, filtered, and concentrated. The crude 3-((4-acetyl-1-oxo-6-(3-(trifluoromethyl)-1H-pyrazol-4-yl)isoquinolin-2(1H)-yl)methyl)-N-methylbenzamide was collected as a white solid in 60% yield (37 mg, 79 µmol) and used without further purification. LC/MS found 469.2 [M+H]⁺.

Step 8: To a solution of 3-((4-acetyl-1-oxo-6-(3-(trifluoromethyl)-1H-pyrazol-4-yl)isoquinolin-2(1H)-yl)methyl)-N-methylbenzamide (37 mg, 79 µmol) in CH₂Cl₂ (2 mL) and CH₃OH (1 mL) was added NaBH₄ (12 mg, 0.32 mmol). The mixture was stirred at RT for 1 hour, quenched with aq. NH₄Cl, and then extracted with EtOAc (×2). The combined organic layer was washed with brine, dried over MgSO₄, filtered, and concentrated. The residue was purified by column chromatography on SiO₂ using a gradient of 1-10% CH₃OH in CH₂Cl₂ to provide compound 532 as a white solid in 35% yield (13 mg). LC/MS found 493.2 [M+Na]⁺, 453.2 [M+H−H₂O]⁺.

Compounds 533-544 in Table 17 below were prepared by the method (General Scheme 17) similar to that described for the preparation of Compound 532 using an appropriate boronic acid by Suzuki reaction condition.

TABLE 17

| Compd | Boronic acid/ester | Structure | MS found [M + H]⁺ |
|---|---|---|---|
| 533 | | 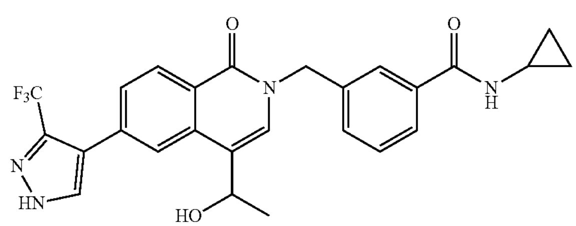 [SMILES: CC(O)c1cn(Cc2cccc(C(=O)NC3CC3)c2)c(=O)c2ccc(-c3c[nH]nc3C(F)(F)F)cc12] | 519.1 [M + Na]⁺ |
| 534 | | 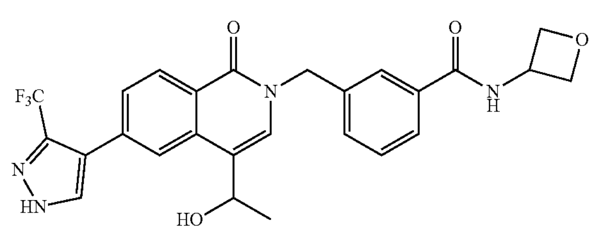 [SMILES: CC(O)c1cn(Cc2cccc(C(=O)NC3COC3)c2)c(=O)c2ccc(-c3c[nH]nc3C(F)(F)F)cc12] | 535.1 [M + Na]⁺ |
| 535 | | 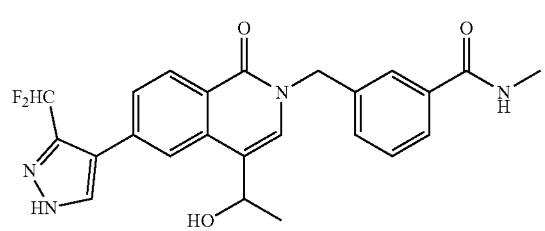 [SMILES: CNC(=O)c1cccc(Cn2cc(C(C)O)c3cc(-c4c[nH]nc4C(F)F)ccc3c2=O)c1] | 475.2 [M + Na]⁺ |

TABLE 17-continued

| Compd | Boronic acid/ester | Structure | MS found [M + H]+ |
|---|---|---|---|
| 536 | | 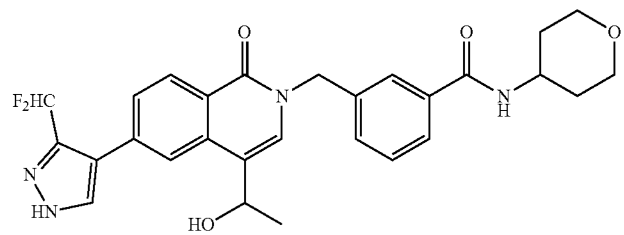 [SMILES: CC(O)c1cn(Cc2cccc(C(=O)NC3CCOCC3)c2)c(=O)c2ccc(-c3c[nH]nc3C(F)F)cc12] | 545.1 [M + Na]+ |
| 537 | | 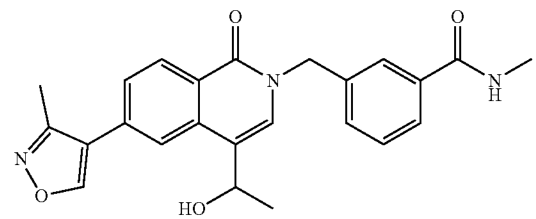 [SMILES: CNC(=O)c1cccc(Cn2cc(C(C)O)c3cc(-c4conc4C)ccc3c2=O)c1] | 440.1 [M + Na]+ |
| 538 | | 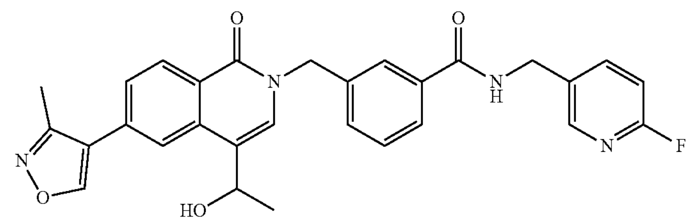 [SMILES: Cc1nocc1-c1ccc2c(=O)n(Cc3cccc(C(=O)NCc4ccc(F)nc4)c3)cc(C(C)O)c2c1] | 513.1 |
| 539 | | 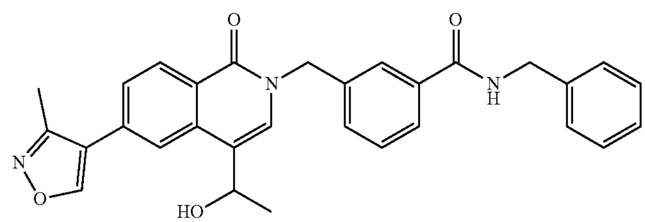 [SMILES: Cc1nocc1-c1ccc2c(=O)n(Cc3cccc(C(=O)NCc4ccccc4)c3)cc(C(C)O)c2c1] | 494.2 |
| 540 | | 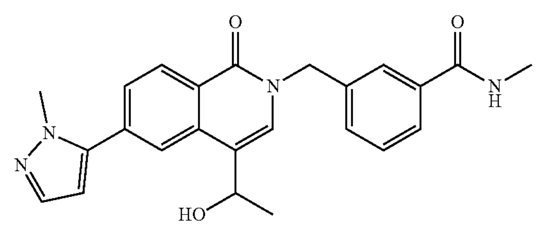 [SMILES: CNC(=O)c1cccc(Cn2cc(C(C)O)c3cc(-c4ccnn4C)ccc3c2=O)c1] | 439.1 [M + Na]+ |
| 541 | | 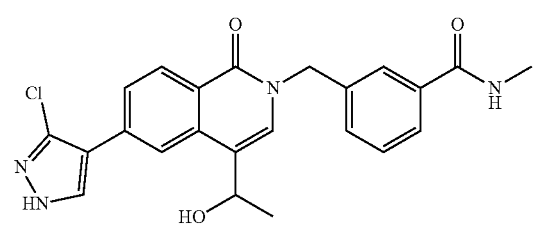 [SMILES: CNC(=O)c1cccc(Cn2cc(C(C)O)c3cc(-c4c[nH]nc4Cl)ccc3c2=O)c1] | 459.4 [M + Na]+ |
| 542 | | 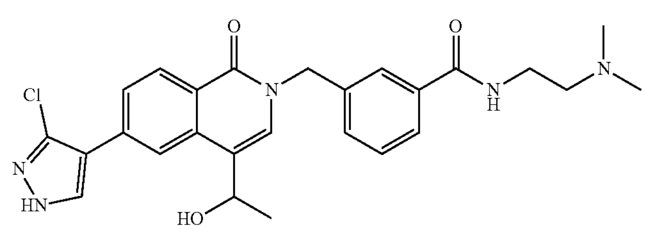 [SMILES: CC(O)c1cn(Cc2cccc(C(=O)NCCN(C)C)c2)c(=O)c2ccc(-c3c[nH]nc3Cl)cc12] | 494.2 |

TABLE 17-continued
| Compd | Boronic acid/ester | Structure | MS found [M + H]+ |
|---|---|---|---|
| 543 | | 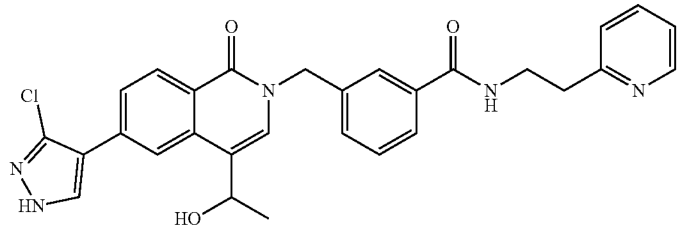 [SMILES: CC(O)c1cn(Cc2cccc(C(=O)NCCc3ccccn3)c2)c(=O)c2ccc(-c3c[nH]nc3Cl)cc12] | 528.1 |
| 544 | | 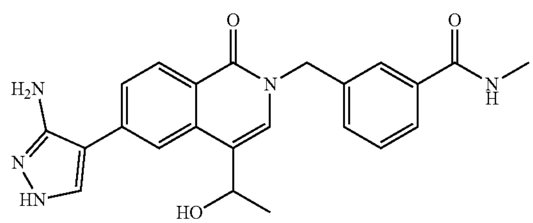 | 418.2 |
| 545 | | 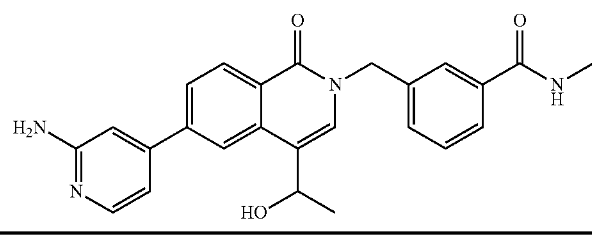 | 451.1 [M + Na]+ |
General Scheme 18
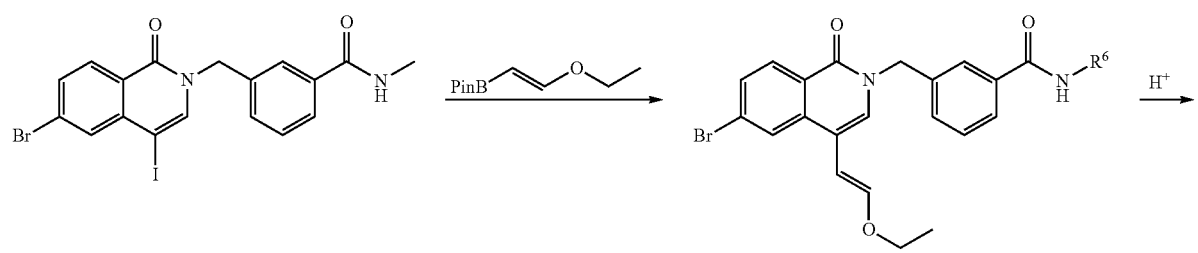

223 224
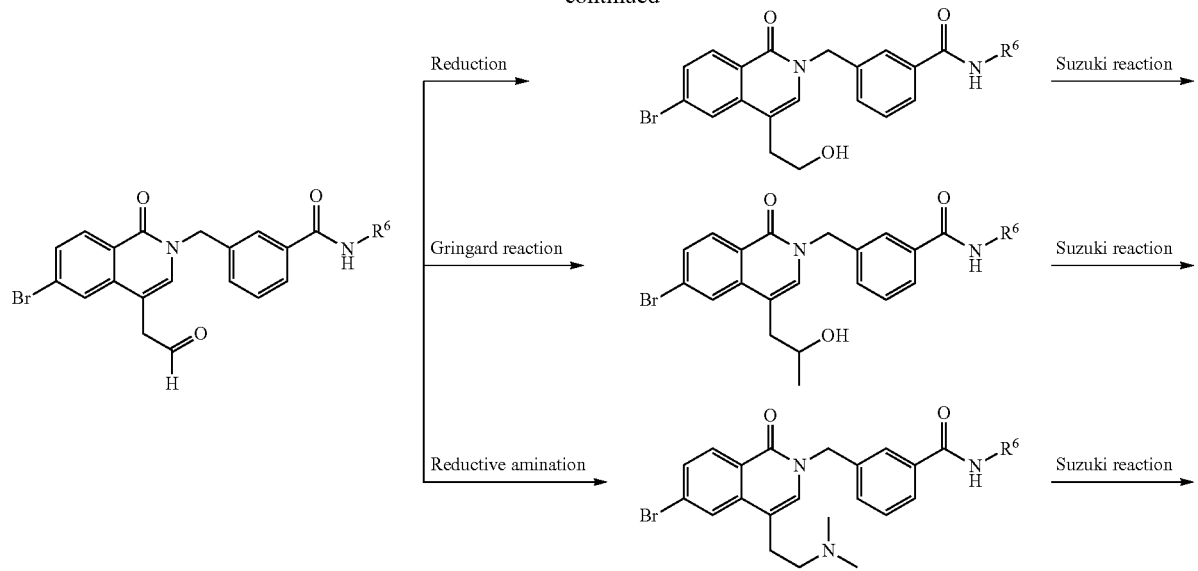
-continued
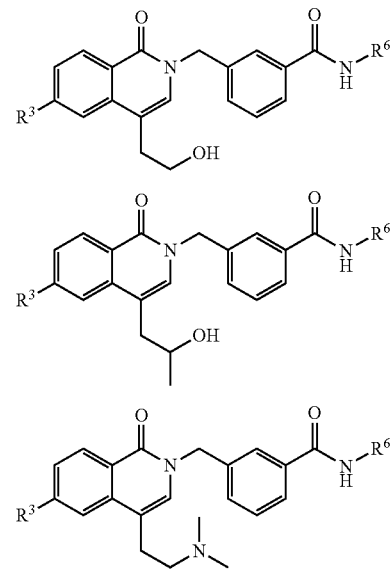
Compound 546: 3-((4-(2-hydroxyethyl)-1-oxo-6-(5-(trifluoromethyl)-1H-pyrazol-4-yl)isoquinolin-2(1H)-yl)methyl)-N-methylbenzamide
Scheme 16
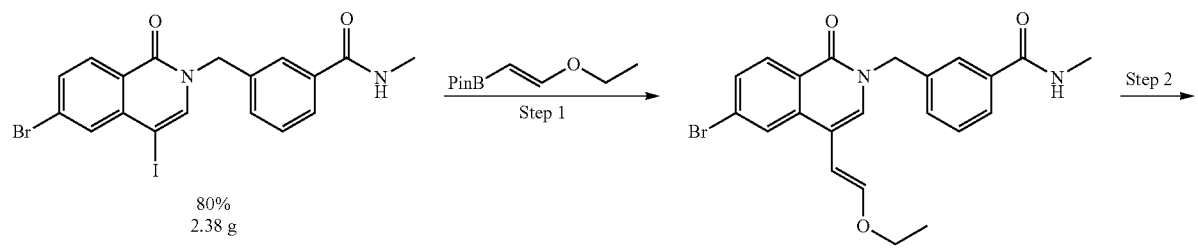

-continued

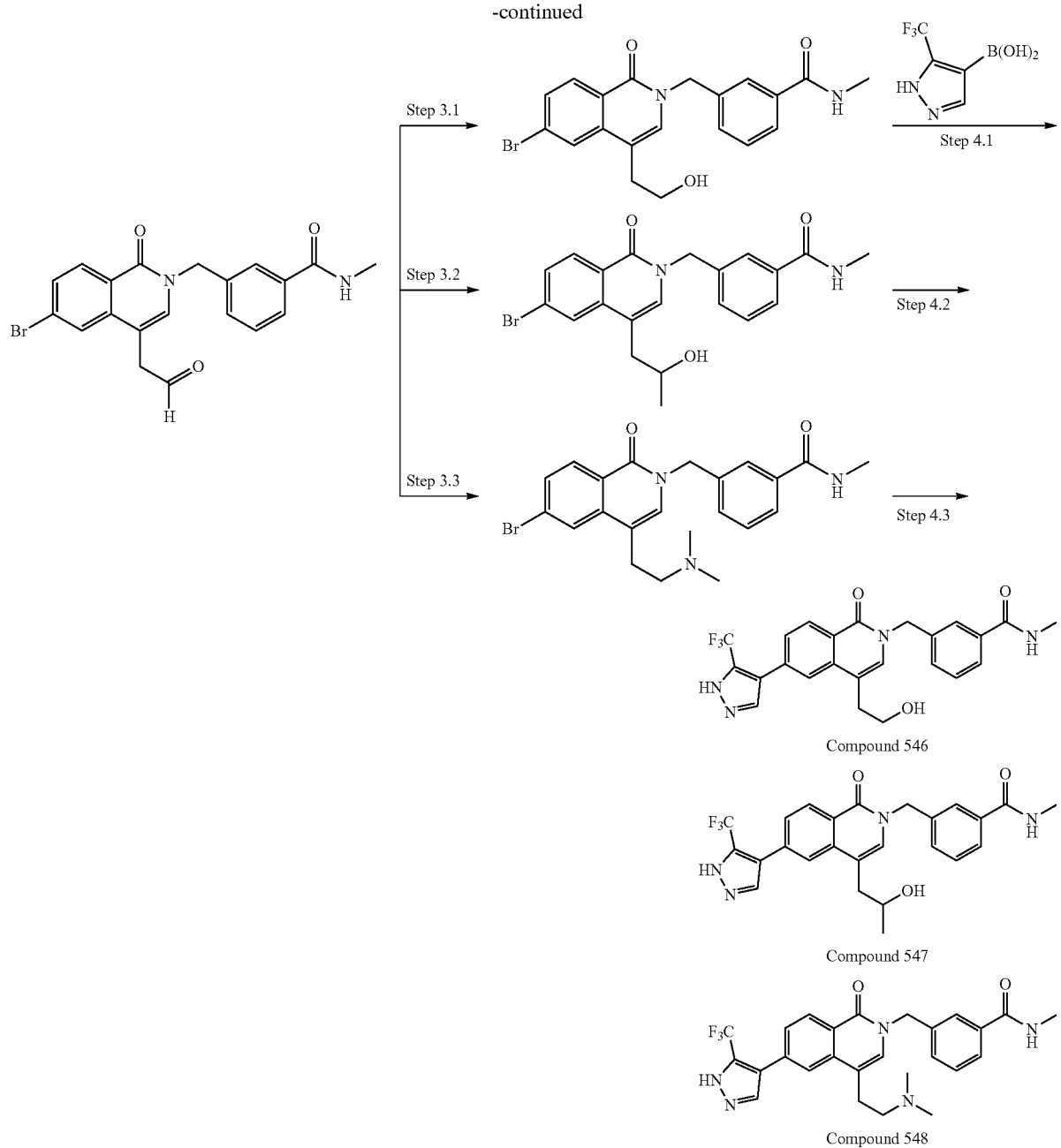

Step 1: A mixture of 3-((6-bromo-4-iodo-1-oxoisoquinolin-2(1H)-yl)methyl)-N-methylbenzamide (2.38 g, 4.8 mmol), 2-(2-ethoxyvinyl)-4,4,5,5-tetramethyl-1,3,2-dioxaborolane (1.90 g, 9.6 mmol), Na$_2$CO$_3$ (1.53 g, 14.4 mmol), and PdCl$_2$(PPh$_3$)$_2$ (350 mg, 0.5 mmol) in 1,4-dioxane (15 mL) and H$_2$O (3 mL) was degassed via sparging with N$_2$ for 10 minutes and then heated to 50° C. with stirring for 1 hour. The mixture was cooled to RT, poured over H$_2$O, and extracted with EtOAc. The organic layer was washed with brine, dried over MgSO$_4$, filtered, and concentrated. The residue was purified silica gel column using a gradient of 50-100% EtOAc in CH$_2$Cl$_2$ to provide (3-((6-bromo-4-(2-ethoxyvinyl)-1-oxoisoquinolin-2(1H)-yl)methyl)-N-methylbenzamide, as a white solid in 50% yield (1.06 g). LC/MS found 441.2 [M+H]$^+$.

Step 2: To a solution of (3-((6-bromo-4-(2-ethoxyvinyl)-1-oxoisoquinolin-2(1H)-yl)methyl)-N-methylbenzamide (1.06 g, 2.4 mmol) in THF (10 mL), was added 1ON aqueous HCl (2.4 mL). After being stirred for 3 hours at RT, volatiles were removed with vacuum. The mixture was extracted with DCM (×2). The combined organic layer was washed with brine, dried over MgSO$_4$, filtered, and concentrated. The residue was purified silica gel column using a gradient of 50-100% EtOAc in CH$_2$Cl$_2$ to provide 3-((6-bromo-1-oxo-4-(2-oxoethyl)isoquinolin-2(1H)-yl)methyl)-N-methylbenzamide as a white solid in quantitative yield (0.99 g). LC/MS found 413.1 [M+H]$^+$.

Step 3.1: To a solution of 3-((6-bromo-1-oxo-4-(2-oxoethyl)isoquinolin-2(1H)-yl)methyl)-N-methylbenzamide (0.99 g, 2.4 mmol) in DCM (20 mL), was added NaBH$_4$ (182 mg, 4.8 mmol) at rt. After being stirred for 2 hours at RT, the mixture was extracted with DCM (×2). The combined organic layer was washed with 1N HCl followed by brine, dried over MgSO$_4$, filtered, and concentrated. The residue was purified silica gel column using a gradient of 70-100% EtOAc in CH$_2$Cl$_2$ to provide 3-((6-bromo-4-(2-hydroxyethyl)-1-oxoisoquinolin-2(1H)-yl)methyl)-N-methylbenzamideas a white solid in 85% yield (0.85 g) g. LC/MS found 415.1 [M+H]$^+$.

Step 3.2: To a solution of 3-((6-bromo-1-oxo-4-(2-oxoethyl)isoquinolin-2(1H)-yl)methyl)-N-methylbenzamide (415 mg, 1.0 mmol) in THF (5 mL), was added 3M solution of MeMgCl (0.5 mL) in THF at 0° C. After being stirred for 2 hours at 0° C., the reaction was quenched by addition of saturated NH$_4$Cl solution and extracted with EtOAc (×2). The combined organic layer was washed with brine, dried over MgSO$_4$, filtered, and concentrated. The residue was purified silica gel column using a gradient of 0-20% MeOH in CH$_2$Cl$_2$ to provide 3-((6-bromo-4-(2-hydroxypropyl)-1-oxoisoquinolin-2(1H)-yl)methyl)-N-methylbenzamide a pale yellow solid in 70% yield (301.0 mg). LC/MS found 430.1 [M+H]$^+$.

Step 3.3: To a mixture of 3-((6-bromo-1-oxo-4-(2-oxoethyl)isoquinolin-2(1H)-yl)methyl)-N-methylbenzamide (415 mg, 1.0 mmol) and dimethylamine-HCl (162 mg, 2 mmol), in CH$_2$Cl$_2$ (10 mL), was added NaBH(OAc)$_3$ (181 mg, 2.5 mmol). After being stirred for 16 hours at RT, the reaction was quenched by addition of saturated NaHCO$_3$ solution and extracted with DCM (×2). The combined organic layer was washed with brine, dried over Na$_2$SO$_4$, filtered, and concentrated. The residue was purified silica gel column using a gradient of 0-50% MeOH in CH$_2$Cl$_2$ to provide 3-((6-bromo-4-(2-(dimethylamino)ethyl)-1-oxoisoquinolin-2(1H)-yl)methyl)-N-methylbenzamide a pale yellow solid in 80% yield (353.7 mg). LC/MS found 443.1 [M+H]$^+$.

Step 4.1: A mixture of 3-((6-bromo-4-(2-hydroxyethyl)-1-oxoisoquinolin-2(1H)-yl)methyl)-N-methylbenzamideas (63 mg, 0.15 mmol), [3-(trifluoromethyl)-1H-pyrazol-4-yl]boronic acid (44 mg, 0.24 mmol), Na$_2$CO$_3$ (34 mg, 0.32 mmol), and PdCl$_2$(PPh$_3$)$_2$ (2.4 mg, 3.4 µmol) in 1,4-dioxane (3 mL) and H$_2$O (1 mL) was degassed via sparging with N$_2$ for 10 minutes and then heated to 100° C. with stirring overnight. The mixture was cooled to RT, poured over H$_2$O, and extracted with in CH$_2$Cl$_2$ (×2). The combined organic layer was washed with brine, dried over MgSO$_4$, filtered, and concentrated. The residue was purified by silica gel column using a gradient of 5-20% MeOH in CH$_2$Cl$_2$ to provide Compound 546, 3-((4-(2-hydroxyethyl)-1-oxo-6-(5-(trifluoromethyl)-1H-pyrazol-4-yl)isoquinolin-2(1H)-yl)methyl)-N-methylbenzamide, as a white solid in 65% yield (69 mg). LC/MS found 471.2 [M+H]$^+$.

Step 4.2: Compound 547 was prepared using 3-((6-bromo-4-(2-hydroxypropyl)-1-oxoisoquinolin-2(1H)-yl)methyl)-N-methylbenzamide by a method similar to the above mentioned method of Step 4.1. LC/MS found 485.1 [M+H]$^+$.

Step 4.3: Compound 548 was prepared using 3-((6-bromo-4-(2-hydroxypropyl)-1-oxoisoquinolin-2(1H)-yl)methyl)-N-methylbenzamide by a method similar to the above mentioned method of Step 4.1. LC/MS found 498.1 [M+H]$^+$.

Compounds 549-567 in Table 18 below were prepared by the method (General Scheme 18) similar to that described in Scheme 16 for the preparation of Compounds 546-548 using an appropriate boronic acid/ester by Suzuki reaction condition.

TABLE 18

| Compd | Boronic acid/ester | Structure | MS found [M + H]$^+$ |
|---|---|---|---|
| 549 | F$_3$C-pyrazole-Bpin | trifluoromethylpyrazole-isoquinolinone-benzamide with CH(CH$_3$) linker and ethanol side chain | 485.1 |
| 550 | Cl-pyrazole-Bpin | chloropyrazole-isoquinolinone-benzamide with CH$_2$ linker and ethanol side chain | 437.1 |
| 551 | Cl-pyrazole-Bpin | chloropyrazole-isoquinolinone-benzamide with CH(CH$_3$) linker and ethanol side chain | 451.3 |

TABLE 18-continued
| Compd | Boronic acid/ester | Structure | MS found [M + H]+ |
|---|---|---|---|
| 552 | 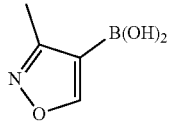 | 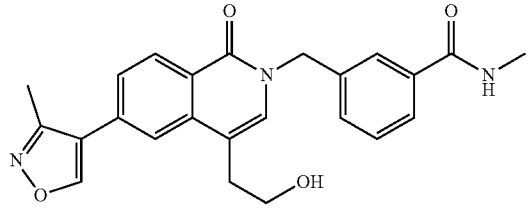 [SMILES: CNC(=O)c1cccc(Cn2cc(CCO)c3cc(-c4conc4C)ccc3c2=O)c1] | 418.1 |
| 553 | 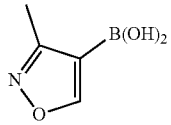 | 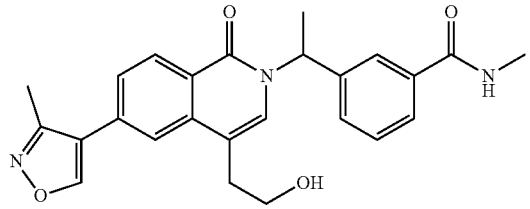 [SMILES: CNC(=O)c1cccc(C(C)n2cc(CCO)c3cc(-c4conc4C)ccc3c2=O)c1] | 432.2 |
| 554 | 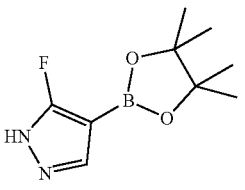 | 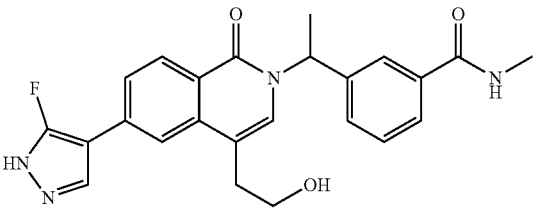 [SMILES: CNC(=O)c1cccc(C(C)n2cc(CCO)c3cc(-c4cn[nH]c4F)ccc3c2=O)c1] | 435 |
| 555 | 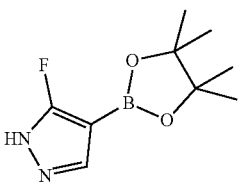 | 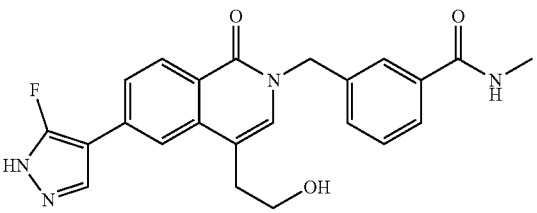 [SMILES: CNC(=O)c1cccc(Cn2cc(CCO)c3cc(-c4cn[nH]c4F)ccc3c2=O)c1] | 421.3 |
| 556 | 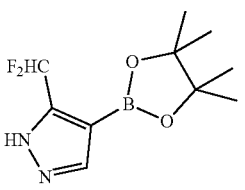 [SMILES: CC1(C)OB(c2cn[nH]c2C(F)F)OC1(C)C] | 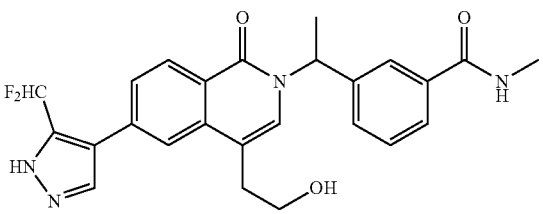 | 453.1 |
| 557 | 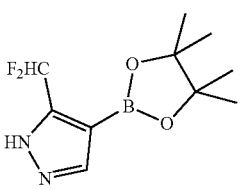 [SMILES: CC1(C)OB(c2cn[nH]c2C(F)F)OC1(C)C] | 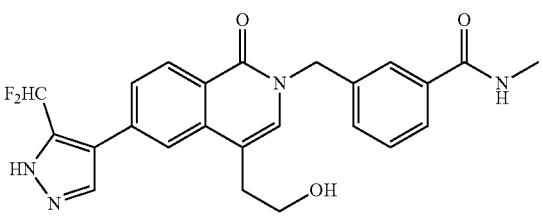 [SMILES: CNC(=O)c1cccc(Cn2cc(CCO)c3cc(-c4cn[nH]c4C(F)F)ccc3c2=O)c1] | 467 |
| 558 | 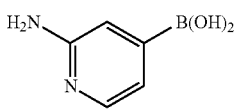 | 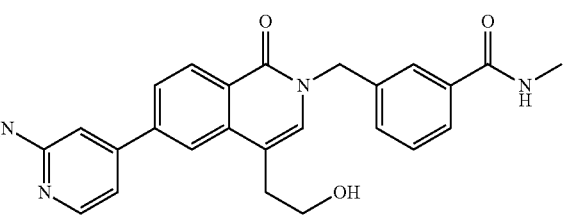 | 429.1 |

TABLE 18-continued

| Compd | Boronic acid/ester | Structure | MS found [M + H]+ |
|---|---|---|---|
| 559 | | 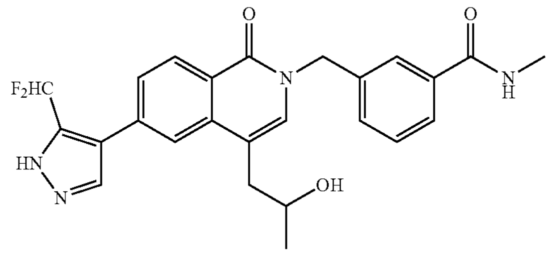 [SMILES: CNC(=O)c1cccc(Cn2cc(CC(C)O)c3cc(-c4cn[nH]c4C(F)F)ccc3c2=O)c1] | 467.1 |
| 560 | | 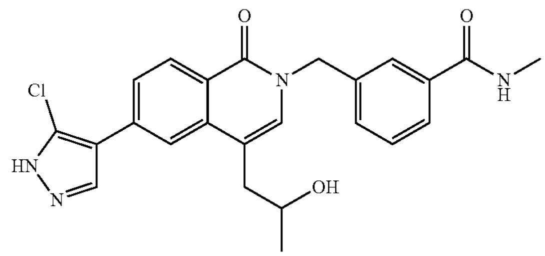 [SMILES: CNC(=O)c1cccc(Cn2cc(CC(C)O)c3cc(-c4cn[nH]c4Cl)ccc3c2=O)c1] | 451.2 |
| 561 | | | 444.1 |
| 561 | | | 432.2 |
| 562 | | 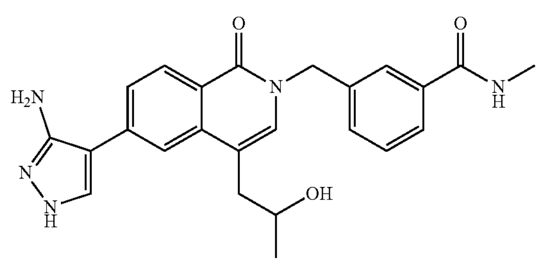 [SMILES: CNC(=O)c1cccc(Cn2cc(CC(C)O)c3cc(-c4c[nH]nc4N)ccc3c2=O)c1] | 432.1 |
| 563 | | 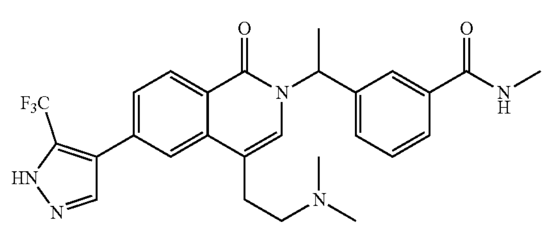 [SMILES: CNC(=O)c1cccc(C(C)n2cc(CCN(C)C)c3cc(-c4cn[nH]c4C(F)(F)F)ccc3c2=O)c1] | 512.2 |

TABLE 18-continued
| Compd | Boronic acid/ester | Structure | MS found [M + H]+ |
|---|---|---|---|
| 564 | | 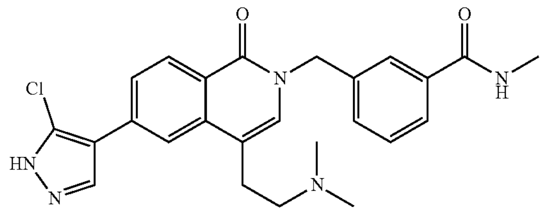 [SMILES: CNC(=O)c1cccc(Cn2cc(CCN(C)C)c3cc(-c4cn[nH]c4Cl)ccc3c2=O)c1] | 464.3 |
| 565 | | 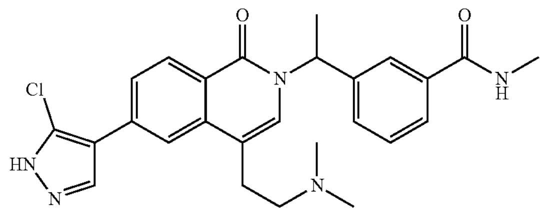 [SMILES: CNC(=O)c1cccc(C(C)n2cc(CCN(C)C)c3cc(-c4cn[nH]c4Cl)ccc3c2=O)c1] | 478.1 |
| 566 | | 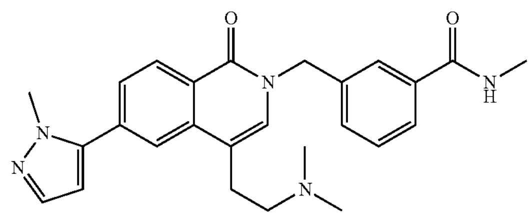 [SMILES: CNC(=O)c1cccc(Cn2cc(CCN(C)C)c3cc(-c4ccnn4C)ccc3c2=O)c1] | 444.3 |
| 567 | | 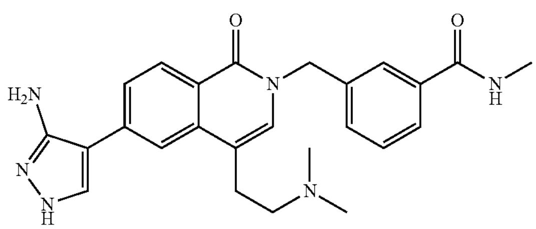 [SMILES: CNC(=O)c1cccc(Cn2cc(CCN(C)C)c3cc(-c4c[nH]nc4N)ccc3c2=O)c1] | 445.1 |
Compound 568: (R)—N-methyl-3-(1-(4-oxo-7-(5-(trifluoromethyl)-1H-pyrazol-4-yl)pyrido[4,3-d]pyrimidin-3(4H)-yl)ethyl)benzamide
General Scheme 19
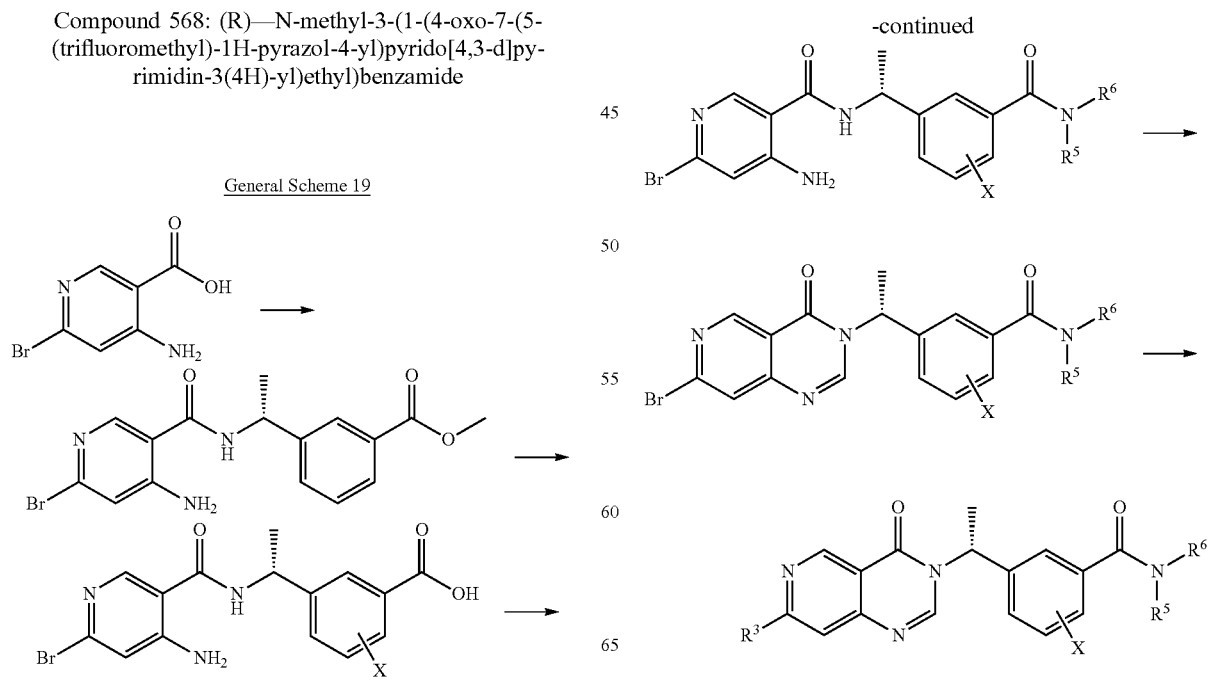

Scheme 17

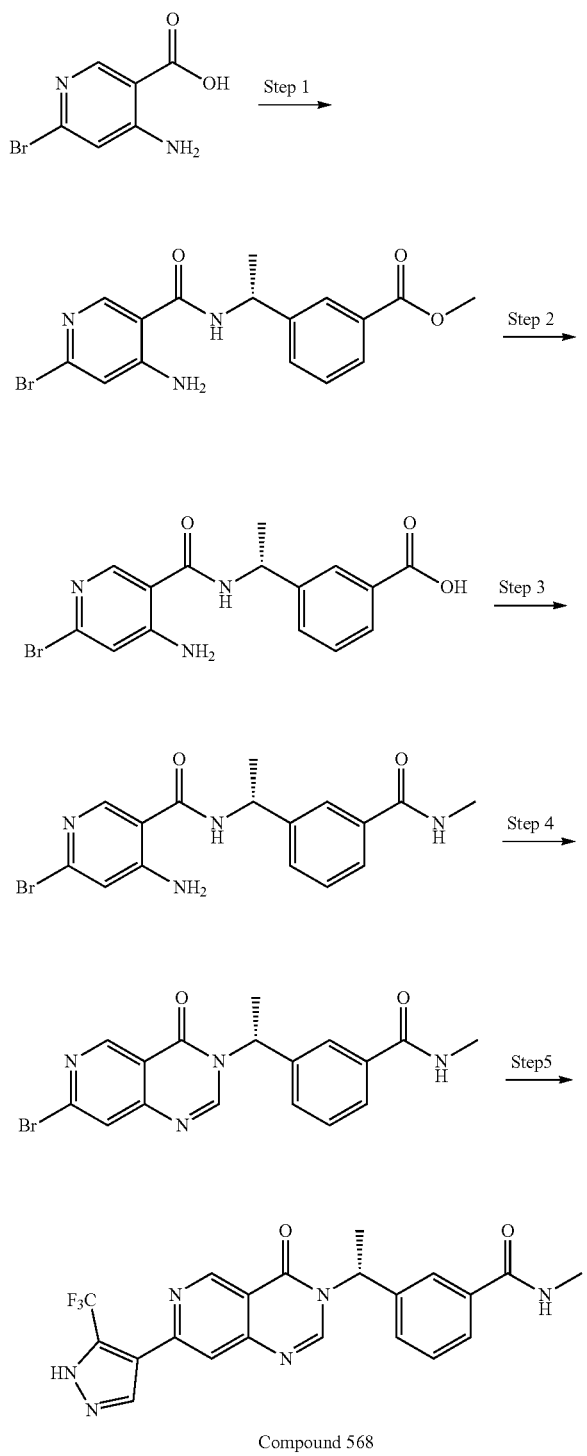

Compound 568

Step 1: A mixture of 4-amino-6-bromonicotinic acid (0.85 g, 4.74 mmol), HBTU (2.52 g, 6.64 mmol), and DIPEA (2.1 mL, 11.9 mmol) in DMF (30 mL) was shaken at ambient temperature for 30 mins. The mixture was treated with methyl (R)-3-(1-aminoethyl)benzoate (0.84 g, 3.92 mmol) and shaken overnight at room temperature. The reaction mixture was diluted with EtOAc and brine, and then the organic layer was separated, washed sequentially with water and brine, dried (Mg$_2$SO$_4$), concentrated, and purified by silica gel column chromatography to provide methyl (R)-3-(1-(4-amino-6-bromonicotinamido)ethyl)benzoate (1.3 g, 87% yield). LC/MS found 378.1 and 380.0 [M+H]$^+$.

Step 2: aq. 2M LiOH solution (13.8 mL, 27.5 mmol) was added to a suspension of methyl (R)-3-(1-(7-bromo-4-oxopyrido[4,3-d]pyrimidin-3(4H)-yl)ethyl)benzoate (1.05 g, 2.8 mmol) in THF (20 mL), and then the mixture was shaken overnight at room temperature. After removing THF in vacuum, the residual solution was acidified with aq. 1N HCl solution to pH 7 and then extracted with CH$_2$Cl$_2$. The organic layer was dried (Na$_2$SO$_4$), filtered, concentrated, and purified by silica gel column chromatography to provide (R)-3-(1-(7-bromo-4-oxopyrido[4,3-d]pyrimidin-3(4H)-yl)ethyl)benzoic acid (1.2 g, 95% yield). LC/MS found 364.0 and 366.0 [M+H]$^+$.

Step 3: A mixture of 3-[(1R)-1-[(4-amino-6-bromo-pyridine-3-carbonyl)amino]ethyl]benzoic acid (1.2 g, 3.29 mmol), HBTU (1.62 g, 4.28 mmol), and DIPEA (1.72 mL, 9.88 mmol) in DMF (15 mL) was shaken at ambient temperature for 30 mins. The mixture was treated with a 2M solution of methyl amine (3.29 mL, 6.59 mmol) in THF and shaken overnight at room temperature. The reaction mixture was diluted with EtOAc and brine, and then the organic layer was separated, washed sequentially with water and brine, dried (Na$_2$SO$_4$), concentrated, and purified by silica gel column chromatography to provide methyl (R)-3-(1-(7-bromo-4-oxopyrido[4,3-d]pyrimidin-3(4H)-yl)ethyl)-N-methylbenzamide (1.15 g, 92% yield). LCMS found 377.0 and 379.0 [M+H]$^+$.

Step 4: A suspension of methyl (R)-3-(1-(4-amino-6-bromonicotinamido)ethyl)benzoate (500 mg, 1.33 mmol) and p-toluenesulfonic acid monohydrate (50 mg, 265 μmol) in neat trimethyl orthoformate (5 mL) was shaken at 100° C. for 48 h. The reaction mixture was diluted with EtOAc, washed sequentially with saturated aqueous NaHCO$_3$ and brine, dried (Na$_2$SO$_4$), filtered, concentrated, and purified by silica gel column chromatography to provide methyl (R)-3-(1-(7-bromo-4-oxopyrido[4,3-d]pyrimidin-3(4H)-yl)ethyl)benzoate (75 mg, 14% yield). LC/MS found 387.0 and 389.0 [M+H]$^+$.

Step 5: (R)-3-(1-(7-bromo-4-oxopyrido[4,3-d]pyrimidin-3(4H)-yl)ethyl)-N-methylbenzamide (30 mg, 77 μmol), 4-(4,4,5,5-tetramethyl-1,3,2-dioxaborolan-2-yl)-5-(trifluoromethyl)-1H-pyrazole (35 mg, 194 μmol), aq. 2M potassium carbonate solution (97 uL, 194 μmol), and tetrakis(triphenylphosphine)palladium(0) (4.5 mg, 3.87 μmol) in dioxane (2 mL) was purged with argon five minutes. The mixture was shaken at 70° C. overnight. The sample was filtered, then the filtrate was evaporated under reduced pressure. The material was dissolved in DCM/MeOH, treated with silica gel, and evaporated under reduced pressure. The material was purified by silica gel column chromatography to provide (R)—N-methyl-3-(1-(4-oxo-7-(5-(trifluoromethyl)-1H-pyrazol-4-yl)pyrido[4,3-d]pyrimidin-3(4H)-yl)ethyl)benzamide, Compound 568, as a pale yellow solid (17 mg, 49%). LC/MS found 443.2 [M+H]$^+$.

Compounds 569-572 shown in Table 19 were prepared by the method (General Scheme 19) similar to that described for the preparation of Compound 568 using (R)-3-(1-(7-bromo-4-oxopyrido[4,3-d]pyrimidin-3(4H)-yl)ethyl)-N-methylbenzamide and appropriate boronic acid/ester.

TABLE 19
| Compd | Boronic acid/ester | Structure | MS found [M + H]+ |
|---|---|---|---|
| 569 | | 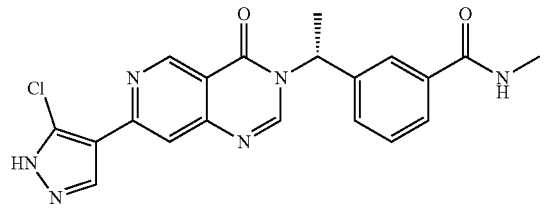 [SMILES: CNC(=O)c1cccc([C@@H](C)n2cnc3cc(-c4cn[nH]c4Cl)ncc3c2=O)c1] | 409.2 |
| 570 | | 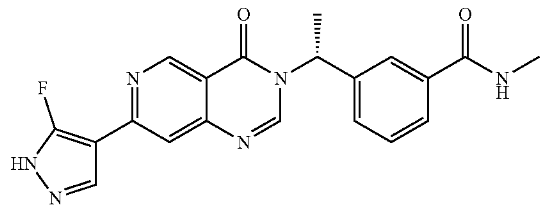 [SMILES: CNC(=O)c1cccc([C@@H](C)n2cnc3cc(-c4cn[nH]c4F)ncc3c2=O)c1] | 393.2 |
| 571 | | 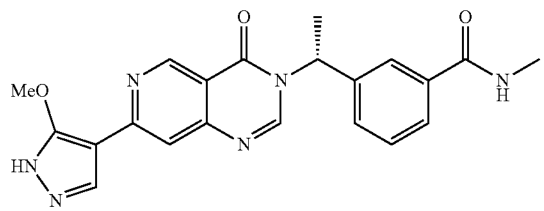 [SMILES: CNC(=O)c1cccc([C@@H](C)n2cnc3cc(-c4cn[nH]c4OC)ncc3c2=O)c1] | 405.2 |
| 572 | | 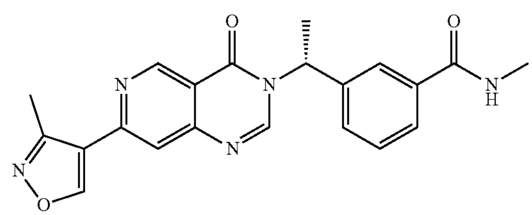 [SMILES: CNC(=O)c1cccc([C@@H](C)n2cnc3cc(-c4conc4C)ncc3c2=O)c1] | 390.1 |
Compound 573: [4-[3-[(1R)-1-[3-(methylcarbamoyl)phenyl]ethyl]-4-oxo-quinazolin-7-yl]-3-(trifluoromethyl)pyrazol-1-yl]methyl dihydrogen phosphate
General Scheme 20
-continued
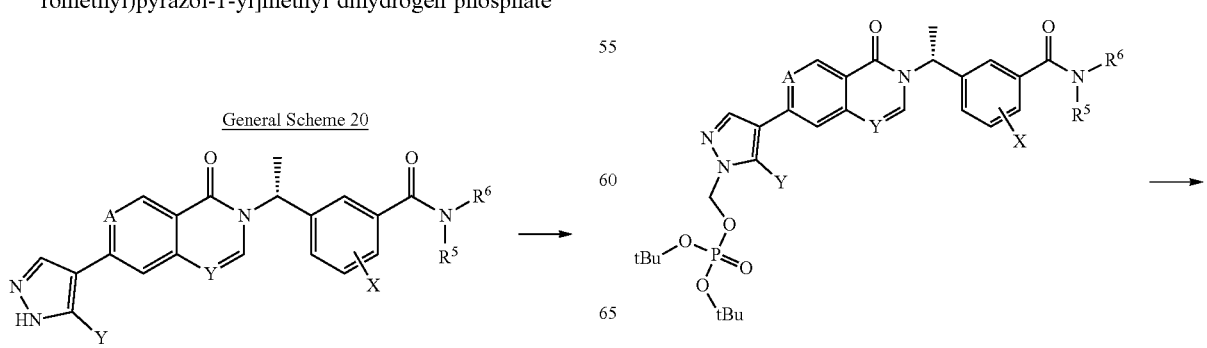

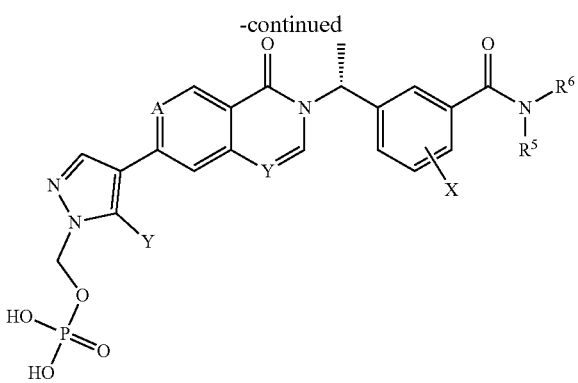

Scheme 18

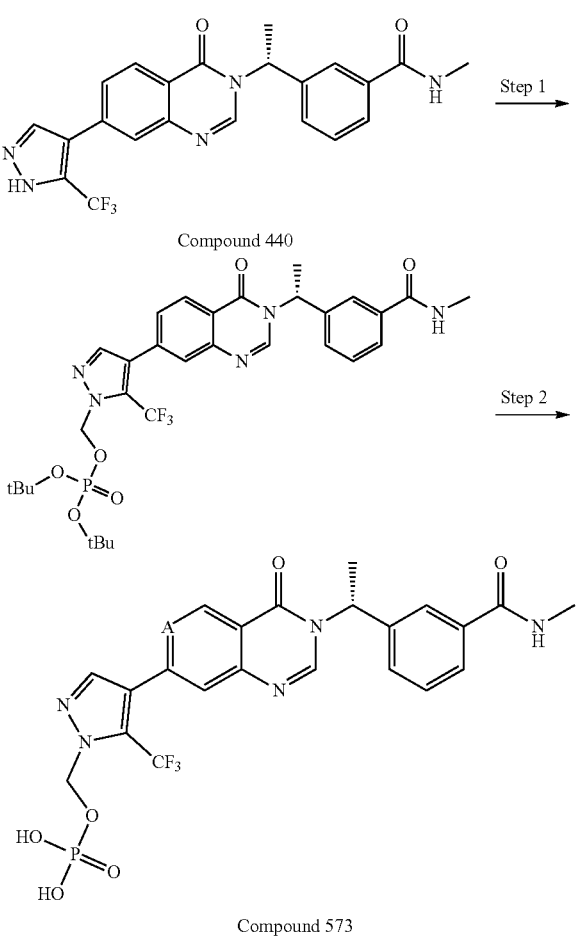

Step 1: A mixture of N-methyl-3-[(1R)-1-[4-oxo-7-[3-(trifluoromethyl)-1H-pyrazol-4-yl]quinazolin-3-yl]ethyl] benzamide, Compound 440 (100 mg, 227 μmol), ditert-butyl chloromethyl phosphate (69 μL, 295 μmol), and cesium carbonate (148 mg, 453 μmol) in acetonitrile (3 mL) was shaken at ambient temperature 48 h. The reaction mixture was concentrated, diluted with EtOAc and brine, and then the organic layer was separated, washed sequentially with water and brine, dried (Mg$_2$SO$_4$), concentrated, and purified by silica gel column chromatography to provide ditert-butyl [4-[3-[(1R)-1-[3-(methylcarbamoyl)phenyl]ethyl]-4-oxo-quinazolin-7-yl]-3-(trifluoromethyl)pyrazol-1-yl]methyl phosphate (125 mg, 83% yield). LC/MS found not observed desired mass. [M+H]$^+$.

Step 2: Trifluoroacetic acid (0.5 mL) was added to a solution of methyl ditert-butyl [4-[3-[(1S)-1-[3-(methylcarbamoyl)phenyl]ethyl]-4-oxo-quinazolin-7-yl]-3-(trifluoromethyl)pyrazol-1-yl]methyl phosphate (1.05 g, 2.8 mmol) in DCM (1.5 mL), and then the mixture was shaken for 1 hour at room temperature. After removing TFA/DCM in vacuum, the residual solution was purified by silica gel column chromatography to provide [4-[3-[(1R)-1-[3-(methylcarbamoyl)phenyl]ethyl]-4-oxo-quinazolin-7-yl]-3-(trifluoromethyl)pyrazol-1-yl]methyl dihydrogen phosphate, Compound 573 (55 mg, 52% yield). LC/MS found 552.2 [M+H]$^+$.

Compound 574: Disodium (R)-(4-(3-(1-(3-(methylcarbamoyl)phenyl)ethyl)-4-oxo-3,4-dihydroquinazolin-7-yl)-5-(trifluoromethyl)-1H-pyrazol-1-yl)methyl phosphate Scheme 19

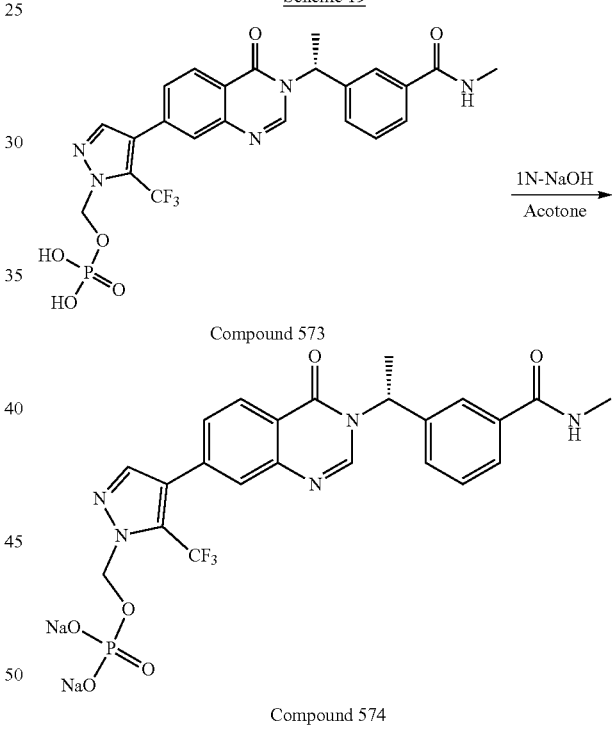

To a solution of Compound 573 (55 mg, 0.1 mmol) in acetone (2 ml) was slowly added of aqueous 1N sodium hydroxide solution (0.22 mL, 0.22 mmol) at room temperature to afford crystalline solids. After being stirred at room temperature for 1 h, the resulted solids were collected by filtration, rinsed with acetone, and then dried in high vacuum to provide a desire Compound 574 (46.7 mg) in 80% yield. LC/MS found 552.2 [M+H]$^+$.

Example 2: ROCK Inhibition Assay

Kinase IC$_{50}$ was determined through an in vitro assay based on LANCE Ultra TR-FRET (Time-Resolved Fluorescence Resonance Energy Transfer) homogeneous technologies method (Perkin Elmer). Recombinant ROCK1 (amino acids 1-477) and ROCK2 (amino acids 5-554) proteins were purchased from Carna Biosciences and SignalChem. Compound activities were measured by Envision and $IC_{50}$s were calculated. The assays were performed in white LUMITRAC™ 200 96 well half-area microplates from Greiner Bio-One. The kinase reaction buffer consisted of 50 mM HEPES pH 7.5, 1 mM EGTA, 10 mM $MgCl_2$, 2 mM DTT and 0.01% Tween-20. Kinases were incubated with 50 nM (ULight-CREBtide) substrate in the presence of 1 (ROCK1) or 4 (ROCK2) µM ATP. The kinase reaction was carried out for 1 hour before addition of a stopping buffer to a final of 10 mM EDTA and 0.6 nM of LANCE Ultra Europium anti-phospho-CREB (Ser133) antibody (PerkinElmer TRF0200) in LANCE detection buffer. All assay incubations were performed at room temperature, and the microplates were sealed with polyester film during that time. The reaction was incubated for 1 hour, and the signal was read in Envision in TR-FRET mode (excitation at 320 nm and emission at 615/665 nm).

The compounds of Formula 1 exhibited useful pharmacological properties. As used herein, a way to describe potency of inhibitory activity (nM) is a value of inhibitory activity at 50% ($IC_{50}$). The results are shown in Table 19 below, where an $IC_{50}$ of less than 10 nM is defined as "A," an $IC_{50}$ of between 11 nM and 100 nM is defined as "B," an $IC_{50}$ of between 101 nM and 500 nM is defined as "C," and an $IC_{50}$ of greater than 501 nM is defined as "D." Table 19 illustrates the inhibition of ROCK1 and ROCK2 by representative compounds of Formula 1.

TABLE 19

Inhibition Activity of ROCK1 and ROCK2

| Compd | ROCK1 | ROCK2 |
| --- | --- | --- |
| 1 | D | C |
| 2 | C | B |
| 3 | C | B |
| 4 | B | A |
| 5 | C | B |
| 6 | B | A |
| 7 | C | B |
| 8 | C | B |
| 9 | B | A |
| 10 | B | A |
| 11 | B | A |
| 12 | B | A |
| 13 | B | A |
| 14 | B | A |
| 15 | B | A |
| 16 | B | A |
| 17 | B | A |
| 18 | B | A |
| 19 | A | A |
| 20 | A | A |
| 21 | B | A |
| 22 | A | A |
| 23 | D | C |
| 24 | D | B |
| 25 | B | A |
| 26 | C | B |
| 27 | B | A |
| 28 | C | B |
| 29 | D | C |
| 30 | D | C |
| 31 | A | A |
| 32 | C | A |
| 33 | D | C |
| 34 | D | C |
| 35 | D | C |
| 36 | D | C |
| 37 | D | C |
| 38 | D | C |
| 39 | C | B |
| 40 | C | B |
| 41 | C | B |
| 42 | C | B |
| 43 | B | A |
| 44 | B | A |
| 45 | C | B |
| 46 | A | A |
| 47 | A | A |
| 48 | C | A |
| 49 | C | A |
| 50 | C | B |
| 51 | A | A |
| 52 | B | A |
| 53 | B | A |
| 54 | B | A |
| 55 | B | A |
| 56 | A | A |
| 57 | A | A |
| 58 | B | A |
| 59 | B | A |
| 60 | B | A |
| 61 | A | A |
| 62 | A | A |
| 63 | B | A |
| 64 | A | A |
| 65 | C | B |
| 66 | B | A |
| 67 | B | B |
| 68 | B | B |
| 69 | C | B |
| 70 | A | A |
| 71 | B | A |
| 72 | C | B |
| 73 | C | B |
| 74 | C | B |
| 75 | C | B |
| 76 | B | A |
| 77 | B | A |
| 78 | B | A |
| 79 | B | A |
| 80 | C | B |
| 81 | C | B |
| 82 | C | B |
| 83 | C | B |
| 84 | C | B |
| 85 | B | A |
| 86 | B | A |
| 87 | B | A |
| 88 | C | B |
| 89 | D | C |
| 90 | D | C |
| 91 | B | A |
| 92 | B | A |
| 93 | A | A |
| 94 | A | A |
| 95 | B | A |
| 96 | A | A |
| 97 | A | A |
| 98 | A | A |
| 99 | A | A |
| 100 | A | A |
| 101 | A | A |
| 102 | D | B |
| 103 | C | B |
| 104 | C | B |
| 105 | A | A |
| 106 | A | A |
| 107 | B | A |
| 108 | B | A |
| 109 | C | B |
| 110 | C | A |
| 111 | C | A |
| 112 | C | B |
| 113 | B | A |

TABLE 19-continued

Inhibition Activity of ROCK1 and ROCK2

| Compd | ROCK1 | ROCK2 |
|---|---|---|
| 114 | B | A |
| 115 | C | B |
| 116 | C | B |
| 117 | C | B |
| 118 | C | B |
| 119 | B | A |
| 120 | C | C |
| 121 | B | A |
| 122 | A | A |
| 123 | A | A |
| 124 | A | A |
| 125 | A | A |
| 126 | B | A |
| 127 | C | B |
| 128 | B | A |
| 129 | C | A |
| 130 | B | B |
| 131 | A | A |
| 132 | A | A |
| 133 | C | B |
| 134 | B | A |
| 135 | C | B |
| 136 | B | A |
| 137 | C | B |
| 138 | C | B |
| 139 | C | C |
| 140 | C | C |
| 141 | D | C |
| 142 | D | C |
| 143 | C | B |
| 144 | B | A |
| 145 | C | B |
| 146 | C | B |
| 147 | B | A |
| 148 | C | B |
| 149 | B | A |
| 150 | B | A |
| 151 | B | A |
| 152 | C | B |
| 153 | C | A |
| 154 | C | A |
| 155 | B | A |
| 156 | B | A |
| 157 | B | A |
| 158 | B | A |
| 159 | B | A |
| 160 | B | A |
| 161 | B | A |
| 162 | A | A |
| 163 | A | A |
| 164 | C | B |
| 165 | C | B |
| 166 | C | B |
| 167 | B | A |
| 168 | A | A |
| 169 | A | A |
| 170 | B | A |
| 171 | B | A |
| 172 | B | A |
| 173 | B | A |
| 174 | B | A |
| 175 | C | B |
| 176 | B | B |
| 177 | B | A |
| 178 | B | A |
| 179 | B | A |
| 180 | B | A |
| 181 | C | B |
| 182 | D | C |
| 183 | C | B |
| 184 | C | B |
| 185 | C | B |
| 186 | B | A |
| 187 | B | A |
| 188 | B | A |
| 189 | A | A |
| 190 | A | A |
| 191 | B | A |
| 192 | B | B |
| 193 | C | B |
| 194 | C | B |
| 195 | C | B |
| 196 | C | B |
| 197 | B | B |
| 198 | D | C |
| 199 | D | C |
| 200 | B | A |
| 201 | B | A |
| 202 | D | C |
| 203 | D | C |
| 204 | D | C |
| 205 | D | C |
| 206 | D | D |
| 207 | B | C |
| 208 | D | C |
| 209 | D | C |
| 210 | D | C |
| 211 | D | C |
| 212 | D | C |
| 213 | D | C |
| 214 | D | C |
| 215 | D | C |
| 216 | C | C |
| 217 | C | B |
| 218 | C | B |
| 219 | C | B |
| 220 | C | B |
| 221 | C | B |
| 222 | C | B |
| 223 | C | B |
| 224 | C | B |
| 225 | C | B |
| 226 | C | B |
| 227 | C | B |
| 228 | C | B |
| 229 | B | B |
| 230 | B | B |
| 231 | B | A |
| 232 | B | A |
| 233 | B | A |
| 234 | B | A |
| 235 | B | A |
| 236 | B | A |
| 237 | B | A |
| 238 | B | A |
| 239 | B | A |
| 240 | C | B |
| 241 | C | B |
| 242 | D | C |
| 243 | D | C |
| 244 | C | B |
| 245 | C | B |
| 246 | B | A |
| 247 | D | D |
| 248 | B | B |
| 249 | A | A |
| 250 | B | A |
| 251 | C | B |
| 252 | B | A |
| 253 | B | A |
| 254 | B | A |
| 255 | B | A |
| 256 | A | A |
| 257 | A | A |
| 258 | B | A |
| 259 | B | A |
| 260 | B | A |
| 261 | A | A |
| 262 | A | A |
| 263 | B | A |
| 264 | B | A |
| 265 | B | A |

TABLE 19-continued

Inhibition Activity of ROCK1 and ROCK2

| Compd | ROCK1 | ROCK2 |
|---|---|---|
| 266 | B | A |
| 267 | B | A |
| 268 | B | A |
| 269 | C | B |
| 270 | B | B |
| 271 | A | A |
| 272 | A | A |
| 273 | A | A |
| 274 | A | A |
| 275 | B | A |
| 276 | B | A |
| 277 | C | A |
| 278 | B | A |
| 279 | B | A |
| 280 | B | A |
| 281 | B | A |
| 282 | B | A |
| 283 | B | A |
| 284 | C | B |
| 285 | C | B |
| 286 | B | A |
| 287 | B | A |
| 288 | B | A |
| 289 | B | A |
| 290 | B | A |
| 291 | B | A |
| 292 | B | A |
| 293 | B | A |
| 294 | B | A |
| 295 | B | A |
| 296 | B | A |
| 297 | B | A |
| 298 | B | A |
| 299 | D | D |
| 300 | D | D |
| 301 | D | D |
| 302 | D | D |
| 303 | D | D |
| 304 | D | D |
| 305 | C | C |
| 306 | C | C |
| 307 | B | A |
| 308 | A | A |
| 309 | B | A |
| 310 | B | A |
| 311 | D | C |
| 312 | C | B |
| 313 | D | C |
| 314 | C | B |
| 315 | B | A |
| 316 | B | A |
| 317 | C | B |
| 318 | B | A |
| 319 | C | B |
| 320 | C | B |
| 321 | C | B |
| 322 | C | B |
| 323 | C | B |
| 324 | C | C |
| 325 | C | B |
| 326 | B | A |
| 327 | D | D |
| 328 | C | B |
| 329 | C | B |
| 330 | D | D |
| 331 | D | C |
| 332 | D | C |
| 333 | D | C |
| 334 | C | B |
| 335 | C | B |
| 336 | C | B |
| 337 | C | B |
| 338 | B | B |
| 339 | C | B |
| 340 | B | A |
| 341 | C | B |
| 342 | C | B |
| 343 | C | B |
| 344 | C | B |
| 345 | B | B |
| 346 | C | B |
| 347 | C | B |
| 348 | B | B |
| 349 | B | B |
| 350 | C | B |
| 351 | C | B |
| 352 | C | B |
| 353 | D | C |
| 354 | B | B |
| 355 | B | B |
| 356 | B | A |
| 357 | B | B |
| 358 | B | B |
| 359 | B | A |
| 360 | B | A |
| 361 | B | A |
| 362 | B | A |
| 363 | B | B |
| 364 | B | B |
| 365 | B | B |
| 366 | B | A |
| 367 | B | A |
| 368 | B | A |
| 369 | B | A |
| 370 | A | A |
| 371 | C | B |
| 372 | A | A |
| 373 | B | A |
| 374 | B | A |
| 375 | C | B |
| 376 | B | A |
| 377 | B | A |
| 378 | A | A |
| 379 | B | A |
| 380 | B | A |
| 381 | A | A |
| 382 | B | A |
| 383 | B | A |
| 384 | B | B |
| 385 | C | B |
| 386 | B | A |
| 387 | B | A |
| 388 | B | A |
| 389 | B | B |
| 390 | B | B |
| 391 | B | A |
| 392 | B | A |
| 393 | B | A |
| 394 | B | B |
| 395 | A | A |
| 396 | B | A |
| 397 | B | A |
| 398 | C | B |
| 399 | C | B |
| 400 | C | B |
| 401 | B | A |
| 402 | B | A |
| 403 | D | C |
| 404 | A | A |
| 405 | A | A |
| 406 | B | A |
| 407 | B | A |
| 408 | A | A |
| 409 | A | A |
| 410 | A | A |
| 411 | B | A |
| 412 | B | A |
| 413 | B | A |
| 414 | C | B |
| 415 | B | A |
| 416 | B | A |
| 417 | A | A |

TABLE 19-continued

Inhibition Activity of ROCK1 and ROCK2

| Compd | ROCK1 | ROCK2 |
|---|---|---|
| 418 | A | A |
| 419 | A | A |
| 420 | B | A |
| 421 | B | A |
| 422 | B | A |
| 423 | B | A |
| 424 | B | A |
| 425 | B | A |
| 426 | B | A |
| 427 | B | A |
| 428 | B | A |
| 429 | B | A |
| 430 | B | A |
| 431 | B | B |
| 432 | C | B |
| 433 | C | B |
| 434 | C | B |
| 435 | C | B |
| 436 | B | A |
| 437 | B | A |
| 438 | B | B |
| 439 | D | D |
| 440 | B | A |
| 441 | B | A |
| 442 | D | D |
| 443 | B | A |
| 444 | B | A |
| 445 | B | A |
| 446 | D | D |
| 447 | A | A |
| 448 | C | N |
| 449 | B | A |
| 450 | A | A |
| 451 | B | A |
| 452 | B | A |
| 453 | B | B |
| 454 | B | A |
| 455 | B | A |
| 456 | C | B |
| 457 | B | A |
| 458 | B | A |
| 459 | C | B |
| 460 | A | A |
| 461 | A | A |
| 462 | B | A |
| 463 | B | A |
| 464 | A | A |
| 465 | A | A |
| 466 | B | A |
| 467 | B | A |
| 468 | C | B |
| 469 | B | A |
| 470 | D | D |
| 471 | B | A |
| 472 | A | A |
| 473 | A | A |
| 474 | B | A |
| 475 | B | A |
| 476 | B | A |
| 477 | B | A |
| 478 | B | A |
| 479 | B | A |
| 480 | C | B |
| 481 | C | B |
| 482 | D | D |
| 483 | C | B |
| 484 | C | B |
| 485 | B | B |
| 486 | B | B |
| 487 | B | B |
| 488 | C | B |
| 489 | B | B |
| 490 | B | B |
| 491 | B | B |
| 492 | B | B |
| 493 | B | A |
| 494 | A | A |
| 495 | A | A |
| 496 | A | A |
| 497 | B | A |
| 498 | A | A |
| 499 | A | A |
| 500 | A | A |
| 501 | D | C |
| 502 | D | C |
| 503 | D | C |
| 504 | D | C |
| 505 | D | C |
| 506 | D | C |
| 507 | D | C |
| 508 | D | C |
| 509 | B | A |
| 510 | B | A |
| 511 | B | A |
| 512 | B | A |
| 513 | B | A |
| 514 | B | A |
| 515 | B | A |
| 516 | A | A |
| 517 | B | A |
| 518 | B | A |
| 519 | B | A |
| 520 | B | A |
| 521 | B | A |
| 522 | A | A |
| 523 | D | C |
| 524 | D | C |
| 525 | D | C |
| 526 | D | D |
| 527 | D | C |
| 528 | D | C |
| 529 | D | D |
| 530 | D | B |
| 531 | D | C |
| 532 | A | A |
| 533 | C | B |
| 534 | B | A |
| 535 | A | A |
| 536 | A | A |
| 537 | B | A |
| 538 | A | A |
| 539 | B | A |
| 540 | B | A |
| 541 | B | A |
| 542 | A | A |
| 543 | A | A |
| 544 | B | A |
| 545 | B | A |
| 546 | B | A |
| 547 | B | A |
| 548 | A | A |
| 549 | B | A |
| 550 | B | A |
| 551 | B | A |
| 552 | C | B |
| 553 | C | B |
| 554 | B | A |
| 555 | B | A |
| 556 | B | A |
| 557 | B | A |
| 558 | A | B |
| 559 | B | A |
| 560 | A | A |
| 561 | B | A |
| 562 | B | A |
| 563 | B | A |
| 564 | B | A |
| 565 | B | A |
| 566 | B | A |
| 567 | B | A |
| 568 | B | A |
| 569 | A | A |

TABLE 19-continued

Inhibition Activity of ROCK1 and ROCK2

| Compd | ROCK1 | ROCK2 |
|---|---|---|
| 570 | A | A |
| 571 | B | A |
| 572 | C | B |

Example 3: Activity of ROCK1/2 Inhibitors in A7r5 Cells

Inhibition of ROCK1/2 in A7r5 cells was measured through cell-based ELISA assay. Rat aortic smooth muscle cell line A7r5 cells were maintained and treated in DMEM medium with 10% fetal bovine serum. Cells were seeded with 5,000 cells/well in 96 well plates for 24 hours and subsequently treated with test compounds for 90 minutes. Cells were then fixed and processed according to the In-Cell ELISA Colrimetric Detection Kit manual (Thermo Scientific). Cellular phospho-myosin light chain (pMLC2, Thr18/Ser19) levels were determined after treatment with DMSO control or a test compound using the In-Cell ELISA kit.

The resulting data was applied to the following formula '[1-(compound/DMSO)]×100%' to calculate the percent inhibition rate. pMLC2 data obtained from 9 points 3-fold serial dilution of compounds were applied to the nonlinear regression curve fit function of the GraphPad Prism software to calculate the cellular $EC_{50}$ values. $EC_{50}$ values of some representative compounds of Formula 1 are shown in Table 20 below, where an $EC_{50}$ of less than 100 nM is defined as "A," an $EC_{50}$ of between 101 nM and 500 nM is defined as "B," an $EC_{50}$ of between 501 nM and 1000 nM is defined as "C," and an $EC_{50}$ of greater than 1000 nM is defined as "D."

TABLE 20 pMCL2 Activity of Selected ROCK1/2 Inhibitors

| Compd | pMLC2 |
|---|---|
| 10 | A |
| 12 | B |
| 22 | A |
| 24 | B |
| 25 | B |
| 31 | A |
| 75 | B |
| 77 | B |
| 82 | A |
| 86 | A |
| 107 | B |
| 108 | B |
| 146 | C |
| 165 | C |
| 184 | A |
| 186 | A |
| 188 | A |
| 191 | A |
| 200 | A |
| 233 | B |
| 277 | C |
| 280 | C |
| 281 | B |
| 315 | C |
| 320 | D |
| 323 | B |
| 326 | B |
| 365 | B |
| 437 | B |
| 440 | B |
| 466 | A |

TABLE 20-continued pMCL2 Activity of Selected ROCK1/2 Inhibitors

| Compd | pMLC2 |
|---|---|
| 469 | A |
| 495 | B |

Although the invention has been described in some detail by way of illustration and example for purposes of clarity of understanding, it will be readily apparent to those of ordinary skill in the art in light of the teachings of this invention that certain changes and modifications may be made thereto without departing from the spirit or scope of the appended claims.

The invention claimed is:

1. A compound of Formula (1), a pharmaceutically acceptable salt, diastereomer, enantiomer, racemate, hydrate, solvate, or prodrug thereof:

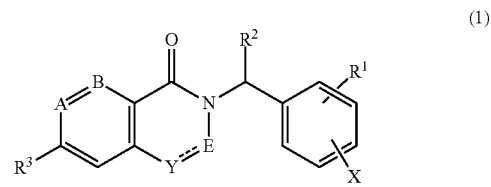

(1)

wherein:

X is H or halogen;

Y is N or $CR^4$;

A, B and E each are independently N or CH;

--- is a single or double bond;

$R^1$ is heteroaryl, $C(O)OR^5$, $NHS(O)_2R^5$, $S(O)_2R^5$, $C(O)NR^5R^6$, or $NHC(O)R^7$, wherein the heteroaryl is optionally substituted with one or more substituents selected from the group consisting of halogen, amino, hydroxyl, alkoxy, and a combination thereof;

$R^2$ is H or $C_1$-$C_3$alkyl, which is optionally substituted with one or more substituents selected from the group consisting of halogen, hydroxyl, $C_1$-$C_3$alkoxy, $NR^5R^6$, and a combination thereof;

$R^3$ is 5-6 membered heteroaryl, wherein one of the carbon atoms within the heteroaryl is connected to the bicyclic ring, wherein the heteroaryl is optionally substituted with one or more substituents selected from the group consisting of halogen, CN, $CHF_2$, $CF_3$, $C_1$-$C_3$alkyl, amino, and a combination thereof, and wherein the 5-6 membered heteroaryl has 1-3 heteroatoms selected from the group consisting of oxygen, nitrogen, and a combination thereof;

$R^4$ is H, halogen, $CF_3$, CN, $C_1$-$C_3$alkyl, $C_1$-$C_3$alkoxy, or $C_2$-$C_6$alkynyl, wherein the $C_1$-$C_3$alkyl or $C_2$-$C_6$alkynyl is optionally substituted with one or more substituents selected from the group consisting of OH, $NH_2$, $C_1$-$C_2$amino, $C_1$-$C_2$hydroxyl, $C_1$-$C_2NR^5R^6$, $C_1$-$C_3$alkoxy, and a combination thereof;

$R^5$ is H or $C_1$-$C_3$alkyl, wherein the $C_1$-$C_3$alkyl is optionally substituted with one or more substituents selected from the group consisting of halogen, amino, hydroxyl, alkoxy, and a combination thereof;

$R^6$ is H, $CD_3$, $C_1$-$C_6$ alkyl, $C_3$-$C_7$cycloalkyl, aryl, heteroaryl, 8-10 membered bicyclic heteroaryl, 8-10 membered saturated or partially unsaturated bicyclic heteroaryl group, or 4-7 membered heterocyclyl comprising 1-2 heteroatoms selected from the group consisting of N, O, S, and a combination thereof, wherein the $C_1$-$C_6$ alkyl, $C_3$-$C_7$cycloalkyl, aryl or heteroaryl is optionally substituted with one or more substituents selected from the group consisting of halogen, $NR^5R^6$, aryl, heteroaryl, and $OR^5$, and a combination thereof, and wherein when the 4-7 membered heterocyclyl has one nitrogen atom, the 4-7 membered heterocyclyl is optionally substituted with $C_1$-$C_3$ alkyl, $CF_3$, $C(O)R^5$, $S(O)_2NH_2$, $OCF_3$, $C(O)OR^5$, or $C(O)NHR^5$ at the nitrogen atom, wherein $R^6$ is independent of each other; and $R^7$ is $C_1$-$C_6$alkyl, $C_3$-$C_7$cycloalkyl, 4-7 membered heterocyclyl comprising 1-2 heteroatoms selected from the group consisting of N, O, and a combination thereof, 5-6 membered aryl, 5-6 membered heteroaryl, 8-10 membered bicyclic heteroaryl, 8-10 membered saturated or partially unsaturated bicyclic heteroaryl group, wherein the $C_1$-$C_6$alkyl or $C_3$-$C_7$ cycloalkyl is optionally substituted with one or more substituents selected from the group consisting of halogen, $C_1$-$C_3$alkyl, $OR^5$, $NH_2$, 5-6 membered heteroaryl, and a combination thereof.

2. The compound, salt, diastereomer, enantiomer, racemate, hydrate, solvate, or prodrug of claim 1, wherein X is H, F, or Cl.

3. The compound, salt, diastereomer, enantiomer, racemate, hydrate, solvate, or prodrug of claim 1, wherein $R^1$ is heteroaryl, $C(O)OR^5$, $NHS(O)_2R^5$, $S(O)_2R^5$, $C(O)NR^5R^6$, or $NHC(O)R^7$, wherein the heteroaryl is optionally substituted with one or more substituents selected from the group consisting of halogen, amino, hydroxyl, alkoxy, and a combination thereof.

4. The compound, salt, diastereomer, enantiomer, racemate, hydrate, solvate, or prodrug of claim 1, wherein $R^2$ is H or $C_1$-$C_3$alkyl, wherein $C_1$-$C_3$alkyl is optionally substituted with one or more substituents selected from the group consisting of hydroxyl, methoxy, ethoxy, $NH_2$, NHMe, $NMe_2$, and a combination thereof.

5. The compound, salt, diastereomer, enantiomer, racemate, hydrate, solvate, or prodrug of claim 1, wherein $R^3$ is selected from the group consisting of:

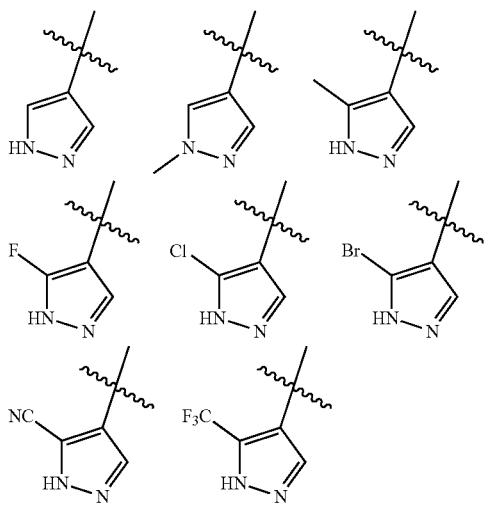

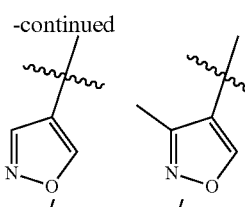

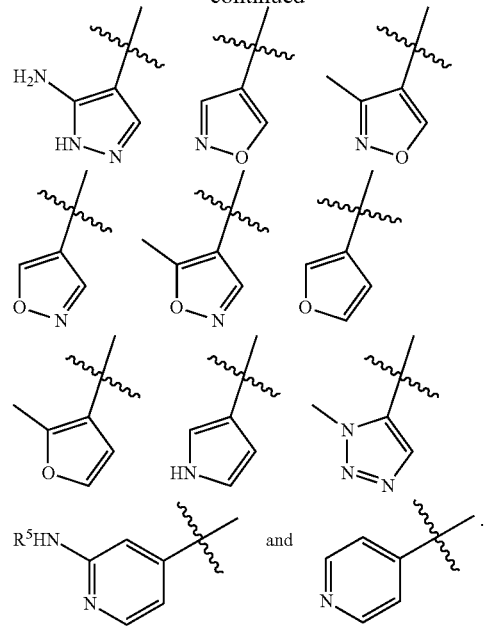

6. The compound, salt, diastereomer, enantiomer, racemate, hydrate, solvate, or prodrug of claim 1, wherein $R^4$ is H, Me, F, Cl, CN, $C_1$-$C_3$alkyl, or $C_2$-$C_4$alkynyl, wherein the $C_1$-$C_3$alkyl or $C_2$-$C_4$alkynyl is optionally substituted with one or more substituents selected from the group consisting of OH, $NH_2$, $NMe_2$, OMe, and a combination thereof.

7. The compound, salt, diastereomer, enantiomer, racemate, hydrate, solvate, or prodrug of claim 1, wherein $R^5$ is H or Me.

8. The compound, salt, diastereomer, enantiomer, racemate, hydrate, solvate, or prodrug of claim 1, wherein $R^6$ is H, $CD_3$, $C_1$-$C_6$alkyl, $C_3$-$C_7$cycloalkyl, phenyl, heteroaryl, 8-10 membered bicyclic heteroaryl, 8-10 membered saturated or partially unsaturated bicyclic heteroaryl group, or 4-7 membered heterocyclyl comprising 1-2 heteroatoms selected from the group consisting of N, O, S, and a combination thereof, wherein the $C_1$-$C_6$ alkyl, $C_3$-$C_7$ cycloalkyl, phenyl, or heteroaryl is optionally substituted with one or more substituents selected from the group consisting of halogen, $CF_3$, OH, OMe, $NR^5R^6$, aryl, heteroaryl, and a combination thereof, and wherein when the 4-7 membered heterocyclyl has one nitrogen atom, the 4-7 membered heterocyclyl is optionally substituted with $C_1$-$C_3$ alkyl, $C(O)R^5$, $S(O)_2NH_2$, $OCF_3$, $C(O)OR^5$, or $C(O)NHR^5$ at the nitrogen atom, wherein $R^6$ is independent of each other.

9. The compound, salt, diastereomer, enantiomer, racemate, hydrate, solvate, or prodrug of claim 1, wherein $R^7$ is H, $C_1$-$C_6$alkyl, $C_3$-$C_7$cycloalkyl, 4-7 membered heterocyclyl comprising 1-2 heteroatoms selected from the group consisting of N, O, and a combination thereof, 5-6 membered aryl, 5-6 membered heteroaryl, 8-10 membered bicyclic heteroaryl, or 8-10 membered saturated or partially unsaturated bicyclic heteroaryl group, wherein the $C_1$-$C_6$ alkyl or $C_3$-$C_7$ cycloalkyl is optionally substituted with one or more substituents selected from the group consisting of halogen, $C_1$-$C_3$ alkyl, OH, OMe, $NH_2$, 5-6 membered heteroaryl, and a combination thereof.

10. A pharmaceutical composition comprising the compound, salt, diastereomer, enantiomer, racemate, hydrate, solvate, or prodrug of claim 1 and at least one additional component selected from the group consisting of a pharmaceutically acceptable carrier, diluent, excipient, adjuvant, and a combination thereof.

11. A compound represented by the following list or a pharmaceutically acceptable salt, diastereomer, enantiomer, racemate, hydrate, solvate, or prodrug thereof:

- 2-(3-Methoxybenzyl)-6-(1H-pyrazol-4-yl)-3,4-dihydroisoquinolin-1(2H)-one;
- 2-(3-Methoxybenzyl)-6-(1H-pyrazol-4-yl)isoquinolin-1(2H)-one;
- 2-(3-Hydroxybenzyl)-6-(1H-pyrazol-4-yl)isoquinolin-1(2H)-one;
- 2-(3-Methoxybenzyl)-6-(3-methyl-1H-pyrazol-4-yl)isoquinolin-1(2H)-one;
- 2-(3-Hydroxybenzyl)-6-(3-methyl-1H-pyrazol-4-yl)isoquinolin-1(2H)-one;
- 2-(3-Methoxybenzyl)-6-(3-(trifluoromethyl)-1H-pyrazol-4-yl)isoquinolin-1(2H)-one;
- 2-(3-Hydroxybenzyl)-6-(3-(trifluoromethyl)-1H-pyrazol-4-yl)isoquinolin-1(2H)-one;
- 2-(1-(3-Hydroxyphenyl)ethyl)-6-(3-(trifluoromethyl)-1H-pyrazol-4-yl)isoquinolin-1(2H)-one;
- 2-(3-Methoxybenzyl)-6-(3-methylisoxazol-4-yl)isoquinolin-1(2H)-one;
- 2-(3-Methoxybenzyl)-6-(1-methyl-1H-pyrazol-5-yl)isoquinolin-1(2H)-one
- 6-(3-(Difluoromethyl)-1H-pyrazol-4-yl)-2-(3-methoxybenzyl)isoquinolin-1(2H)-one;
- 2-(3-Hydroxybenzyl)-6-(3-methylisoxazol-4-yl)isoquinolin-1(2H)-one;
- 6-(3-(Difluoromethyl)-1H-pyrazol-4-yl)-2-(3-hydroxybenzyl)isoquinolin-1(2H)-one;
- 6-(3-(Difluoromethyl)-1H-pyrazol-4-yl)-2-(1-(3-hydroxyphenyl)ethyl)isoquinolin-1(2H)-one;
- 2-(3-Hydroxybenzyl)-6-(1-methyl-1H-pyrazol-5-yl)isoquinolin-1(2H)-one;
- 6-(2-Aminopyridin-4-yl)-2-(3-methoxybenzyl)isoquinolin-1(2H)-one;
- 6-(3-(Difluoromethyl)-1H-pyrazol-4-yl)-2-(3-fluoro-5-methoxybenzyl)isoquinolin-1(2H)-one;
- 6-(3-Chloro-1H-pyrazol-4-yl)-2-(3-fluoro-5-methoxybenzyl)isoquinolin-1(2H)-one;
- 6-(3-Chloro-1H-pyrazol-4-yl)-2-(3-methoxybenzyl)isoquinolin-1(2H)-one;
- 6-(3-Chloro-1H-pyrazol-4-yl)-2-(1-(3-methoxyphenyl)ethyl)isoquinolin-1(2H)-one;
- 6-(3-Chloro-1H-pyrazol-4-yl)-2-(3-hydroxybenzyl)isoquinolin-1(2H)-one;
- 6-(3-Chloro-1H-pyrazol-4-yl)-2-(1-(3-hydroxyphenyl)ethyl)isoquinolin-1(2H)-one;
- 2-(3-Methoxybenzyl)-6-(pyridin-4-yl)isoquinolin-1(2H)-one;
- 2-(3-Hydroxybenzyl)-6-(pyridin-4-yl)isoquinolin-1(2H)-one;
- 6-(2-Aminopyridin-4-yl)-2-(3-methoxybenzyl)isoquinolin-1(2H)-one;
- 6-(2-Aminopyridin-4-yl)-2-(1-(3-methoxyphenyl)ethyl)isoquinolin-1(2H)-one;
- 3-((1-Oxo-6-(1H-pyrazol-4-yl)isoquinolin-2(1H)-yl)methyl)-N-(2-(pyridin-2-yl)ethyl)benzamide;
- N-Isopropyl-3-((1-oxo-6-(1H-pyrazol-4-yl)isoquinolin-2(1H)-yl)methyl)benzamide;
- 3-((1-Oxo-6-(1H-pyrazol-4-yl)isoquinolin-2(1H)-yl)methyl)-N-phenylbenzamide;
- N-Benzyl-3-((1-oxo-6-(1H-pyrazol-4-yl)isoquinolin-2(1H)-yl)methyl)benzamide;
- 3-((6-(3-Methyl-1H-pyrazol-4-yl)-1-oxoisoquinolin-2(1H)-yl)methyl)-N-(2-(pyridin-2-yl)ethyl)benzamide;
- N-(1-Methyl-1H-pyrazol-3-yl)-3-((6-(3-methyl-1H-pyrazol-4-yl)-1-oxoisoquinolin-2(1H)-yl)methyl)benzamide;
- 3-((6-(3-Methyl-1H-pyrazol-4-yl)-1-oxoisoquinolin-2(1H)-yl)methyl)-N-(3-(methylsulfonamido)benzyl)benzamide;
- 3-((6-(3-Methyl-1H-pyrazol-4-yl)-1-oxoisoquinolin-2(1H)-yl)methyl)-N-(3-sulfamoylphenyl)benzamide;
- 3-((6-(3-Methyl-1H-pyrazol-4-yl)-1-oxoisoquinolin-2(1H)-yl)methyl)-N-(3-(trifluoromethoxy)phenyl)benzamide;
- 3-((6-(3-Methyl-1H-pyrazol-4-yl)-1-oxoisoquinolin-2(1H)-yl)methyl)-N-(4-sulfamoylphenyl)benzamide;
- 3-((6-(3-Methyl-1H-pyrazol-4-yl)-1-oxoisoquinolin-2(1H)-yl)methyl)-N-(4-(methylsulfonamido)phenyl)benzamide;
- 3-((6-(3-Methyl-1H-pyrazol-4-yl)-1-oxoisoquinolin-2(1H)-yl)methyl)-N-(2-(trifluoromethoxy)phenyl)benzamide;
- N-(6-Fluoropyridin-3-yl)-3-((6-(3-methyl-1H-pyrazol-4-yl)-1-oxoisoquinolin-2(1H)-yl)methyl)benzamide;
- N-((6-Fluoropyridin-3-yl)methyl)-3-((6-(3-methyl-1H-pyrazol-4-yl)-1-oxoisoquinolin-2(1H)-yl)methyl)benzamide;
- 3-((6-(3-Methyl-1H-pyrazol-4-yl)-1-oxoisoquinolin-2(1H)-yl)methyl)-N-(2,2,2-trifluoroethyl)benzamide;
- 3-((1-Oxo-6-(3-(trifluoromethyl)-1H-pyrazol-4-yl)isoquinolin-2(1H)-yl)methyl)-N-(4-sulfamoylphenyl)benzamide;
- N-(1-Methyl-1H-pyrazol-3-yl)-3-((1-oxo-6-(5-(trifluoromethyl)-1H-pyrazol-4-yl)isoquinolin-2(1H)-yl)methyl)benzamide;
- N-((6-Fluoropyridin-3-yl)methyl)-3-((1-oxo-6-(3-(trifluoromethyl)-1H-pyrazol-4-yl)isoquinolin-2(1H)-yl)methyl)benzamide;
- 3-((1-Oxo-6-(3-(trifluoromethyl)-1H-pyrazol-4-yl)isoquinolin-2(1H)-yl)methyl)-N-(tetrahydro-2H-pyran-4-yl)benzamide;
- 3-((1-Oxo-6-(3-(trifluoromethyl)-1H-pyrazol-4-yl)isoquinolin-2(1H)-yl)methyl)-N-(piperidin-4-yl)benzamide;
- N-(1-Methylpiperidin-4-yl)-3-((1-oxo-6-(3-(trifluoromethyl)-1H-pyrazol-4-yl)isoquinolin-2(1H)-yl)methyl)benzamide;
- N-(1-(Oxetan-3-yl)piperidin-4-yl)-3-((1-oxo-6-(3-(trifluoromethyl)-1H-pyrazol-4-yl)isoquinolin-2(1H)-yl)methyl)benzamide;
- N-(1-(2,2-Difluoroethyl)piperidin-4-yl)-3-((1-oxo-6-(3-(trifluoromethyl)-1H-pyrazol-4-yl)isoquinolin-2(1H)-yl)methyl)benzamide;
- N-Cyclopropyl-3-((1-oxo-6-(3-(trifluoromethyl)-1H-pyrazol-4-yl)isoquinolin-2(1H)-yl)methyl)benzamide;
- N-((1-Methylpiperidin-4-yl)methyl)-3-((1-oxo-6-(3-(trifluoromethyl)-1H-pyrazol-4-yl)isoquinolin-2(1H)-yl)methyl)benzamide;
- 3-((1-Oxo-6-(3-(trifluoromethyl)-1H-pyrazol-4-yl)isoquinolin-2(1H)-yl)methyl)-N-((tetrahydro-2H-pyran-4-yl)methyl)benzamide;
- N-(Oxetan-3-ylmethyl)-3-((1-oxo-6-(3-(trifluoromethyl)-1H-pyrazol-4-yl)isoquinolin-2(1H)-yl)methyl)benzamide;
- N-(2-(6-Fluoropyridin-2-yl)ethyl)-3-((1-oxo-6-(3-(trifluoromethyl)-1H-pyrazol-4-yl)isoquinolin-2(1H)-yl)methyl)benzamide;

3-((6-(3-(Difluoromethyl)-1H-pyrazol-4-yl)-1-oxoisoqui-
nolin-2(1H)-yl)methyl)-N-((tetrahydro-2H-pyran-4-yl)
methyl)benzamide;
3-((6-(3-(Difluoromethyl)-1H-pyrazol-4-yl)-1-oxoisoqui-
nolin-2(1H)-yl)methyl)-N-((1-methylpiperidin-4-yl)
methyl)benzamide;
3-((6-(3-(Difluoromethyl)-1H-pyrazol-4-yl)-1-oxoisoqui-
nolin-2(1H)-yl)methyl)-N-(piperidin-4-ylmethyl)benz-
amide;
3-((6-(3-(Difluoromethyl)-1H-pyrazol-4-yl)-1-oxoisoqui-
nolin-2(1H)-yl)methyl)-N-(oxetan-3-ylmethyl)benz-
amide;
3-((6-(3-(Difluoromethyl)-1H-pyrazol-4-yl)-1-oxoisoqui-
nolin-2(1H)-yl)methyl)-5-fluoro-N-(oxetan-3-ylm-
ethyl)benzamide;
3-((6-(3-(Difluoromethyl)-1H-pyrazol-4-yl)-1-oxoisoqui-
nolin-2(1H)-yl)methyl)-5-fluoro-N-((tetrahydro-2H-
pyran-4-yl)methyl)benzamide;
3-((6-(3-(Difluoromethyl)-1H-pyrazol-4-yl)-1-oxoisoqui-
nolin-2(1H)-yl)methyl)-5-fluoro-N-(piperidin-4-ylm-
ethyl)benzamide;
3-((6-(3-(Difluoromethyl)-1H-pyrazol-4-yl)-1-oxoisoqui-
nolin-2(1H)-yl)methyl)-5-fluoro-N-((1-methylpiperi-
din-4-yl)methyl)benzamide;
3-((6-(3-Chloro-1H-pyrazol-4-yl)-1-oxoisoquinolin-2
(1H)-yl)methyl)-N-(oxetan-3-ylmethyl)benzamide;
3-((6-(3-Chloro-1H-pyrazol-4-yl)-1-oxoisoquinolin-2
(1H)-yl)methyl)-N-((1-methylpiperidin-4-yl)methyl)
benzamide;
3-((6-(3-Chloro-1H-pyrazol-4-yl)-1-oxoisoquinolin-2
(1H)-yl)methyl)-5-fluoro-N-(2-hydroxyethyl)benz-
amide;
3-((6-(1-Methyl-1H-pyrazol-5-yl)-1-oxoisoquinolin-2
(1H)-yl)methyl)-N-((1-methylpiperidin-4-yl)methyl)
benzamide;
3-Fluoro-5-((6-(1-methyl-1H-pyrazol-5-yl)-1-oxoisoqui-
nolin-2(1H)-yl)methyl)-N-((1-methylpiperidin-4-yl)
methyl)benzamide;
3-((6-(3-Chloro-1H-pyrazol-4-yl)-1-oxoisoquinolin-2
(1H)-yl)methyl)-5-fluoro-N-((1S,4S)-4-hydroxycyclo-
hexyl)benzamide;
3-Fluoro-5-((6-(1-methyl-1H-pyrazol-5-yl)-1-oxoisoqui-
nolin-2(1H)-yl)methyl)-N-(piperidin-4-ylmethyl)benz-
amide hydrochloride;
3-((6-(3-Methylisoxazol-4-yl)-1-oxoisoquinolin-2(1H)-
yl)methyl)-N-(2,2,2-trifluoroethyl)benzamide;
N-(Cyclopropylmethyl)-3-((6-(3-methylisoxazol-4-yl)-1-
oxoisoquinolin-2(1H)-yl)methyl)benzamide;
3-((6-(3-Methylisoxazol-4-yl)-1-oxoisoquinolin-2(1H)-
yl)methyl)-N-(2-morpholinoethyl)benzamide;
3-((6-(3-Methylisoxazol-4-yl)-1-oxoisoquinolin-2(1H)-
yl)methyl)-N-(2-(4-methylpiperazin-1-yl)ethyl)benz-
amide;
3-((6-(3-Methylisoxazol-4-yl)-1-oxoisoquinolin-2(1H)-
yl)methyl)-N-(oxetan-3-ylmethyl)benzamide;
N-((1S,3S)-3-Hydroxycyclobutyl)-3-((6-(3-methylisoxa-
zol-4-yl)-1-oxoisoquinolin-2(1H)-yl)methyl)benz-
amide;
N-((1R,3R)-3-Hydroxycyclobutyl)-3-((6-(3-methylisoxa-
zol-4-yl)-1-oxoisoquinolin-2(1H)-yl)methyl)benz-
amide;
N-((1S,4S)-4-Hydroxycyclohexyl)-3-((6-(3-methylisoxa-
zol-4-yl)-1-oxoisoquinolin-2(1H)-yl)methyl)benz-
amide;
N-((1R,4R)-4-Hydroxycyclohexyl)-3-((6-(3-methyl-
isoxazol-4-yl)-1-oxoisoquinolin-2(1H)-yl)methyl)ben-
zamide;
N-((6-Fluoropyridin-3-yl)methyl)-3-((6-(3-methylisoxa-
zol-4-yl)-1-oxoisoquinolin-2(1H)-yl)methyl)benz-
amide;
3-((6-(3-Methylisoxazol-4-yl)-1-oxoisoquinolin-2(1H)-
yl)methyl)-N-(tetrahydro-2H-pyran-4-yl)benzamide;
3-((6-(3-Methylisoxazol-4-yl)-1-oxoisoquinolin-2(1H)-
yl)methyl)-N-((1-methylpiperidin-4-yl)methyl)benz-
amide;
3-((6-(3-Methylisoxazol-4-yl)-1-oxoisoquinolin-2(1H)-
yl)methyl)-N-(piperidin-4-ylmethyl)benzamide hydro-
chloride;
[3-((6-(3-Methylisoxazol-4-yl)-1-oxoisoquinolin-2(1H)-
yl)methyl)-N-(piperidin-4-ylmethyl)benzamide;
N-((1-Cyclopropylpiperidin-4-yl)methyl)-3-((6-(3-meth-
ylisoxazol-4-yl)-1-oxoisoquinolin-2(1H)-yl)methyl)
benzamide;
N-((1-Isopropylpiperidin-4-yl)methyl)-3-((6-(3-methyl-
isoxazol-4-yl)-1-oxoisoquinolin-2(1H)-yl)methyl)ben-
zamide;
N-((1-(3,3-Difluoroallyl)piperidin-4-yl)methyl)-3-((6-(3-
methylisoxazol-4-yl)-1-oxoisoquinolin-2(1H)-yl)
methyl)benzamide;
3-((6-(3-Methylisoxazol-4-yl)-1-oxoisoquinolin-2(1H)-
yl)methyl)-N-((1-(2,2,2-trifluoroethyl)piperidin-4-yl)
methyl)benzamide;
3-((6-(3-Methylisoxazol-4-yl)-1-oxoisoquinolin-2(1H)-
yl)methyl)-N-((1-(oxetan-3-yl)piperidin-4-yl)methyl)
benzamide;
3-((6-(3-Methylisoxazol-4-yl)-1-oxoisoquinolin-2(1H)-
yl)methyl)-N-(piperidin-4-yl)benzamide;
N-((1-(2,2Difluoroethyl)piperidin-4-yl)methyl)-3-((6-(3-
methylisoxazol-4-yl)-1-oxoisoquinolin-2(1H)-yl)
methyl)benzamide;
3-((6-(3-Methylisoxazol-4-yl)-1-oxoisoquinolin-2(1H)-
yl)methyl)-N-(1-(2,2,2-trifluoroethyl)piperidin-4-yl)
benzamide;
3-((6-(3-Methylisoxazol-4-yl)-1-oxoisoquinolin-2(1H)-
yl)methyl)-N-(1-(oxetan-3-yl)piperidin-4-yl)benz-
amide;
N-(1-Methyl-1H-pyrazol-3-yl)-3-((6-(3-methylisoxazol-
4-yl)-1-oxoisoquinolin-2(1H)-yl)methyl)benzamide;
N-(Isoxazol-3-yl)-3-((6-(3-methylisoxazol-4-yl)-1-
oxoisoquinolin-2(1H)-yl)methyl)benzamide;
N-(Isochroman-6-yl)-3-((6-(3-methylisoxazol-4-yl)-1-
oxoisoquinolin-2(1H)-yl)methyl)benzamide;
N-(Isochroman-7-yl)-3-((6-(3-methylisoxazol-4-yl)-1-
oxoisoquinolin-2(1H)-yl)methyl)benzamide;
3-((6-(3-Methylisoxazol-4-yl)-1-oxoisoquinolin-2(1H)-
yl)methyl)-N-(4,5,6,7-tetrahydrothiazolo[4,5-c]pyri-
din-2-yl)benzamide;
N-(5-Methyl-4,5,6,7-tetrahydrothiazolo[4,5-c]pyridin-2-
yl)-3-((6-(3-methylisoxazol-4-yl)-1-oxoisoquinolin-2
(1H)-yl)methyl)benzamide;
N-(5-Isopropyl-4,5,6,7-tetrahydrothiazolo[4,5-c]pyridin-
2-yl)-3-((6-(3-methylisoxazol-4-yl)-1-oxoisoquinolin-
2(1H)-yl)methyl)benzamide;
3-((6-(3-Methylisoxazol-4-yl)-1-oxoisoquinolin-2(1H)-
yl)methyl)-N-(1,2,3,4-tetrahydroisoquinolin-6-yl)ben-
zamide;
N-(2-Methyl-1,2,3,4-tetrahydroisoquinolin-6-yl)-3-((6-
(3-methylisoxazol-4-yl)-1-oxoisoquinolin-2(1H)-yl)
methyl)benzamide;
N-(2-Isopropyl-1,2,3,4-tetrahydroisoquinolin-6-yl)-3-
((6-(3-methylisoxazol-4-yl)-1-oxoisoquinolin-2(1H)-
yl)methyl)benzamide;

N-(2-Cyclopropyl-1,2,3,4-tetrahydroisoquinolin-6-yl)-3-((6-(3-methylisoxazol-4-yl)-1-oxoisoquinolin-2(1H)-yl)methyl)benzamide;

3-((6-(3-Methylisoxazol-4-yl)-1-oxoisoquinolin-2(1H)-yl)methyl)-N-(1,2,3,4-tetrahydroisoquinolin-7-yl)benzamide;

N-(2-Methyl-1,2,3,4-tetrahydroisoquinolin-7-yl)-3-((6-(3-methylisoxazol-4-yl)-1-oxoisoquinolin-2(1H)-yl)methyl)benzamide;

N-(2-Hydroxyethyl)-3-((6-(3-methylisoxazol-4-yl)-1-oxoisoquinolin-2(1H)-yl)methyl)benzamide;

3-((6-(1-Methyl-1H-pyrazol-5-yl)-1-oxoisoquinolin-2(1H)-yl)methyl)-N-(2,2,2-trifluoroethyl)benzamide;

3-((6-(1-Methyl-1H-pyrazol-5-yl)-1-oxoisoquinolin-2(1H)-yl)methyl)-N-(tetrahydro-2H-pyran-4-yl)benzamide;

3-((6-(1-Methyl-1H-pyrazol-5-yl)-1-oxoisoquinolin-2(1H)-yl)methyl)-N-(piperidin-4-yl)benzamide;

3-((6-(1-Methyl-1H-pyrazol-5-yl)-1-oxoisoquinolin-2(1H)-yl)methyl)-N-(1-methylpiperidin-4-yl)benzamide;

N-(1-(2,2-Difluoroethyl)piperidin-4-yl)-3-((6-(1-methyl-1H-pyrazol-5-yl)-1-oxoisoquinolin-2(1H)-yl)methyl)benzamide;

3-((6-(1-Methyl-1H-pyrazol-5-yl)-1-oxoisoquinolin-2(1H)-yl)methyl)-N-(1-(2,2,2-trifluoroethyl)piperidin-4-yl)benzamide;

3-((6-(1-Methyl-1H-pyrazol-5-yl)-1-oxoisoquinolin-2(1H)-yl)methyl)-N-(1-(oxetan-3-yl)piperidin-4-yl)benzamide;

3-((6-(1-Methyl-1H-pyrazol-5-yl)-1-oxoisoquinolin-2(1H)-yl)methyl)-N-(oxetan-3-yl)benzamide;

3-((6-(1-Methyl-1H-pyrazol-5-yl)-1-oxoisoquinolin-2(1H)-yl)methyl)-N-(oxetan-3-ylmethyl)benzamide;

N-((3-Hydroxycyclobutyl)methyl)-3-((6-(1-methyl-1H-pyrazol-5-yl)-1-oxoisoquinolin-2(1H)-yl)methyl)benzamide;

3-((6-(1-Methyl-1H-pyrazol-5-yl)-1-oxoisoquinolin-2(1H)-yl)methyl)-N-((1-methylazetidin-3-yl)methyl)benzamide;

N-((6-Fluoropyridin-3-yl)methyl)-3-((6-(1-methyl-1H-pyrazol-5-yl)-1-oxoisoquinolin-2(1H)-yl)methyl)benzamide;

N-((1R,4R)-4-Hydroxycyclohexyl)-3-((6-(1-methyl-1H-pyrazol-5-yl)-1-oxoisoquinolin-2(1H)-yl)methyl)benzamide;

N-((1S,4S)-4-Hydroxycyclohexyl)-3-((6-(1-methyl-1H-pyrazol-5-yl)-1-oxoisoquinolin-2(1H)-yl)methyl)benzamide;

N-((2-Fluoropyridin-4-yl)methyl)-3-((6-(1-methyl-1H-pyrazol-5-yl)-1-oxoisoquinolin-2(1H)-yl)methyl)benzamide;

N-(1-Isopropylpiperidin-4-yl)-3-((6-(1-methyl-1H-pyrazol-5-yl)-1-oxoisoquinolin-2(1H)-yl)methyl)benzamide;

N-(2-(Dimethylamino)ethyl)-3-((6-(1-methyl-1H-pyrazol-5-yl)-1-oxoisoquinolin-2(1H)-yl)methyl)benzamide;

N-Methyl-3-((1-oxo-6-(5-(trifluoromethyl)-1H-pyrazol-4-yl)isoquinolin-2(1H)-yl)methyl)benzamide;

N-(2-Methoxyethyl)-3-((6-(1-methyl-1H-pyrazol-5-yl)-1-oxoisoquinolin-2(1H)-yl)methyl)benzamide;

3-((6-(1-Methyl-1H-pyrazol-5-yl)-1-oxoisoquinolin-2(1H)-yl)methyl)-N-(5-methyl-4,5,6,7-tetrahydrothiazolo[4,5-c]pyridin-2-yl)benzamide;

3-((6-(1-Methyl-1H-pyrazol-5-yl)-1-oxoisoquinolin-2(1H)-yl)methyl)-N-(4,5,6,7-tetrahydrothiazolo[4,5-c]pyridin-2-yl)benzamide;

3-((6-(1-Methyl-1H-pyrazol-5-yl)-1-oxoisoquinolin-2(1H)-yl)methyl)-N-(1,2,3,4-tetrahydroisoquinolin-6-yl)benzamide;

N-(2-Methyl-1,2,3,4-tetrahydroisoquinolin-6-yl)-3-((6-(1-methyl-1H-pyrazol-5-yl)-1-oxoisoquinolin-2(1H)-yl)methyl)benzamide;

3-((6-(1-Methyl-1H-pyrazol-5-yl)-1-oxoisoquinolin-2(1H)-yl)methyl)-N-(1,2,3,4-tetrahydroisoquinolin-7-yl)benzamide;

N-(2-Cyclopropyl-1,2,3,4-tetrahydroisoquinolin-7-yl)-3-((6-(1-methyl-1H-pyrazol-5-yl)-1-oxoisoquinolin-2(1H)-yl)methyl)benzamide;

3-Fluoro-5-((1-oxo-6-(3-(trifluoromethyl)-1H-pyrazol-4-yl)isoquinolin-2(1H)-yl)methyl)-N-(4-sulfamoylphenyl)benzamide;

3-Fluoro-N-(1-methyl-1H-pyrazol-3-yl)-5-((1-oxo-6-(5-(trifluoromethyl)-1H-pyrazol-4-yl)isoquinolin-2(1H)-yl)methyl)benzamide;

3-Fluoro-N-((6-fluoropyridin-3-yl)methyl)-5-((1-oxo-6-(3-(trifluoromethyl)-1H-pyrazol-4-yl)isoquinolin-2(1H)-yl)methyl)benzamide;

3-Fluoro-5-((1-oxo-6-(3-(trifluoromethyl)-1H-pyrazol-4-yl)isoquinolin-2(1H)-yl)methyl)-N-(tetrahydro-2H-pyran-4-yl)benzamide;

3-Fluoro-5-((1-oxo-6-(3-(trifluoromethyl)-1H-pyrazol-4-yl)isoquinolin-2(1H)-yl)methyl)-N-(piperidin-4-yl)benzamide;

3-Fluoro-N-(1-methylpiperidin-4-yl)-5-((1-oxo-6-(3-(trifluoromethyl)-1H-pyrazol-4-yl)isoquinolin-2(1H)-yl)methyl)benzamide;

N-Cyclopropyl-3-fluoro-5-((1-oxo-6-(3-(trifluoromethyl)-1H-pyrazol-4-yl)isoquinolin-2(1H)-yl)methyl)benzamide;

3-Fluoro-N-((1-methylpiperidin-4-yl)methyl)-5-((1-oxo-6-(3-(trifluoromethyl)-1H-pyrazol-4-yl)isoquinolin-2(1H)-yl)methyl)benzamide;

3-Fluoro-5-((1-oxo-6-(3-(trifluoromethyl)-1H-pyrazol-4-yl)isoquinolin-2(1H)-yl)methyl)-N-((tetrahydro-2H-pyran-4-yl)methyl)benzamide;

3-Fluoro-N-(oxetan-3-ylmethyl)-5-((1-oxo-6-(3-(trifluoromethyl)-1H-pyrazol-4-yl)isoquinolin-2(1H)-yl)methyl)benzamide;

3-Fluoro-N-((1S,3S)-3-hydroxycyclobutyl)-5-((6-(3-methylisoxazol-4-yl)-1-oxoisoquinolin-2(1H)-yl)methyl)benzamide;

3-Fluoro-N-((1R,3R)-3-hydroxycyclobutyl)-5-((6-(3-methylisoxazol-4-yl)-1-oxoisoquinolin-2(1H)-yl)methyl)benzamide;

3-Fluoro-N-((1R,4R)-4-hydroxycyclohexyl)-5-((6-(3-methylisoxazol-4-yl)-1-oxoisoquinolin-2(1H)-yl)methyl)benzamide;

3-Fluoro-N-((1S,4S)-4-hydroxycyclohexyl)-5-((6-(3-methylisoxazol-4-yl)-1-oxoisoquinolin-2(1H)-yl)methyl)benzamide;

3-Fluoro-N-((1S,4R)-4-methoxycyclohexyl)-5-((6-(3-methylisoxazol-4-yl)-1-oxoisoquinolin-2(1H)-yl)methyl)benzamide;

3-Fluoro-N-((1S,4S)-4-methoxycyclohexyl)-5-((6-(3-methylisoxazol-4-yl)-1-oxoisoquinolin-2(1H)-yl)methyl)benzamide;

3-Fluoro-5-((6-(3-methylisoxazol-4-yl)-1-oxoisoquinolin-2(1H)-yl)methyl)-N-(2-morpholinoethyl)benzamide;

3-Fluoro-5-((6-(3-methylisoxazol-4-yl)-1-oxoisoquino-lin-2(1H)-yl)methyl)-N-(2-(4-methylpiperazin-1-yl)ethyl)benzamide;

3-Fluoro-5-((6-(3-methylisoxazol-4-yl)-1-oxoisoquino-lin-2(1H)-yl)methyl)-N-(oxetan-3-ylmethyl)benzamide;

3-Fluoro-N-((6-fluoropyridin-3-yl)methyl)-5-((6-(3-methylisoxazol-4-yl)-1-oxoisoquinolin-2(1H)-yl)methyl)benzamide;

3-Fluoro-5-((6-(3-methylisoxazol-4-yl)-1-oxoisoquino-lin-2(1H)-yl)methyl)-N-(tetrahydro-2H-pyran-4-yl)benzamide;

3-Fluoro-5-((6-(3-methylisoxazol-4-yl)-1-oxoisoquino-lin-2(1H)-yl)methyl)-N-((1-methylpiperidin-4-yl)methyl)benzamide;

3-Fluoro-5-((6-(3-methylisoxazol-4-yl)-1-oxoisoquino-lin-2(1H)-yl)methyl)-N-(piperidin-4-ylmethyl)benzamide;

N-((1-Cyclopropylpiperidin-4-yl)methyl)-3-fluoro-5-((6-(3-methylisoxazol-4-yl)-1-oxoisoquinolin-2(1H)-yl)methyl)benzamide;

3-Fluoro-N-((1-isopropylpiperidin-4-yl)methyl)-5-((6-(3-methylisoxazol-4-yl)-1-oxoisoquinolin-2(1H)-yl)methyl)benzamide;

3-Fluoro-5-((6-(3-methylisoxazol-4-yl)-1-oxoisoquino-lin-2(1H)-yl)methyl)-N-((1-(2,2,2-trifluoroethyl)pip-eridin-4-yl)methyl)benzamide;

3-Fluoro-5-((6-(3-methylisoxazol-4-yl)-1-oxoisoquino-lin-2(1H)-yl)methyl)-N-((1-(oxetan-3-yl)piperidin-4-yl)methyl)benzamide;

3-Fluoro-5-((6-(3-methylisoxazol-4-yl)-1-oxoisoquino-lin-2(1H)-yl)methyl)-N-(1-methylpiperidin-4-yl)benzamide;

3-Fluoro-N-(1-methyl-1H-pyrazol-3-yl)-5-((6-(3-methyl-isoxazol-4-yl)-1-oxoisoquinolin-2(1H)-yl)methyl)benzamide;

3-Fluoro-5-((6-(3-methylisoxazol-4-yl)-1-oxoisoquino-lin-2(1H)-yl)methyl)-N-(4,5,6,7-tetrahydrothiazolo[4,5-c]pyridin-2-yl)benzamide;

3-Fluoro-N-(5-methyl-4,5,6,7-tetrahydrothiazolo[4,5-c]pyridin-2-yl)-5-((6-(3-methylisoxazol-4-yl)-1-oxoiso-quinolin-2(1H)-yl)methyl)benzamide;

3-Fluoro-N-(5-isopropyl-4,5,6,7-tetrahydrothiazolo[4,5-c]pyridin-2-yl)-5-((6-(3-methylisoxazol-4-yl)-1-oxoisoquinolin-2(1H)-yl)methyl)benzamide;

3-Fluoro-5-((6-(3-methylisoxazol-4-yl)-1-oxoisoquino-lin-2(1H)-yl)methyl)-N-(1,2,3,4-tetrahydroisoquino-lin-7-yl)benzamide;

N-(2-Cyclopropyl-1,2,3,4-tetrahydroisoquinolin-7-yl)-3-fluoro-5-((6-(3-methylisoxazol-4-yl)-1-oxoisoquinolin-2(1H)-yl)methyl)benzamide;

3-Fluoro-5-((6-(3-methylisoxazol-4-yl)-1-oxoisoquino-lin-2(1H)-yl)methyl)-N-(1,2,3,4-tetrahydroisoquino-lin-6-yl)benzamide;

3-Fluoro-N-(2-methyl-1,2,3,4-tetrahydroisoquinolin-6-yl)-5-((6-(3-methylisoxazol-4-yl)-1-oxoisoquinolin-2(1H)-yl)methyl)benzamide;

3-Fluoro-N-((1R,4R)-4-hydroxycyclohexyl)-5-((6-(1-methyl-1H-pyrazol-5-yl)-1-oxoisoquinolin-2(1H)-yl)methyl)benzamide;

3-Fluoro-N-((1S,4S)-4-hydroxycyclohexyl)-5-((6-(1-methyl-1H-pyrazol-5-yl)-1-oxoisoquinolin-2(1H)-yl)methyl)benzamide;

3-Fluoro-5-((6-(1-methyl-1H-pyrazol-5-yl)-1-oxoisoqui-nolin-2(1H)-yl)methyl)-N-(tetrahydro-2H-pyran-4-yl)benzamide;

N-((3-Hydroxycyclobutyl)methyl)-3-((6-(1-methyl-1H-pyrazol-5-yl)-1-oxoisoquinolin-2(1H)-yl)methyl)benz-amide;

3-((6-(1-Methyl-1H-pyrazol-5-yl)-1-oxoisoquinolin-2(1H)-yl)methyl)-N-((1-methylazetidin-3-yl)methyl)benzamide;

3-Fluoro-5-((6-(1-methyl-1H-pyrazol-5-yl)-1-oxoisoqui-nolin-2(1H)-yl)methyl)-N-((1-methylpiperidin-4-yl)methyl)benzamide;

3-Fluoro-5-((6-(1-methyl-1H-pyrazol-5-yl)-1-oxoisoqui-nolin-2(1H)-yl)methyl)-N-(piperidin-4-ylmethyl)benz-amide;

3-Fluoro-N-((6-fluoropyridin-3-yl)methyl)-5-((6-(1-methyl-1H-pyrazol-5-yl)-1-oxoisoquinolin-2(1H)-yl)methyl)benzamide;

3-Fluoro-N-(1-isopropylpiperidin-4-yl)-5-((6-(1-methyl-1H-pyrazol-5-yl)-1-oxoisoquinolin-2(1H)-yl)methyl)benzamide;

3-Fluoro-5-((6-(1-methyl-1H-pyrazol-5-yl)-1-oxoisoqui-nolin-2(1H)-yl)methyl)-N-(1-methylpiperidin-4-yl)benzamide;

3-Fluoro-5-((6-(1-methyl-1H-pyrazol-5-yl)-1-oxoisoqui-nolin-2(1H)-yl)methyl)-N-(piperidin-4-yl)benzamide;

N-(2-(Dimethylamino)ethyl)-3-fluoro-5-((6-(1-methyl-1H-pyrazol-5-yl)-1-oxoisoquinolin-2(1H)-yl)methyl)benzamide;

3-Fluoro-N-(1-methyl-1H-pyrazol-3-yl)-5-((6-(1-methyl-1H-pyrazol-5-yl)-1-oxoisoquinolin-2(1H)-yl)methyl)benzamide;

N-(2-(2-Fluoropyridin-4-yl)ethyl)-3-((1-oxo-6-(pyridin-4-yl)isoquinolin-2(1H)-yl)methyl)benzamide;

3-((6-(2-Aminopyridin-4-yl)-1-oxoisoquinolin-2(1H)-yl)methyl)-N-benzylbenzamide;

3-((6-(2-Aminopyridin-4-yl)-1-oxoisoquinolin-2(1H)-yl)methyl)-N-(naphthalen-2-ylmethyl)benzamide;

N-(2-(Aminomethyl)benzyl)-3-((6-(2-aminopyridin-4-yl)-1-oxoisoquinolin-2(1H)-yl)methyl)benzamide;

3-((6-(2-Aminopyridin-4-yl)-1-oxoisoquinolin-2(1H)-yl)methyl)-N-(2-(hydroxymethyl)benzyl)benzamide;

3-((6-(2-Aminopyridin-4-yl)-1-oxoisoquinolin-2(1H)-yl)methyl)-N-phenethylbenzamide;

3-((6-(2-Aminopyridin-4-yl)-1-oxoisoquinolin-2(1H)-yl)methyl)-N-(2-(pyridin-2-yl)ethyl)benzamide;

3-((6-(2-Aminopyridin-4-yl)-1-oxoisoquinolin-2(1H)-yl)methyl)-N-(1,2,3,4-tetrahydroisoquinolin-7-yl)benz-amide;

3-((6-(2-Aminopyridin-4-yl)-1-oxoisoquinolin-2(1H)-yl)methyl)-N-(1,2,3,4-tetrahydroisoquinolin-6-yl)benz-amide;

3-((6-(2-Aminopyridin-4-yl)-1-oxoisoquinolin-2(1H)-yl)methyl)-N-(2-methyl-1,2,3,4-tetrahydroisoquinolin-6-yl)benzamide;

3-((6-(2-Aminopyridin-4-yl)-1-oxoisoquinolin-2(1H)-yl)methyl)-N-(4,5,6,7-tetrahydrothiazolo[5,4-c]pyridin-2-yl)benzamide;

3-((6-(2-Aminopyridin-4-yl)-1-oxoisoquinolin-2(1H)-yl)methyl)-N-(5-methyl-4,5,6,7-tetrahydrothiazolo[5,4-c]pyridin-2-yl)benzamide;

3-((6-(2-Aminopyridin-4-yl)-1-oxoisoquinolin-2(1H)-yl)methyl)-N-((1S,4S)-4-hydroxycyclohexyl)benzamide;

3-((6-(2-Aminopyridin-4-yl)-1-oxoisoquinolin-2(1H)-yl)methyl)-N-((1R,4R)-4-hydroxycyclohexyl)benzamide;

3-((6-(2-Aminopyridin-4-yl)-1-oxoisoquinolin-2(1H)-yl)methyl)-N-(tetrahydro-2H-pyran-4-yl)benzamide;

3-((6-(2-Aminopyridin-4-yl)-1-oxoisoquinolin-2(1H)-yl)methyl)-N-(oxetan-3-yl)benzamide;

3-((6-(2-Aminopyridin-4-yl)-1-oxoisoquinolin-2(1H)-yl)
  methyl)-N-(isochroman-6-yl)benzamide;
3-((6-(2-Aminopyridin-4-yl)-1-oxoisoquinolin-2(1H)-yl)
  methyl)-N-(isochroman-7-yl)benzamide;
3-((6-(2-Aminopyridin-4-yl)-1-oxoisoquinolin-2(1H)-yl)
  methyl)-N-cyclopentylbenzamide;
3-((6-(2-Aminopyridin-4-yl)-1-oxoisoquinolin-2(1H)-yl)
  methyl)-N-(1H-imidazol-2-yl)benzamide;
3-((6-(2-Aminopyridin-4-yl)-1-oxoisoquinolin-2(1H)-yl)
  methyl)-N-(1-methyl-1H-pyrazol-3-yl)benzamide;
3-((6-(2-Aminopyridin-4-yl)-1-oxoisoquinolin-2(1H)-yl)
  methyl)-5-fluoro-N-(1-methyl-1H-pyrazol-3-yl)benzamide;
3-((6-(2-Aminopyridin-4-yl)-1-oxoisoquinolin-2(1H)-yl)
  methyl)-5-fluoro-N-(oxetan-3-yl)benzamide;
3-((6-(2-Aminopyridin-4-yl)-1-oxoisoquinolin-2(1H)-yl)
  methyl)-N-(isoxazol-5-yl)benzamide;
3-((6-(2-Aminopyridin-4-yl)-1-oxoisoquinolin-2(1H)-yl)
  methyl)-N-(isoxazol-3-yl)benzamide;
3-((6-(2-Aminopyridin-4-yl)-1-oxoisoquinolin-2(1H)-yl)
  methyl)-5-fluoro-N-(isoxazol-3-yl)benzamide;
N-(Isoxazol-5-yl)-3-((6-morpholino-1-oxoisoquinolin-2
  (1H)-yl)methyl)benzamide;
3-((6-Morpholino-1-oxoisoquinolin-2(1H)-yl)methyl)-N-
  (oxetan-3-yl)benzamide;
3-Fluoro-5-((6-morpholino-1-oxoisoquinolin-2(1H)-yl)
  methyl)-N-(oxetan-3-yl)benzamide;
3-Fluoro-N-((1S,3S)-3-hydroxycyclobutyl)-5-((6-morpholino-1-oxoisoquinolin-2(1H)-yl)methyl)benzamide;
3-Fluoro-N-((1R,3R)-3-hydroxycyclobutyl)-5-((6-morpholino-1-oxoisoquinolin-2(1H)-yl)methyl)benzamide;
3-Fluoro-5-((6-morpholino-1-oxoisoquinolin-2(1H)-yl)
  methyl)-N-(tetrahydro-2H-pyran-4-yl)benzamide;
3-((6-Morpholino-1-oxoisoquinolin-2(1H)-yl)methyl)-N-
  (tetrahydro-2H-pyran-4-yl)benzamide;
N-Methyl-3-((6-(2-methyl-1H-pyrrol-3-yl)-1-oxo-2,7-
  naphthyridin-2(1H)-yl)methyl)benzamide;
N-(Methyl-d3)-3-((6-(2-methyl-1H-pyrrol-3-yl)-1-oxo-2,
  7-naphthyridin-2(1H)-yl)methyl)benzamide;
N-Methyl-3-((6-(2-methyl-1H-pyrrol-3-yl)-1-oxo-2,7-
  naphthyridin-2(1H)-yl)methyl)benzamide;
N-Methyl-3-((6-(2-methyl-1H-pyrrol-3-yl)-1-oxo-2,7-
  naphthyridin-2(1H)-yl)methyl)benzamide;
N-(Methyl-D3)-3-((1-oxo-6-(5-(trifluoromethyl)-1H-
  pyrazol-4-yl)-2,7-naphthyridin-2(1H)-yl)methyl)benzamide;
N-Methyl-3-((1-oxo-6-(5-(trifluoromethyl)-1H-pyrazol-
  4-yl)-2,7-naphthyridin-2(1H)-yl)methyl)benzamide;
N-(Methyl-D3)-3-((1-oxo-6-(5-(trifluoromethyl)-1H-
  pyrazol-4-yl)-2,7-naphthyridin-2(1H)-yl)methyl)benzamide;
3-((6-(3-Chloro-1H-pyrazol-4-yl)-1-oxo-2,7-naphthyridin-2(1H)-yl)methyl)-N-methylbenzamide;
3-((6-(3-Chloro-1H-pyrazol-4-yl)-1-oxo-2,7-naphthyridin-2(1H)-yl)methyl)-N-(methyl-d3)benzamide;
3-((6-(5-(Difluoromethyl)-1H-pyrazol-4-yl)-1-oxo-2,7-
  naphthyridin-2(1H)-yl)methyl)-N-methylbenzamide;
3-((6-(5-(Difluoromethyl)-1H-pyrazol-4-yl)-1-oxo-2,7-
  naphthyridin-2(1H)-yl)methyl)-N-(methyl-D3)benzamide;
N-Methyl-3-((6-(3-methyl-1H-pyrazol-4-yl)-1-oxo-2,7-
  naphthyridin-2(1H)-yl)methyl)benzamide;
N-Methyl-3-((6-(1-methyl-1H-pyrazol-5-yl)-1-oxo-2,7-
  naphthyridin-2(1H)-yl)methyl)benzamide;
N-Methyl-3-((6-(3-methylisoxazol-4-yl)-1-oxo-2,7-
  naphthyridin-2(1H)-yl)methyl)benzamide;
N-Methyl-3-((8-oxo-3-(5-(trifluoromethyl)-1H-pyrazol-
  4-yl)-1,7-naphthyridin-7(8H)-yl)methyl)benzamide;
N-Methyl-3-((3-(3-methylisoxazol-4-yl)-8-oxo-1,7-
  naphthyridin-7(8H)-yl)methyl)benzamide;
3-((6-(2-Aminopyridin-4-yl)-1-oxo-2,7-naphthyridin-2
  (1H)-yl)methyl)-N-methylbenzamide;
3-Fluoro-N-methyl-5-((6-(1-methyl-1H-pyrazol-5-yl)-1-
  oxo-2,7-naphthyridin-2(1H)-yl)methyl)benzamide;
3-Fluoro-N-methyl-5-((1-oxo-6-(5-(trifluoromethyl)-1H-
  pyrazol-4-yl)-2,7-naphthyridin-2(1H)-yl)methyl)benzamide;
3-Fluoro-N-methyl-5-((6-(2-methylfuran-3-yl)-1-oxo-2,
  7-naphthyridin-2(1H)-yl)methyl)benzamide;
3-Fluoro-N-methyl-5-((6-(5-methyl-1H-pyrazol-4-yl)-1-
  oxo-2,7-naphthyridin-2(1H)-yl)methyl)benzamide;
3-((6-(3-Chloro-1H-pyrazol-4-yl)-1-oxo-2,7-naphthyridin-2(1H)-yl)methyl)-5-fluoro-N-methylbenzamide;
3-Fluoro-N-methyl-5-((1-oxo-6-(3-(trifluoromethyl)-1H-
  pyrazol-4-yl)-2,7-naphthyridin-2(1H)-yl)methyl)benzamide;
3-((6-(2-Aminopyridin-4-yl)-1-oxoisoquinolin-2(1H)-yl)
  methyl)-5-fluoro-N-methylbenzamide;
3-((6-(3-(Difluoromethyl)-1H-pyrazol-4-yl)-1-oxo-2,7-
  naphthyridin-2(1H)-yl)methyl)-5-fluoro-N-methylbenzamide;
3-Fluoro-5-((6-(3-methyl-1H-pyrazol-4-yl)-1-oxo-2,7-
  naphthyridin-2(1H)-yl)methyl)-N-(tetrahydro-2H-
  pyran-4-yl)benzamide;
N-Ethyl-3-fluoro-5-((6-(3-methyl-1H-pyrazol-4-yl)-1-
  oxo-2,7-naphthyridin-2(1H)-yl)methyl)benzamide;
3-Fluoro-5-((6-(3-methyl-1H-pyrazol-4-yl)-1-oxo-2,7-
  naphthyridin-2(1H)-yl)methyl)-N-(tetrahydro-2H-
  pyran-4-yl)benzamide;
3-Fluoro-5-((6-(3-methyl-1H-pyrazol-4-yl)-1-oxo-2,7-
  naphthyridin-2(1H)-yl)methyl)-N-((1-methylpiperidin-
  4-yl)methyl)benzamide;
3-Fluoro-N-((1-methylpiperidin-4-yl)methyl)-5-((1-oxo-
  6-(3-(trifluoromethyl)-1H-pyrazol-4-yl)-2,7-naphthyridin-2(1H)-yl)methyl)benzamide;
3-Fluoro-N-(oxetan-3-ylmethyl)-5-((1-oxo-6-(3-(trifluoromethyl)-1H-pyrazol-4-yl)-2,7-naphthyridin-2(1H)-
  yl)methyl)benzamide;
3-Fluoro-N-(1-methylpiperidin-4-yl)-5-((1-oxo-6-(3-(trifluoromethyl)-1H-pyrazol-4-yl)-2,7-naphthyridin-2
  (1H)-yl)methyl)benzamide;
3-Fluoro-N-((1R,4R)-4-hydroxycyclohexyl)-5-((1-oxo-
  6-(3-(trifluoromethyl)-1H-pyrazol-4-yl)-2,7-naphthyridin-2(1H)-yl)methyl)benzamide;
3-((6-(3-Chloro-1H-pyrazol-4-yl)-1-oxo-2,7-naphthyridin-2(1H)-yl)methyl)-5-fluoro-N-(1-methylpiperidin-
  4-yl)benzamide;
3-((6-(3-Chloro-1H-pyrazol-4-yl)-1-oxo-2,7-naphthyridin-2(1H)-yl)methyl)-5-fluoro-N-((1S,4S)-4-hydroxycyclohexyl)benzamide;
3-((6-(3-Chloro-1H-pyrazol-4-yl)-1-oxo-2,7-naphthyridin-2(1H)-yl)methyl)-5-fluoro-N-((1R,4R)-4-hydroxycyclohexyl)benzamide;
3-((6-(3-Chloro-1H-pyrazol-4-yl)-1-oxo-2,7-naphthyridin-2(1H)-yl)methyl)-5-fluoro-N-isopropylbenzamide;
3-Fluoro-5-((6-(3-methylisoxazol-4-yl)-1-oxo-2,7-naphthyridin-2(1H)-yl)methyl)-N-((1-methylpiperidin-4-yl)
  methyl)benzamide;
3-Fluoro-5-((6-(3-methylisoxazol-4-yl)-1-oxo-2,7-naphthyridin-2(1H)-yl)methyl)-N-((tetrahydro-2H-pyran-4-
  yl)methyl)benzamide;

3-Fluoro-5-((6-(3-methylisoxazol-4-yl)-1-oxo-2,7-naph-thyridin-2(1H)-yl)methyl)-N-(2-morpholinoethyl)benzamide;
3-Fluoro-5-((6-(1-methyl-1H-pyrazol-5-yl)-1-oxo-2,7-naphthyridin-2(1H)-yl)methyl)-N-(2-(4-methylpiperazin-1-yl)ethyl)benzamide;
3-Fluoro-5-((6-(1-methyl-1H-pyrazol-5-yl)-1-oxo-2,7-naphthyridin-2(1H)-yl)methyl)-N-(oxetan-3-ylmethyl)benzamide;
3-Fluoro-5-((6-(1-methyl-1H-pyrazol-5-yl)-1-oxo-2,7-naphthyridin-2(1H)-yl)methyl)-N-((tetrahydro-2H-pyran-4-yl)methyl)benzamide;
3-Fluoro-5-((6-(1-methyl-1H-pyrazol-5-yl)-1-oxo-2,7-naphthyridin-2(1H)-yl)methyl)-N-(2-(pyridin-3-yl)ethyl)benzamide;
3-((6-(3-Bromo-1H-pyrazol-4-yl)-1-oxo-2,7-naphthyridin-2(1H)-yl)methyl)-5-fluoro-N-isopropylbenzamide;
3-((6-(3-Bromo-1H-pyrazol-4-yl)-1-oxo-2,7-naphthyridin-2(1H)-yl)methyl)-5-fluoro-N-((1-methylpiperidin-4-yl)methyl)benzamide;
3-((6-(3-(Difluoromethyl)-1H-pyrazol-4-yl)-1-oxo-2,7-naphthyridin-2(1H)-yl)methyl)-5-fluoro-N-((1-methylpiperidin-4-yl)methyl)benzamide;
N-Methyl-3-((6-(3-methylisoxazol-4-yl)-1-oxoisoquinolin-2(1H)-yl)methyl)benzamide;
N-Methyl-3-((1-oxo-6-(5-(trifluoromethyl)-1H-pyrazol-4-yl)isoquinolin-2(1H)-yl)methyl)benzamide;
N-(Methyl-D3)-3-((1-oxo-6-(5-(trifluoromethyl)-1H-pyrazol-4-yl)isoquinolin-2(1H)-yl)methyl)benzamide;
N-Methyl-3-(1-(1-oxo-6-(5-(trifluoromethyl)-1H-pyrazol-4-yl)isoquinolin-2(1H)-yl)ethyl)benzamide;
3-((4-Chloro-1-oxo-6-(5-(trifluoromethyl)-1H-pyrazol-4-yl)isoquinolin-2(1H)-yl)methyl)-N-methylbenzamide;
3-Fluoro-N-methyl-5-((1-oxo-6-(5-(trifluoromethyl)-1H-pyrazol-4-yl)isoquinolin-2(1H)-yl)methyl)benzamide;
3-Fluoro-N-(methyl-d3)-5-((1-oxo-6-(5-(trifluoromethyl)-1H-pyrazol-4-yl)isoquinolin-2(1H)-yl)methyl)benzamide;
3-Fluoro-N-methyl-5-(1-(1-oxo-6-(5-(trifluoromethyl)-1H-pyrazol-4-yl)isoquinolin-2(1H)-yl)ethyl)benzamide;
2-Fluoro-N-methyl-5-((1-oxo-6-(5-(trifluoromethyl)-1H-pyrazol-4-yl)isoquinolin-2(1H)-yl)methyl)benzamide;
3-Chloro-N-methyl-5-((1-oxo-6-(5-(trifluoromethyl)-1H-pyrazol-4-yl)isoquinolin-2(1H)-yl)methyl)benzamide;
3-((6-(5-(Difluoromethyl)-1H-pyrazol-4-yl)-1-oxoisoquinolin-2(1H)-yl)methyl)-N-methylbenzamide;
3-(1-(6-(5-(Difluoromethyl)-1H-pyrazol-4-yl)-1-oxoisoquinolin-2(1H)-yl)ethyl)-N-methylbenzamide;
N-(Methyl-d3)-3-(1-(6-(3-methylisoxazol-4-yl)-1-oxoisoquinolin-2(1H)-yl)ethyl)benzamide;
3-(1-(6-(5-(Difluoromethyl)-1H-pyrazol-4-yl)-1-oxoisoquinolin-2(1H)-yl)ethyl)-N-(methyl-D3)benzamide;
3-((6-(5-(Difluoromethyl)-1H-pyrazol-4-yl)-1-oxoisoquinolin-2(1H)-yl)methyl)-5-fluoro-N-methylbenzamide;
3-((6-(5-Chloro-1H-pyrazol-4-yl)-1-oxoisoquinolin-2(1H)-yl)methyl)-N-methylbenzamide;
3-((6-(5-Chloro-1H-pyrazol-4-yl)-1-oxoisoquinolin-2(1H)-yl)methyl)-N-(methyl-D3)benzamide;
3-(1-(6-(5-Chloro-1H-pyrazol-4-yl)-1-oxoisoquinolin-2(1H)-yl)ethyl)-N-methylbenzamide;
3-((6-(5-Chloro-1H-pyrazol-4-yl)-1-oxoisoquinolin-2(1H)-yl)methyl)-5-fluoro-N-methylbenzamide;
3-(1-(6-(5-Chloro-1H-pyrazol-4-yl)-1-oxoisoquinolin-2(1H)-yl)ethyl)-5-fluoro-N-methylbenzamide;
3-(1-(6-(5-Fluoro-1H-pyrazol-4-yl)-1-oxoisoquinolin-2(1H)-yl)ethyl)-N-methylbenzamide;
3-((6-(5-Fluoro-1H-pyrazol-4-yl)-1-oxoisoquinolin-2(1H)-yl)methyl)-N-(methyl-D3)benzamide;
3-((6-(5-Fluoro-1H-pyrazol-4-yl)-1-oxoisoquinolin-2(1H)-yl)methyl)-N-methylbenzamide;
3-Fluoro-5-(1-(6-(5-fluoro-1H-pyrazol-4-yl)-1-oxoisoquinolin-2(1H)-yl)ethyl)-N-methylbenzamide;
N-Methyl-3-((6-(1-methyl-1H-pyrazol-4-yl)-1-oxoisoquinolin-2(1H)-yl)methyl)benzamide;
3-((6-(Isoxazol-4-yl)-1-oxoisoquinolin-2(1H)-yl)methyl)-N-methylbenzamide;
N-Methyl-3-((6-(5-methylisoxazol-4-yl)-1-oxoisoquinolin-2(1H)-yl)methyl)benzamide;
3-((6-(Furan-3-yl)-1-oxoisoquinolin-2(1H)-yl)methyl)-N-methylbenzamide;
N-Methyl-3-((6-(2-methylfuran-3-yl)-1-oxoisoquinolin-2(1H)-yl)methyl)benzamide;
3-((6-(2,5-Dihydrofuran-3-yl)-1-oxoisoquinolin-2(1H)-yl)methyl)-N-methylbenzamide;
N-Methyl-3-((1-oxo-6-(1H-pyrrol-3-yl)isoquinolin-2(1H)-yl)methyl)benzamide;
N-Methyl-3-((6-(3-methylisoxazol-4-yl)-1-oxoisoquinolin-2(1H)-yl)methyl)benzamide;
N-(Methyl-d3)-3-((6-(3-methylisoxazol-4-yl)-1-oxoisoquinolin-2(1H)-yl)methyl)benzamide;
N-Methyl-3-(1-(6-(3-methylisoxazol-4-yl)-1-oxoisoquinolin-2(1H)-yl)ethyl)benzamide;
3-((4-Chloro-6-(3-methylisoxazol-4-yl)-1-oxoisoquinolin-2(1H)-yl)methyl)-N-methylbenzamide;
N-Methyl-6-((6-(3-methylisoxazol-4-yl)-1-oxoisoquinolin-2(1H)-yl)methyl)picolinamide;
N-Methyl-5-((6-(3-methylisoxazol-4-yl)-1-oxoisoquinolin-2(1H)-yl)methyl)nicotinamide;
N-Methyl-4-((6-(3-methylisoxazol-4-yl)-1-oxoisoquinolin-2(1H)-yl)methyl)picolinamide;
2-Fluoro-N-methyl-3-((6-(3-methylisoxazol-4-yl)-1-oxoisoquinolin-2(1H)-yl)methyl)benzamide;
3-Fluoro-N-methyl-5-((6-(3-methylisoxazol-4-yl)-1-oxoisoquinolin-2(1H)-yl)methyl)benzamide;
3-Fluoro-N-methyl-5-(1-(6-(3-methylisoxazol-4-yl)-1-oxoisoquinolin-2(1H)-yl)ethyl)benzamide;
2-Fluoro-N-methyl-5-((6-(3-methylisoxazol-4-yl)-1-oxoisoquinolin-2(1H)-yl)methyl)benzamide;
3-((4-Chloro-6-(3-methylisoxazol-4-yl)-1-oxoisoquinolin-2(1H)-yl)methyl)-5-fluoro-N-methylbenzamide;
3-Chloro-N-methyl-5-((6-(3-methylisoxazol-4-yl)-1-oxoisoquinolin-2(1H)-yl)methyl)benzamide;
N-Methyl-3-((6-(1-methyl-1H-pyrazol-5-yl)-1-oxoisoquinolin-2(1H)-yl)methyl)benzamide;
N-(Methyl-D3)-3-((6-(1-methyl-1H-pyrazol-5-yl)-1-oxoisoquinolin-2(1H)-yl)methyl)benzamide;
N-Methyl-3-(1-(6-(1-methyl-1H-pyrazol-5-yl)-1-oxoisoquinolin-2(1H)-yl)ethyl)benzamide;
3-Fluoro-N-methyl-5-((6-(1-methyl-1H-pyrazol-5-yl)-1-oxoisoquinolin-2(1H)-yl)methyl)benzamide;
3-Chloro-N-methyl-5-((6-(1-methyl-1H-pyrazol-5-yl)-1-oxoisoquinolin-2(1H)-yl)methyl)benzamide;
N-Methyl-3-((1-oxo-6-(pyridin-4-yl)isoquinolin-2(1H)-yl)methyl)benzamide;
3-((6-(2-Aminopyridin-4-yl)-1-oxoisoquinolin-2(1H)-yl)methyl)-N-methylbenzamide;
N-Methyl-3-((1-oxo-6-(pyridin-4-yl)isoquinolin-2(1H)-yl)methyl)benzamide;
3-((6-(2-Aminopyridin-4-yl)-1-oxoisoquinolin-2(1H)-yl)methyl)-N-methylbenzamide;
N-Methyl-3-((6-(1-methyl-1H-1,2,3-triazol-5-yl)-1-oxoisoquinolin-2(1H)-yl)methyl)benzamide;

N-Methyl-3-((6-morpholino-1-oxoisoquinolin-2(1H)-yl)methyl)benzamide;
3-Fluoro-N-methyl-5-((6-morpholino-1-oxoisoquinolin-2(1H)-yl)methyl)benzamide;
3-((6-(6-Oxa-3-azabicyclo[3.1.1]heptan-3-yl)-1-oxoisoquinolin-2(1H)-yl)methyl)-N-methylbenzamide;
(S)—N-Methyl-3-((6-(2-methylmorpholino)-1-oxoisoquinolin-2(1H)-yl)methyl)benzamide;
N-(3-((6-(2-Methylfuran-3-yl)-1-oxoisoquinolin-2(1H)-yl)methyl)phenyl)acetamide;
N-(3-Fluoro-5-((6-(2-methylfuran-3-yl)-1-oxoisoquinolin-2(1H)-yl)methyl)phenyl)acetamide;
N-(3-((6-(5-Methylisoxazol-4-yl)-1-oxoisoquinolin-2(1H)-yl)methyl)phenyl)acetamide;
N-(2-Fluoro-5-((6-(5-methylisoxazol-4-yl)-1-oxoisoquinolin-2(1H)-yl)methyl)phenyl)acetamide;
N-(3-((6-(3-Methyl-1H-pyrazol-4-yl)-1-oxoisoquinolin-2(1H)-yl)methyl)phenyl)acetamide;
N-(3-((1-Oxo-6-(3-(trifluoromethyl)-1H-pyrazol-4-yl)isoquinolin-2(1H)-yl)methyl)phenyl)acetamide;
N-(3-((1-Oxo-6-(3-(trifluoromethyl)-1H-pyrazol-4-yl)isoquinolin-2(1H)-yl)methyl)phenyl)isobutyramide;
N-(3-((1-Oxo-6-(3-(trifluoromethyl)-1H-pyrazol-4-yl)isoquinolin-2(1H)-yl)methyl)phenyl)tetrahydro-2H-pyran-4-carboxamide;
N-(3-((1-Oxo-6-(3-(trifluoromethyl)-1H-pyrazol-4-yl)isoquinolin-2(1H)-yl)methyl)phenyl)-3-(pyridin-2-yl)propenamide;
N-(3-((6-(3-(Difluoromethyl)-1H-pyrazol-4-yl)-1-oxoisoquinolin-2(1H)-yl)methyl)phenyl)acetamide;
N-(3-((6-(3-(Difluoromethyl)-1H-pyrazol-4-yl)-1-oxoisoquinolin-2(1H)-yl)methyl)phenyl)nicotinamide;
N-(3-((6-(3-(Difluoromethyl)-1H-pyrazol-4-yl)-1-oxoisoquinolin-2(1H)-yl)methyl)phenyl)oxetane-3-carboxamide;
N-(3-((6-(3-(Difluoromethyl)-1H-pyrazol-4-yl)-1-oxoisoquinolin-2(1H)-yl)methyl)phenyl)benzamide;
N-(3-((6-(3-Chloro-1H-pyrazol-4-yl)-1-oxoisoquinolin-2(1H)-yl)methyl)phenyl)acetamide;
N-(3-((6-(3-Chloro-1H-pyrazol-4-yl)-1-oxoisoquinolin-2(1H)-yl)methyl)phenyl)oxetane-3-carboxamide;
N-(3-((6-(3-Methylisoxazol-4-yl)-1-oxoisoquinolin-2(1H)-yl)methyl)phenyl)acetamide;
N-(3-((6-(3-Methylisoxazol-4-yl)-1-oxoisoquinolin-2(1H)-yl)methyl)phenyl)oxetane-3-carboxamide;
4-Fluoro-N-(3-((6-(3-methylisoxazol-4-yl)-1-oxoisoquinolin-2(1H)-yl)methyl)phenyl)benzamide;
N-(3-Fluoro-5-((6-(3-methylisoxazol-4-yl)-1-oxoisoquinolin-2(1H)-yl)methyl)phenyl)picolinamide;
N-(3-Fluoro-5-((6-(3-methylisoxazol-4-yl)-1-oxoisoquinolin-2(1H)-yl)methyl)phenyl)acetamide;
N-(3-((1-Oxo-6-(1H-pyrazol-4-yl)isoquinolin-2(1H)-yl)methyl)phenyl)acetamide;
N-(3-((6-(2-Aminopyridin-4-yl)-1-oxoisoquinolin-2(1H)-yl)methyl)-5-fluorophenyl)acetamide;
3-(3-Methoxybenzyl)-7-(1H-pyrazol-4-yl)quinazolin-4(3H)-one;
3-(3-Methoxybenzyl)-7-(3-methyl-1H-pyrazol-4-yl)quinazolin-4(3H)-one;
3-(3-Methoxybenzyl)-7-(3-(trifluoromethyl)-1H-pyrazol-4-yl)quinazolin-4(3H)-one;
3-(3-Methoxybenzyl)-7-(3-methylisoxazol-4-yl)quinazolin-4(3H)-one;
3-(3-Methoxybenzyl)-7-(1-methyl-1H-pyrazol-5-yl)quinazolin-4(3H)-one;
7-(3-(Difluoromethyl)-1H-pyrazol-4-yl)-3-(3-methoxybenzyl)quinazolin-4(3H)-one;
7-(3-(Difluoromethyl)-1H-pyrazol-4-yl)-3-(3-fluoro-5-methoxybenzyl)quinazolin-4(3H)-one;
7-(3-Chloro-1H-pyrazol-4-yl)-3-(3-fluoro-5-methoxybenzyl)quinazolin-4(3H)-one;
7-(3-Chloro-1H-pyrazol-4-yl)-3-(3-methoxybenzyl)quinazolin-4(3H)-one;
3-(3-Methoxybenzyl)-7-(pyridin-4-yl)quinazolin-4(3H)-one;
7-(2-Aminopyridin-4-yl)-3-(3-methoxybenzyl)quinazolin-4(3H)-one;
(R)-7-(2-Aminopyridin-4-yl)-3-(1-(3-methoxyphenyl)ethyl)quinazolin-4(3H)-one;
N-Methyl-3-((4-oxo-7-(1H-pyrazol-4-yl)quinazolin-3(4H)-yl)methyl)benzamide;
N-Methyl-3-((4-oxo-7-(5-(trifluoromethyl)-1H-pyrazol-4-yl)quinazolin-3(4H)-yl)methyl)benzamide;
N-(Methyl-D3)-3-((4-oxo-7-(5-(trifluoromethyl)-1H-pyrazol-4-yl)quinazolin-3(4H)-yl)methyl)benzamide;
N-Isopropyl-3-((4-oxo-7-(5-(trifluoromethyl)-1H-pyrazol-4-yl)quinazolin-3(4H)-yl)methyl)benzamide;
3-((4-Oxo-7-(5-(trifluoromethyl)-1H-pyrazol-4-yl)quinazolin-3(4H)-yl)methyl)-N-(2-(pyridin-4-yl)ethyl)benzamide;
N-Benzyl-3-((4-oxo-7-(5-(trifluoromethyl)-1H-pyrazol-4-yl)quinazolin-3(4H)-yl)methyl)benzamide;
3-((4-Oxo-7-(5-(trifluoromethyl)-1H-pyrazol-4-yl)quinazolin-3(4H)-yl)methyl)-N-(pyridin-4-ylmethyl)benzamide;
N-(4-(Methylsulfonamido)benzyl)-3-((4-oxo-7-(5-(trifluoromethyl)-1H-pyrazol-4-yl)quinazolin-3(4H)-yl)methyl)benzamide;
N-(1-Methyl-1H-pyrazol-3-yl)-3-((4-oxo-7-(5-(trifluoromethyl)-1H-pyrazol-4-yl)quinazolin-3(4H)-yl)methyl)benzamide;
N-(Isoxazol-3-yl)-3-((4-oxo-7-(5-(trifluoromethyl)-1H-pyrazol-4-yl)quinazolin-3(4H)-yl)methyl)benzamide;
3-((4-Oxo-7-(5-(trifluoromethyl)-1H-pyrazol-4-yl)quinazolin-3(4H)-yl)methyl)-N-(tetrahydro-2H-pyran-4-yl)benzamide;
N-(1-(Oxetan-3-yl)piperidin-4-yl)-3-((4-oxo-7-(5-(trifluoromethyl)-1H-pyrazol-4-yl)quinazolin-3(4H)-yl)methyl)benzamide;
N-(1-Methylpiperidin-4-yl)-3-((4-oxo-7-(5-(trifluoromethyl)-1H-pyrazol-4-yl)quinazolin-3(4H)-yl)methyl)benzamide;
3-((4-Oxo-7-(5-(trifluoromethyl)-1H-pyrazol-4-yl)quinazolin-3(4H)-yl)methyl)-N-((tetrahydro-2H-pyran-4-yl)methyl)benzamide;
N-(Oxetan-3-ylmethyl)-3-((4-oxo-7-(5-(trifluoromethyl)-1H-pyrazol-4-yl)quinazolin-3(4H)-yl)methyl)benzamide;
3-((4-Oxo-7-(5-(trifluoromethyl)-1H-pyrazol-4-yl)quinazolin-3(4H)-yl)methyl)-N-(piperidin-4-ylmethyl)benzamide;
N-((1S,4S)-4-Hydroxycyclohexyl)-3-((4-oxo-7-(5-(trifluoromethyl)-1H-pyrazol-4-yl)quinazolin-3(4H)-yl)methyl)benzamide;
N-((1R,4R)-4-Hydroxycyclohexyl)-3-((4-oxo-7-(5-(trifluoromethyl)-1H-pyrazol-4-yl)quinazolin-3(4H)-yl)methyl)benzamide;
N-(2-Hydroxyethyl)-3-((4-oxo-7-(5-(trifluoromethyl)-1H-pyrazol-4-yl)quinazolin-3(4H)-yl)methyl)benzamide;
N-(4-(Methylsulfonamido)phenyl)-3-((4-oxo-7-(5-(trifluoromethyl)-1H-pyrazol-4-yl)quinazolin-3(4H)-yl)methyl)benzamide;

3-Fluoro-N-methyl-5-((4-oxo-7-(5-(trifluoromethyl)-1H-pyrazol-4-yl)quinazolin-3(4H)-yl)methyl)benzamide;
3-Fluoro-N-(methyl-d3)-5-((4-oxo-7-(5-(trifluoromethyl)-1H-pyrazol-4-yl)quinazolin-3(4H)-yl)methyl)benzamide;
3-Fluoro-N-methyl-5-(1-(4-oxo-7-(5-(trifluoromethyl)-1H-pyrazol-4-yl)quinazolin-3(4H)-yl)ethyl)benzamide;
2-Fluoro-N-methyl-5-((4-oxo-7-(5-(trifluoromethyl)-1H-pyrazol-4-yl)quinazolin-3(4H)-yl)methyl)benzamide;
3-Chloro-N-methyl-5-((4-oxo-7-(5-(trifluoromethyl)-1H-pyrazol-4-yl)quinazolin-3(4H)-yl)methyl)benzamide;
3-((7-(5-(Difluoromethyl)-1H-pyrazol-4-yl)-4-oxoquinazolin-3(4H)-yl)methyl)-N-methylbenzamide;
3-((7-(5-(Difluoromethyl)-1H-pyrazol-4-yl)-4-oxoquinazolin-3(4H)-yl)methyl)-N-(methyl-d3)benzamide;
3-((7-(5-(Difluoromethyl)-1H-pyrazol-4-yl)-4-oxoquinazolin-3(4H)-yl)methyl)-N-(2-hydroxyethyl)benzamide;
3-((7-(5-(Difluoromethyl)-1H-pyrazol-4-yl)-4-oxoquinazolin-3(4H)-yl)methyl)-N-(2-(dimethylamino)ethyl)benzamide;
3-((7-(5-(Difluoromethyl)-1H-pyrazol-4-yl)-4-oxoquinazolin-3(4H)-yl)methyl)-N-((1-methylpiperidin-4-yl)methyl)benzamide;
3-((7-(5-(Difluoromethyl)-1H-pyrazol-4-yl)-4-oxoquinazolin-3(4H)-yl)methyl)-N-((tetrahydro-2H-pyran-4-yl)methyl)benzamide;
3-((7-(5-(Difluoromethyl)-1H-pyrazol-4-yl)-4-oxoquinazolin-3(4H)-yl)methyl)-N-((2-fluoropyridin-4-yl)methyl)benzamide;
3-((7-(5-(Difluoromethyl)-1H-pyrazol-4-yl)-4-oxoquinazolin-3(4H)-yl)methyl)-N-(3-(methylsulfonyl)benzyl)benzamide;
3-((7-(5-(Difluoromethyl)-1H-pyrazol-4-yl)-4-oxoquinazolin-3(4H)-yl)methyl)-N-(3-(methylsulfonamido)benzyl)benzamide;
3-((7-(5-(Difluoromethyl)-1H-pyrazol-4-yl)-4-oxoquinazolin-3(4H)-yl)methyl)-N-(3-(dimethylamino)benzyl)benzamide;
3-((7-(5-(Difluoromethyl)-1H-pyrazol-4-yl)-4-oxoquinazolin-3(4H)-yl)methyl)-5-fluoro-N-methylbenzamide;
3-((7-(5-(Difluoromethyl)-1H-pyrazol-4-yl)-4-oxoquinazolin-3(4H)-yl)methyl)-5-fluoro-N-(methyl-D3)benzamide;
5-((7-(5-Chloro-1H-pyrazol-4-yl)-4-oxoquinazolin-3(4H)-yl)methyl)-N-methylnicotinamide;
3-((7-(5-Chloro-1H-pyrazol-4-yl)-4-oxoquinazolin-3(4H)-yl)methyl)-N-methylbenzamide;
3-((7-(5-Chloro-1H-pyrazol-4-yl)-4-oxoquinazolin-3(4H)-yl)methyl)-N-(methyl-D3)benzamide;
3-(1-(7-(5-Chloro-1H-pyrazol-4-yl)-4-oxoquinazolin-3(4H)-yl)ethyl)-N-methylbenzamide;
3-((7-(5-Chloro-1H-pyrazol-4-yl)-4-oxoquinazolin-3(4H)-yl)methyl)-N-((1S,4S)-4-hydroxycyclohexyl)benzamide;
3-((7-(5-Chloro-1H-pyrazol-4-yl)-4-oxoquinazolin-3(4H)-yl)methyl)-N-(1-methylpiperidin-4-yl)benzamide;
3-((7-(5-Chloro-1H-pyrazol-4-yl)-4-oxoquinazolin-3(4H)-yl)methyl)-N-(piperidin-4-yl)benzamide;
3-((7-(5-Chloro-1H-pyrazol-4-yl)-4-oxoquinazolin-3(4H)-yl)methyl)-N-((1-methylpiperidin-4-yl)methyl)benzamide;
N-Methyl-3-((7-(3-methylisoxazol-4-yl)-4-oxoquinazolin-3(4H)-yl)methyl)benzamide;
N-(Methyl-d3)-3-((7-(3-methylisoxazol-4-yl)-4-oxoquinazolin-3(4H)-yl)methyl)benzamide;
N-methyl-3-(1-(7-(3-methylisoxazol-4-yl)-4-oxoquinazolin-3(4H)-yl)ethyl)benzamide;
N-Isopropyl-3-((7-(3-methylisoxazol-4-yl)-4-oxoquinazolin-3(4H)-yl)methyl)benzamide;
3-((7-(3-Methylisoxazol-4-yl)-4-oxoquinazolin-3(4H)-yl)methyl)-N-(oxetan-3-ylmethyl)benzamide;
3-((7-(3-Methylisoxazol-4-yl)-4-oxoquinazolin-3(4H)-yl)methyl)-N-((tetrahydro-2H-pyran-4-yl)methyl)benzamide;
3-((7-(3-Methylisoxazol-4-yl)-4-oxoquinazolin-3(4H)-yl)methyl)-N-((1-methylpiperidin-4-yl)methyl)benzamide;
3-((7-(3-Methylisoxazol-4-yl)-4-oxoquinazolin-3(4H)-yl)methyl)-N-(piperidin-4-ylmethyl)benzamide;
3-((7-(3-Methylisoxazol-4-yl)-4-oxoquinazolin-3(4H)-yl)methyl)-N-(2-(pyridin-3-yl)ethyl)benzamide;
3-((7-(3-Methylisoxazol-4-yl)-4-oxoquinazolin-3(4H)-yl)methyl)-N-(2-morpholinoethyl)benzamide;
3-((7-(3-Methylisoxazol-4-yl)-4-oxoquinazolin-3(4H)-yl)methyl)-N-(2,2,2-trifluoroethyl)benzamide;
3-Fluoro-N-methyl-5-((7-(3-methylisoxazol-4-yl)-4-oxoquinazolin-3(4H)-yl)methyl)benzamide;
3-Fluoro-N-(methyl-D3)-5-((7-(3-methylisoxazol-4-yl)-4-oxoquinazolin-3(4H)-yl)methyl)benzamide;
N-Methyl-3-((7-(1-methyl-1H-pyrazol-5-yl)-4-oxoquinazolin-3(4H)-yl)methyl)benzamide;
N-(Methyl-D3)-3-((7-(1-methyl-1H-pyrazol-5-yl)-4-oxoquinazolin-3(4H)-yl)methyl)benzamide;
N-Methyl-3-(1-(7-(1-methyl-1H-pyrazol-5-yl)-4-oxoquinazolin-3(4H)-yl)ethyl)benzamide;
N-((1S,3S)-3-Hydroxycyclobutyl)-3-((7-(1-methyl-1H-pyrazol-5-yl)-4-oxoquinazolin-3(4H)-yl)methyl)benzamide;
N-((1R,3R)-3-Hydroxycyclobutyl)-3-((7-(1-methyl-1H-pyrazol-5-yl)-4-oxoquinazolin-3(4H)-yl)methyl)benzamide;
N-((1S,4S)-4-Hydroxycyclohexyl)-3-((7-(1-methyl-1H-pyrazol-5-yl)-4-oxoquinazolin-3(4H)-yl)methyl)benzamide;
3-((7-(1-Methyl-1H-pyrazol-5-yl)-4-oxoquinazolin-3(4H)-yl)methyl)-N-(1-methylpiperidin-4-yl)benzamide;
3-((7-(1-Methyl-1H-pyrazol-5-yl)-4-oxoquinazolin-3(4H)-yl)methyl)-N-(oxetan-3-ylmethyl)benzamide;
N-(2-Hydroxyethyl)-3-((7-(1-methyl-1H-pyrazol-5-yl)-4-oxoquinazolin-3(4H)-yl)methyl)benzamide;
3-((7-(2-Aminopyridin-4-yl)-4-oxoquinazolin-3(4H)-yl)methyl)-N-methylbenzamide;
3-((7-(2-Aminopyridin-4-yl)-4-oxoquinazolin-3(4H)-yl)methyl)-N-(oxetan-3-yl)benzamide;
3-((7-(2-Aminopyridin-4-yl)-4-oxoquinazolin-3(4H)-yl)methyl)-N-(tetrahydro-2H-pyran-4-yl)benzamide;
3-((7-(2-Aminopyridin-4-yl)-4-oxoquinazolin-3(4H)-yl)methyl)-N-(1-methylpiperidin-4-yl)benzamide;
3-((7-(2-Aminopyridin-4-yl)-4-oxoquinazolin-3(4H)-yl)methyl)-N-(2-(pyridin-2-yl)ethyl)benzamide;
3-((7-(2-Aminopyridin-4-yl)-4-oxoquinazolin-3(4H)-yl)methyl)-N-((tetrahydro-2H-pyran-4-yl)methyl)benzamide;
N-Methyl-3-((7-(1-methyl-1H-1,2,3-triazol-5-yl)-4-oxoquinazolin-3(4H)-yl)methyl)benzamide;
(R)—N-Methyl-3-(1-(7-(5-methyl-1H-pyrazol-4-yl)-4-oxoquinazolin-3(4H)-yl)ethyl)benzamide;
(R)—N-Methyl-3-(1-(4-oxo-7-(5-(trifluoromethyl)-1H-pyrazol-4-yl)quinazolin-3(4H)-yl)ethyl)benzamide;

(R)—N-(Methyl-d3)-3-(1-(4-oxo-7-(5-(trifluoromethyl)-1H-pyrazol-4-yl)quinazolin-3(4H)-yl)ethyl)benzamide;

(S)—N-Methyl-3-(1-(4-oxo-7-(5-(trifluoromethyl)-1H-pyrazol-4-yl)quinazolin-3(4H)-yl)ethyl)benzamide;

(R)—N-Isopropyl-3-(1-(4-oxo-7-(5-(trifluoromethyl)-1H-pyrazol-4-yl)quinazolin-3(4H)-yl)ethyl)benzamide;

(R)-3-(1-(4-Oxo-7-(5-(trifluoromethyl)-1H-pyrazol-4-yl)quinazolin-3(4H)-yl)ethyl)-N-(pyridin-4-ylmethyl)benzamide;

(R)—N-(Isoxazol-3-yl)-3-(1-(4-oxo-7-(5-(trifluoromethyl)-1H-pyrazol-4-yl)quinazolin-3(4H)-yl)ethyl)benzamide;

(R)-3-(1-(4-Oxo-7-(5-(trifluoromethyl)-1H-pyrazol-4-yl)quinazolin-3(4H)-yl)ethyl)-N-(tetrahydro-2H-pyran-4-yl)benzamide;

(R)—N-(1-Methylpiperidin-4-yl)-3-(1-(4-oxo-7-(5-(trifluoromethyl)-1H-pyrazol-4-yl)quinazolin-3(4H)-yl)ethyl)benzamide;

(R)-3-(1-(4-Oxo-7-(5-(trifluoromethyl)-1H-pyrazol-4-yl)quinazolin-3(4H)-yl)ethyl)-N-((tetrahydro-2H-pyran-4-yl)methyl)benzamide;

(R)—N-(Oxetan-3-ylmethyl)-3-(1-(4-oxo-7-(5-(trifluoromethyl)-1H-pyrazol-4-yl)quinazolin-3(4H)-yl)ethyl)benzamide;

(R)—N-(2-Hydroxyethyl)-3-(1-(4-oxo-7-(5-(trifluoromethyl)-1H-pyrazol-4-yl)quinazolin-3(4H)-yl)ethyl)benzamide;

(R)-3-Fluoro-N-methyl-5-(1-(4-oxo-7-(5-(trifluoromethyl)-1H-pyrazol-4-yl)quinazolin-3(4H)-yl)ethyl)benzamide;

(R)-3-Fluoro-N-(methyl-d3)-5-(1-(4-oxo-7-(5-(trifluoromethyl)-1H-pyrazol-4-yl)quinazolin-3(4H)-yl)ethyl)benzamide;

(R)-2-Fluoro-N-methyl-5-(1-(4-oxo-7-(5-(trifluoromethyl)-1H-pyrazol-4-yl)quinazolin-3(4H)-yl)ethyl)benzamide;

(R)-3-(1-(7-(5-(Difluoromethyl)-1H-pyrazol-4-yl)-4-oxoquinazolin-3(4H)-yl)ethyl)-N-methylbenzamide;

(R)-3-(1-(7-(5-(Difluoromethyl)-1H-pyrazol-4-yl)-4-oxoquinazolin-3(4H)-yl)ethyl)-N-(methyl-D3)benzamide;

(R)-3-(1-(7-(5-(D)-1H-pyrazol-4-yl)-4-oxoquinazolin-3(4H)-yl)ethyl)-N-(2-hydroxyethyl)benzamide;

(R)-3-(1-(7-(5-(Difluoromethyl)-1H-pyrazol-4-yl)-4-oxoquinazolin-3(4H)-yl)ethyl)-N-(2-(dimethylamino)ethyl)benzamide;

(R)-3-(1-(7-(5-(Difluoromethyl)-1H-pyrazol-4-yl)-4-oxoquinazolin-3(4H)-yl)ethyl)-N-((1-methylpiperidin-4-yl)methyl)benzamide;

(R)-3-(1-(7-(5-(Difluoromethyl)-1H-pyrazol-4-yl)-4-oxoquinazolin-3(4H)-yl)ethyl)-N-((tetrahydro-2H-pyran-4-yl)methyl)benzamide;

(R)-3-(1-(7-(5-(Difluoromethyl)-1H-pyrazol-4-yl)-4-oxoquinazolin-3(4H)-yl)ethyl)-5-fluoro-N-methylbenzamide;

(R)-3-(1-(7-(5-Chloro-1H-pyrazol-4-yl)-4-oxoquinazolin-3(4H)-yl)ethyl)-N-(1-methylpiperidin-4-yl)benzamide;

(R)-3-(1-(7-(5-Chloro-1H-pyrazol-4-yl)-4-oxoquinazolin-3(4H)-yl)ethyl)-N-((1-methylpiperidin-4-yl)methyl)benzamide;

(R)-3-(1-(7-(5-Chloro-1H-pyrazol-4-yl)-4-oxoquinazolin-3(4H)-yl)ethyl)-N-methylbenzamide;

(R)-3-(1-(7-(5-Chloro-1H-pyrazol-4-yl)-4-oxoquinazolin-3(4H)-yl)ethyl)-N-(methyl-d3)benzamide;

(S)-3-(1-(7-(5-Chloro-1H-pyrazol-4-yl)-4-oxoquinazolin-3(4H)-yl)ethyl)-N-methylbenzamide;

(R)—N-Methyl-3-(1-(7-(3-methylisoxazol-4-yl)-4-oxoquinazolin-3(4H)-yl)ethyl)benzamide;

(R)—N-(Methyl-d3)-3-(1-(7-(3-methylisoxazol-4-yl)-4-oxoquinazolin-3(4H)-yl)ethyl)benzamide;

(R)-3-(1-(7-(3-Methylisoxazol-4-yl)-4-oxoquinazolin-3(4H)-yl)ethyl)-N-((1-methylpiperidin-4-yl)methyl)benzamide;

(R)-3-(1-(7-(3-Methylisoxazol-4-yl)-4-oxoquinazolin-3(4H)-yl)ethyl)-N-(piperidin-4-ylmethyl)benzamide;

(R)-3-(1-(7-(3-Methylisoxazol-4-yl)-4-oxoquinazolin-3(4H)-yl)ethyl)-N-(2-morpholinoethyl)benzamide;

(R)-3-(1-(7-(3-Methylisoxazol-4-yl)-4-oxoquinazolin-3(4H)-yl)ethyl)-N-(2,2,2-trifluoroethyl)benzamide;

(R)—N-Methyl-3-(1-(7-(1-methyl-1H-pyrazol-5-yl)-4-oxoquinazolin-3(4H)-yl)ethyl)benzamide;

(R)—N-(Methyl-d3)-3-(1-(7-(1-methyl-1H-pyrazol-5-yl)-4-oxoquinazolin-3(4H)-yl)ethyl)benzamide;

N-((1S,3S)-3-Hydroxycyclobutyl)-3-((R)-1-(7-(1-methyl-1H-pyrazol-5-yl)-4-oxoquinazolin-3(4H)-yl)ethyl)benzamide;

(R)-3-(1-(7-(1-Methyl-1H-pyrazol-5-yl)-4-oxoquinazolin-3(4H)-yl)ethyl)-N-(oxetan-3-ylmethyl)benzamide;

(R)—N-(2-Hydroxyethyl)-3-(1-(7-(1-methyl-1H-pyrazol-5-yl)-4-oxoquinazolin-3(4H)-yl)ethyl)benzamide;

(R)-3-(1-(7-(2-Aminopyridin-4-yl)-4-oxoquinazolin-3(4H)-yl)ethyl)-N-methylbenzamide;

3-(1-(3-Chlorophenyl)-2-hydroxyethyl)-7-(pyridin-4-yl)quinazolin-4(3H)-one;

7-(2-Aminopyridin-4-yl)-3-(1-(3-chlorophenyl)-2-hydroxyethyl)quinazolin-4(3H)-one;

3-(1-(3-Chlorophenyl)-2-hydroxyethyl)-7-(5-methyl-1H-pyrazol-4-yl)quinazolin-4(3H)-one;

3-(1-(3-Chlorophenyl)-2-hydroxyethyl)-7-(5-(trifluoromethyl)-1H-pyrazol-4-yl)quinazolin-4(3H)-one;

7-(5-Chloro-1H-pyrazol-4-yl)-3-(1-(3-chlorophenyl)-2-hydroxyethyl)quinazolin-4(3H)-one;

3-(1-(3-Chlorophenyl)-2-hydroxyethyl)-7-(3-methylisoxazol-4-yl)quinazolin-4(3H)-one;

3-(2-Hydroxy-1-(3-methoxyphenyl)ethyl)-7-(5-methyl-1H-pyrazol-4-yl)quinazolin-4(3H)-one;

3-(2-Hydroxy-1-(3-methoxyphenyl)ethyl)-7-(5-(trifluoromethyl)-1H-pyrazol-4-yl)quinazolin-4(3H)-one;

7-(5-Chloro-1H-pyrazol-4-yl)-3-(2-hydroxy-1-(3-methoxyphenyl)ethyl)quinazolin-4(3H)-one;

3-(2-Amino-1-(3-chlorophenyl)ethyl)-7-(2-aminopyridin-4-yl)quinazolin-4(3H)-one;

3-(2-Amino-1-(3-chlorophenyl)ethyl)-7-(5-methyl-1H-pyrazol-4-yl)quinazolin-4(3H)-one;

3-(2-Amino-1-(3-chlorophenyl)ethyl)-7-(5-(trifluoromethyl)-1H-pyrazol-4-yl)quinazolin-4(3H)-one;

3-(2-Amino-1-(3-chlorophenyl)ethyl)-7-(5-chloro-1H-pyrazol-4-yl)quinazolin-4(3H)-one;

3-(2-Amino-1-(3-chlorophenyl)ethyl)-7-(3-methylisoxazol-4-yl)quinazolin-4(3H)-one;

3-(2-Amino-1-(3-methoxyphenyl)ethyl)-7-(5-methyl-1H-pyrazol-4-yl)quinazolin-4(3H)-one;

3-(2-Amino-1-(3-methoxyphenyl)ethyl)-7-(5-(trifluoromethyl)-1H-pyrazol-4-yl)quinazolin-4(3H)-one;

3-(2-Amino-1-(3-methoxyphenyl)ethyl)-7-(5-chloro-1H-pyrazol-4-yl)quinazolin-4(3H)-one;

3-(2-Amino-1-(2-aminopyridin-4-yl)-4-oxoquinazolin-3(4H)-yl)ethyl)benzonitrile;

3-(2-Amino-1-(2-fluoropyridin-4-yl)-4-oxoquinazolin-3(4H)-yl)ethyl)benzonitrile;

3-(2-Amino-1-(4-oxo-7-(5-(trifluoromethyl)-1H-pyrazol-4-yl)quinazolin-3(4H)-yl)ethyl)benzonitrile;
3-(2-Amino-1-(7-(5-chloro-1H-pyrazol-4-yl)-4-oxoquinazolin-3(4H)-yl)ethyl)benzonitrile;
3-(2-Amino-1-(7-(3-fluoropyridin-4-yl)-4-oxoquinazolin-3(4H)-yl)ethyl)benzamide;
3-(2-Amino-1-(7-(2-aminopyridin-4-yl)-4-oxoquinazolin-3(4H)-yl)ethyl)benzamide;
3-(2-Amino-1-(4-oxo-7-(5-(trifluoromethyl)-1H-pyrazol-4-yl)quinazolin-3(4H)-yl)ethyl)benzamide;
3-(2-Amino-1-(7-(5-chloro-1H-pyrazol-4-yl)-4-oxoquinazolin-3(4H)-yl)ethyl)benzamide;
(R)-3-(1-(7-(5-Bromo-1H-pyrazol-4-yl)-4-oxoquinazolin-3(4H)-yl)ethyl)-N-methylbenzamide;
(R)-3-(1-(7-(5-Bromo-1H-pyrazol-4-yl)-4-oxoquinazolin-3(4H)-yl)ethyl)-N-(methyl-D3)benzamide;
3-((7-(5-Bromo-1H-pyrazol-4-yl)-4-oxoquinazolin-3(4H)-yl)methyl)-N-(methyl-d3)benzamide;
3-((6-(5-Bromo-1H-pyrazol-4-yl)-1-oxoisoquinolin-2(1H)-yl)methyl)-N-methylbenzamide;
3-((6-(5-Bromo-1H-pyrazol-4-yl)-1-oxoisoquinolin-2(1H)-yl)methyl)-N-(methyl-d3)benzamide;
(R)-3-(1-(7-(5-Bromo-1H-pyrazol-4-yl)-4-oxoquinazolin-3(4H)-yl)ethyl)-N-(oxetan-3-yl)benzamide;
(R)-3-(1-(7-(5-Bromo-1H-pyrazol-4-yl)-4-oxoquinazolin-3(4H)-yl)ethyl)-N-cyclopropylbenzamide;
(R)-3-(1-(7-(5-Bromo-1H-pyrazol-4-yl)-4-oxoquinazolin-3(4H)-yl)ethyl)-N-((6-fluoropyridin-3-yl)methyl)benzamide;
(R)-3-(1-(7-(5-Bromo-1H-pyrazol-4-yl)-4-oxoquinazolin-3(4H)-yl)ethyl)-N-(4-fluorophenyl)benzamide;
(R)-3-(1-(7-(5-Amino-1H-pyrazol-4-yl)-4-oxoquinazolin-3(4H)-yl)ethyl)-N-methylbenzamide;
(R)-3-(1-(7-(5-Amino-1H-pyrazol-4-yl)-4-oxoquinazolin-3(4H)-yl)ethyl)-N-(methyl-D3)benzamide;
(R)-3-(1-(7-(5-Amino-1H-pyrazol-4-yl)-4-oxoquinazolin-3(4H)-yl)ethyl)-N-(oxetan-3-yl)benzamide;
(R)-3-(1-(7-(5-Amino-1H-pyrazol-4-yl)-4-oxoquinazolin-3(4H)-yl)ethyl)-N-cyclopropylbenzamide;
(R)-3-(1-(7-(5-Amino-1H-pyrazol-4-yl)-4-oxoquinazolin-3(4H)-yl)ethyl)-N-((6-fluoropyridin-3-yl)methyl)benzamide;
(R)-3-(1-(7-(5-Amino-1H-pyrazol-4-yl)-4-oxoquinazolin-3(4H)-yl)ethyl)-N-methylbenzamide;
(R)-3-(1-(7-(5-Amino-1H-pyrazol-4-yl)-4-oxoquinazolin-3(4H)-yl)ethyl)-N-(methyl-D3)benzamide;
(R)-3-(1-(7-(5-Amino-1H-pyrazol-4-yl)-4-oxoquinazolin-3(4H)-yl)ethyl)-N-(oxetan-3-yl)benzamide;
(R)-3-(1-(7-(5-Amino-1H-pyrazol-4-yl)-4-oxoquinazolin-3(4H)-yl)ethyl)-N-cyclopropylbenzamide;
(R)-3-(1-(7-(5-Amino-1H-pyrazol-4-yl)-4-oxoquinazolin-3(4H)-yl)ethyl)-N-((6-fluoropyridin-3-yl)methyl)benzamide;
(S)-3-(1-(3-Chlorophenyl)-2-hydroxyethyl)-7-(5-methyl-1H-pyrazol-4-yl)-2,3-dihydroquinazolin-4(1H)-one;
(S)-3-(1-(3-Chlorophenyl)-2-hydroxyethyl)-7-(5-(trifluoromethyl)-1H-pyrazol-4-yl)-2,3-dihydroquinazolin-4(1H)-one;
(S)-7-(5-Chloro-1H-pyrazol-4-yl)-3-(1-(3-chlorophenyl)-2-hydroxyethyl)-2,3-dihydroquinazolin-4(1H)-one;
(S)-3-(1-(3-Chlorophenyl)-2-hydroxyethyl)-7-(1-methyl-1H-pyrazol-5-yl)-2,3-dihydroquinazolin-4(1H)-one;
(S)-3-(2-Hydroxy-1-(3-methoxyphenyl)ethyl)-7-(pyridin-4-yl)-2,3-dihydroquinazolin-4(1H)-one;
(S)-3-(2-Hydroxy-1-(3-methoxyphenyl)ethyl)-7-(5-(trifluoromethyl)-1H-pyrazol-4-yl)-2,3-dihydroquinazolin-4(1H)-one;
(S)-3-(2-Hydroxy-1-(3-methoxyphenyl)ethyl)-7-(5-methylisoxazol-4-yl)-2,3-dihydroquinazolin-4(1H)-one;
(S)-7-(5-Chloro-1H-pyrazol-4-yl)-3-(2-hydroxy-1-(3-methoxyphenyl)ethyl)-2,3-dihydroquinazolin-4(1H)-one;
(S)-3-(2-Hydroxy-1-(3-methoxyphenyl)ethyl)-7-(1-methyl-1H-pyrazol-5-yl)-2,3-dihydroquinazolin-4(1H)-one;
3-((4-(1-Hydroxyethyl)-1-oxo-6-(3-(trifluoromethyl)-1l2-pyrazol-4-yl)isoquinolin-2(1H)-yl)methyl)-N-methylbenzamide;
N-Cyclopropyl-3-((4-(1-hydroxyethyl)-1-oxo-6-(3-(trifluoromethyl)-1H-pyrazol-4-yl)isoquinolin-2(1H)-yl)methyl)benzamide;
3-((4-(1-Hydroxyethyl)-1-oxo-6-(3-(trifluoromethyl)-1H-pyrazol-4-yl)isoquinolin-2(1H)-yl)methyl)-N-(oxetan-3-yl)benzamide;
3-((6-(3-(Difluoromethyl)-1H-pyrazol-4-yl)-4-(1-hydroxyethyl)-1-oxoisoquinolin-2(1H)-yl)methyl)-N-methylbenzamide;
3-((6-(3-(Difluoromethyl)-1H-pyrazol-4-yl)-4-(1-hydroxyethyl)-1-oxoisoquinolin-2(1H)-yl)methyl)-N-(tetrahydro-2H-pyran-4-yl)benzamide;
3-((4-(1-Hydroxyethyl)-6-(3-methylisoxazol-4-yl)-1-oxoisoquinolin-2(1H)-yl)methyl)-N-methylbenzamide;
N-((6-Fluoropyridin-3-yl)methyl)-3-((4-(1-hydroxyethyl)-6-(3-methylisoxazol-4-yl)-1-oxoisoquinolin-2(1H)-yl)methyl)benzamide;
N-Benzyl-3-((4-(1-hydroxyethyl)-6-(3-methylisoxazol-4-yl)-1-oxoisoquinolin-2(1H)-yl)methyl)benzamide;
3-((4-(1-Hydroxyethyl)-6-(1-methyl-1H-pyrazol-5-yl)-1-oxoisoquinolin-2(1H)-yl)methyl)-N-methylbenzamide;
3-((6-(3-Chloro-1H-pyrazol-4-yl)-4-(1-hydroxyethyl)-1-oxoisoquinolin-2(1H)-yl)methyl)-N-methylbenzamide;
3-((6-(3-Chloro-1H-pyrazol-4-yl)-4-(1-hydroxyethyl)-1-oxoisoquinolin-2(1H)-yl)methyl)-N-(2-(dimethylamino)ethyl)benzamide;
3-((6-(3-Chloro-1H-pyrazol-4-yl)-4-(1-hydroxyethyl)-1-oxoisoquinolin-2(1H)-yl)methyl)-N-(2-(pyridin-2-yl)ethyl)benzamide;
3-((6-(2-Aminopyridin-4-yl)-4-(1-hydroxyethyl)-1-oxoisoquinolin-2(1H)-yl)methyl)-N-methylbenzamide;
3-((6-(3-(Difluoromethyl)-1H-pyrazol-4-yl)-4-(1-hydroxyethyl)-1-oxoisoquinolin-2(1H)-yl)methyl)-N-(tetrahydro-2H-pyran-4-yl)benzamide;
3-((4-(1-Hydroxyethyl)-6-(3-methylisoxazol-4-yl)-1-oxoisoquinolin-2(1H)-yl)methyl)-N-methylbenzamide;
N-((6-Fluoropyridin-3-yl)methyl)-3-((4-(1-hydroxyethyl)-6-(3-methylisoxazol-4-yl)-1-oxoisoquinolin-2(1H)-yl)methyl)benzamide;
N-Benzyl-3-((4-(1-hydroxyethyl)-6-(3-methylisoxazol-4-yl)-1-oxoisoquinolin-2(1H)-yl)methyl)benzamide;
3-((4-(1-Hydroxyethyl)-6-(1-methyl-1H-pyrazol-5-yl)-1-oxoisoquinolin-2(1H)-yl)methyl)-N-methylbenzamide;
3-((6-(3-Chloro-1H-pyrazol-4-yl)-4-(1-hydroxyethyl)-1-oxoisoquinolin-2(1H)-yl)methyl)-N-methylbenzamide;
3-((6-(3-Chloro-1H-pyrazol-4-yl)-4-(1-hydroxyethyl)-1-oxoisoquinolin-2(1H)-yl)methyl)-N-(2-(dimethylamino)ethyl)benzamide;

3-((6-(3-Chloro-1H-pyrazol-4-yl)-4-(1-hydroxyethyl)-1-oxoisoquinolin-2(1H)-yl)methyl)-N-(2-(pyridin-2-yl)ethyl)benzamide;

3-((6-(2-Aminopyridin-4-yl)-4-(1-hydroxyethyl)-1-oxoisoquinolin-2(1H)-yl)methyl)-N-methylbenzamide;

3-((4-(1-Hydroxyethyl)-1-oxo-6-(3-(trifluoromethyl)-1H-pyrazol-4-yl)isoquinolin-2(1H)-yl)methyl)-N-methylbenzamide;

N-Cyclopropyl-3-((4-(1-hydroxyethyl)-1-oxo-6-(3-(trifluoromethyl)-1H-pyrazol-4-yl)isoquinolin-2(1H)-yl)methyl)benzamide;

3-((4-(1-Hydroxyethyl)-1-oxo-6-(3-(trifluoromethyl)-1H-pyrazol-4-yl)isoquinolin-2(1H)-yl)methyl)-N-(oxetan-3-yl)benzamide;

3-((6-(3-(Difluoromethyl)-1H-pyrazol-4-yl)-4-(1-hydroxyethyl)-1-oxoisoquinolin-2(1H)-yl)methyl)-N-methylbenzamide;

3-((6-(3-(Difluoromethyl)-1H-pyrazol-4-yl)-4-(1-hydroxyethyl)-1-oxoisoquinolin-2(1H)-yl)methyl)-N-methylbenzamide;

3-((6-(3-(Difluoromethyl)-1H-pyrazol-4-yl)-4-(1-hydroxyethyl)-1-oxoisoquinolin-2(1H)-yl)methyl)-N-(tetrahydro-2H-pyran-4-yl)benzamide;

3-((4-(1-Hydroxyethyl)-6-(3-methylisoxazol-4-yl)-1-oxoisoquinolin-2(1H)-yl)methyl)-N-methylbenzamide;

N-((6-Fluoropyridin-3-yl)methyl)-3-((4-(1-hydroxyethyl)-6-(3-methylisoxazol-4-yl)-1-oxoisoquinolin-2(1H)-yl)methyl)benzamide;

N-Benzyl-3-((4-(1-hydroxyethyl)-6-(3-methylisoxazol-4-yl)-1-oxoisoquinolin-2(1H)-yl)methyl)benzamide;

3-((4-(1-Hydroxyethyl)-6-(1-methyl-1H-pyrazol-5-yl)-1-oxoisoquinolin-2(1H)-yl)methyl)-N-methylbenzamide;

3-((6-(3-Chloro-1H-pyrazol-4-yl)-4-(1-hydroxyethyl)-1-oxoisoquinolin-2(1H)-yl)methyl)-N-methylbenzamide;

3-((6-(3-Chloro-1H-pyrazol-4-yl)-4-(1-hydroxyethyl)-1-oxoisoquinolin-2(1H)-yl)methyl)-N-(2-(dimethylamino)ethyl)benzamide;

3-((6-(3-Chloro-1H-pyrazol-4-yl)-4-(1-hydroxyethyl)-1-oxoisoquinolin-2(1H)-yl)methyl)-N-(2-(pyridin-2-yl)ethyl)benzamide;

3-((6-(3-Amino-1H-pyrazol-4-yl)-4-(1-hydroxyethyl)-1-oxoisoquinolin-2(1H)-yl)methyl)-N-methylbenzamide;

3-((6-(2-Aminopyridin-4-yl)-4-(1-hydroxyethyl)-1-oxoisoquinolin-2(1H)-yl)methyl)-N-methylbenzamide;

3-((4-(2-Hydroxyethyl)-1-oxo-6-(5-(trifluoromethyl)-1H-pyrazol-4-yl)isoquinolin-2(1H)-yl)methyl)-N-methylbenzamide;

3-((4-(2-Hydroxypropyl)-1-oxo-6-(5-(trifluoromethyl)-1H-pyrazol-4-yl)isoquinolin-2(1H)-yl)methyl)-N-methylbenzamide;

3-((4-(2-(Dimethylamino)ethyl)-1-oxo-6-(5-(trifluoromethyl)-1H-pyrazol-4-yl)isoquinolin-2(1H)-yl)methyl)-N-methylbenzamide;

3-(1-(4-(2-Hydroxyethyl)-1-oxo-6-(5-(trifluoromethyl)-1H-pyrazol-4-yl)isoquinolin-2(1H)-yl)ethyl)-N-methylbenzamide;

3-((6-(5-Chloro-1H-pyrazol-4-yl)-4-(2-hydroxyethyl)-1-oxoisoquinolin-2(1H)-yl)methyl)-N-methylbenzamide;

3-(1-(6-(5-Chloro-1H-pyrazol-4-yl)-4-(2-hydroxyethyl)-1-oxoisoquinolin-2(1H)-yl)ethyl)-N-methylbenzamide;

3-((4-(2-Hydroxyethyl)-6-(3-methylisoxazol-4-yl)-1-oxoisoquinolin-2(1H)-yl)methyl)-N-methylbenzamide;

3-(1-(4-(2-Hydroxyethyl)-6-(3-methylisoxazol-4-yl)-1-oxoisoquinolin-2(1H)-yl)ethyl)-N-methylbenzamide;

3-(1-(6-(5-Fluoro-1H-pyrazol-4-yl)-4-(2-hydroxyethyl)-1-oxoisoquinolin-2(1H)-yl)ethyl)-N-methylbenzamide;

3-((6-(5-Fluoro-1H-pyrazol-4-yl)-4-(2-hydroxyethyl)-1-oxoisoquinolin-2(1H)-yl)methyl)-N-methylbenzamide;

3-(1-(6-(5-(Difluoromethyl)-1H-pyrazol-4-yl)-4-(2-hydroxyethyl)-1-oxoisoquinolin-2(1H)-yl)ethyl)-N-methylbenzamide;

3-((6-(5-(Difluoromethyl)-1H-pyrazol-4-yl)-4-(2-hydroxyethyl)-1-oxoisoquinolin-2(1H)-yl)methyl)-N-methylbenzamide;

3-(1-(6-(5-(Difluoromethyl)-1H-pyrazol-4-yl)-4-(2-hydroxyethyl)-1-oxoisoquinolin-2(1H)-yl)ethyl)-N-methylbenzamide;

3-((6-(5-(Difluoromethyl)-1H-pyrazol-4-yl)-4-(2-hydroxyethyl)-1-oxoisoquinolin-2(1H)-yl)methyl)-N-methylbenzamide;

3-((6-(2-Aminopyridin-4-yl)-4-(2-hydroxyethyl)-1-oxoisoquinolin-2(1H)-yl)methyl)-N-methylbenzamide;

3-((6-(5-(Difluoromethyl)-1H-pyrazol-4-yl)-4-(2-hydroxypropyl)-1-oxoisoquinolin-2(1H)-yl)methyl)-N-methylbenzamide;

3-((6-(5-Chloro-1H-pyrazol-4-yl)-4-(2-hydroxypropyl)-1-oxoisoquinolin-2(1H)-yl)methyl)-N-methylbenzamide;

3-((6-(2-Fluoro-1H-pyrrol-3-yl)-4-(2-hydroxypropyl)-1-oxoisoquinolin-2(1H)-yl)methyl)-N-methylbenzamide;

3-((4-(2-Hydroxypropyl)-6-(3-methylisoxazol-4-yl)-1-oxoisoquinolin-2(1H)-yl)methyl)-N-methylbenzamide;

3-((6-(3-Amino-1H-pyrazol-4-yl)-4-(2-hydroxypropyl)-1-oxoisoquinolin-2(1H)-yl)methyl)-N-methylbenzamide;

3-(1-(4-(2-(Dimethylamino)ethyl)-1-oxo-6-(5-(trifluoromethyl)-1H-pyrazol-4-yl)isoquinolin-2(1H)-yl)ethyl)-N-methylbenzamide;

3-(1-(4-(2-(Dimethylamino)ethyl)-1-oxo-6-(5-(trifluoromethyl)-1H-pyrazol-4-yl)isoquinolin-2(1H)-yl)ethyl)-N-methylbenzamide;

3-(1-(6-(5-Chloro-1H-pyrazol-4-yl)-4-(2-(dimethylamino)ethyl)-1-oxoisoquinolin-2(1H)-yl)ethyl)-N-methylbenzamide;

3-((4-(2-(Dimethylamino)ethyl)-6-(1-methyl-1H-pyrazol-5-yl)-1-oxoisoquinolin-2(1H)-yl)methyl)-N-methylbenzamide;

3-((6-(3-Amino-1H-pyrazol-4-yl)-4-(2-(dimethylamino)ethyl)-1-oxoisoquinolin-2(1H)-yl)methyl)-N-methylbenzamide;

(R)-3-(1-(7-(5-chloro-1H-pyrazol-4-yl)-4-oxopyrido[4,3-d]pyrimidin-3(4H)-yl)ethyl)-N-methylbenzamide;

(R)-3-(1-(7-(5-fluoro-1H-pyrazol-4-yl)-4-oxopyrido[4,3-d]pyrimidin-3(4H)-yl)ethyl)-N-methylbenzamide;

(R)-3-(1-(7-(5-methoxy-1H-pyrazol-4-yl)-4-oxopyrido[4,3-d]pyrimidin-3(4H)-yl)ethyl)-N-methylbenzamide;

(R)—N-methyl-3-(1-(7-(3-methylisoxazol-4-yl)-4-oxopyrido[4,3-d]pyrimidin-3(4H)-yl)ethyl)benzamide;

(R)-(4-(3-(1-(3-(methylcarbamoyl)phenyl)ethyl)-4-oxo-3,4-dihydroquinazolin-7-yl)-5-(trifluoromethyl)-1H-pyrazol-1-yl)methyl dihydrogen phosphate; or Disodium (R)-(4-(3-(1-(3-(methylcarbamoyl)phenyl)ethyl)-4-oxo-3,4-dihydroquinazolin-7-yl)-5-(trifluoromethyl)-1H-pyrazol-1-yl)methyl phosphate.

12. A method for treating or alleviating a ROCK-mediated disease or disorder, the method comprising administering to a subject in need the compound, salt, diastereomer, enantiomer, racemate, hydrate, solvate, or prodrug of claim 1.

13. The method of claim 12, wherein ROCK-mediated disease or disorder is a fibrotic disease or disorder, a cardiovascular disease or disorder, an inflammatory disease or disorder, a neurological disease or disorder, or a proliferative disease or disorder.

14. The method of claim 13, wherein the fibrotic disease or disorder is pulmonary fibrosis selected from the group consisting of cystic and idiopathic pulmonary fibrosis, radiation induced lung injury, liver fibrosis including cirrhosis, cardiac fibrosis including arterial fibrosis, endomyocardial fibrosis, old myocardial infraction, arterial stiffness, atherosclerosis, restenosis, arthrofibrosis, Crohn's disease, myelofibrosis, Peyronie's diseases, nephrogenic systemic fibrosis, progressive massive fibrosis, retroperitoneal cavity fibrosis, scleroderma/systemic sclerosis, mediastinal fibrosis, Keloids and hypertrophic scars, glial scaring, and renal fibrosis.

15. The method of claim 13, wherein the cardiovascular disease or disorder is selected from the group consisting of angina, atherosclerosis, cerebral vasospasm, cerebrovascular contraction, coronary vasospasm, endothelial dysfunction, erectile dysfunction, glaucoma, hypertension, ischemic/reperfusion injury, myocardial hypertrophy, myocardial infarction, peripheral circulation disorder, preterm labor, Raynaud's Disease, renal disease, and stroke.

16. The method of claim 13, wherein the proliferative disease or disorder is an invasive or metastatic cancer selected from the group consisting of adenocarcinoma, adrenocortical cancer, bladder cancer, bone cancer, brain cancer, breast cancer, cancer of the buccal cavity, cervical cancer, colon cancer, colorectal cancer, endometrial or uterine carcinoma, epidermoid carcinoma, esophageal cancer, eye cancer, follicular carcinoma, gallbladder cancer, gastrointestinal cancer, cancer of the genitourinary tract, glioblastoma, hairy cell carcinoma, head and neck cancer, hepatic carcinoma, hepatocellular cancer, Hodgkin's disease, keratoacanthoma, kidney cancer, large cell carcinoma, cancer of the large intestine, laryngeal cancer, liver cancer, adenocarcinoma of the lung, small-cell lung cancer, squamous carcinoma of the lung, non-small cell lung cancer, melanoma, a myeloproliferative disorder, neuroblastoma, ovarian cancer, papillary carcinoma, pancreatic cancer, cancer of the peritoneum, prostate cancer, rectal cancer, salivary gland carcinoma, sarcoma, squamous cell cancer, small cell carcinoma, cancer of the small intestine, stomach cancer, testicular cancer, thyroid cancer, and vulval cancer.

17. The method of claim 13, wherein the neurological disease or disorder is selected from the group consisting of Huntington's disease, Parkinson's Disease, Alzheimer's, Amyotrophic lateral sclerosis (ALS), Batten disease, dementia, spinal muscular atrophy, motor neuron diseases, spinocerebellar ataxia, acute or chronic pain, dementia, neuronal degeneration, spinal cord injury, cerebral vasospasm, and multiple sclerosis.

18. A method of treating cancer comprising administering to a subject in need a composition comprising a therapeutically effective amount of at least one of the compound, salt, diastereomer, enantiomer, racemate, hydrate, solvate, or prodrug of claim 1 and a therapeutically effective amount of at least one immune checkpoint inhibitor, wherein the cancer is adenocarcinoma, adrenocortical cancer, bladder cancer, bone cancer, brain cancer, breast cancer, buccal cavity cancer, cervical cancer, colon cancer, colorectal cancer, endometrial or uterine carcinoma, epidermoid carcinoma, esophageal cancer, eye cancer, follicular carcinoma, gallbladder cancer, gastrointestinal cancer, genitourinary tract cancer, glioblastoma, hairy cell carcinoma, head and neck cancer, hepatic carcinoma, hepatocellular cancer, Hodgkin's disease, keratoacanthoma, kidney cancer, large cell carcinoma, large intestine cancer, laryngeal cancer, liver cancer, lung adenocarcinoma, small-cell lung cancer, lung squamous carcinoma, non-small cell lung cancer, melanoma, a myeloproliferative disorder, neuroblastoma, ovarian cancer, papillary carcinoma, pancreatic cancer, peritoneal cancer, prostate cancer, rectal cancer, salivary gland carcinoma, sarcoma, squamous cell cancer, small cell carcinoma, small intestine cancer, stomach cancer, testicular cancer, thyroid cancer, vulvar cancer, or any combination thereof.

19. The method of claim 18, wherein the checkpoint inhibitor is a PD-1 inhibitor, a PD-L1 inhibitor, or a CTLA-4 inhibitor.

20. A method of treating a cancer comprising administering to a subject in need a composition comprising a therapeutically effective amount of at least one of the compound, salt, diastereomer, enantiomer, racemate, hydrate, solvate, or prodrug of claim 1 and a therapeutically effective amount of at least one immunogenic cell death (ICD)-inducing chemotherapeutic, wherein the cancer is adenocarcinoma, adrenocortical cancer, bladder cancer, bone cancer, brain cancer, breast cancer, buccal cavity cancer, cervical cancer, colon cancer, colorectal cancer, endometrial or uterine carcinoma, epidermoid carcinoma, esophageal cancer, eye cancer, follicular carcinoma, gallbladder cancer, gastrointestinal cancer, genitourinary tract cancer, glioblastoma, hairy cell carcinoma, head and neck cancer, hepatic carcinoma, hepatocellular cancer, Hodgkin's disease, keratoacanthoma, kidney cancer, large cell carcinoma, large intestine cancer, laryngeal cancer, liver cancer, lung adenocarcinoma, small-cell lung cancer, lung squamous carcinoma, non-small cell lung cancer, melanoma, a myeloproliferative disorder, neuroblastoma, ovarian cancer, papillary carcinoma, pancreatic cancer, peritoneal cancer, prostate cancer, rectal cancer, salivary gland carcinoma, sarcoma, squamous cell cancer, small cell carcinoma, small intestine cancer, stomach cancer, testicular cancer, thyroid cancer, vulvar cancer, or any combination thereof.

21. The method of claim 20, wherein the immunogenic cell death (ICD)-inducing chemotherapeutic is doxorubicin, idarubicin, mitoxantrone, tautomycin, calyculin A, salubrinal, oxaliplatin, bleomycin, or cyclophosphamide.

* * * * *